(12) United States Patent
Jones et al.

(10) Patent No.: US 9,085,581 B2
(45) Date of Patent: Jul. 21, 2015

(54) PROCESSES FOR THE PREPARATION OF S1P1 RECEPTOR MODULATORS AND CRYSTALLINE FORMS THEREOF

(75) Inventors: Robert M. Jones, San Diego, CA (US); Daniel J. Buzard, San Diego, CA (US); Tawfik Gharbaoui, Escondido, CA (US); Benjamin R. Johnson, San Diego, CA (US); Michelle Kasem, Chula Vista, CA (US); Thomas O. Schrader, San Diego, CA (US); Scott Stirn, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/581,846

(22) PCT Filed: Mar. 2, 2011

(86) PCT No.: PCT/US2011/026806
§ 371 (c)(1),
(2), (4) Date: Aug. 30, 2012

(87) PCT Pub. No.: WO2011/109471
PCT Pub. Date: Sep. 9, 2011

(65) Prior Publication Data
US 2012/0329848 A1 Dec. 27, 2012

Related U.S. Application Data

(60) Provisional application No. 61/339,362, filed on Mar. 3, 2010.

(51) Int. Cl.
C07D 487/16 (2006.01)
A61K 31/403 (2006.01)
C07D 487/04 (2006.01)

(52) U.S. Cl.
CPC .................................. *C07D 487/04* (2013.01)

(58) Field of Classification Search
None
See application file for complete search history.

(56) References Cited

U.S. PATENT DOCUMENTS

| | | | |
|---|---|---|---|
| 3,206,470 A * | 9/1965 | Remers et al. ............... | 548/428 |
| 4,057,559 A | 11/1977 | Asselin et al. | |
| 4,782,076 A | 11/1988 | Mobilio et al. | |
| 4,810,699 A | 3/1989 | Sabatucci et al. | |
| 5,221,678 A | 6/1993 | Atkinson et al. | |
| 5,776,967 A | 7/1998 | Kreft et al. | |
| 5,830,911 A | 11/1998 | Failli et al. | |
| 6,410,583 B1 | 6/2002 | Labelle et al. | |
| 6,960,692 B2 | 11/2005 | Kohno et al. | |
| 7,250,441 B2 | 7/2007 | Gopalsamy et al. | |
| 8,415,484 B2 * | 4/2013 | Jones et al. ................ | 548/302.4 |
| 2003/0083269 A1 | 5/2003 | Brouillette et al. | |
| 2003/0211421 A1 | 11/2003 | Hanabata et al. | |
| 2004/0224941 A1 | 11/2004 | Seko et al. | |
| 2004/0254222 A1 | 12/2004 | Kohno et al. | |
| 2005/0004114 A1 | 1/2005 | Whitehouse et al. | |
| 2005/0009786 A1 | 1/2005 | Pan et al. | |
| 2005/0014724 A1 | 1/2005 | Marsilje et al. | |
| 2005/0014725 A1 | 1/2005 | Mi et al. | |

(Continued)

FOREIGN PATENT DOCUMENTS

| | | |
|---|---|---|
| EP | 0468785 | 1/1992 |
| EP | 1650186 | 4/2006 |

(Continued)

OTHER PUBLICATIONS

Schafiee et al., "An efficent enzyme-catalyzed kinetic resolution: large-scale preparation of an enantiomerically pure indole-ethyl ester derivative, a key component for the synthesis of a prostaglandin D2 receptor antagonist, an anti-allergic rhinitis drug candidate," *Tetrahedron: Asymmetry*, 2005, 16:3094-3098.
Actelion, Clinical Trials.gov, "Multicenter, Randomized, Double-blind, Placebo-controlled, Phase IIa Study to Evaluate the Efficacy, Safety, and Tolerability of ACT-128800, an S1P1 Receptor Agonist, Administered for 6 Weeks to Subjects With Moderate to Severe Chronic Plaque Psoriasis" http://clinicaltrials.gov/ct2/show/NCT00852670, 2009.
Arbiser, "Why targeted therapy hasn't worked in advanced cancer," J Clinical Invest., 117(10):2762-2765, (2007).
Balatoni et al., "FTY720 sustains and restores neuronal function in the DA rat model of MOG-induced experimental autoimmunue encephalomyelitis," Brain Res. Bull., 2007, 74:307-316.
Bar-Haim et al., "Interrelationship between Dendritic Cell Trafficking and *Francisella tularensis* Dissemination following Airway Infection," PLoS Pathog., 2008, 4(11):e1000211, 15 pages.

(Continued)

*Primary Examiner* — Nyeemah A Grazier
(74) *Attorney, Agent, or Firm* — Fish & Richardson P.C.; Lyle W. Spruce

(57) ABSTRACT

The present invention relates to salts, processes, and process intermediates useful in the preparation of (R)-2-(9-chloro-7-(4-isopropoxy-3-(trifluoromethyl)benzyloxy)-2,3-dihydro-1H-pyrrolo[1,2-a]indol-1-yl)acetic acid of Formula (Ia), salts, and crystalline forms thereof. The compound (R)-2-(9-chloro-7-(4-isopropoxy-3-(trifluoromethyl)benzyloxy)-2,3-dihydro-1H-pyrrolo[1,2-a]indol-1-yl)acetic acid has been identified as an S1P1 receptor modulator that is useful in the treatment of S1P1 receptor-associated disorders, for example, diseases and disorders mediated by lymphocytes, transplant rejection, autoimmune diseases and disorders, inflammatory diseases and disorders (e.g., acute and chronic inflammatory conditions), cancer, and conditions characterized by an underlying defect in vascular integrity or that are associated with angiogenesis such as may be pathologic (e.g., as may occur in inflammation, tumor development, and atherosclerosis).

(Ia)

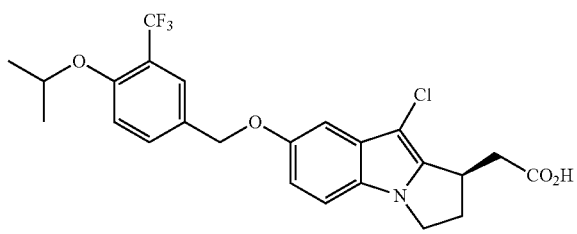

30 Claims, 17 Drawing Sheets

(56) References Cited

U.S. PATENT DOCUMENTS

| | | |
|---|---|---|
| 2005/0014728 A1 | 1/2005 | Pan et al. |
| 2005/0033055 A1 | 2/2005 | Bugianesi et al. |
| 2005/0239899 A1 | 10/2005 | Fecke et al. |
| 2006/0004010 A1 | 1/2006 | Habashita et al. |
| 2006/0063821 A1 | 3/2006 | Gopalsamy et al. |
| 2006/0079542 A1 | 4/2006 | Nestor |
| 2006/0122222 A1 | 6/2006 | Whitehouse et al. |
| 2006/0160771 A1 | 7/2006 | Kohno et al. |
| 2006/0211656 A1 | 9/2006 | Albert et al. |
| 2006/0223866 A1 | 10/2006 | Evindar et al. |
| 2007/0010494 A1 | 1/2007 | Ehrhardt et al. |
| 2007/0043014 A1 | 2/2007 | Doherty et al. |
| 2007/0060573 A1 | 3/2007 | Wortmann et al. |
| 2007/0149595 A1 | 6/2007 | Tanaka et al. |
| 2007/0149597 A1 | 6/2007 | Nishi et al. |
| 2007/0167425 A1 | 7/2007 | Nakade et al. |
| 2007/0173487 A1 | 7/2007 | Saha et al. |
| 2007/0173507 A1 | 7/2007 | Hirata |
| 2007/0191313 A1 | 8/2007 | Beard et al. |
| 2007/0191371 A1 | 8/2007 | Bennett et al. |
| 2007/0191468 A1 | 8/2007 | Nishi et al. |
| 2007/0244155 A1 | 10/2007 | Sharma et al. |
| 2007/0254886 A1 | 11/2007 | Habashita et al. |
| 2008/0051418 A1 | 2/2008 | Maekawa et al. |
| 2008/0153882 A1 | 6/2008 | Nishi et al. |
| 2008/0200535 A1 | 8/2008 | Ohmori et al. |
| 2008/0207584 A1 | 8/2008 | Habashita et al. |
| 2008/0319077 A1 | 12/2008 | Suzuki et al. |
| 2009/0012093 A1 | 1/2009 | Fukatsu et al. |
| 2009/0076070 A1 | 3/2009 | Harada et al. |
| 2009/0131438 A1 | 5/2009 | Ono et al. |
| 2009/0137685 A1 | 5/2009 | Kojima et al. |
| 2009/0325907 A1 | 12/2009 | Kohno et al. |
| 2010/0267778 A1 | 10/2010 | Kusuda et al. |
| 2010/0273806 A1 | 10/2010 | Jones et al. |
| 2010/0292233 A1 | 11/2010 | Jones et al. |
| 2011/0130409 A1 | 6/2011 | Jones et al. |
| 2011/0160243 A1 | 6/2011 | Jones et al. |
| 2012/0064060 A1 | 3/2012 | Habashita et al. |
| 2012/0295947 A1 | 11/2012 | Montalban et al. |
| 2013/0184307 A1 | 7/2013 | Jones et al. |

FOREIGN PATENT DOCUMENTS

| | | |
|---|---|---|
| EP | 1826197 | 8/2007 |
| EP | 2003132 | 12/2008 |
| EP | 1772145 | 3/2011 |
| EP | 2017263 | 11/2011 |
| GB | 1436893 | 5/1976 |
| JP | 2007262009 | 10/2007 |
| WO | WO 91/06537 | 5/1991 |
| WO | WO 97/14674 | 4/1997 |
| WO | WO 00/64888 | 11/2000 |
| WO | WO 02/39987 | 5/2002 |
| WO | WO 02/064616 | 8/2002 |
| WO | WO 02/092068 | 11/2002 |
| WO | WO 03/029205 | 4/2003 |
| WO | WO 03/062252 | 7/2003 |
| WO | WO 03/074008 | 9/2003 |
| WO | WO 03/061567 | 12/2003 |
| WO | WO 03/105771 | 12/2003 |
| WO | WO 03/073986 | 5/2004 |
| WO | WO 2004/058149 | 9/2004 |
| WO | WO 2004/074297 | 9/2004 |
| WO | WO 2004/010949 | 10/2004 |
| WO | WO 2004/071442 | 10/2004 |
| WO | WO 2004/096752 | 11/2004 |
| WO | WO 2004/103309 | 12/2004 |
| WO | WO 2004/104205 | 12/2004 |
| WO | WO 2004/096757 | 1/2005 |
| WO | WO 2005/000833 | 1/2005 |
| WO | WO 2004/110979 | 2/2005 |
| WO | WO 2004/103306 | 3/2005 |
| WO | WO 2005/021503 | 3/2005 |
| WO | WO 2005/020882 | 4/2005 |
| WO | WO 2005/032465 | 4/2005 |
| WO | WO 2004/103279 | 5/2005 |
| WO | WO 2005/041899 | 5/2005 |
| WO | WO 2005/044780 | 5/2005 |
| WO | WO 2005/058848 | 6/2005 |
| WO | WO 2005/070886 | 8/2005 |
| WO | WO 2005/079788 | 9/2005 |
| WO | WO 2005/082089 | 9/2005 |
| WO | WO 2005/082841 | 9/2005 |
| WO | WO 2005/085179 | 9/2005 |
| WO | WO 2005/097745 | 10/2005 |
| WO | WO 2005/058295 | 11/2005 |
| WO | WO 2005/123677 | 12/2005 |
| WO | WO 2006/001463 | 1/2006 |
| WO | WO 2006/009092 | 1/2006 |
| WO | WO 2006/010379 | 2/2006 |
| WO | WO 2006/011554 | 2/2006 |
| WO | WO 2006/013948 | 2/2006 |
| WO | WO 2006/020951 | 2/2006 |
| WO | WO 2004/113330 | 3/2006 |
| WO | WO 2006/010544 | 3/2006 |
| WO | WO 2006/034337 | 3/2006 |
| WO | WO 2006/043149 | 4/2006 |
| WO | WO 2006/047195 | 5/2006 |
| WO | WO 2006/064757 | 6/2006 |
| WO | WO 2006/079406 | 8/2006 |
| WO | WO 2006/088944 | 8/2006 |
| WO | WO 2006/100631 | 9/2006 |
| WO | WO 2006/100633 | 9/2006 |
| WO | WO 2006/063033 | 11/2006 |
| WO | WO 2006/131336 | 12/2006 |
| WO | WO 2006/137019 | 12/2006 |
| WO | WO 2006/137509 | 12/2006 |
| WO | WO 2006/100635 | 1/2007 |
| WO | WO 2007/024922 | 3/2007 |
| WO | WO 2007/037196 | 4/2007 |
| WO | WO 2007/060626 | 5/2007 |
| WO | WO 2007/080542 | 7/2007 |
| WO | WO 2007/083089 | 7/2007 |
| WO | WO 2007/085451 | 8/2007 |
| WO | WO 2007/086001 | 8/2007 |
| WO | WO 2007/091396 | 8/2007 |
| WO | WO 2007/091501 | 8/2007 |
| WO | WO 2007/092638 | 8/2007 |
| WO | WO 2007/109330 | 9/2007 |
| WO | WO 2007/095561 | 10/2007 |
| WO | WO 2007/115820 | 10/2007 |
| WO | WO 2007/116866 | 10/2007 |
| WO | WO 2007/061458 | 11/2007 |
| WO | WO 2007/092190 | 11/2007 |
| WO | WO 2007/129473 | 11/2007 |
| WO | WO 2007/129745 | 11/2007 |
| WO | WO 2007/132307 | 11/2007 |
| WO | WO 2007/100617 | 1/2008 |
| WO | WO 2007/109334 | 1/2008 |
| WO | WO 2008/016674 | 2/2008 |
| WO | WO 2008/018427 | 2/2008 |
| WO | WO 2008/019090 | 2/2008 |
| WO | WO 2008/023783 | 2/2008 |
| WO | WO 2008/024196 | 2/2008 |
| WO | WO 2008/016692 | 3/2008 |
| WO | WO 2008/028937 | 3/2008 |
| WO | WO 2008/029371 | 3/2008 |
| WO | WO 2008/030843 | 3/2008 |
| WO | WO 2008/035239 | 3/2008 |
| WO | WO 2008/029306 | 5/2008 |
| WO | WO 2008/074820 | 6/2008 |
| WO | WO 2008/074821 | 6/2008 |
| WO | WO 2008/076356 | 6/2008 |
| WO | WO 2008/079382 | 7/2008 |
| WO | WO 2008/089015 | 7/2008 |
| WO | WO 2008/091967 | 7/2008 |
| WO | WO 2008/114157 | 9/2008 |
| WO | WO 2008/128951 | 10/2008 |
| WO | WO 2007/098474 | 11/2008 |
| WO | WO 2008/097819 | 11/2008 |
| WO | WO 2008/152149 | 12/2008 |
| WO | WO 2009/019167 | 2/2009 |

(56) References Cited

FOREIGN PATENT DOCUMENTS

| WO | WO 2009/019506 | 2/2009 |
|---|---|---|
| WO | WO 2009/011850 | 3/2009 |
| WO | WO 2009/064250 | 5/2009 |
| WO | WO 2009/078983 | 6/2009 |
| WO | WO 2009/094157 | 7/2009 |
| WO | WO 2009/103552 | 8/2009 |
| WO | WO 2009/151529 | 12/2009 |
| WO | WO 2009/151621 | 12/2009 |
| WO | WO 2009/151626 | 12/2009 |
| WO | WO 2010/011316 | 1/2010 |
| WO | WO 2010/027431 | 3/2010 |
| WO | WO 2010/093704 | 8/2010 |
| WO | WO 2011/005290 | 1/2011 |
| WO | WO 2011/005295 | 1/2011 |
| WO | WO 2011/059784 | 5/2011 |
| WO | WO 2011/094008 | 8/2011 |
| WO | WO 2011/109471 | 9/2011 |
| WO | WO 2012/015758 | 2/2012 |

OTHER PUBLICATIONS

Baumruker et al., "FTY720, an immunomodulatory sphingolipid mimetic: translation of a novel mechanism into clinical benefit in multiple sclerosis," Expert Opin. Investig. Drugs, 2007, 16(3):283-289.

Berge et al., "Pharmaceutical Salts," J Pharma Sci., 1977, 66(1):1-19.

Biopharmatiques, "Merging Pharma and Biotech", http://www.biopharmaceutiques.com/fr/tables/clinical_studies_709.html, 2009.

Bioreversible Carriers in Drug Design, ed. Edward B. Roche, American Pharmaceutical Association and Pergamon Press 1987 *too voluminous.

Boismenu et al., "Insights from mouse models of colitis," K. Leukoc Biol, 67:267-278, 2000.

Bolick et al., "Sphingosine-l-Phosphate Prevents Tumor Necrosis Factor-alpha-Mediated Monocyte Adhesion to Aortic Endothelium in Mice," Arterioscler. Thromb. Vasc. Biol., 2005, 25:976-981.

Brinkman, "Sphingosine 1-phosphate receptors in health and disease: Mechanistic insights from gene deletion studies and reverse pharmacology," Pharmacol. Ther., 2007, 115:84-105.

Brinkmann et al., "FTY720 Alters Lymphocyte Homing and Protects Allografts Without Inducing General Immunosuppression," Transplantation Proc., 2001, 33:530-531.

Brinkmann et al., "FTY720: Altered Lymphocyte Traffic Results in Allograft Protection," Transplantation, Sep. 2001, 72(5):764-769.

Brinkmann et al., "The Immune Modulator FTY720 Targets Sphingosine 1-Phosphate Receptors," J Biol. Chem., 2002, 277(24):21453-21457.

Brinkmann, "FTY720 (fingolimod) in Multiple Sclerosis: therapeutic effects in the immune and the central nervous system", British Journal of Pharmacology, 158: 1173-1182, 2009.

Budde et al., "First Human Trial of FTY720, a Novel Immunomodulator, in Stable Renal Transplant Patients," J Am Soc. Nephrol., 2002, 13:1073-1083.

Buzard, Daniel J. et al., "Discovery and Characterization of Potent and Selective 4-Oxo-4-(5-(5-phenyl-1,2,4-oxadiazol-3-ypindolin-l-yl)butanoic acids as S1P1 Receptor Agonists", Arena Pharmaceuticals, Inc., MEDI099, ACS, Mar. 2011.

Buzard et al., "Discovery and Characterization of Potent and Selective 4-Oxo-4-(5-(5-phenyl-1,2,4-oxadiazol-3-ypindolin-l-yl)butanoic acids as S1P1 Agonists", Biorganic Med. Chem. Lett., 2011, 6013-6018.

Buzard, Daniel J. et al, "Recent Progress in the Development of Selective S1P1 Receptor Agonists for the Treatment of Inflammatory and Autoimmune Disorders", Expert Opinion, 1141-1159, 2008.

Chawla et al., Challenges in Polymorphism of Pharmaceuticals, CRIPS, Jan.-Mar. 2004, vol. 5, No. 1, 4 pages.

Chiba et al., "Role of Sphingosine 1-Phosphate Receptor Type 1 in Lumphocyte Egress from Secondary Lymphoid Tissues and Thymus," Cell Mole Immunol., Feb. 2006, 3(1):11-19.

Chiba, "FTY720, a new class of immunomodulator, inhibits lymphocyte egress from secondary lymphoid tissues and thymus by agonistic activity at sphingosine 1-phosphate receptors," Pharmacol. Ther., 2005, 108:308-319.

Chun et al., "International Union of Pharmacology. XXXIV. Lysophospholipid Receptor Nomenclature," Pharmacol. Rev., 2002, 54(2):256-269.

Hoffman, "Crohns disease and ulcerative colitis," Sep. 1995, http://www.drhoffman.com/page.cfm/171, 5 pages.

Coelho et al., "The Immunomodulator FTY720 has a direct cytoprotective effect in oligodendrocyte Progenitors," J Pharmacol. Exp. Ther., 2007, 323:626-635.

Collier et al, "Radiosynthesis and in-vivo Evaluation of the Psuedopeptide 8-pioid Antagonist [$^{125}$I]-ITIPP(Ψ)," J. Labelled Compd. Radiopharm., 1999, 42, S264-S266.

Coste et al., "Antinociceptive activity of the S1P-receptor agonist FTY720," J Cell Moll Med., 2008, 12(3):995-1004.

Daniel et al., "FTY720 Ameliorates Th1-Mediated Colitis in Mice by Directly Affecting the Functional Activity of DC4+CD25+ Regulatory T Cell1," J Immunol., 2007, 178:2458-2468.

Deguchi et al., "The S1P receptor modulator FTY720 prevents the development of experimental colitis in mice," Oncol. Rep., 2006, 16:699-703.

Dev et al., "Brain sphingosine-1-phosphate receptors: Implication for FTY720 in the treatment of multiple sclerosis," Pharmacol Ther., 2008, 117:77-93.

Fischer et al., "Targeting receptor tyrosine kinase signalling in small cell lung cancer (SCLC): What have we learned so far?" Cancer Treatment Revs., 2007, 33:391-406.

Fu et al., "Long-term islet graft survival in streptozotocin- and autoimmune-induced diabetes models by immunosuppressive and potential insulinotropic agent FTY720," Transplantation, May 2002, 73(9):1425-1430.

Fujii et al., "FTY720 suppresses CD4+CD44highCD62L− effector memory T cell-mediated colitis," Am J Physiol Gastrointest Liver Physiol., 2006, 291:G267-G274.

Fujino et al., "Amerlioration of Experimental Autoimmune Encephalomyelitis in Lewis Rats by FTY720 Treatment," J Pharmacol. Exp. Ther., 2003, 305(1):70-77.

Fujishiro et al., "Change from Cyclosporine to Combination Therapy of Mycophenolic Acid with the New Sphinogosine-1-phosphate Receptor Agonist, KRP-203, Prevents Host Nephrotoxicity and Transplant Vasculopathy in Rats," J Heart Lung Transplant, 2006, 25:825-833.

Gabriel et al, "High Throughput Screening Technologies for Direct Cyclic AMP Measurement," ASSAY and Drug Development Technologies, 1:291-303, 2003.

Golub et al., "Molecular Classification of Cancer: Class Discovery and Class Prediction by Gene Expression Monitoring," Science, 1999, 286:531-537.

Gottlieb, et al., "NMR Chemical Shifts of Common Laboratory Solvents as trace Impurities," *J. Org. Chem.* 1997, 62, 7512-7515.

Greene, T.W. and Wuts, P.G.M., *Protective Groups in Organic Synthesis*, 3$^{rd}$ Edition, 1999 [Wiley].

Griesser, "The Importance of Solvates" in *Polymorphism in the Pharmaceutical Industry*, 211-233 (Rolf Hilfiker, ed., 2006).

Groeneveld, "Vascular pharmacology of acute lung injury and acute respiratory distress syndrome," Vascular Pharmacol., 2003, 39:247-256.

Guillory, "Generation of Polymorphs, Hydrates, Solvates, and Amorphous Solids," in:Polymorphism in Pharmaceutical Solids, ed. Harry

(56) References Cited

OTHER PUBLICATIONS

G. Brittan, vol. 95, Marcel Dekker, Inc. New York, 1999, pp. 202-209.

Hale et al., "Potent S1P receptor agonists replicate the pharmacologic actions of the novel immune modulator FTY720," Bioorganic Med Chem. Lett., 2004, 14:3351-335.

Han, Sangdon et al., "Discovery of 2-(7-(5-phenyl-1,2,4-oxadiazol-3-yl)-1,2,3,4-tetrahydrocyclopenta[b]indol-3-yl)acetic acids: Potent and Selective Sphingosine-1-phosphate (S1P1) Receptor Agonists", Arena Pharmaceuticals, Inc., MEDI098, ACS Poster, Mar. 2011.

Herzinger et al., "Sphingosine-1-Phosphate Signaling and the Skin," Am J Clin Dermatol., 2007, 8(6):329-336.

Higuchi and Stella, Pro-drugs as Novel Delivery Systems vol. 14 of the A.C.S. Symposium Series, 1975, 129 pages.

Hwang et al., "FTY720, a New Immunosuppressant, Promotes Long-Term Graft Survival and Inhibits the Progression of Graft Coronary Artery Disease in a Murine Model of Cardiac Transplantation," Circulation, 1999, 100:1322-1329.

Idzko et al., "Local application of FTY720 to the lung abrogates experimental asthma by altering dendritic cell function," J Clinc Invest., Nov. 2006, 116(11):2935-2944.

Ishii et al., "Sphingosine-1-phosphate mobilizes osteoclast precursors and regulates bone homeostasis," Nature, Mar. 2009, 458(7237):524-528.

Jones, Robert M. "Discovery of Potent and Selective Sphingosine-1-Phosphate 1 (S1P1) Receptor Agonists", CHI $6^{th}$ Annual Drug Discovery Chemistry, San Diego, CA, Apr. 12, 2011.

Jones, Robert M. "Discovery of Potent and Selective Sphingosine-1-Phosphate 1(S1P1) Receptor Agonists", CHI $6^{th}$ Annual Discovery on Target, Boston, MA, Nov. 3, 2011.

Jung et al., "Functional Consequences of S1P Receptor Modulation in Rat Oligodendroglial Lineage Cells," Glia, 2007, 55:1656-1667.

Kaneider et al., "The immune modulator FTY720 targets sphingosine-kinase-dependent migration of human monocytes in response to amyloid beta-protein and its precursor," FASEB J, 2004, 18:309-311.

Kappos et al., "Oral Fingolimod (FTY720) for Relapsing Multiple Sclerosis," N Engl J Med., 2006, 355:1124-1140.

Kataoka et al., "FTY720, Sphingosine 1-Phosphate Receptor Modulator, Ameliorates Experimental Autoimmune Encephalomyelitis by Inhibition of T Cell Infiltration," Cell Mol. Immunol, Dec. 2005, 2(6):439-448.

Kaudel et al., "FTY720 for Treatment of Ischemia-Reperfusion Injury Following Complete Renal Ischemia; Impact on Long-Term Survival and T-Lymphocyte Tissue Infiltration," Transplantation Proc., 2007, 39:499-502.

Kawasaki, Andrew et al., "Discovery and Characterization of 2-(7-(5-phenyl-1,2,4-oxadiazol-3-yl)-2,3-dihydro-1H-pyrrolo[1,2-a]indol-1-yl)acetic acid Derivatives as Potent & Selective Human S1P1 Receptor Agonists", Arena Pharmaceuticals, Inc., MEDI254, ACS, Mar. 2011.

Keul et al., "The Sphinogosine-1-Phosphate Analogue FTY720 Reduces Atherosclerosis in Apolipoprotein E-Deficient Mice," Arterioscler Thromb Vasc Biol., 2007, 27:607-613.

Kim et al., "Sphingosine-1-phosphate inhibits human keratinocyte proliferation via Akt/protein kinase B inactivation," Cell Signal, 2004, 16:89-95.

Kimura et al., "Essential Roles of Sphingosine 1-Phosphate/S1P1 Receptor Axis in the Migration of Neural Stem Cells Toward a Site of Spinal Cord Injury," Stem Cells, 2007, 25:115-124.

Kitabayashi et al., "FTY720 Prevents Development of Experimental Autoimmune Myocarditis Through Reduction of Circulating Lymphocytes," J Cardiovasc. Pharmacol. 2000, 35:410-416.

Kohno et al., "A Novel Immunomodulator, FTY720, Prevents Development of Experimental Autoimmune Myasthenia Gravis in C57BL/6 Mice," Biol Pharma Bull., 2005, 28(4):736-739.

Kohno et al., "A Novel Immunomodulator, FTY720, Prevents Spontaneous Dermatitis in NC/Nga Mice," Biol. Pharm. Bull., 2004, 27(9):1392-1396.

Koreck et al., "The Role of Innate Immunity in the Pathogensis of Acne," Dermatol., 2003, 206:96-105.

Kurose et al., "Effects of FTY720, a novel immunosuppressant, on experimental autoimmune uveoretinitis in rats," Exp. Eye Res., 2000, 70:7-15.

Lala et al., "Role of nitric oxide in tumor progression: Lessons from experimental tumors," Cancer Metastasis Rev., 1998, 17:91-106.

LaMontagne et al., "Antagonism of Sphingosine-1-Phosphate Receptors by FTY720 Inhibits Angiogenesis and Tumor Vascularization," Cancer Res., 2006, 66:221-231.

Le Bas, et al, "Radioiodinated Analogs of EP 00652218 for the Exploration of the Tachykinin NK1 Receptor by Spect," J. Labelled Compl. Radiopharm. 2001, 44, S280-S282.

Lee et al., "FTY720: A Promising Agent for Treatment of Metastatic Hepatocellular Carcinoma," Clin. Cancer Res., 2005, 11:8458-8466.

Lima et al., "FTY720 Treatment Prolongs Skin Graft Survival in a Completely Incompatible Strain Combination," Transplant Proc., 2004, 36:1015-1017.

Liu et al., "Long-Term Effect of FTY720 on Lymphocyte Count and Islet Allograft Survival in Mice," Microsurgery, 2007, 27:300-304.

Madhusudan et al., "Tyrosine kinase inhibitors in cancer therapy," Clinical Biochem., 2004, 37:618-635.

Maki et al., "Prevention and Cure of Autoimmune Diabetes in Nonobese Diabetic Mice by Continuous Administration of FTY720," Transplantation, 2005, 79:1051-1055.

Maki et al., "Prevention of autoimmune diabetes by FTY720 in Nonobese diabetic mice," Transplantation, Dec. 2002, 74(12):1684-1686.

Martini et al., "Current perspectives on FTY720," Expert Opin. Investig. Drugs, 2007, 16:505-518.

Martini et al., "S1P modulator FTY720 limits matrix expansion in acute anti-thyl mesangioproliferative glomerulonephritis," Am J Physiol Renal Physiol., 2007, 292:F1761-F1770.

Matloubian et al., "Lymphocyte egress from thymus and peripheral lymphoid organs in dependent on SIP receptor 1," Nature, Jan. 2004, 427:355-360.

Matsuura et al., "Effect of FTY720, a novel immunosuppressant, on adjuvant- and collagen-induced arthritis in rats," Int. J Immunopharmacol. 2000, 22:323-331.

Matsuura et al., "Effect of FTY720, a novel immunosuppressant, on adjuvant-induced arthritis in rats," Inflamm. Res. 2000, 49:404-410.

Miron et al., "FTY720 Modulates Human Oligodendrocyte Progenitor Process Extension and Survival," Ann Neurol, 2008, 63:61-71.

Miyamoto et al., "Therapeutic Effects of FTY720, a New Immunosuppressive Agent, in a Murine Model of Acute Viral Myocarditis," J Am Coll Cardiol., 2001, 37(6):1713-1718.

Mizushima et al., "Therapeutic Effects of a New Lymphocyte Homing Reagent FTY720 in Interleukin-10 Gene-deficient Mice with Colitis," Inflamm Bowel Dis., May 2004, 10(3):182-192.

Morissette, et al., "High-Throughput Crystallization: Polymorphs, Salts, Co-Crystals and Solvates", *Adv. Drug Delivery Rev.*, 56:275-300 (2004).

Nakashima et al., "Impaired Initiation of Contact Hypersensitivity by FTY720," J Invest Dermatol., 2008, 128:2833-2841.

Neurath et al., "Antibodies to Interleukin 12 Abrogate Established Experimental Colitis in Mice," J. Exp. Med, 182:1281-1290, 1995.

Newman et al., "Solid-state analysis of active pharmaceutical ingredient in drug products," DDT, Oct. 2003, 8(19):898-905.

Nofer et al., "FTY720, a Synthetic Sphingosine 1 Phosphate Analogue, Inhibits Development of Atherosclerosis in Low-Density Lipoprotein Receptor Deficient Mice," Circulation, 2007, 115:501-508.

Ogawa et al., "A novel sphingosine-l-phosphate receptor agonist KRP-203 attenuates rate autoimmune myocarditis," Biochem. Biophys. Res. Commun., 2007, 361:621-628.

Okayasu et al, "A Novel Method in the Induction of Reliable Experimental Acute and Chronic Ulcerative Colitis in Mice," Gastroenterology, 98:694-702, 1990.

Okazaki et al., "Effects of FTY720 in MRL-Ipr/Ipr mice: therapeutic potential in systemic lupus erythematosus," J Rheumatol., 2002, 29:707-716.

(56) References Cited

OTHER PUBLICATIONS

Oo et al , "Immunosuppressive and Anti-angiogenic Sphingosine 1-Phosphate Receptor-1 Agonists Induce Ubiquitinylation and Proteasomal Degradation of the Receptor," J Biol Chem., 2007, 282(12):9082-9089.

Pan et al., "A Monoselective Sphingosine-1-Phosphate Receptor-1 Agonist Prevents Allograft Rejection in a Stringent Rat Heart Transplantation Model," Chem. Biol., 2006, 13:1227-1234.

Pheilschifter et al., "Treatment with immunomodulator FTY720 does not promote spontaneous bacterial infections after experimental stroke mice," Experimental Translational Stroke Med., 2011, 3, 6 pages.

Premenko-Lanier et al., "Transient FTY720 treatment promotes immune-mediated clearance of a chronic viral infection," Nature, Aug. 2008, 454:894-899.

Rausch et al., "Predictability of FTY720 Efficacy in Experimental Autoimmune Encephalomyelitis by in Vivo Macrophage Tracking: Clinical Implications for Ultrasmall Superparamagnetic Iron Oxide-Enhanced Magnetic Resonance Imaging," 2004, J Magn. Reson. Imaging, 2004, 20:16-24.

Raveney et al., "Fingolimod (FTY720) as an Acute Rescue Therapy for Intraocular Inflammatory Disease," Arch Ophthalmol, 2008, 126(10):1390-1395.

Remington, The Science and Practice of Pharmacy, 20th Edition, 2000, Lippincott Williams & Wilkins, (Editors: Gennaro et al).

Rheumatoid Arthritis Health Center—Most Common Types of Arthritis, WebMD, http://www.webmd.com/rheumatoid-arthritis/guide/most-common-arthritis-types, 2012, 2 pages.

Rosen et al., "Egress: a receptor-regulated step in lymphocyte trafficking," Immunol. Rev. 2003, 195:160-177.

Sakagawa et al., "Rejection following donor or recipient preoperative treatment with FTY720 in rat small bowel transplantation," Transpl. Immunol., 2004, 13:161-168.

Sanchez et al., "Phosphorylation and Action of the Immunomodulator FTY720 Inhibits Vascular Endothelial Cell Growth Factor-induced Vascular Permeability," J Biol Chem., 2003, 278(47):47281-47290.

Sanna et al., "Enhancement of cappillary leakage and restoration of lymphocyte egress by a chiral S1P1 antagonist in vivo," Nature Chem Biol., Aug. 2006, 2(8):434-441.

Sanna et al., "Sphingosine 1-Phosphate (S1P) Receptor Subtypes S1P1 and S1P3, Respectively, Regulate Lymphocyte Recirculation and Heart Rate," J. Biol Chem., 2004, 279(14):13839-13848.

Sauer et al., "Involvement of Smad Signlaing in Sphingosine 1-Phosphate-mediated Biological Responses of Keratinocytes," J Biol. Chem., 2004, 279:38471-38479.

Sawicka et al , "Inhibition of Th1- and Th2-Mediated Airway Inflammation by the Sphingosine 1-Phosphate Receptor Agonist FTY720," J Immunol., 2003, 171:6206-6214.

Schmid et al., "The Immunosuppressant FTY720 inhibits tumor Angiogenesis via the Sphingosine 1-Phosphate Receptor 1," J Cell Biochem., 2007, 101:259-270.

Schwab and Cyster, "Finding a way out: lymphocyte egress from lymphoid organs," Nature Immunol., Dec. 2007, 8(12):1295-1301.

Shimizu et al., "KRP-203, a Novel Synthetic Immunosuppressant, Prolongs Graft Survival and Attenuates Chronic Rejection in Rat Skin and Heart Allografts," Circulation, 2005, 111:222-229.

Stahly, "Diversity in Single- and Multiple-Component Crystals. The Search for and Prevalence of Polymorphs and Cocrystals," Crystal Growth & Design (2007), 7(6), 1007-1026.

Storey, et al., "Automation of Solid Form Screening Procedures in the Pharmaceutical Industry—How to Avoid the Bottlenecks", Crystallography Reviews, 10(1):45-46 (2004).

Sturino et al: "Discovery of a potent and selective prostaglandin D2 receptor antagonist, [(3R)-4-(4-chloro-benzyl)-7-Fluoro-5-(methylsulfonyl)-1,2,3,4-tetrahydrocyclopenta[b]indol-3-yl]-acetic acid (MK-0524)", Journal of Medicinal Chemistry, Feb. 22, 2007, pp. 794-806.

Suzuki et al., "Efficacy of Mycophenolic Acid Combined with KRP-203, a Novel Immunomodulator, in a Rat Heart Transplantation Model," J Heart Lung Transplant, 2006, 25:302-309.

Suzuki et al , "Immunosuppressive effect of a new drug, FTY720, on lymphocyte responses in vitro and cardiac allograft survival in rats," Transplant Immunol., 1996, 4:252-255.

Taylor et al., "Insights into the mechanism of FTY720 and compatibility with regulatory T cells for the inhibition of graft-versus-host disease (GVHD)," Blood, 2007, 110:3480-3488.

Truong et al., "Human Islet Function is not Impaired by the Sphingosine-1-Phosphate Receptor Modulator FTY720," Am J Transplantation, 2007, 7:2031-2038.

Vachal et al., "Highly selective and potent agonists of sphinogosin-1-phosphate 1 (S1P1) receptor," Bioorganic Med Chem Lett., Jul. 2006, 16(14):3684-3687.

Villullas et al, "Characterisation of a Sphingosine 1-Phosphate-Activated Ca2+ Signalling Pathway in Human Neuroblastoma Cells," J. Neurosci. Res, 73:215-226, 2003.

Avoiding Fatal Responses to Flu Infection, ScienceDaily, http://www.sciencedaily.com/releases/2011/09/110915134410.htm, Sep. 15, 2011, 2 pages.

Vippagunta, et al., "Crystalline Solids," *Adv. Drug Delivery Rev.*, 48:3-26 (2001).

Webb et al., "Sphingosine 1-phosphate receptors agonists attenuate relapsing—remitting experimental autoimmune encephalitis in SJL mice," J Neuroimmunol., 2004, 153:108-121.

Webster, "The Pathophysiology of Acne," Cutis, 2005, 76(suppl. 2):4-7.

Whetzel et al., "Sphingosine-1 Phosphate Prevents Monocyte/Endothelial Interactions in Type 1 Diabetic NOD Mice Through Activation of the S1P1 Receptor," Circ. Res., 2006, 99:731-739.

Yan et al., "Discovery of 3-arylpropionic acids as potent agonists of sphingosine-1-phosphate receptor-1 (S1P1) with high selectivity against all other known S1P receptor subtypes," Bioorg. Med. Chem. Left., 2006, 16:3679-3683.

Yanagawa et al., "FTY720, a Novel Immunosuppressant, Induces Sequestration of Circulating Mature Lymphocytes by Acceleration of Lymphocyte Homing in Rats. II. FTY720 Prolongs Skin Allograft Survival by Decreasing T Cell Infiltration into Grafts But not cytokine production in vivo," J Immunol., 1998, 160:5493-5499.

Yang et al., "The immune modulator FYT720 prevents autoimmune diabetes in nonobese diabetic mice," Clin. Immunol., 2003, 107:30-35.

Zhang et al., "FTY720 attenuates accumulation of EMAP-II+ and MHC-II+ monocytes in early lesions of rat traumatic brain injury," J Cell Mol Med., 2007, 11(2):307-314.

Zhang et al., "FTY720: A Most Promising Immunosuppressant Modulating Immune Cell Functions," Mini Rev. Med Chem., 2007, 7:845-850.

Zhu et al, "Synthesis and Mode of Action of 125I-and 3H- Labeled Thieno[2,3-c]pyridine Antagonists of Cell Adhesion Molecule Expression," J. Org. Chem., 2002, 67, 943-948.

Truppo et al., "Optimization and Scale-Up of a Lipase-Catalyzed Enzymatic Resolution of an Indole Ester Intermediate for a Prostaglandin D2 (DP) Receptor Antagonist Targeting Allergic Rhinitis," Organic Process Research and Development, Feb. 2006, 10(3):592-598.

\* cited by examiner

DSC and TGA Thermograms of Crystalline (R)-2-(9-Chloro-7-(4-isopropoxy-3-(trifluoromethyl)benzyloxy)-2,3-dihydro-1H-pyrrolo[1,2-a]indol-1-yl)acetic Acid DSC and TGA Thermograms of
(R)-2-(9-Chloro-7-(4-isopropoxy-3-(trifluoromethyl)benzyloxy)-
2,3-dihydro-1H-pyrrolo[1,2-a]indol-1-yl)acetic Acid L-Lysine Salt DSC and TGA Thermograms of
(R)-2-(9-Chloro-7-(4-isopropoxy-3-(trifluoromethyl)benzyloxy)-2,3-dihydro-1H-pyrrolo[1,2-a]indol-1-yl)acetic Acid Sodium Salt Hydrate DSC and TGA Thermograms of
(R)-2-(9-Chloro-7-(4-isopropoxy-3-(trifluoromethyl)benzyloxy)-2,3-dihydro-1H-pyrrolo[1,2-a]indol-1-yl)acetic Acid Ethylenediamine Salt Hydrate DSC and TGA Thermograms of (R)-2-(9-Chloro-7-(4-isopropoxy-3-(trifluoromethyl)benzyloxy)-2,3-dihydro-1H-pyrrolo[1,2-a]indol-1-yl)acetic Acid 2-Amino-2-hydroxymethyl-propane-1,3-diol (TRIS) Salt

US 9,085,581 B2

PROCESSES FOR THE PREPARATION OF S1P1 RECEPTOR MODULATORS AND CRYSTALLINE FORMS THEREOF

This application is a §371 National Stage Application of PCT/US2011/026806, filed Mar. 2, 2011, which claims the benefit of priority of U.S. Provisional No. 61/339,362, filed Mar. 3, 2010, each of which is incorporated herein by reference it in its entirety.

FIELD OF THE INVENTION

The present invention relates to salts, processes, and process intermediates useful in the preparation of (R)-2-(9-chloro-7-(4-isopropoxy-3-(trifluoromethyl)benzyloxy)-2,3-dihydro-1H-pyrrolo[1,2-a]indol-1-yl)acetic acid of Formula (Ia), salts, and crystalline forms thereof. The compound (R)-2-(9-chloro-7-(4-isopropoxy-3-(trifluoromethyl)benzyloxy)-2,3-dihydro-1H-pyrrolo[1,2-a]indol-1-yl)acetic acid has been identified as an S1P1 receptor modulator that is useful in the treatment of S1P1 receptor-associated disorders, for example, diseases and disorders mediated by lymphocytes, transplant rejection, autoimmune diseases and disorders, inflammatory diseases and disorders (e.g., acute and chronic inflammatory conditions), cancer, and conditions characterized by an underlying defect in vascular integrity or that are associated with angiogenesis such as may be pathologic (e.g., as may occur in inflammation, tumor development, and atherosclerosis).

BACKGROUND OF THE INVENTION

S1P1 receptor agonists have been shown to possess at least immunosuppressive, anti-inflammatory, and/or hemostatic activities, e.g. by virtue of modulating leukocyte trafficking, sequestering lymphocytes in secondary lymphoid tissues, and/or enhancing vascular integrity. Accordingly, S1P1 receptor agonists can be useful as immunosuppressive agents for at least autoimmune diseases and disorders, inflammatory diseases and disorders (e.g., acute and chronic inflammatory conditions), transplant rejection, cancer, and/or conditions that have an underlying defect in vascular integrity or that are associated with angiogenesis such as may be pathologic (e.g., as may occur in inflammation, tumor development, and atherosclerosis) with fewer side effects such as the impairment of immune responses to systemic infection.

The sphingosine-1-phosphate (SIP) receptors 1-5 constitute a family of G protein-coupled receptors containing a seven-transmembrane domain. These receptors, referred to as S1P1 to S1P5 (formerly termed endothelial differentiation gene (EDG) receptor-1, -5, -3, -6, and -8, respectively; Chun et al., *Pharmacological Reviews*, 54:265-269, 2002), are activated via binding by sphingosine-1-phosphate, which is produced by the sphingosine kinase-catalyzed phosphorylation of sphingosine. S1P1, S1P4, and S1P5 receptors activate Gi but not Gq, whereas S1P2 and S1P3 receptors activate both Gi and Gq. The S1P3 receptor, but not the S1P1 receptor, responds to an agonist with an increase in intracellular calcium.

In view of the growing demand for S1P1 agonists useful in the treatment of S1P1 receptor-associated disorders, the compound (R)-2-(9-chloro-7-(4-isopropoxy-3-(trifluoromethyl) benzyloxy)-2,3-dihydro-1H-pyrrolo[1,2-a]indol-1-yl)acetic acid of Formula (Ia):

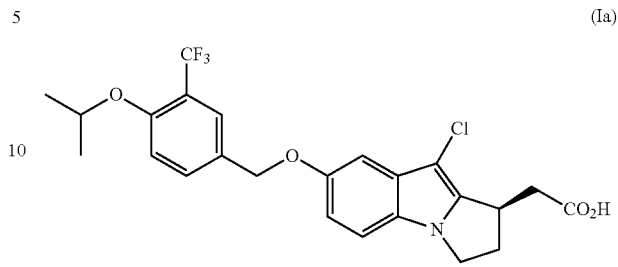

has emerged as an important new compound, see PCT patent application, Serial No. PCT/US2009/004851 hereby incorporated by reference in its entirety. Accordingly, new and efficient routes leading to (R)-2-(9-chloro-7-(4-isopropoxy-3-(trifluoromethyl)benzyloxy)-2,3-dihydro-1H-pyrrolo[1,2-a]indol-1-yl)acetic acid, salts, intermediates, and crystalline forms related thereto are needed. The processes and compounds described herein help meet these and other needs.

SUMMARY OF THE INVENTION

The present invention provides, inter alia, salts, crystalline forms, and processes for the preparation (R)-2-(9-chloro-7-(4-isopropoxy-3-(trifluoromethyl)benzyloxy)-2,3-dihydro-1H-pyrrolo[1,2-a]indol-1-yl)acetic acid of Formula (Ia).

The processes and intermediates of the present invention are useful in preparing (R)-2-(9-chloro-7-(4-isopropoxy-3-(trifluoromethyl)benzyloxy)-2,3-dihydro-1H-pyrrolo[1,2-a] indol-1-yl)acetic acid. The compound (R)-2-(9-chloro-7-(4-isopropoxy-3-(trifluoromethyl)benzyloxy)-2,3-dihydro-1H-pyrrolo[1,2-a]indol-1-yl)acetic acid is useful in the treatment of S1P1 receptor-associated disorders, such as, psoriasis and multiple sclerosis.

One aspect of the present invention is directed to salts and crystalline forms thereof selected from the group consisting of:
(R)-2-(9-chloro-7-(4-isopropoxy-3-(trifluoromethyl)benzyloxy)-2,3-dihydro-1H-pyrrolo[1,2-a]indol-1-yl)acetic acid L-lysine salt;
(R)-2-(9-chloro-7-(4-isopropoxy-3-(trifluoromethyl)benzyloxy)-2,3-dihydro-1H-pyrrolo[1,2-a]indol-1-yl)acetic acid sodium salt;
(R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate;
(R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate;
(R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt;
(R)-2-(9-chloro-7-(4-isopropoxy-3-(trifluoromethyl)benzyloxy)-2,3-dihydro-1H-pyrrolo[1,2-a]indol-1-yl)acetic acid L-arginine salt;
(R)-2-(9-chloro-7-(4-isopropoxy-3-(trifluoromethyl)benzyloxy)-2,3-dihydro-1H-pyrrolo[1,2-a]indol-1-yl)acetic acid zinc salt;
(R)-2-(9-chloro-7-(4-isopropoxy-3-(trifluoromethyl)benzyloxy)-2,3-dihydro-1H-pyrrolo[1,2-a]indol-1-yl)acetic acid calcium salt;

(R)-2-(9-chloro-7-(4-isopropoxy-3-(trifluoromethyl)benzyloxy)-2,3-dihydro-1H-pyrrolo[1,2-a]indol-1-yl)acetic acid N-methylglucamine salt;
(R)-2-(9-chloro-7-(4-isopropoxy-3-(trifluoromethyl)benzyloxy)-2,3-dihydro-1H-pyrrolo[1,2-a]indol-1-yl)acetic acid potassium salt; and
(R)-2-(9-chloro-7-(4-isopropoxy-3-(trifluoromethyl)benzyloxy)-2,3-dihydro-1H-pyrrolo[1,2-a]indol-1-yl)acetic acid magnesium salt.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid sodium salt.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid L-arginine salt.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid zinc salt.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid calcium salt.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid N-methylglucamine salt.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid potassium salt.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid magnesium salt.

One aspect of the present invention is directed a crystalline form of (R)-2-(9-chloro-7-(4-isopropoxy-3-(trifluoromethyl)benzyloxy)-2,3-dihydro-1H-pyrrolo[1,2-a]indol-1-yl) acetic acid.

One aspect of the present invention is directed to compositions comprising a salt or a crystalline form, each as described herein.

One aspect of the present invention is directed to pharmaceutical compositions comprising a salt or a crystalline form, each as described herein, and a pharmaceutically acceptable carrier.

One aspect of the present invention is directed to methods for treating an S1P1 receptor-associated disorder in an individual comprising administering to the individual in need thereof a therapeutically effective amount of a salt, a crystalline form, or a pharmaceutical composition, each as described herein.

One aspect of the present invention is directed to methods for treating a disease or disorder mediated by lymphocytes in an individual comprising administering to the individual in need thereof a therapeutically effective amount of a salt, a crystalline form, or a pharmaceutical composition, each as described herein.

One aspect of the present invention is directed to methods for treating an autoimmune disease or disorder in an individual comprising administering to the individual in need thereof a therapeutically effective amount of a salt, a crystalline form, or a pharmaceutical composition, each as described herein.

One aspect of the present invention is directed to methods for treating an inflammatory disease or disorder in an individual comprising administering to the individual in need thereof a therapeutically effective amount of a salt, a crystalline form, or a pharmaceutical composition, each as described herein.

One aspect of the present invention is directed to methods for treating a microbial infection or disease in an individual comprising administering to the individual in need thereof a therapeutically effective amount of a salt, a crystalline form, or a pharmaceutical composition, each as described herein.

One aspect of the present invention is directed to methods for treating a viral infection or disease in an individual comprising administering to the individual in need thereof a therapeutically effective amount of a salt, a crystalline form, or a pharmaceutical composition, each as described herein.

One aspect of the present invention is directed to methods for treating cancer in an individual comprising administering to the individual in need thereof a therapeutically effective amount of a salt, a crystalline form, or a pharmaceutical composition, each as described herein.

One aspect of the present invention is directed to methods for treating a disorder in an individual comprising administering to said individual in need thereof a therapeutically effective amount of a salt, a crystalline form, or a pharmaceutical composition, each as described herein, wherein said disorder is selected from the group consisting of psoriasis, psoriatic arthritis, inflammatory bowel disease, rheumatoid arthritis, Crohn's disease, transplant rejection, multiple sclerosis, systemic lupus erythematosus, ulcerative colitis, type I diabetes, acne, myocardial ischemia-reperfusion injury, hypertensive nephropathy, glomerulosclerosis, gastritis, polymyositis, thyroiditis, vitiligo, hepatitis, and biliary cirrhosis.

One aspect of the present invention pertains to the use of a salt or a crystalline form, each as described herein, in the manufacture of a medicament for the treatment of an S1P1 receptor-associated disorder.

One aspect of the present invention pertains to the use of a salt or a crystalline form, each as described herein, in the manufacture of a medicament for the treatment of a disease or disorder mediated by lymphocytes.

One aspect of the present invention pertains to the use of a salt or a crystalline form, each as described herein, in the manufacture of a medicament for the treatment of an autoimmune disease or disorder.

One aspect of the present invention pertains to the use of a salt or a crystalline form, each as described herein, in the manufacture of a medicament for the treatment of an inflammatory disease or disorder.

One aspect of the present invention pertains to the use of a salt or a crystalline form, each as described herein, in the manufacture of a medicament for the treatment of a microbial infection or disease.

One aspect of the present invention pertains to the use of a salt or a crystalline form, each as described herein, in the manufacture of a medicament for the treatment of a viral infection or disease.

One aspect of the present invention pertains to the use of a salt or a crystalline form, each as described herein, in the manufacture of a medicament for the treatment of cancer.

One aspect of the present invention pertains to the use of a salt or a crystalline form, each as described herein, in the manufacture of a medicament for the treatment of an S1P1 receptor-associated disorder selected from the group consisting of psoriasis, rheumatoid arthritis, Crohn's disease, transplant rejection, multiple sclerosis, systemic lupus erythematosus, ulcerative colitis, type I diabetes, acne, myocardial ischemia-reperfusion injury, hypertensive nephropathy, glomerulosclerosis, gastritis, polymyositis, thyroiditis, vitiligo, hepatitis, and biliary cirrhosis.

One aspect of the present invention pertains to a salt, a crystalline form, or pharmaceutical composition, each as described herein, for use in a method for the treatment of the human or animal body by therapy.

One aspect of the present invention pertains to a salt, a crystalline form, or pharmaceutical composition, each as described herein, for use in a method for the treatment of an S1P1 receptor-associated disorder.

One aspect of the present invention pertains to a salt, a crystalline form, or pharmaceutical composition, each as described herein, for use in a method for the treatment of a disease or disorder mediated by lymphocytes.

One aspect of the present invention pertains to a salt, a crystalline form, or pharmaceutical composition, each as described herein, for use in a method for the treatment of an autoimmune disease or disorder.

One aspect of the present invention pertains to a salt, a crystalline form, or pharmaceutical composition, each as described herein, for use in a method for the treatment of an inflammatory disease or disorder.

One aspect of the present invention pertains to a salt, a crystalline form, or pharmaceutical composition, each as described herein, for use in a method for the treatment of a microbial infection or disease.

One aspect of the present invention pertains to a salt, a crystalline form, or pharmaceutical composition, each as described herein, for use in a method for the treatment of a viral infection or disease.

One aspect of the present invention pertains to a salt, a crystalline form, or pharmaceutical composition, each as described herein, for use in a method for the treatment of cancer.

One aspect of the present invention pertains to a salt, a crystalline form, or pharmaceutical composition, each as described herein, for use in a method for the treatment of an S1P1 receptor-associated disorder selected from the group consisting of psoriasis, rheumatoid arthritis, Crohn's disease, transplant rejection, multiple sclerosis, systemic lupus erythematosus, ulcerative colitis, type I diabetes, acne, myocardial ischemia-reperfusion injury, hypertensive nephropathy, glomerulosclerosis, gastritis, polymyositis, thyroiditis, vitiligo, hepatitis, and biliary cirrhosis.

One aspect of the present invention pertains to processes for preparing compositions comprising admixing a salt or a crystalline form, each as described herein, and a pharmaceutically acceptable carrier.

The present invention further provides, inter alia, processes for preparing an L-lysine salt of (R)-2-(9-chloro-7-(4-isopropoxy-3-(trifluoromethyl)benzyloxy)-2,3-dihydro-1H-pyrrolo[1,2-a]indol-1-yl)acetic acid of Formula (Ia):

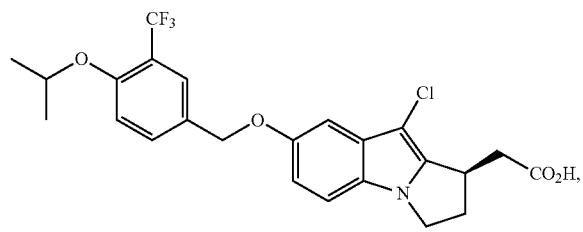

comprising the following steps:

a) reacting a compound of Formula (IIa) or a salt thereof:

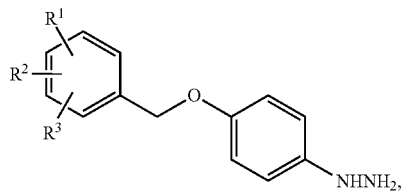

wherein $R^1$, $R^2$, and $R^3$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro; with a compound of:

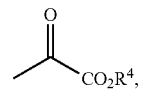

wherein $R^4$ is $C_1$-$C_4$ alkyl;

in the presence of an indole-forming-step acid and an indole-forming-step solvent to form a compound of Formula (IIc):

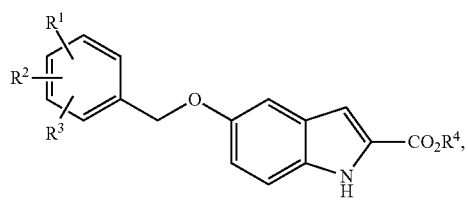

b) cyclizing the compound of Formula (IIc) with a compound of Formula (IId):

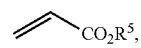

wherein $R^5$ is $C_1$-$C_4$ alkyl;
in the presence of an alkali metal $C_1$-$C_4$ alkoxide base and a cyclizing-step solvent to form a compound of Formula (IIe), or a keto tautomer thereof:

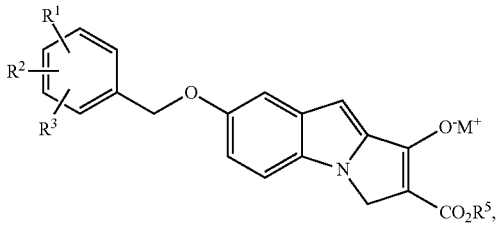
(IIe)

wherein M is an alkali metal or H;

c) decarboxylating the compound of Formula (IIe), or a keto tautomer thereof, in the presence of a Brønsted acid and water to form a compound of Formula (IIf):

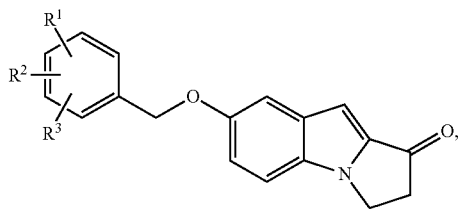
(IIf)

d) olefinating the compound of Formula (IIf) with a compound of Formula (IIg):

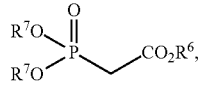
(IIg)

wherein $R^6$ is $C_1$-$C_4$ alkyl; and each $R^7$ is independently $C_1$-$C_4$ alkyl;
in the presence of an olefinating-step base and an olefinating-step solvent to form a compound of Formula (IIh):

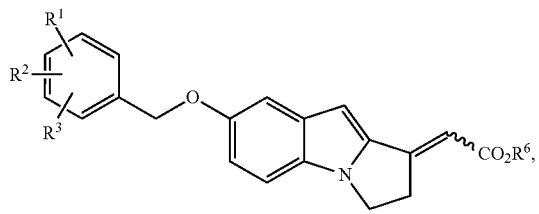
(IIh)

e) reducing the compound of Formula (IIh) in the presence of:
  i) a chiral phosphine ligand;
  ii) a Cu-catalyst;
  iii) hydride-reagent;
  iv) a reducing-step solvent; and
  v) optionally a sterically-hindered $C_3$-$C_8$ alkylalcohol, to form a compound of Formula (IIi):

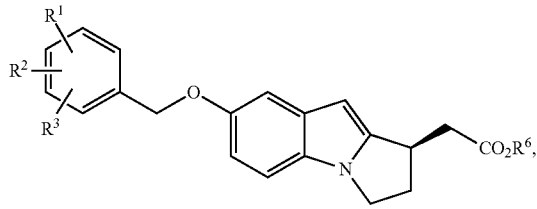
(IIi)

f) deprotecting the compound of Formula (IIi) in the presence of hydrogen, a palladium catalyst, and a deprotecting-step solvent, to form a compound of Formula (IIj), or a salt thereof:

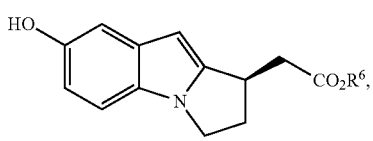
(IIj)

g) alkylating the compound of Formula (IIj) or a salt thereof, with 4-(chloromethyl)-1-isopropoxy-2-(trifluoromethyl)benzene of Formula (IIk):

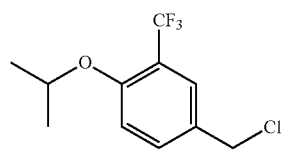
(IIk)

in the presence of an alkylating-step base, and an alkylating-step solvent to form a compound of Formula (IIm) or a salt thereof:

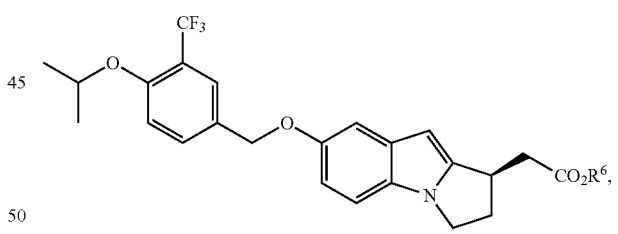
(IIm)

h) chlorinating the compound of Formula (IIm) or a salt thereof, with a chlorinating agent in the presence of a chlorinating-step solvent to form a compound of Formula (IIn):

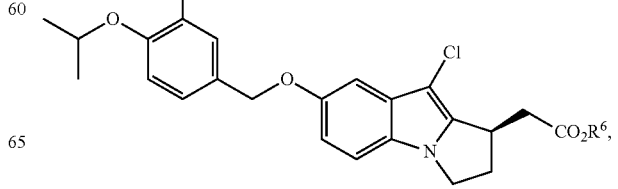
(IIn)

i) hydrolyzing the compound of Formula (IIn) in the presence of a hydrolyzing-step base and a hydrolyzing-step solvent to form the (R)-2-(9-chloro-7-(4-isopropoxy-3-(trifluoromethyl)benzyloxy)-2,3-dihydro-1H-pyrrolo[1,2-a]indol-1-yl)acetic acid;
and j) contacting the (R)-2-(9-chloro-7-(4-isopropoxy-3-(trifluoromethyl)benzyloxy)-2,3-dihydro-1H-pyrrolo[1,2-a]indol-1-yl)acetic acid with L-lysine or a salt thereof, in the presence of a contacting-step solvent and H₂O to form the L-lysine salt of (R)-2-(9-chloro-7-(4-isopropoxy-3-(trifluoromethyl)benzyloxy)-2,3-dihydro-1H-pyrrolo[1,2-a]indol-1-yl)acetic acid.

One aspect of the present invention pertains to one or more of the processes as described above in Steps a) through j), either provided separately or together, that are useful in the preparation of an intermediate for use directly or indirectly in the preparation of (R)-2-(9-chloro-7-(4-isopropoxy-3-(trifluoromethyl)benzyloxy)-2,3-dihydro-1H-pyrrolo[1,2-a]indol-1-yl)acetic acid of Formula (Ia), salts, and/or crystalline forms thereof.

These and other aspects of the invention disclosed herein will be set forth in greater detail as the patent disclosure proceeds.

BRIEF DESCRIPTION OF THE DRAWINGS

FIG. 2 also depicts a thermogravimetric analysis (TGA) thermogram for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid (TA Instruments TGA Q50000 in open cell; 10° C./min).

FIG. 5 also depicts a thermogravimetric analysis (TGA) thermogram for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt (TA Instruments TGA Q50000 in open cell; 10° C./min).

FIG. 8 also depicts a thermogravimetric analysis (TGA) thermogram for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate (TA Instruments TGA Q50000 in open cell; 10° C./min).

FIG. 11 also depicts a thermogravimetric analysis (TGA) thermogram for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate (TA Instruments TGA Q50000 in open cell; 10° C./min).

FIG. 14 also depicts a thermogravimetric analysis (TGA) thermogram for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt (TA Instruments TGA Q5000 in open cell; 10° C./min)

DETAILED DESCRIPTION OF THE INVENTION

Definitions

Figure 1:
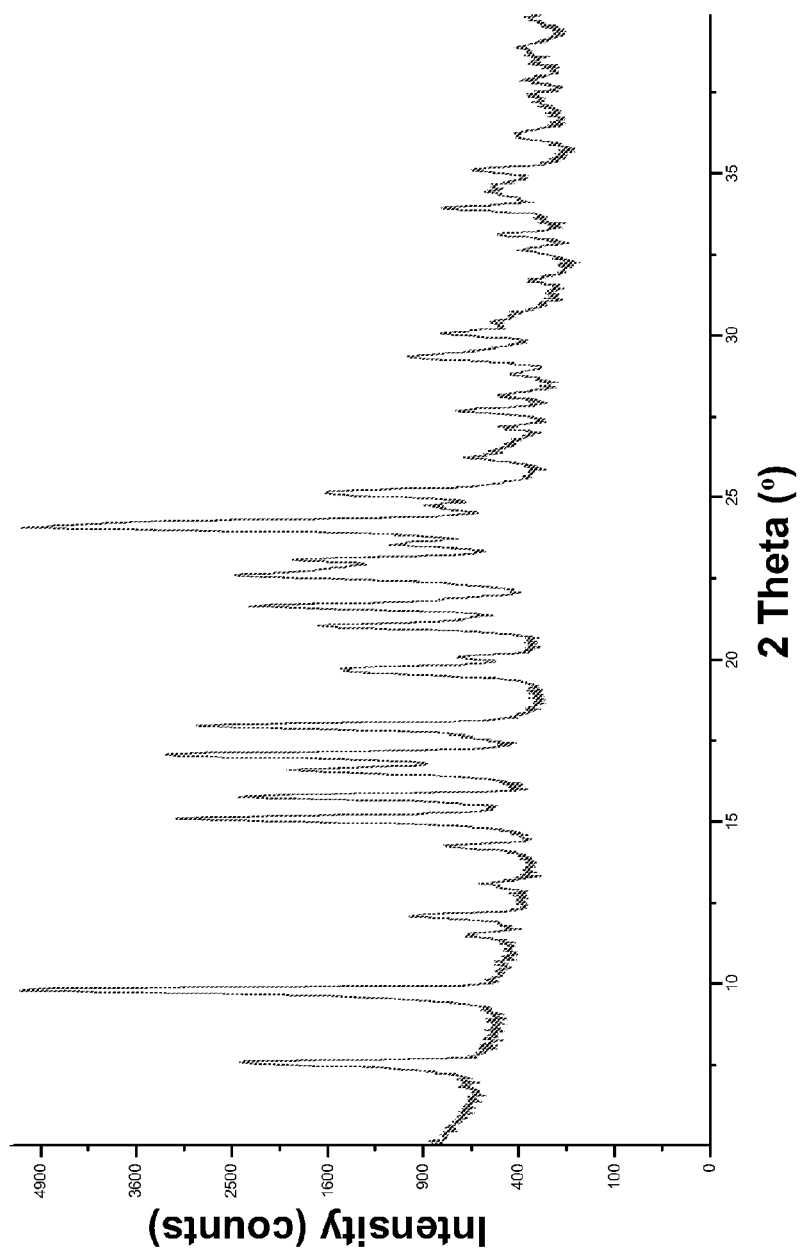
FIG. 1 shows a powder X-ray diffraction pattern (PXRD) for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid (PANalytical X'Pert Plus Powder X-Ray Diffractometer; 5.0 to 40.0° 2θ).

For clarity and consistency, the following definitions will be used throughout this patent document.

The term "agonist" refers to a moiety that interacts and activates the receptor, such as, the S1P1 receptor and initiate a physiological or pharmacological response characteristic of that receptor. For example, when moieties activate the intracellular response upon binding to the receptor, or enhance GTP binding to membranes.

The term "hydrate" as used refers to a compound of the invention or a salt thereof, that further includes a stoichiometric or non-stoichiometric amount of water bound by non-covalent intermolecular forces.

The term "in need of treatment" and the term "in need thereof," when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

The term "individual" refers to any animal, including mammals, preferably mice, rats, other rodents, rabbits, dogs, cats, swine, cattle, sheep, horses, or primates and most preferably humans.

The term "modulate or modulating" refers to an increase or decrease in the amount, quality, response or effect of a particular activity, function or molecule.

The term "pharmaceutical composition" refers to a composition comprising at least one active ingredient; including but not limited to, salts, solvates and hydrates of compounds of the present invention; whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "therapeutically effective amount" refers to the amount of active compound or pharmaceutical agent that elicits the biological or medicinal response in a tissue, system, animal, individual or human that is being sought by a researcher, veterinarian, medical doctor or other clinician or caregiver; or in an individual, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology) and (3) Ameliorating the disease; for example, ameliorating a disease, condition or disorder in an individual that is experiencing or displaying the pathology or symptomatology of the disease, condition or disorder (i.e., reversing the pathology and/or symptomatology).

The term "reacting" is used herein as known in the art and generally refers to the bringing together of chemical reagents in such a manner so as to allow their interaction at the molecular level to achieve a chemical or physical transformation of at least one chemical reagent.

Chemical Group, Moiety or Radical

The term "$C_1$-$C_4$ alkoxy" refers to a $C_1$-$C_4$ alkyl radical, as defined herein, attached directly to an oxygen atom. In some embodiments, the term alkoxy refers to 1 to 3 carbons; some embodiments 1 to 3 carbons; and some embodiments 1 or 2 carbons. Examples include methoxy, ethoxy, n-propoxy, isopropoxy, n-butoxy, t-butoxy, isobutoxy, sec-butoxy, and the like.

The term "alkyl" refers to a straight or branched carbon radical. In some embodiments, the term "$C_3$-$C_8$ alkyl" refers to an alkyl radical containing 3 to 8 carbons. In some embodiments, the term "$C_1$-$C_6$ alkyl" refers to an alkyl radical containing 1 to 6 carbons. In some embodiments, the term "$C_1$-$C_5$ alkyl" refers to a radical containing 1 to 5 carbons. In some embodiments, the term "$C_1$-$C_4$ alkyl" refers to an alkyl radical containing 1 to 4 carbons. Examples of an alkyl include, but are not limited to, methyl, ethyl, n-propyl, isopropyl, n-butyl, sec-butyl, isobutyl, t-butyl, pentyl, isopentyl, t-pentyl, neo-pentyl, 1-methylbutyl [i.e., —CH(CH$_3$)CH$_2$CH$_2$CH$_3$], 2-methylbutyl [i.e., —CH$_2$CH(CH$_3$)CH$_2$CH$_3$], n-hexyl, and the like.

The term "halogen" or "halo" refers to a fluoro, chloro, bromo or iodo group.

The term "$C_1$-$C_4$ haloalkoxy" refers to a $C_1$-$C_4$ haloalkyl, as defined herein, which is directly attached to an oxygen atom. Examples include, but are not limited to, difluoromethoxy, trifluoromethoxy, 2,2,2-trifluoroethoxy, pentafluoroethoxy, and the like.

The term "$C_1$-$C_4$ haloalkyl" refers to a $C_1$-$C_4$ alkyl group, defined herein, wherein the alkyl is substituted with one halogen up to fully substituted and a fully substituted $C_1$-$C_4$ haloalkyl can be represented by the formula $C_nL_{2n+1}$ wherein L is a halogen and "n" is 1, 2, 3, 4, 5 or 6; when more than one halogen is present then they may be the same or different and selected from the group consisting of F, Cl, Br and I, preferably F, some embodiments are 1 to 5 carbons, some embodiments are 1 to 4 carbons, some embodiments are 1 to 3 carbons, and some embodiments are 1 or 2 carbons. Examples of haloalkyl groups include, but are not limited to, fluoromethyl, difluoromethyl, trifluoromethyl, chlorodifluoromethyl, 2,2,2-trifluoroethyl, pentafluoroethyl, and the like.

The term "nitro" refers to the group —NO$_2$.

The term "sterically-hindered C$_3$-C$_8$ alkylalcohol" refers to a 2° alcohol or a 3° alcohol containing C$_3$ to C$_8$ carbons. Examples of a "sterically-hindered C$_3$-C$_8$ alkylalcohol" include, isopropanol, t-butyl alcohol, 2-methylbutan-2-ol, 2,3-dimethylbutan-2-ol, 2,3,3-trimethylbutan-2-ol, 3-methylpentan-3-ol, 3-ethylpentan-3-ol, and the like.

Salts and Crystalline Forms

The present invention is directed to, inter alia, salts of (R)-2-(9-chloro-7-(4-isopropoxy-3-(trifluoromethyl)benzyloxy)-2,3-dihydro-1H-pyrrolo[1,2-a]indol-1-yl)acetic acid of Formula (Ia) and crystalline forms thereof.

The present invention is further directed to a crystalline form of (R)-2-(9-chloro-7-(4-isopropoxy-3-(trifluoromethyl)benzyloxy)-2,3-dihydro-1H-pyrrolo[1,2-a]indol-1-yl) acetic acid.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid sodium salt.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid L-arginine salt.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid zinc salt.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid calcium salt.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid N-methylglucamine salt.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid potassium salt.

One aspect of the present invention is directed to (R)-2-(9-chloro-7-(4-isopropoxy-3-(trifluoromethyl)benzyloxy)-2,3-dihydro-1H-pyrrolo[1,2-a]indol-1-yl)acetic acid magnesium salt.

Salts and Crystalline Forms

The crystalline forms of the salts and free acid of (R)-2-(9-chloro-7-(4-isopropoxy-3-(trifluoromethyl)benzyloxy)-2,3-dihydro-1H-pyrrolo[1,2-a]indol-1-yl)acetic acid can be identified by their unique solid state signatures with respect to, for example, differential scanning calorimetry (DSC), powder X-ray diffraction (PXRD), and other solid state methods. Further characterization with respect to water or solvent content of the crystalline forms can be gauged by any of the following methods for example, thermogravimetric analysis (TGA), DSC and the like. For DSC, it is known that the temperatures observed for thermal events will depend upon sample purity, and may also depend on the rate of temperature change, as well as sample preparation technique and the particular instrument employed. Thus, the values reported herein relating to DSC thermograms can vary by plus or minus about 5° C. The values reported herein relating to DSC thermograms can also vary by plus or minus about 20 joules per gram. For PXRD, the relative intensities of the peaks can vary, depending upon the sample preparation technique, the sample mounting procedure and the particular instrument employed. Moreover, instrument variation and other factors can often affect the 2θ values. Therefore, the peak assignments of diffraction patterns can vary by plus or minus about 0.2°. For TGA, the temperature features reported herein can vary by plus or minus about 5° C. The TGA % weight changes reported herein over a specified temperature range can vary by plus or minus about 2% weight change due to, for example, variations in sample quality and sample size. Further characterization with respect to hygroscopicity of the crystalline form can be gauged by, for example, dynamic moisture sorption (DMS). The DMS features reported herein can vary by plus or minus about 5% relative humidity. The DMS features reported herein can also vary by plus or minus about 2% weight change.

A) (R)-2-(9-Chloro-7-(4-isopropoxy-3-(trifluoromethyl)benzyloxy)-2,3-dihydro-1H-pyrrolo[1,2-a]indol-1-yl)acetic acid One aspect of the present invention relates to the crystalline form of (R)-2-(9-chloro-7-(4-isopropoxy-3-(trifluoromethyl)benzyloxy)-2,3-dihydro-1H-pyrrolo[1,2-a]indol-1-yl) acetic acid. The physical properties of the crystalline form of (R)-2-(9-chloro-7-(4-isopropoxy-3-(trifluoromethyl)benzyloxy)-2,3-dihydro-1H-pyrrolo[1,2-a]indol-1-yl)acetic acid are summarized in Table 1 below.

TABLE 1

| Analytical Method | Crystalline form of (R)-2-(9-chloro-7-(4-isopropoxy-3-(trifluoromethyl)benzyloxy)-2,3-dihydro-1H-pyrrolo[1,2-a]indol-1-yl)acetic acid |
|---|---|
| PXRD | FIG. 1: Peaks of ≥20% relative intensity at: 7.6, 9.8, 15.1, 15.8, 16.6, 17.1, 18.0, 19.7, 21.1, 21.6, 22.6, 23.1, 24.1, 24.3, and 25.2 in terms of °2θ. |
| TGA | FIG. 2: <0.2% weight loss up to about 100° C.; and <1.4% weight loss up to about 150° C. |
| DSC | FIG. 2: endotherm extrapolated onset temperature: 179° C. |
| DMS | FIG. 3: gains less than about 0.1% weight over the full range of % RH tested (10% RH to 90% RH) at 25° C. |

The small weight loss observed in the TGA data suggests that the crystalline form of (R)-2-(9-chloro-7-(4-isopropoxy-3-(trifluoromethyl)benzyloxy)-2,3-dihydro-1H-pyrrolo[1,2-a]indol-1-yl)acetic acid is an anhydrous, non-solvated crystalline form. The DSC thermogram further reveals an endotherm with an onset at about 179° C.

The DMS data suggests that the crystalline form of (R)-2-(9-chloro-7-(4-isopropoxy-3-(trifluoromethyl)benzyloxy)-2,3-dihydro-1H-pyrrolo[1,2-a]indol-1-yl)acetic acid is non-hygroscopic with adsorption of less than about 0.1% weight gain over the full range of % RH tested (10% RH to 90% RH) at 25° C. The maximum weight gain of about 0.06% occurred during the adsorption phase of the DMS cycle at about 70% RH.

Certain X-ray powder diffraction peaks for a representative crystalline form of (R)-2-(9-chloro-7-(4-isopropoxy-3-(trifluoromethyl)benzyloxy)-2,3-dihydro-1H-pyrrolo[1,2-a]indol-1-yl)acetic acid are shown in Table 2 below.

TABLE 2

Crystalline form of (R)-2-(9-chloro-7-(4-isopropoxy-3-(trifluoromethyl)benzyloxy)-2,3-dihydro-1H-pyrrolo[1,2-a]indol-1-yl)acetic acid;
PXRD Peaks with Relative Intensity of 20% or Higher (°2θ)

| Peak Position (°2θ) | d-spacing [Å] | Relative Intensity (%) |
|---|---|---|
| 7.6 | 11.67 | 38.6 |
| 9.8 | 9.02 | 97.4 |
| 15.1 | 5.87 | 57.5 |
| 15.8 | 5.62 | 43.1 |
| 16.6 | 5.34 | 33.5 |
| 17.1 | 5.20 | 60.4 |
| 18.0 | 4.94 | 52.7 |
| 19.7 | 4.52 | 23.9 |
| 21.1 | 4.22 | 28.0 |
| 21.6 | 4.11 | 41.9 |
| 22.6 | 3.93 | 44.8 |
| 23.1 | 3.85 | 33.0 |
| 24.1 | 3.70 | 100.0 |
| 24.3 | 3.67 | 60.9 |
| 25.2 | 3.54 | 27.4 |

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having an X-ray powder diffraction pattern comprising a peak, in terms of 2θ, at about 24.1°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having an X-ray powder diffraction pattern comprising a peak, in terms of 2θ, at about 9.8°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having an X-ray powder diffraction pattern comprising peaks, in terms of 2θ, at about 9.8° and about 24.1°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having an X-ray powder diffraction pattern comprising peaks, in terms of 2θ, at about 7.6°, about 9.8°, about 15.1°, about 17.1°, and 24.1°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having an X-ray powder diffraction pattern comprising peaks, in terms of 2θ, at about 7.6°, about 9.8°, about 15.1°, about 15.8°, about 17.1°, about 18.0°, about 21.6°, about 22.6°, and about 24.1°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having an X-ray powder diffraction pattern comprising peaks, in terms of 2θ, at about 7.6°, about 9.8°, about 15.1°, about 15.8°, about 16.6°, about 17.1°, about 18.0°, about 21.6°, about 22.6°, about 23.1°, about 24.1°, and about 25.2°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having an X-ray powder diffraction pattern comprising peaks, in terms of 2θ, at about 7.6°, about 9.8°, about 15.1°, about 15.8°, about 16.6°, about 17.1°, about 18.0°, about 19.7°, about 21.1°, about 21.6°, about 22.6°, about 23.1°, about 24.1°, about 24.3°, and about 25.2°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having an X-ray powder diffraction pattern substantially as shown in FIG. 1.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having a differential scanning calorimetry thermogram comprising an endotherm with an extrapolated onset temperature between about 174° C. and about 184° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having a differential scanning calorimetry thermogram comprising an endotherm with an extrapolated onset temperature between about 177° C. and about 181° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having a differential scanning calorimetry thermogram comprising an endotherm with an extrapolated onset temperature of about 179° C.

Figure 2:
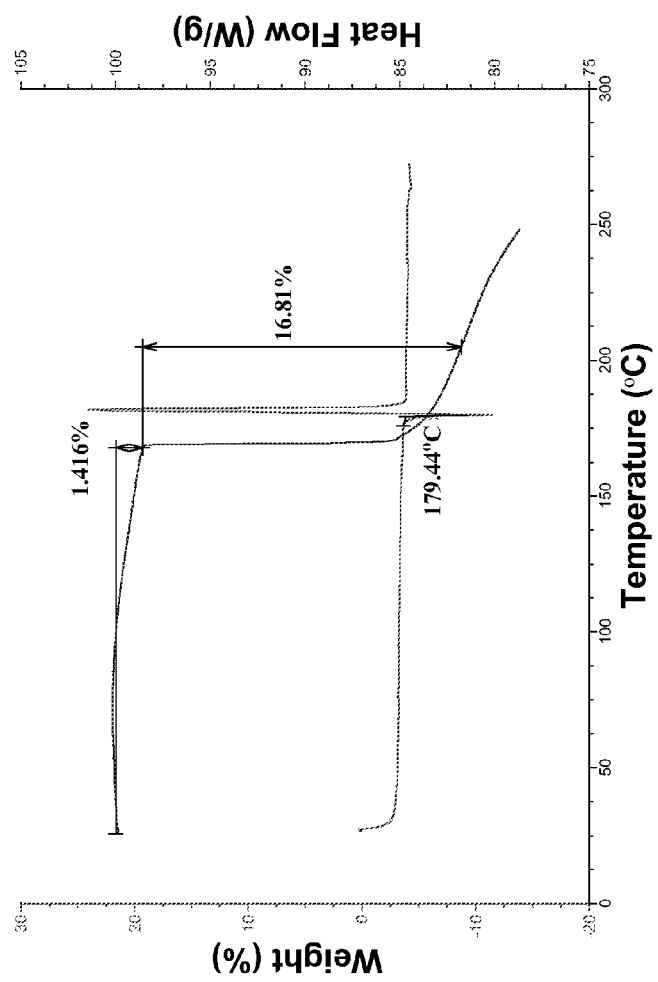
FIG. 2 shows a differential scanning calorimetry (DSC) thermogram for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid (TA Instruments DSC Q2000; 10° C./min).

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having a differential scanning calorimetry thermogram substantially as shown in FIG. 2.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having a thermogravimetric analysis profile showing less than about 0.2% weight loss up to about 100° C.

In some embodiments, the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having a thermogravimetric analysis profile showing less than about 0.2% weight loss up to about 100° C. when scanned at 10° C. per minute One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having a thermogravimetric analysis profile substantially as shown in FIG. 2.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having:

1) an X-ray diffraction pattern comprising peaks, expressed in terms of 2θ, at about 9.8° and about 24.1°; and
2) a differential scanning calorimetry thermogram comprising an endotherm with an extrapolated onset temperature between about 174° C. and about 184° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having:

1) an X-ray diffraction pattern comprising peaks, expressed in terms of 2θ, at about 7.6°, about 9.8°, about 15.1°, about 15.8°, about 17.1°, about 18.0°, about 21.6°, about 22.6°, and about 24.10;
2) a differential scanning calorimetry thermogram comprising an endotherm with an extrapolated onset temperature between about 177° C. and about 181° C.; and
3) a thermogravimetric analysis profile showing less than about 0.2% weight loss up to about 100° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid having:
1) an X-ray diffraction pattern comprising peaks, expressed in terms of 2θ, at about 7.6°, about 9.8°, about 15.1°, about 15.8°, about 16.6°, about 17.1°, about 18.0°, about 19.7°, about 21.1°, about 21.6°, about 22.6°, about 23.1°, about 24.1°, about 24.3°, and about 25.20;
2) a differential scanning calorimetry thermogram comprising an endotherm with an extrapolated onset temperature of about 179° C.; and
3) a thermogravimetric analysis profile showing less than about 0.2% weight loss up to about 100° C.

B) (R)-2-(9-Chloro-7-(4-isopropoxy-3-(trifluoromethyl)benzyloxy)-2,3-dihydro-1H-pyrrolo[1,2-a]indol-1-yl)acetic acid L-lysine salt One aspect of the present invention relates to (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt.

Another aspect of the present invention relates to a crystal form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt. The physical properties of a representative crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt are summarized in Table 3 below.

TABLE 3

Figure 4:
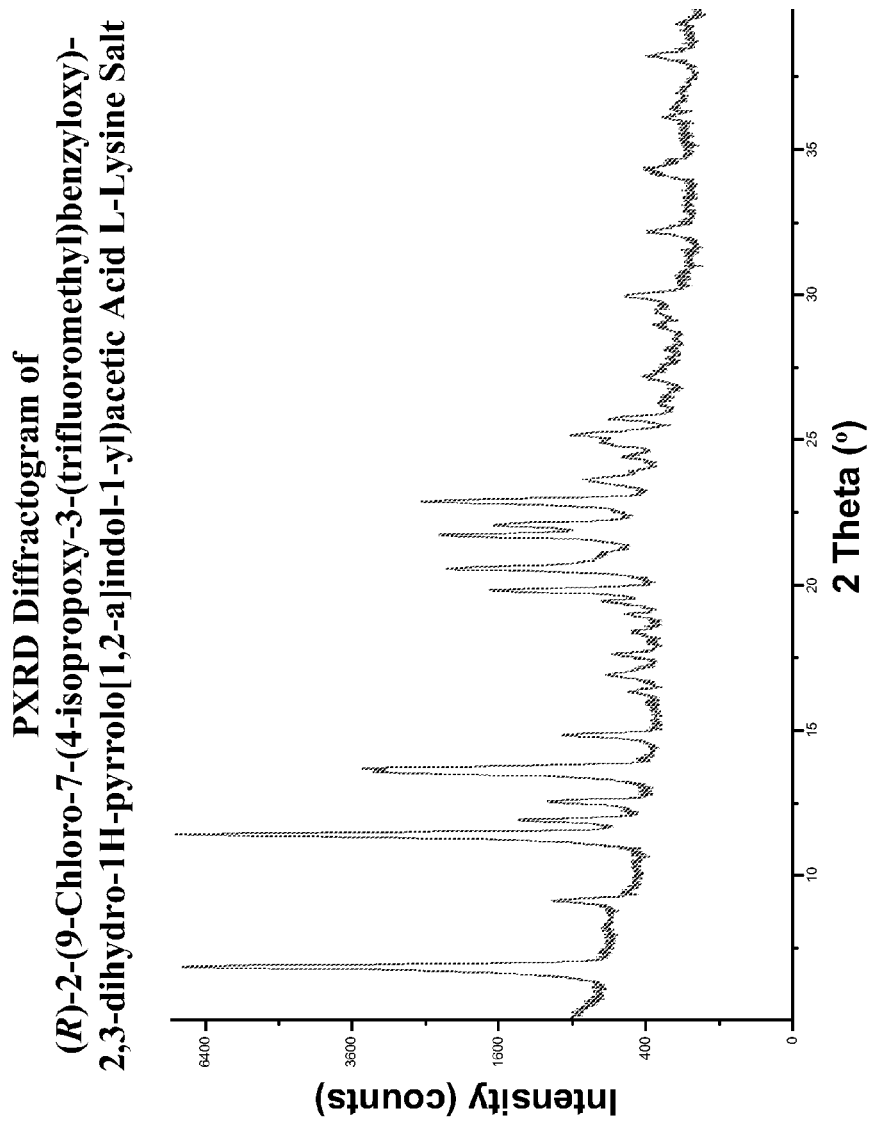
FIG. 4 shows a powder X-ray diffraction pattern (PXRD) for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt (PANalytical X'Pert Plus Powder X-Ray Diffractometer; 5.0 to 40.0° 2θ).

| Analytical Method | Crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt |
|---|---|
| PXRD | FIG. 4: Peaks of ≥20% relative intensity at: 6.9, 11.4, 13.6, 13.7, 19.8, 20.6, 21.7, 22.1, and 22.9 in terms of °2θ. |
| TGA | FIG. 5: <0.1% weight loss up to about 110° C. |
| DSC | FIG. 5: a first endotherm extrapolated onset temperature: 215° C.; a second extrapolated onset temperature: 222° C. |
| DMS | FIG. 6: gains less than about 2.2% weight at a 90% RH hold at 25° C.; gains less than about 0.25% weight after undergoing a dynamic moisture-sorption adsorption cycle to about 90% RH followed by a desorption cycle back to about 10% RH. |

The insignificant weight loss observed in the TGA data suggests that the crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt is an anhydrous, non-solvated crystalline form. The DSC thermogram further reveals an endotherm with an onset temperature at about 215° C.

Certain X-ray powder diffraction peaks for a representative crystalline form of the (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt of the present invention are shown in Table 4 below.

TABLE 4

Crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt; PXRD Peaks with Relative Intensity of 20% or Higher (°2θ)

| Peak Position (°2θ) | d-spacing [Å] | Relative Intensity (%) |
|---|---|---|
| 6.9 | 12.90 | 94.6 |
| 11.4 | 7.76 | 100.0 |
| 13.6 | 6.52 | 43.4 |
| 13.7 | 6.47 | 47.0 |
| 19.8 | 4.48 | 21.1 |
| 20.6 | 4.32 | 28.7 |
| 21.7 | 4.09 | 30.9 |
| 22.1 | 4.03 | 20.7 |
| 22.9 | 3.89 | 34.6 |

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having an X-ray powder diffraction pattern comprising peaks, in terms of 2θ, at about 11.4°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having an X-ray powder diffraction pattern comprising peaks, in terms of 2θ, at about 6.9°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having an X-ray powder diffraction pattern comprising peaks, in terms of 2θ, at about 6.9° and about 11.4°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having an X-ray powder diffraction pattern comprising peaks, in terms of 2θ, at about 6.9°, about 11.4°, and about 22.9°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having an X-ray powder diffraction pattern comprising peaks, in terms of 2θ, at about 6.9°, about 11.4°, about 13.7°, about 21.7°, and about 22.9°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having an X-ray powder diffraction pattern comprising peaks, in terms of 2θ, at about 6.9°, about 11.4°, about 13.6°, about 13.7°, about 19.8°, about 21.7°, and about 22.9°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having an X-ray powder diffraction pattern comprising peaks, in terms of 2θ, at about 6.9°, about 11.4°, about 13.6°, about 13.7°, about 19.8°, about 20.6°, about 21.7°, about 22.1°, and about 22.9°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having an X-ray powder diffraction pattern substantially as shown in FIG. 4.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having a differential scanning calorimetry thermogram comprising an endotherm with an extrapolated onset temperature between about 210° C. and about 220° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having a differential scanning calorimetry thermogram comprising an endotherm with an extrapolated onset temperature between about 213° C. and about 217° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having a differential scanning calorimetry thermogram comprising an endotherm with an extrapolated onset temperature of about 215° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having a differential scanning calorimetry thermogram comprising an endotherm with an extrapolated onset temperature between about 217° C. and about 227° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having a differential scanning calorimetry thermogram comprising an endotherm with an extrapolated onset temperature between about 220° C. and about 224° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having a differential scanning calorimetry thermogram comprising an endotherm with an extrapolated onset temperature of about 222° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having a differential scanning calorimetry thermogram comprising an endotherm with a first extrapolated onset temperature between about 213° C. and about 217° C.; and a second extrapolated onset temperature between about 220° C. and about 224° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having a differential scanning calorimetry thermogram comprising an endotherm with a first extrapolated onset temperature of about 215° C. and a second extrapolated onset temperature of about 222° C.

Figure 5:
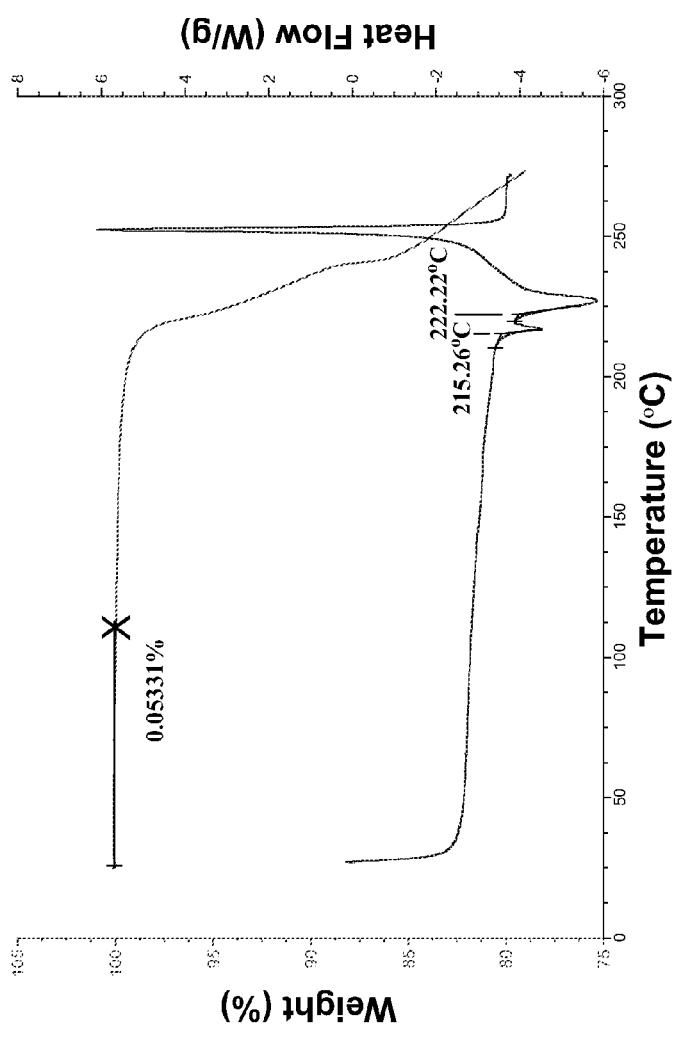
FIG. 5 shows a differential scanning calorimetry (DSC) thermogram for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt (TA Instruments DSC Q2000; 10° C./min).

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having a differential scanning calorimetry thermogram substantially as shown in FIG. 5.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having a dynamic moisture-adsorption profile comprising a weight gain of less than about 2.2% at a 90% RH hold at 25° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having a dynamic moisture-adsorption profile comprising a weight gain of less than about 0.25% after undergoing an absorption dynamic moisture-sorption cycle up to about 90% RH and a desorption cycle back to about 10% RH.

Figure 6:
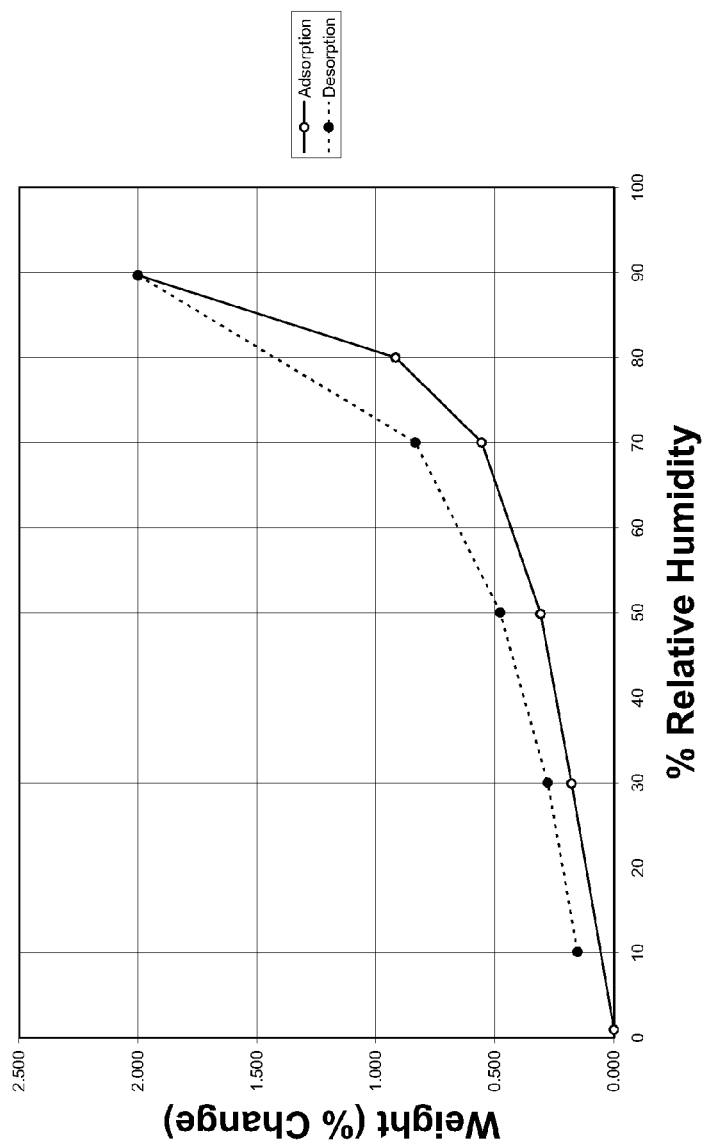
FIG. 6 shows a dynamic moisture sorption profile for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having a dynamic moisture-sorption profile substantially as shown in FIG. 6.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having a thermogravimetric analysis profile showing less than about 0.1% weight loss up to about 110° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having a thermogravimetric analysis profile substantially as shown in FIG. 5.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having:
  1) an X-ray diffraction pattern comprising peaks, expressed in terms of 2θ, at about 6.9° and about 11.40; and
  2) a differential scanning calorimetry thermogram comprising an endotherm with an extrapolated onset temperature between about 210° C. and about 220° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having:
  1) an X-ray diffraction pattern comprising peaks, expressed in terms of 2θ, at about 6.9° and about 11.40; and/or
  2) a differential scanning calorimetry thermogram comprising an endotherm with an extrapolated onset temperature between about 210° C. and about 220° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having:
  1) an X-ray diffraction pattern comprising peaks, expressed in terms of 2θ, at about 6.9°, about 11.4°, about 13.7°, about 21.7°, and about 22.90;
  2) a differential scanning calorimetry thermogram comprising an endotherm with an extrapolated onset temperature between about 213° C. and about 217° C.; and
  3) a thermogravimetric analysis profile showing less than about 0.1% weight loss up to about 110° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having:
  1) an X-ray diffraction pattern comprising peaks, expressed in terms of 2θ, at about 6.9°, about 11.4°, about 13.7°, about 21.7°, and about 22.90;

2) a differential scanning calorimetry thermogram comprising an endotherm with an extrapolated onset temperature between about 213° C. and about 217° C.; and/or 3) a thermogravimetric analysis profile showing less than about 0.1% weight loss up to about 110° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having:

1) an X-ray diffraction pattern comprising peaks, expressed in terms of 2θ, at about 6.9°, about 11.4°, about 13.6°, about 13.7°, about 19.8°, about 20.6°, about 21.7°, about 22.1°, and about 22.9°;

2) a differential scanning calorimetry thermogram comprising an endotherm with a first extrapolated onset temperature between about 213° C. and about 217° C.; and a second extrapolated onset temperature between about 220° C. and about 224° C.; and 3) a thermogravimetric analysis profile showing less than about 0.1% weight loss up to about 110° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt having:

1) an X-ray diffraction pattern comprising peaks, expressed in terms of 2θ, at about 6.9°, about 11.4°, about 13.6°, about 13.7°, about 19.8°, about 20.6°, about 21.7°, about 22.1°, and about 22.9°;

2) a differential scanning calorimetry thermogram comprising an endotherm with a first extrapolated onset temperature between about 213° C. and about 217° C.; and a second extrapolated onset temperature between about 220° C. and about 224° C.; and/or 3) a thermogravimetric analysis profile showing less than about 0.1% weight loss up to about 110° C.

C) (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate One aspect of the present invention relates to (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate.

Another aspect of the present invention relates to a crystal form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate. The physical properties of a representative crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate are summarized in Table 5 below.

TABLE 5

Figure 7:
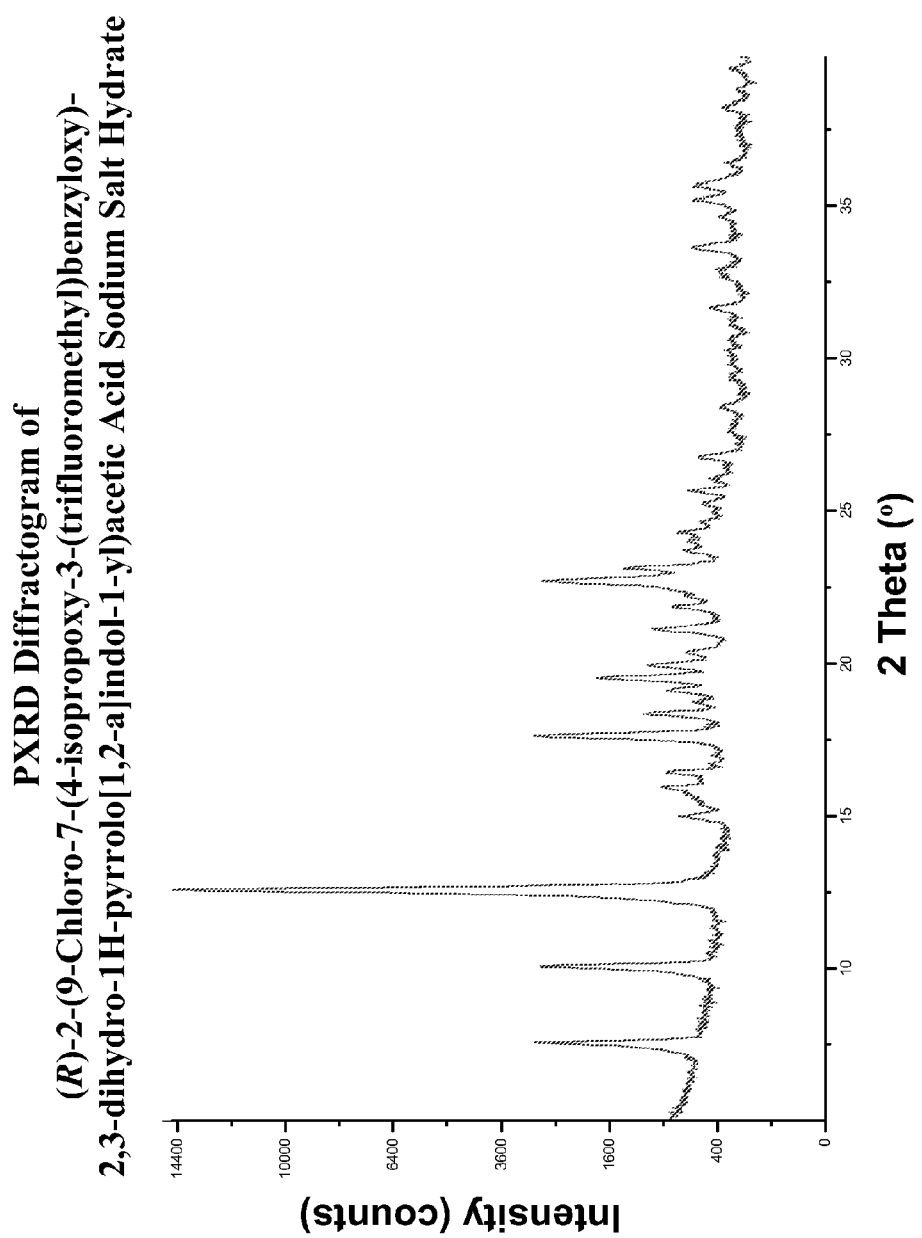
FIG. 7 shows a powder X-ray diffraction pattern (PXRD) for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate (PANalytical X'Pert Plus Powder X-Ray Diffractometer; 5.0 to 40.0° 2θ).

| Analytical Method | Crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate |
|---|---|
| PXRD | FIG. 7: Peaks of ≥7% relative intensity at: 7.6, 10.1, 12.6, 17.6, 19.5, 22.7, 23.1 in terms of °2θ. |
| TGA | FIG. 8: 6.6% weight loss up to about 130° C. |
| DSC | FIG. 8: endotherm extrapolated onset temperature: 75° C.; endotherm peak temperature: 90° C.; associated heat flow 150 J/g. |

TABLE 5-continued

Figure 9:
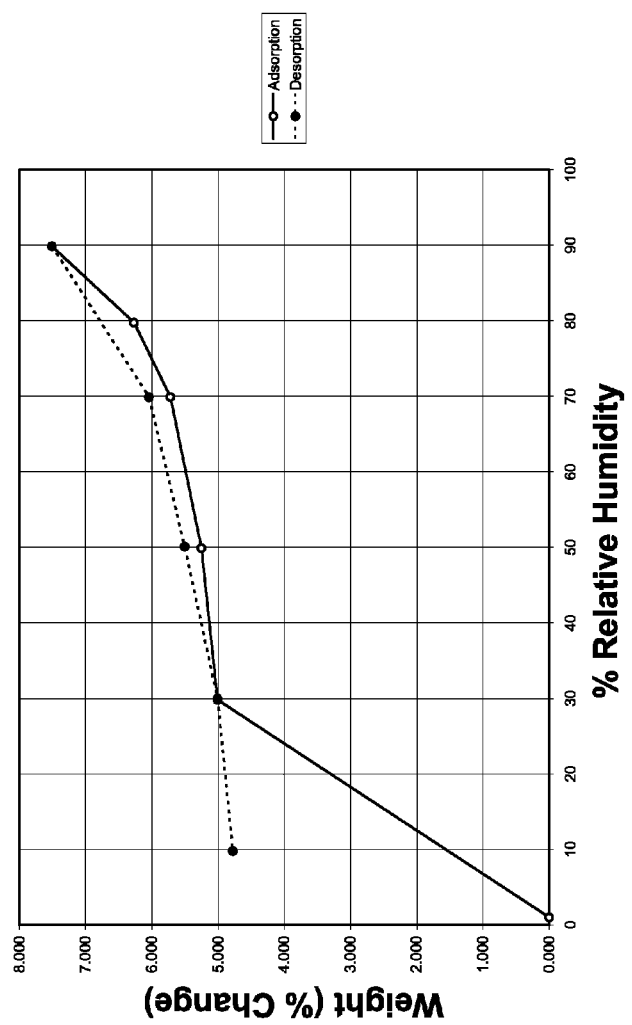
FIG. 9 shows a dynamic moisture sorption profile for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate.

| Analytical Method | Crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate |
|---|---|
| DMS | FIG. 9: gains about 2.5% weight at about 90% relative humidity from about 30% RH to about 90% RH at 25° C. |

The significant weight loss observed in the TGA data indicates that the crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate is a channel hydrate as shown by the loss of weight at low temperatures. This particular channel hydrate holds about 6.6% weight as water at humidities 30%-50% and 25° C. The DSC thermogram further reveals a dehydration endotherm with an onset temperature at 75° C. when scanned at 10° C. per minute.

Certain X-ray powder diffraction peaks for the crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate of the present invention are shown in Table 6 below.

TABLE 6

Crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate;
PXRD Peaks with Relative Intensity of 7% or Higher (°2θ)

| Peak Position (°2θ) | d-spacing [Å] | Relative Intensity (%) |
|---|---|---|
| 7.6 | 11.68 | 16.5 |
| 10.1 | 8.78 | 16.6 |
| 12.6 | 7.03 | 100.0 |
| 17.6 | 5.03 | 18.4 |
| 19.5 | 4.55 | 10.2 |
| 22.7 | 3.92 | 17.4 |
| 23.1 | 3.85 | 7.7 |

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having an X-ray powder diffraction pattern comprising a peak, in terms of 2θ, at about 12.6°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having an X-ray powder diffraction pattern comprising a peak, in terms of 2θ, at about 17.6°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having an X-ray powder diffraction pattern comprising peaks, in terms of 2θ, at about 12.6° and about 17.6°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having an X-ray powder diffraction pattern comprising peaks, in terms of 2θ, at about 12.6°, about 17.6°, and about 22.7°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having an X-ray powder diffraction pattern comprising peaks, in terms of 2θ, at about 7.6°, about 12.6°, about 17.6°, and about 22.7°, and about 23.1°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having an X-ray powder diffraction pattern comprising peaks, in terms of 2θ, at about 7.6°, about 10.1°, about 12.6°, about 17.6°, about 19.5°, about 22.7°, and about 23.1°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having an X-ray powder diffraction pattern substantially as shown in FIG. 7.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having a differential scanning calorimetry thermogram comprising an endotherm with an extrapolated onset temperature between about 65° C. and about 85° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having a differential scanning calorimetry thermogram comprising an endotherm with an extrapolated onset temperature between about 70° C. and about 80° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having a differential scanning calorimetry thermogram comprising an endotherm with an extrapolated onset temperature of about 75° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having a differential scanning calorimetry thermogram comprising an endotherm with a peak temperature between about 85° C. and about 95° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having a differential scanning calorimetry thermogram comprising an endotherm with a peak temperature at about 90° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having a differential scanning calorimetry thermogram comprising an endotherm with an associated heat flow of about 150 joules per gram.

Figure 8:
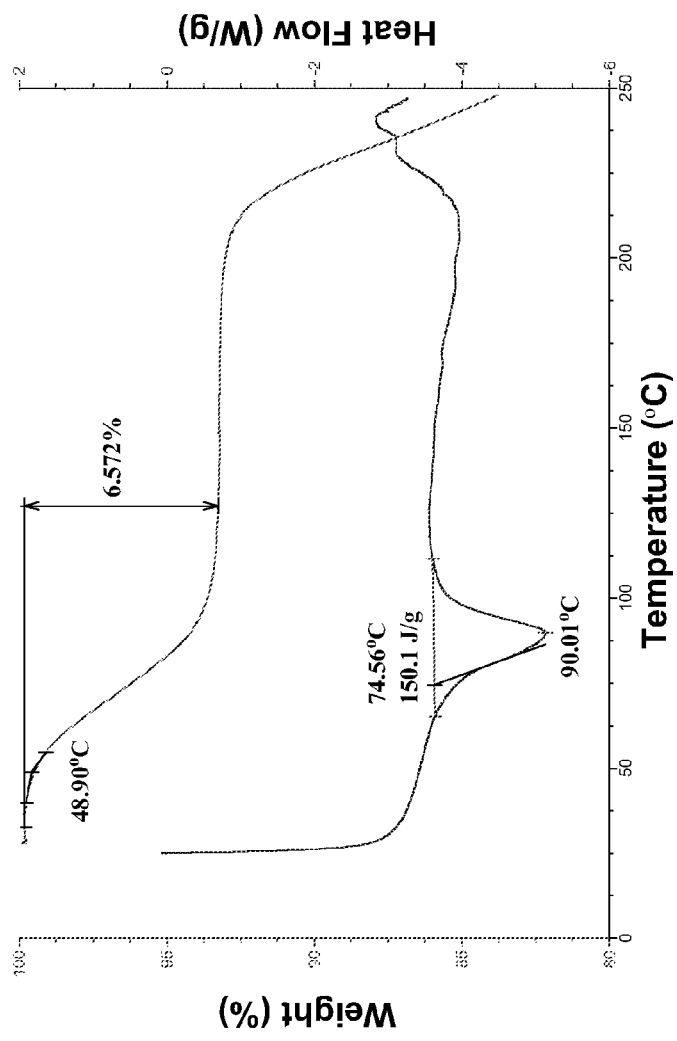
FIG. 8 shows a differential scanning calorimetry (DSC) thermogram for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate (TA Instruments DSC Q2000; 10° C./min).

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having a differential scanning calorimetry thermogram substantially as shown in FIG. 8.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having a dynamic moisture-sorption profile comprising a weight gain of about 2.0% to about 3.0% weight above the nominal water of hydration at about 85% to about 92% RH.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having a dynamic moisture-sorption profile comprising a weight gain of about 2.4% to about 2.6% weight above the nominal water of hydration at about 89% to about 91% RH.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having a dynamic moisture-sorption profile substantially as shown in FIG. 9.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having a thermogravimetric analysis profile comprising about 6.6% weight loss up to about 130° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having a thermogravimetric analysis profile substantially as shown in FIG. 8.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having:
 1) an X-ray diffraction pattern comprising peaks, expressed in terms of 2θ, at about 12.6° and about 17.60; and
 2) a thermogravimetric analysis profile comprising about 6.6% weight loss up to about 130° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having:
 1) an X-ray diffraction pattern comprising peaks, expressed in terms of 2θ, at about 7.6°, about 12.6°, about 17.6°, and about 22.7°, and about 23.10; and
 2) a thermogravimetric analysis profile comprising about 6.6% weight loss up to about 130° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate having:
 1) an X-ray diffraction pattern comprising peaks, expressed in terms of 2θ, at about 7.6°, about 10.1°, about 12.6°, about 17.6°, about 19.5°, about 22.7°, and about 23.1°; and
 2) a thermogravimetric analysis profile comprising about 6.6% weight loss up to about 130° C.

D) (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate One aspect of the present invention relates to (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate.

Another aspect of the present invention relates to a crystal form of (R)-2-(9-chloro-7-(4-isopropoxy-3-(trifluoromethyl)benzyloxy)-2,3-dihydro-1H-pyrrolo[1,2-a]indol-1-yl) acetic acid ethylenediamine salt hydrate. The physical properties of a representative crystalline form of (R)-2-(9-chloro-7-(4-isopropoxy-3-(trifluoromethyl)benzyloxy)-2,3- dihydro-1H-pyrrolo[1,2-a]indol-1-yl)acetic acid ethylenediamine salt hydrate are summarized in Table 7 below.

TABLE 7

Figure 10:
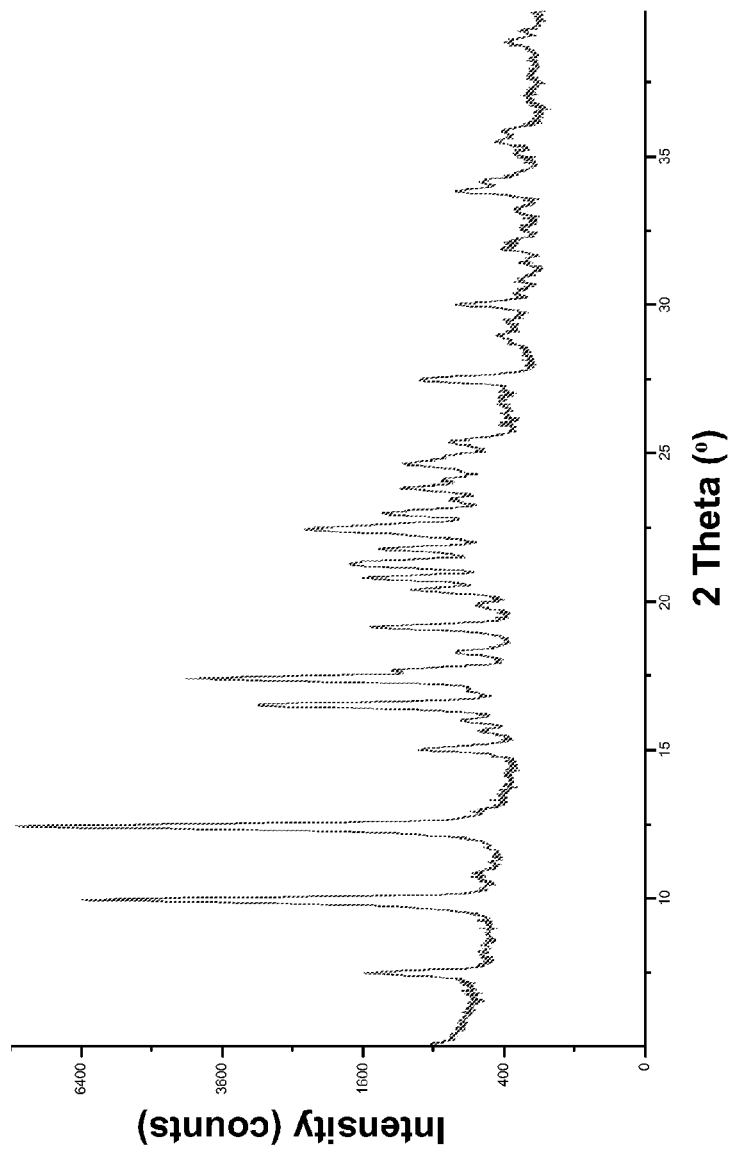
FIG. 10 shows a powder X-ray diffraction pattern (PXRD) for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate (PANalytical X'Pert Plus Powder X-Ray Diffractometer; 5.0 to 40.0° 2θ).

| Analytical Method | Crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate |
|---|---|
| PXRD | FIG. 10: Peaks of ≥14% relative intensity at: 7.5, 10.0, 12.4, 16.5, 17.4, 19.1, 20.8, 21.1, 21.4, and 22.4 in terms of °2θ. |
| TGA | FIG. 11: about 2.2% weight loss up to about 120° C. |
| DSC | FIG. 11: an endotherm extrapolated onset temperature at 152° C. |
| DMS | FIG. 12: gains less than about 3.2% weight at a 90% RH hold at 25° C.; gains less than about 1.5% weight after undergoing an adsorption cycle up to about 90% RH and a desorption cycle back to about 10% RH. |

Weight loss was observed in the TGA data for the crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate. The TGA data indicates a channel hydrate as shown by the loss of weight at low temperatures. This particular channel hydrate holds about 2.2% weight as water.

The DSC thermogram further reveals an endotherm with an onset temperature at 152° C.

Certain X-ray powder diffraction peaks for a representative crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate of the present invention are shown in Table 8 below.

TABLE 8

Crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate; PXRD Peaks with Relative Intensity of 14% or Higher (°2θ)

| Peak Position (°2θ) | d-spacing [Å] | Relative Intensity (%) |
|---|---|---|
| 7.5 | 11.81 | 14.4 |
| 10.0 | 8.88 | 79.6 |
| 12.4 | 7.12 | 100.0 |
| 16.5 | 5.37 | 35.8 |
| 17.4 | 5.09 | 49.9 |
| 19.1 | 4.64 | 15.4 |
| 20.8 | 4.27 | 16.6 |
| 21.1 | 4.19 | 16.3 |
| 21.4 | 4.16 | 14.3 |
| 22.4 | 3.96 | 25.7 |

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having an X-ray powder diffraction pattern comprising a peak, in terms of 2θ, at about 12.4°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having an X-ray powder diffraction pattern comprising a peak, in terms of 2θ, at about 10.0°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having an X-ray powder diffraction pattern comprising peaks, in terms of 2θ, at about 10.0° and about 12.4°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having an X-ray powder diffraction pattern comprising peaks, in terms of 2θ, at about 10.0°, about 12.4° and about 17.4°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having an X-ray powder diffraction pattern comprising peaks, in terms of 2θ, at about 10.0°, about 12.4°, about 16.5°, and about 17.4°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having an X-ray powder diffraction pattern comprising peaks, in terms of 2θ, at about 10.0°, about 12.4°, about 16.5°, about 17.4°, about 19.1°, and about 22.4°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having an X-ray powder diffraction pattern comprising peaks, in terms of 2θ, at about 7.5°, about 10.0°, about 12.4°, about 16.5°, about 17.4°, about 19.1°, about 20.8°, about 21.1°, about 21.4°, and about 22.4°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having an X-ray powder diffraction pattern substantially as shown in FIG. 10.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having a differential scanning calorimetry thermogram comprising an endotherm with an extrapolated onset temperature between about 147° C. and about 157° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having a differential scanning calorimetry thermogram comprising an endotherm with an extrapolated onset temperature between about 150° C. and about 154° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having a differential scanning calorimetry thermogram comprising an endotherm with an extrapolated onset temperature of about 152° C.

Figure 11:
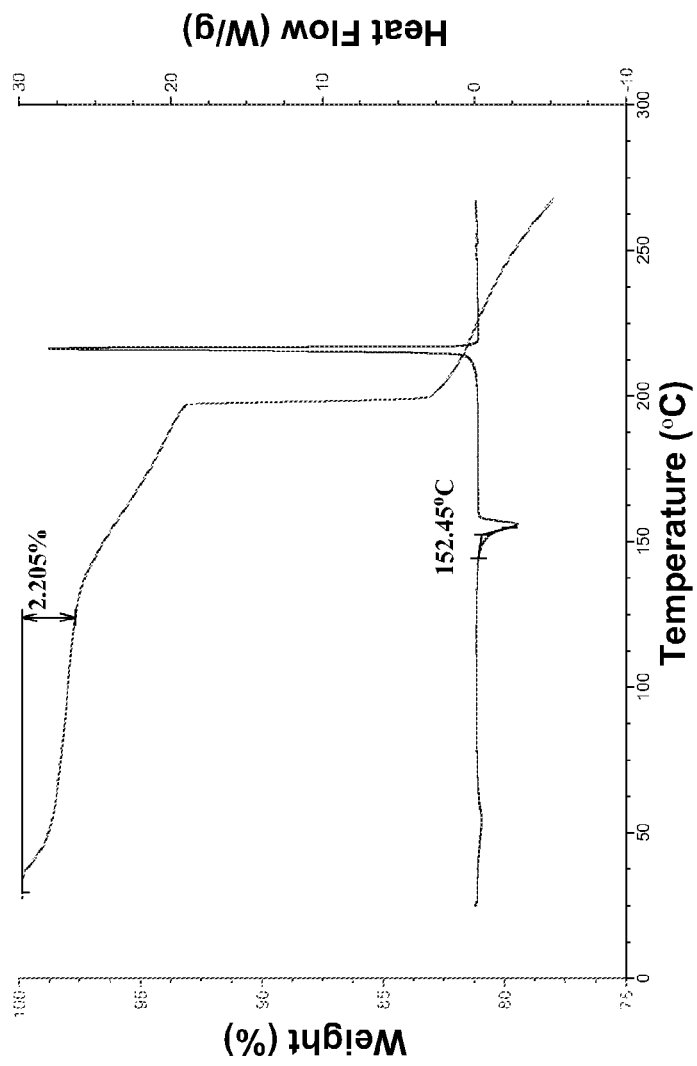
FIG. 11 shows a differential scanning calorimetry (DSC) thermogram for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate (TA Instruments DSC Q2000; 10° C./min).

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having a differential scanning calorimetry thermogram substantially as shown in FIG. 11.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate wherein said compound gains less than about 3.2% weight after undergoing a dynamic moisture-adsorption cycle up to and held at about 90% RH.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate wherein said compound gains less than about 1.5% weight after undergoing a dynamic moisture-sorption cycle from about 1% RH to about 90% RH and back to about 10% RH.

Figure 12:
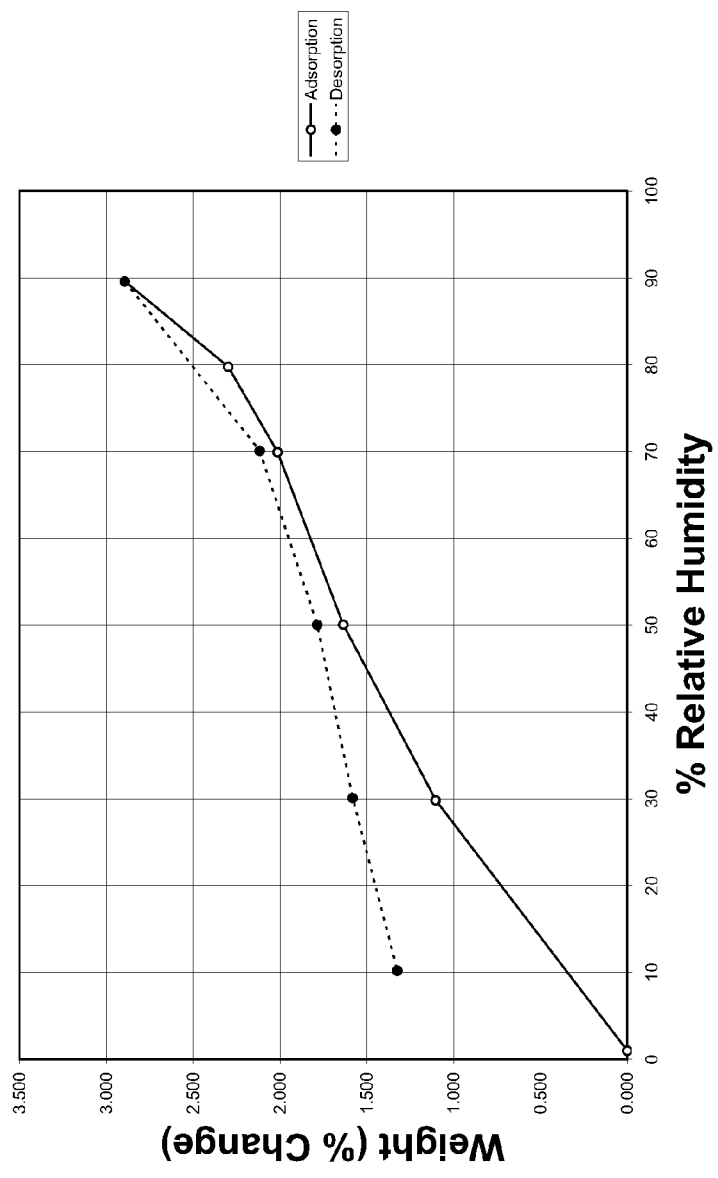
FIG. 12 shows a dynamic moisture sorption profile for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having a dynamic moisture-sorption profile substantially as shown in FIG. 12.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having a thermogravimetric analysis profile comprising about 2.2% weight loss up to about 120° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having a thermogravimetric analysis profile substantially as shown in FIG. 11.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having:
1) an X-ray diffraction pattern comprising peaks, expressed in terms of 2θ, at about 10.0° and about 12.40; and
2) a differential scanning calorimetry thermogram comprising an endotherm with an extrapolated onset temperature between about 147° C. and about 157° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having:
1) an X-ray diffraction pattern comprising peaks, expressed in terms of 2θ, at about 10.0°, about 12.4°, about 16.5°, about 17.4°, about 19.1°, and about 22.40; and
2) a differential scanning calorimetry thermogram comprising an endotherm with an extrapolated onset temperature between about 150° C. and about 154° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate having:
1) an X-ray diffraction pattern comprising peaks, expressed in terms of 2θ, at about 7.5°, about 10.0°, about 12.4°, about 16.5°, about 17.4°, about 19.1°, about 20.8°, about 21.1°, about 21.4°, and about 22.40;
2) a differential scanning calorimetry thermogram comprising an endotherm with an extrapolated onset temperature of about 152° C.; and
3) a thermogravimetric analysis profile comprising about 2.2% weight loss up to about 120° C.

E) (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt One aspect of the present invention relates to (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt. It is understood that TRIS refers to 2-amino-2-hydroxymethyl-propane-1,3-diol.

Another aspect of the present invention relates to a crystal form of (R)-2-(9-chloro-7-(4-isopropoxy-3-(trifluoromethyl)benzyloxy)-2,3-dihydro-1H-pyrrolo[1,2-a]indol-1-yl) acetic acid 2-amino-2-hydroxymethyl-propane-1,3-diol (TRIS) salt. The physical properties of a representative crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt are summarized in Table 9 below.

TABLE 9

Figure 13:
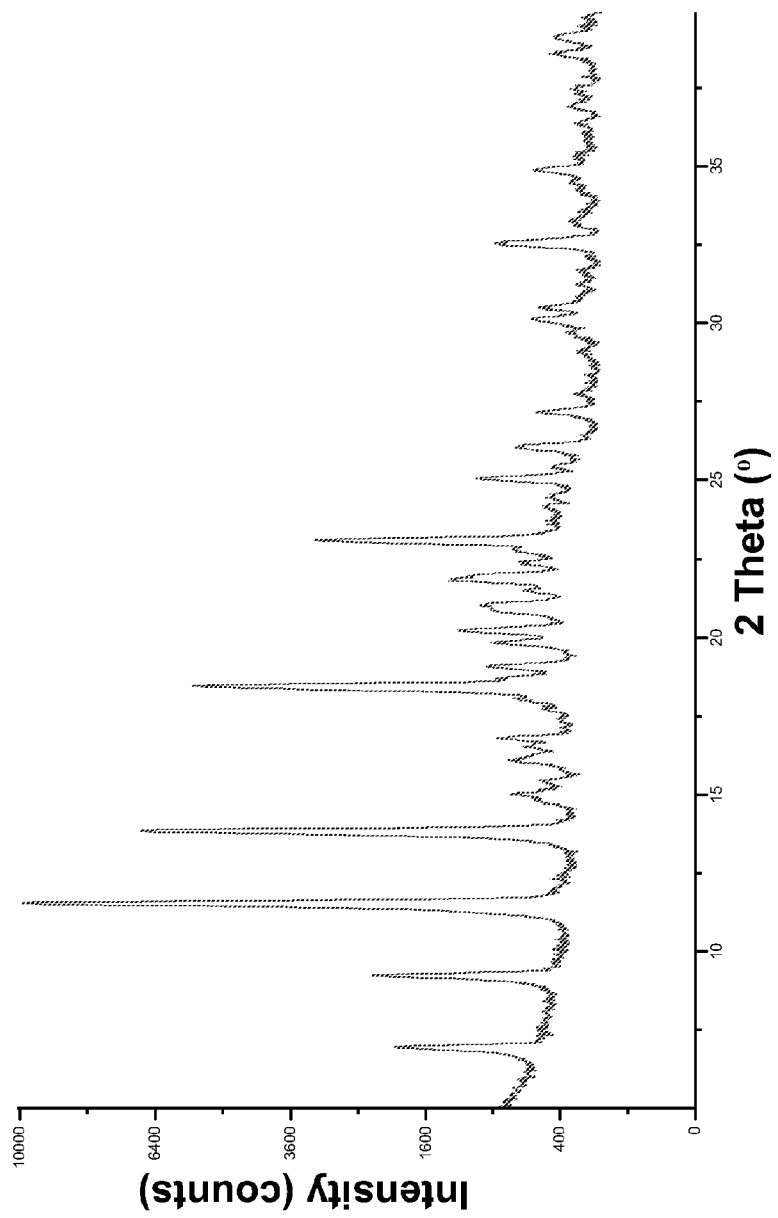
FIG. 13 shows a powder X-ray diffraction pattern (PXRD) for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt (PANalytical X'Pert Plus Powder X-Ray Diffractometer; 5.0 to 40.0° 2θ).

| Analytical Method | Crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt |
|---|---|
| PXRD | FIG. 13: Peaks of ≥15% relative intensity at: 7.0, 9.3, 11.5, 13.8, 18.4, and 23.1 in terms of °2θ. |
| TGA | FIG. 14: <0.1% weight loss up to about 110° C. |
| DSC | FIG. 14: an extrapolated onset temperature: 140° C.; endotherm peak temperature: 142° C. (maximum); associated heat flow 97 J/g. |

The insignificant weight loss observed in the TGA data suggests that the crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt is an anhydrous, non-solvated crystalline form. The DSC thermogram further reveals a melting endotherm with an onset temperature at 140° C.

Certain X-ray powder diffraction peaks for the crystalline form of (R)-2-(9-chloro-7-(4-isopropoxy-3-(trifluoromethyl)benzyloxy)-2,3-dihydro-1H-pyrrolo[1,2-a]indol-1-yl) acetic acid 2-amino-2-hydroxymethyl-propane-1,3-diol (TRIS) salt of the present invention are shown in Table 10 below.

TABLE 10

Crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt; PXRD Peaks with Relative Intensity of 15% or Higher (°2θ)

| Peak Position (°2θ) | d-spacing [Å] | Relative Intensity (%) |
|---|---|---|
| 7.0 | 12.68 | 15.4 |
| 9.3 | 9.56 | 19.7 |
| 11.5 | 7.66 | 100.0 |
| 13.8 | 6.40 | 67.8 |
| 18.4 | 4.81 | 54.8 |
| 23.1 | 3.85 | 30.4 |

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having an X-ray powder diffraction pattern comprising a peak, in terms of 2θ, at about 11.5°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having an X-ray powder diffraction pattern comprising a peak, in terms of 2θ, at about 13.8°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having an X-ray powder diffraction pattern comprising peaks, in terms of 2θ, at about 11.5° and about 13.8°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having an X-ray powder diffraction pattern comprising peaks, in terms of 2θ, at about 11.5°, about 13.8°, and about 18.4°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having an X-ray powder diffraction pattern comprising peaks, in terms of 2θ, at about 9.3°, about 11.5°, about 13.8°, about 18.4°, and about 23.1°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having an X-ray powder diffraction pattern comprising peaks, in terms of 2θ, at about 7.0°, about 9.3°, about 11.5°, about 13.8°, about 18.4°, and about 23.1°.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having an X-ray powder diffraction pattern substantially as shown in FIG. 13.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having a differential scanning calorimetry thermogram comprising an endotherm with an extrapolated onset temperature between about 135° C. and about 145° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having a differential scanning calorimetry thermogram comprising an endotherm with an extrapolated onset temperature between about 138° C. and about 142° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having a differential scanning calorimetry thermogram comprising an endotherm with an extrapolated onset temperature of about 140° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having a differential scanning calorimetry thermogram comprising an endotherm with a peak temperature between about 140° C. and about 144° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having a differential scanning calorimetry thermogram comprising an endotherm with a peak temperature at about 142° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having a differential scanning calorimetry thermogram comprising an endotherm with an associated heat flow of about 97 joules per gram.

Figure 14:
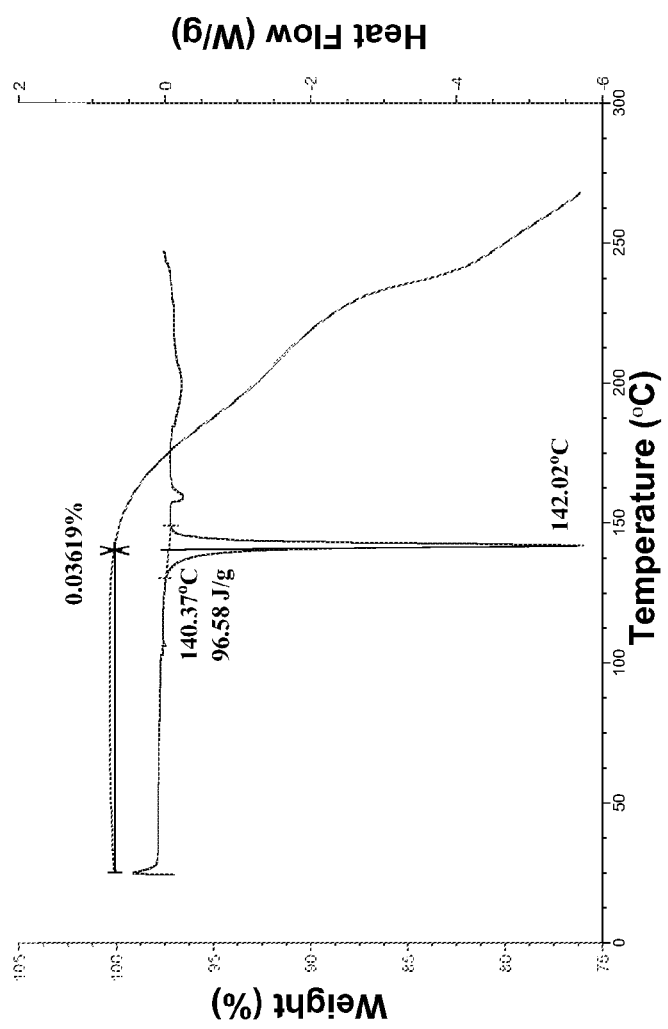
FIG. 14 shows a differential scanning calorimetry (DSC) thermogram for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt (TA Instruments DSC Q2000; 10° C./min).

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having a differential scanning calorimetry thermogram substantially as shown in FIG. 14.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having a thermogravimetric analysis profile showing less than about 0.1% weight loss up to about 110° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having a thermogravimetric analysis profile substantially as shown in FIG. 14.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having:
1) an X-ray diffraction pattern comprising peaks, expressed in terms of 2θ, at about 11.5° and about 13.8°; and
2) a differential scanning calorimetry thermogram comprising an endotherm with an extrapolated onset temperature between about 135° C. and about 145° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having:
1) an X-ray diffraction pattern comprising peaks, expressed in terms of 2θ, at about 11.5°, about 13.8°, and about 18.4°;
2) a differential scanning calorimetry thermogram comprising an endotherm with an extrapolated onset temperature between about 138° C., and about 142° C., and a peak temperature between about 140° C. and about 144° C.; and
2) a thermogravimetric analysis profile showing less than about 0.1% weight loss up to about 110° C.

One embodiment of the present invention is directed to a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt having:
1) an X-ray diffraction pattern comprising peaks, expressed in terms of 2θ, at about 7.0°, about 9.3°, about 11.5°, about 13.8°, about 18.4°, and about 23.1°;
2) a differential scanning calorimetry thermogram comprising an endotherm with an extrapolated onset temperature of about 140° C., and a peak temperature at about 142° C.; and 3) a thermogravimetric analysis profile showing less than about 0.1% weight loss up to about 110° C.

F) (R)-2-(9-chloro-7-(4-isopropoxy-3-(trifluoromethyl)benzyloxy)-2,3-dihydro-1H-pyrrolo[1,2-a] indol-1-yl)acetic acid sodium salt One aspect of the present invention relates to (R)-2-(9-chloro-7-(4-isopropoxy-3-(trifluoromethyl)benzyloxy)-2,3-dihydro-1H-pyrrolo[1,2-a]indol-1-yl)acetic acid sodium salt.

G) (R)-2-(9-chloro-7-(4-isopropoxy-3-(trifluoromethyl)benzyloxy)-2,3-dihydro-1H-pyrrolo[1,2-a] indol-1-yl)acetic acid L-arginine salt One aspect of the present invention relates to (R)-2-(9-chloro-7-(4-isopropoxy-3-(trifluoromethyl)benzyloxy)-2,3-dihydro-1H-pyrrolo[1,2-a]indol-1-yl)acetic acid L-arginine salt.

H) (R)-2-(9-chloro-7-(4-isopropoxy-3-(trifluoromethyl)benzyloxy)-2,3-dihydro-1H-pyrrolo[1,2-a] indol-1-yl)acetic acid zinc salt One aspect of the present invention relates to (R)-2-(9-chloro-7-(4-isopropoxy-3-(trifluoromethyl)benzyloxy)-2,3-dihydro-1H-pyrrolo[1,2-a]indol-1-yl)acetic acid zinc salt.

I) (R)-2-(9-chloro-7-(4-isopropoxy-3-(trifluoromethyl)benzyloxy)-2,3-dihydro-1H-pyrrolo[1,2-a] indol-1-yl)acetic acid calcium salt One aspect of the present invention relates to (R)-2-(9-chloro-7-(4-isopropoxy-3-(trifluoromethyl)benzyloxy)-2,3-dihydro-1H-pyrrolo[1,2-a]indol-1-yl)acetic acid calcium salt.

J) (R)-2-(9-chloro-7-(4-isopropoxy-3-(trifluoromethyl)benzyloxy)-2,3-dihydro-1H-pyrrolo[1,2-a] indol-1-yl)acetic acid N-methylglucamine salt One aspect of the present invention relates to (R)-2-(9-chloro-7-(4-isopropoxy-3-(trifluoromethyl)benzyloxy)-2,3-dihydro-1H-pyrrolo[1,2-a]indol-1-yl)acetic acid N-methylglucamine salt.

K) (R)-2-(9-chloro-7-(4-isopropoxy-3-(trifluoromethyl)benzyloxy)-2,3-dihydro-1H-pyrrolo[1,2-a] indol-1-yl)acetic acid potassium salt One aspect of the present invention relates to (R)-2-(9-chloro-7-(4-isopropoxy-3-(trifluoromethyl)benzyloxy)-2,3-dihydro-1H-pyrrolo[1,2-a]indol-1-yl)acetic acid potassium salt.

K) (R)-2-(9-chloro-7-(4-isopropoxy-3-(trifluoromethyl)benzyloxy)-2,3-dihydro-1H-pyrrolo[1,2-a] indol-1-yl)acetic acid magnesium salt One aspect of the present invention relates to (R)-2-(9-chloro-7-(4-isopropoxy-3-(trifluoromethyl)benzyloxy)-2,3-dihydro-1H-pyrrolo[1,2-a]indol-1-yl)acetic acid magnesium salt.

Indications and Methods of Prophylaxis and/or Treatment

The present application is in part focused on addressing an unmet need for immunosuppressive agents such as may be orally available which have therapeutic efficacy for at least autoimmune diseases and disorders, inflammatory diseases and disorders (e.g., acute and chronic inflammatory conditions), transplant rejection, cancer, and/or conditions that have an underlying defect in vascular integrity or that are associated with angiogenesis such as may be pathologic (e.g., as may occur in inflammation, tumor development, and atherosclerosis) with fewer side effects such as the impairment of immune responses to systemic infection.

The sphingosine-1-phosphate (SIP) receptors 1-5 constitute a family of G protein-coupled receptors with a seven-transmembrane domain. These receptors, referred to as S1P1 to SIPS (formerly termed endothelial differentiation gene (EDG) receptor-1, -5, -3, -6, and -8, respectively; Chun et al., *Pharmacological Reviews*, 54:265-269, 2002), are activated via binding by sphingosine-1-phosphate, which is produced by the sphingosine kinase-catalyzed phosphorylation of sphingosine. S1P1, S1P4, and S1P5 receptors activate Gi but not Gq, whereas S1P2 and S1P3 receptors activate both Gi and Gq. The S1P3 receptor, but not the S1P1 receptor, responds to an agonist with an increase in intracellular calcium.

S1P receptor agonists having agonist activity on the S1P1 receptor have been shown to rapidly and reversibly induce lymphopenia (also referred to as peripheral lymphocyte lowering (PLL); Hale et al., *Bioorg. Med. Chem. Lett.*, 14:3351-3355, 2004). This is attended by clinically useful immunosuppression by virtue of sequestering T- and B-cells in secondary lymphoid tissue (lymph nodes and Peyer's patches) and thus apart from sites of inflammation and organ grafts (Rosen et al., *Immunol. Rev.*, 195:160-177, 2003; Schwab et al., *Nature Immunol.*, 8:1295-1301, 2007). This lymphocyte sequestration, for example in lymph nodes, is thought to be a consequence of concurrent agonist-driven functional antagonism of the S1P1 receptor on T-cells (whereby the ability of S1P to mobilize T-cell egress from lymph nodes is reduced) and persistent agonism of the S1P1 receptor on lymph node endothelium (such that barrier function opposing transmigration of lymphocytes is increased) (Matloubian et al., *Nature*, 427:355-360, 2004; Baumruker et al., *Expert Opin. Investig. Drugs*, 16:283-289, 2007). It has been reported that agonism of the S1P1 receptor alone is sufficient to achieve lymphocyte sequestration (Sanna et al., *J Biol Chem.*, 279:13839-13848, 2004) and that this occurs without impairment of immune responses to systemic infection (Brinkmann et al., *Transplantation*, 72:764-769, 2001; Brinkmann et al., *Transplant Proc.*, 33:530-531, 2001).

That agonism of endothelial S1P1 receptors has a broader role in promoting vascular integrity is supported by work implicating the S1P1 receptor in capillary integrity in mouse skin and lung (Sanna et al., *Nat Chem Biol.*, 2:434-441, 2006). Vascular integrity can be compromised by inflammatory processes, for example as may derive from sepsis, major trauma and surgery so as to lead to acute lung injury or respiratory distress syndrome (Johan Groeneveld, *Vascul. Pharmacol.*, 39:247-256, 2003).

An exemplary S1P receptor agonist having agonist activity on the S1P1 receptor is FTY720 (fingolimod), an immunosuppressive agent currently in clinical trials (Martini et al., *Expert Opin. Investig. Drugs*, 16:505-518, 2007). FTY720 acts as a prodrug which is phosphorylated in vivo; the phosphorylated derivative is an agonist for S1P1, S1P3, S1P4, and SIPS receptors (but not the S1P2 receptor) (Chiba, *Pharmacology & Therapeutics*, 108:308-319, 2005). FTY720 has been shown to rapidly and reversibly induce lymphopenia (also referred to as peripheral lymphocyte lowering (PLL); Hale et al., *Bioorg. Med. Chem. Lett.*, 14:3351-3355, 2004). This is attended by clinically useful immunosuppression by virtue of sequestering T- and B-cells in secondary lymphoid tissue (lymph nodes and Peyer's patches) and thus apart from sites of inflammation and organ grafts (Rosen et al., *Immunol. Rev.*, 195:160-177, 2003; Schwab et al., *Nature Immunol.*, 8:1295-1301, 2007).

In clinical trials, FTY720 elicited an adverse event (i.e., transient asymptomatic bradycardia) due to its agonism of the S1P3 receptor (Budde et al., *J. Am. Soc. Nephrol.*, 13:1073-1083, 2002; Sanna et al., *J. Biol. Chem.*, 279:13839-13848, 2004; Ogawa et al., *BBRC*, 361:621-628, 2007).

FTY720 has been reported to have therapeutic efficacy in at least: a rat model for autoimmune myocarditis and a mouse model for acute viral myocarditis (Kiyabayashi et al., *J. Cardiovasc. Pharmacol.*, 35:410-416, 2000; Miyamoto et al., *J. Am. Coll. Cardiol.*, 37:1713-1718, 2001); mouse models for inflammatory bowel disease including colitis (Mizushima et al., *Inflamm. Bowel Dis.*, 10:182-192, 2004; Deguchi et al., *Oncology Reports*, 16:699-703, 2006; Fujii et al., *Am. J. Physiol. Gastrointest. Liver Physiol.*, 291:G267-G274, 2006; Daniel et al., *J. Immunol.*, 178:2458-2468, 2007); a rat model for progressive mesangioproliferative glomerulonephritis (Martini et al., *Am. J. Physiol. Renal Physiol.*, 292:F1761-F1770, 2007); a mouse model for asthma, suggested to be primarily through the S1P1 receptor on the basis of work using the S1P1 receptor agonist SEW2871 (Idzko et al., *J. Clin. Invest.*, 116:2935-2944, 2006); a mouse model for airway inflammation and induction of bronchial hyperresponsiveness (Sawicka et al., *J. Immunol.*, 171; 6206-6214, 2003); a mouse model for atopic dermatitis (Kohno et al., *Biol. Pharm. Bull.*, 27:1392-1396, 2004); a mouse model for ischemia-reperfusion injury (Kaudel et al., *Transplant. Proc*, 39:499-502, 2007); a mouse model for systemic lupus erythematosus (SLE) (Okazaki et al., *J. Rheumatol.*, 29:707-716, 2002; Herzinger et al, Am. J. Clin. Dermatol., 8:329-336, 2007); rat models for rheumatoid arthritis (Matsuura et al., *Int. J. Immunopharmacol.*, 22:323-331, 2000; Matsuura et al., *Inflamm. Res.*, 49:404-410, 2000); a rat model for autoimmune uveitis (Kurose et al., *Exp. Eye Res.*, 70:7-15, 2000); mouse models for type I diabetes (Fu et al, *Transplantation*, 73:1425-1430, 2002; Maki et al., *Transplantation*, 74:1684-1686, 2002; Yang et al., *Clinical Immunology*, 107:30-35, 2003; Maki et al., *Transplantation*, 79:1051-1055, 2005); mouse models for atherosclerosis (Nofer et al., *Circulation*, 115:501-508, 2007; Keul et al., *Arterioscler. Thromb. Vasc. Biol.*, 27:607-613, 2007); a rat model for brain inflammatory reaction following traumatic brain injury (TBI) (Zhang et al., *J. Cell. Mol. Med.*, 11:307-314, 2007); and mouse models for graft coronary artery disease and graft-versus-host disease (GVHD) (Hwang et al., *Circulation*, 100:1322-1329, 1999; Taylor et al., *Blood*, 110:3480-3488, 2007). In vitro results suggest that FTY720 may have therapeutic efficacy for β-amyloid-related inflammatory diseases including Alzheimer's disease (Kaneider et al., *FASEB J.*, 18:309-311, 2004). KRP-203, an SIP receptor agonist having agonist activity on the S1P1 receptor, has been reported to have therapeutic efficacy in a rat model for autoimmune myocarditis (Ogawa et al., *BBRC*, 361:621-628, 2007). Using the S1P1 receptor agonist SEW2871, it has been shown that agonism of endothelial S1P1 receptors prevents proinflammatory monocyte/endothelial interactions in type I diabetic vascular endothelium (Whetzel et al., *Circ. Res.*, 99:731-739, 2006) and protects the vasculature against TNFα-mediated monocyte/endothelial interactions (Bolick et al., *Arterioscler. Thromb. Vasc. Biol.*, 25:976-981, 2005).

Additionally, FTY720 has been reported to have therapeutic efficacy in experimental autoimmune encephalomyelitis (EAE) in rats and mice, a model for human multiple sclerosis (Brinkmann et al., *J. Biol. Chem.*, 277:21453-21457, 2002; Fujino et al., *J. Pharmacol. Exp. Ther.*, 305:70-77, 2003; Webb et al., *J. Neuroimmunol.*, 153:108-121, 2004; Rausch et al., *J. Magn. Reson. Imaging*, 20:16-24, 2004; Kataoka et al., *Cellular & Molecular Immunology*, 2:439-448, 2005; Brinkmann et al., *Pharmacology & Therapeutics*, 115:84-105, 2007; Baumruker et al., *Expert Opin. Investig. Drugs*, 16:283-289, 2007; Balatoni et al., *Brain Research Bulletin*, 74:307-316, 2007). Furthermore, FTY720 has been found to have therapeutic efficacy for multiple sclerosis in clinical trials. In Phase II clinical trials for relapsing-remitting multiple sclerosis, FTY720 was found to reduce the number of lesions detected by magnetic resonance imaging (MRI) and clinical disease activity in patients with multiple sclerosis (Kappos et al., N. Engl. J. Med., 355:1124-1140, 2006; Martini et al., *Expert Opin. Investig. Drugs*, 16:505-518, 2007; Zhang et al., *Mini-Reviews in Medicinal Chemistry*, 7:845-850, 2007; Brinkmann, *Pharmacology & Therapeutics*, 115: 84-105, 2007). FTY720 is currently in Phase III studies of remitting-relapsing multiple sclerosis (Brinkmann, *Pharmacology & Therapeutics*, 115:84-105, 2007; Baumruker et al., *Expert. Opin. Investig. Drugs*, 16:283-289, 2007; Dev et al., *Pharmacology and Therapeutics*, 117:77-93, 2008).

Recently, FTY720 has been reported to have anti-viral activity. Specific data has been presented in the lymphocytic choriomeningitis virus (LCMV) mouse model, wherein the mice were infected with either the Armstrong or the clone 13 strain of LCMV (Premenko-Lanier et al., Nature, 454, 894, 2008).

FTY720 has been reported to impair migration of dendritic cells infected with Francisella tularensis to the mediastinal lymph node, thereby reducing the bacterial colonization of it. Francisella tularensis is associated with tularemia, ulceroglandular infection, respiratory infection and a typhoidal disease (E. Bar-Haim et al, PLoS Pathogens, 4(11): e1000211. doi:10.1371/journal.ppat.1000211, 2008).

It has also been recently reported that a short-term high dose of FTY720 rapidly reduced ocular infiltrates in experimental autoimmune uveoretinitis. When given in the early stages of ocular inflammation, FTY720 rapidly prevented retinal damage. It was reported to not only prevent infiltration of target organs, but also reduce existing infiltration (Raveney et al., Arch. Ophthalmol. 126(10), 1390, 2008).

It has been reported that treatment with FTY720 relieved ovariectomy-induced osteoporosis in mice by reducing the number of mature osteoclasts attached to the bone surface. The data provided evidence that S1P controlled the migratory behaviour of osteoclast precursors, dynamically regulating bone mineral homeostasis (Ishii et al., *Nature,* 458(7237), 524-528, 2009).

Agonism of the S1P1 receptor has been implicated in enhancement of survival of oligodendrocyte progenitor cells. Survival of oligodendrocyte progenitor cells is a required component of the remyelination process. Remyelination of multiple sclerosis lesions is considered to promote recovery from clinical relapses. (Miron et al., *Ann. Neurol.,* 63:61-71, 2008; Coelho et al., *J. Pharmacol. Exp. Ther.,* 323:626-635, 2007; Dev et al., *Pharmacology and Therapeutics,* 117:77-93, 2008). It also has been shown that the S1P1 receptor plays a role in platelet-derived growth factor (PDGF)-induced oligodendrocyte progenitor cell mitogenesis (Jung et al., *Glia,* 55:1656-1667, 2007).

Agonism of the S1P1 receptor has also been reported to mediate migration of neural stem cells toward injured areas of the central nervous system (CNS), including in a rat model of spinal cord injury (Kimura et al., *Stem Cells,* 25:115-124, 2007).

Agonism of the S1P1 receptor has been implicated in the inhibition of keratinocyte proliferation (Sauer et al., *J. Biol. Chem.*, 279:38471-38479, 2004), consistent with reports that SIP inhibits keratinocyte proliferation (Kim et al., *Cell Signal*, 16:89-95, 2004). The hyperproliferation of keratinocytes at the entrance to the hair follicle, which can then become blocked, and an associated inflammation are significant pathogenetic factors of acne (Koreck et al., *Dermatology*, 206:96-105, 2003; Webster, *Cutis*, 76:4-7, 2005).

FTY720 has been reported to have therapeutic efficacy in inhibiting pathologic angiogenesis, such as that as may occur in tumor development. Inhibition of angiogenesis by FTY720 is thought to involve agonism of the S1P1 receptor (Oo et al., *J. Biol. Chem.*, 282; 9082-9089, 2007; Schmid et al., *J. Cell Biochem.*, 101:259-270, 2007). FTY720 has been reported to have therapeutic efficacy for inhibiting primary and metastatic tumor growth in a mouse model of melanoma (LaMontagne et al., *Cancer Res.*, 66:221-231, 2006). FTY720 has been reported to have therapeutic efficacy in a mouse model for metastatic hepatocellular carcinoma (Lee et al., *Clin. Cancer Res.*, 11:84588466, 2005).

It has been reported that oral administration of FTY720 to mice potently blocked VEGF-induced vascular permeability, an important process associated with angiogenesis, inflammation, and pathological conditions such as sepsis, hypoxia, and solid tumor growth (T Sanchez et al, J. Biol. Chem., 278(47), 47281-47290, 2003).

Cyclosporin A and FK506 (calcineurin inhibitors) are drugs used to prevent rejection of transplanted organs. Although they are effective in delaying or suppressing transplant rejection, classical immunosuppressants such as cyclosporin A and FK506 are known to cause several undesirable side effects including nephrotoxicity, neurotoxicity, β-cell toxicity and gastrointestinal discomfort. There is an unmet need in organ transplantation for an immunosuppressant without these side effects which is effective as a monotherapy or in combination with a classical immunosuppressant for inhibiting migration of, e.g., alloantigen-reactive T-cells to the grafted tissue, thereby prolonging graft survival.

FTY720 has been shown to have therapeutic efficacy in transplant rejection both as a monotherapy and in synergistic combination with a classical immunosuppressant, including cyclosporin A, FK506 and RAD (an mTOR inhibitor). It has been shown that, unlike the classical immunosuppressants cyclosporin A, FK506 and RAD, FTY720 has efficacy for prolonging graft survival without inducing general immunosuppression, and this difference in drug action is believed to be relevant to the synergism observed for the combination (Brinkmann et al., *Transplant Proc.*, 33:530-531, 2001; Brinkmann et al., *Transplantation*, 72:764-769, 2001).

Agonism of the S1P1 receptor has been reported to have therapeutic efficacy for prolonging allograft survival in mouse and rat skin allograft models (Lima et al., *Transplant Proc.*, 36:1015-1017, 2004; Yan et al., *Bioorg. & Med. Chem. Lett.*, 16:3679-3683, 2006). FTY720 has been reported to have therapeutic efficacy for prolonging allograft survival in a rat cardiac allograft model (Suzuki et al., *Transpl. Immunol.*, 4:252-255, 1996). FTY720 has been reported to act synergistically with cyclosporin A to prolong rat skin allograft survival (Yanagawa et al., *J. Immunol.*, 160:5493-5499, 1998), to act synergistically with cyclosporin A and with FK506 to prolong rat cardiac allograft survival, and to act synergistically with cyclosporin A to prolong canine renal allograft survival and monkey renal allograft survival (Chiba et al., *Cell Mol. Biol.*, 3:11-19, 2006). KRP-203, an S1P receptor agonist has been reported to have therapeutic efficacy for prolonging allograft survival in a rat skin allograft model and both as monotherapy and in synergistic combination with cyclosporin A in a rat cardiac allograft model (Shimizu et al., *Circulation*, 111:222-229, 2005). KRP-203 also has been reported to have therapeutic efficacy in combination with mycophenolate mofetil (MMF; a prodrug for which the active metabolite is mycophenolic acid, an inhibitor of purine biosynthesis) for prolonging allograft survival both in a rat renal allograft model and in a rat cardiac allograft model (Suzuki et al., *J. Heart Lung Transplant*, 25:302-209, 2006; Fujishiro et al., *J. Heart Lung Transplant*, 25:825-833, 2006). It has been reported that an agonist of the S1P1 receptor, AUY954, in combination with a subtherapeutic dose of RAD001 (Certican/Everolimus, an mTOR inhibitor) can prolong rat cardiac allograft survival (Pan et al., *Chemistry & Biology*, 13:1227-1234, 2006). In a rat small bowel allograft model, FTY720 has been reported to act synergistically with cyclosporin A to prolong small bowel allograft survival (Sakagawa et al., *Transpl. Immunol.*, 13:161-168, 2004). FTY720 has been reported to have therapeutic efficacy in a mouse islet graft model (Fu et al., *Transplantation*, 73:1425-1430, 2002; Liu et al., *Microsurgery*, 27:300-304; 2007) and in a study using human islet cells to evidence no detrimental effects on human islet function (Truong et al., *American Journal of Transplantation*, 7:2031-2038, 2007).

FTY720 has been reported to reduce the nociceptive behavior in the spared nerve injury model for neuropathic pain which does not depend on prostaglandin synthesis (O. Costu et al, Journal of Cellular and Molecular Medicine 12(3), 995-1004, 2008).

FTY720 has been reported to impair initiation of murine contact hypersensitivity (CHS). Adoptive transfer of immunized lymph node cells from mice treated with FTY720 during the sensitization phase was virtually incapable of inducing CHS response in recipients (D. Nakashima et al., J. Investigative Dermatology (128(12), 2833-2841, 2008).

It has been reported that prophylactic oral administration of FTY720 (1 mg/kg, three times a week), completely prevented the development of experimental autoimmune myasthenia gravis (EAMG) in C57BL/6 mice (T. Kohono et al, Biological & Pharmaceutical Bulletin, 28(4), 736-739, 2005).

In one embodiment, the present invention encompasses compounds which are agonists of the S1P1 receptor having selectivity over the S1P3 receptor. The S1P3 receptor, and not the S1P1 receptor, has been directly implicated in bradycardia (Sanna et al., *J. Biol. Chem.*, 279:13839-13848, 2004). An S1P1 receptor agonist selective over at least the S1P3 receptor has advantages over current therapies by virtue of an enhanced therapeutic window, allowing better tolerability with higher dosing and thus improving efficacy as therapy. The present invention encompasses compounds which are agonists of the S1P1 receptor and which exhibit no or substantially no activity for bradycardia.

In one embodiment, compounds of the present invention can be used in the treatment of chronic heart failure, congestive heart failure, arrhythmia or tachyarrhythmia, unstable angina, acute myocardial infarction or complications from cardiac surgery or for improving heart energy efficiency or cardiac output.

S1P1 receptor agonists are useful to treat or prevent conditions where suppression of the immune system or agonism of the S1P1 receptor is in order, such as diseases and disorders mediated by lymphocytes, transplant rejection, autoimmune diseases and disorders, inflammatory diseases and disorders, and conditions that have an underlying defect in vascular integrity or that relate to angiogenesis such as may be pathologic.

In one embodiment, the present invention encompasses compounds which are agonists of the S1P1 receptor having good overall physical properties and biological activities and having an effectiveness that is substantially at least that of prior compounds with activity at the S1P1 receptor.

One aspect of the present invention is directed to methods for treating an S1P1 receptor-associated disorder in an individual comprising administering to said individual in need thereof a therapeutically effective amount of a salt, a crystalline form, or a pharmaceutical composition as described herein.

One aspect of the present invention is directed to methods for treating psoriasis in an individual comprising administering to said individual in need thereof a therapeutically effective amount of a salt, a crystalline form, or a pharmaceutical composition as described herein.

One aspect of the present invention is directed to methods for treating rheumatoid arthritis in an individual comprising administering to said individual in need thereof a therapeutically effective amount of a salt, a crystalline form, or a pharmaceutical composition as described herein.

One aspect of the present invention is directed to methods for treating Crohn's disease in an individual comprising administering to said individual in need thereof a therapeutically effective amount of a salt, a crystalline form, or a pharmaceutical composition as described herein.

One aspect of the present invention is directed to methods for treating transplant rejection in an individual comprising administering to said individual in need thereof a therapeutically effective amount of a salt, a crystalline form, or a pharmaceutical composition as described herein.

One aspect of the present invention is directed to methods for treating multiple sclerosis in an individual comprising administering to said individual in need thereof a therapeutically effective amount of a salt, a crystalline form, or a pharmaceutical composition as described herein.

One aspect of the present invention is directed to methods for treating systemic lupus erythematosus in an individual comprising administering to said individual in need thereof a therapeutically effective amount of a salt, a crystalline form, or a pharmaceutical composition as described herein.

One aspect of the present invention is directed to methods for treating ulcerative colitis in an individual comprising administering to said individual in need thereof a therapeutically effective amount of a salt, a crystalline form, or a pharmaceutical composition as described herein.

One aspect of the present invention is directed to methods for treating type I diabetes in an individual comprising administering to said individual in need thereof a therapeutically effective amount of a salt, a crystalline form, or a pharmaceutical composition as described herein.

One aspect of the present invention is directed to methods for treating acne in an individual comprising administering to said individual in need thereof a therapeutically effective amount of a salt, a crystalline form, or a pharmaceutical composition as described herein.

One aspect of the present invention is directed to methods for treating myocardial ischemia-reperfusion injury in an individual comprising administering to said individual in need thereof a therapeutically effective amount of a salt, a crystalline form, or a pharmaceutical composition as described herein.

One aspect of the present invention is directed to methods for treating hypertensive nephropathy in an individual comprising administering to said individual in need thereof a therapeutically effective amount of a salt, a crystalline form, or a pharmaceutical composition as described herein.

One aspect of the present invention is directed to methods for treating glomerulosclerosis in an individual comprising administering to said individual in need thereof a therapeutically effective amount of a salt, a crystalline form, or a pharmaceutical composition as described herein.

One aspect of the present invention is directed to methods for treating gastritis in an individual comprising administering to said individual in need thereof a therapeutically effective amount of a salt, a crystalline form, or a pharmaceutical composition as described herein.

One aspect of the present invention is directed to methods for treating polymyositis in an individual comprising administering to said individual in need thereof a therapeutically effective amount of a salt, a crystalline form, or a pharmaceutical composition as described herein.

One aspect of the present invention is directed to methods for treating thyroiditis in an individual comprising administering to said individual in need thereof a therapeutically effective amount of a salt, a crystalline form, or a pharmaceutical composition as described herein.

One aspect of the present invention is directed to methods for treating vitiligo in an individual comprising administering to said individual in need thereof a therapeutically effective amount of a salt, a crystalline form, or a pharmaceutical composition as described herein.

One aspect of the present invention is directed to methods for treating hepatitis in an individual comprising administering to said individual in need thereof a therapeutically effective amount of a salt, a crystalline form, or a pharmaceutical composition as described herein.

One aspect of the present invention is directed to methods for treating biliary cirrhosis in an individual comprising administering to said individual in need thereof a therapeutically effective amount of a salt, a crystalline form, or a pharmaceutical composition as described herein.

One aspect of the present invention pertains to the use of a salt or a crystalline form, as described herein, in the manufacture of a medicament for the treatment of psoriasis.

One aspect of the present invention pertains to the use of a salt or a crystalline form, as described herein, in the manufacture of a medicament for the treatment of rheumatoid arthritis.

One aspect of the present invention pertains to the use of a salt or a crystalline form, as described herein, in the manufacture of a medicament for the treatment of Crohn's disease.

One aspect of the present invention pertains to the use of a salt or a crystalline form, as described herein, in the manufacture of a medicament for the treatment of transplant rejection.

One aspect of the present invention pertains to the use of a salt or a crystalline form, as described herein, in the manufacture of a medicament for the treatment of multiple sclerosis.

One aspect of the present invention pertains to the use of a salt or a crystalline form, as described herein, in the manufacture of a medicament for the treatment of systemic lupus erythematosus.

One aspect of the present invention pertains to the use of a salt or a crystalline form, as described herein, in the manufacture of a medicament for the treatment of ulcerative colitis.

One aspect of the present invention pertains to the use of a salt or a crystalline form, as described herein, in the manufacture of a medicament for the treatment of type I diabetes.

One aspect of the present invention pertains to the use of a salt or a crystalline form, as described herein, in the manufacture of a medicament for the treatment of acne.

One aspect of the present invention pertains to the use of a salt or a crystalline form, as described herein, in the manufacture of a medicament for the treatment of myocardial ischemia-reperfusion injury.

One aspect of the present invention pertains to the use of a salt or a crystalline form, as described herein, in the manufacture of a medicament for the treatment of hypertensive nephropathy.

One aspect of the present invention pertains to the use of a salt or a crystalline form, as described herein, in the manufacture of a medicament for the treatment of glomerulosclerosis.

One aspect of the present invention pertains to the use of a salt or a crystalline form, as described herein, in the manufacture of a medicament for the treatment of gastritis.

One aspect of the present invention pertains to the use of a salt or a crystalline form, as described herein, in the manufacture of a medicament for the treatment of polymyositis.

One aspect of the present invention pertains to the use of a salt or a crystalline form, as described herein, in the manufacture of a medicament for the treatment of thyroiditis.

One aspect of the present invention pertains to the use of a salt or a crystalline form, as described herein, in the manufacture of a medicament for the treatment of vitiligo.

One aspect of the present invention pertains to the use of a salt or a crystalline form, as described herein, in the manufacture of a medicament for the treatment of hepatitis.

One aspect of the present invention pertains to the use of a salt or a crystalline form, as described herein, in the manufacture of a medicament for the treatment of biliary cirrhosis.

One aspect of the present invention pertains to a salt, a crystalline form, or a pharmaceutical composition, as described herein, for use in a method for the treatment of the human or animal body by therapy.

One aspect of the present invention pertains to a salt, a crystalline form, or a pharmaceutical composition, as described herein, for use in a method for the treatment of psoriasis.

One aspect of the present invention pertains to a salt, a crystalline form, or a pharmaceutical composition, as described herein, for use in a method for the treatment of rheumatoid arthritis.

One aspect of the present invention pertains to a salt, a crystalline form, or a pharmaceutical composition, as described herein, for use in a method for the treatment of Crohn's disease.

One aspect of the present invention pertains to a salt, a crystalline form, or a pharmaceutical composition, as described herein, for use in a method for the treatment of transplant rejection.

One aspect of the present invention pertains to a salt, a crystalline form, or a pharmaceutical composition, as described herein, for use in a method for the treatment of multiple sclerosis.

One aspect of the present invention pertains to a salt, a crystalline form, or a pharmaceutical composition, as described herein, for use in a method for the treatment of systemic lupus erythematosus.

One aspect of the present invention pertains to a salt, a crystalline form, or a pharmaceutical composition, as described herein, for use in a method for the treatment of ulcerative colitis.

One aspect of the present invention pertains to a salt, a crystalline form, or a pharmaceutical composition, as described herein, for use in a method for the treatment of type I diabetes.

One aspect of the present invention pertains to a salt, a crystalline form, or a pharmaceutical composition, as described herein, for use in a method for the treatment of acne.

One aspect of the present invention pertains to a salt, a crystalline form, or a pharmaceutical composition, as described herein, for use in a method for the treatment of myocardial ischemia-reperfusion injury.

One aspect of the present invention pertains to a salt, a crystalline form, or a pharmaceutical composition, as described herein, for use in a method for the treatment of hypertensive nephropathy.

One aspect of the present invention pertains to a salt, a crystalline form, or a pharmaceutical composition, as described herein, for use in a method for the treatment of glomerulosclerosis.

One aspect of the present invention pertains to a salt, a crystalline form, or a pharmaceutical composition, as described herein, for use in a method for the treatment of gastritis.

One aspect of the present invention pertains to a salt, a crystalline form, or a pharmaceutical composition, as described herein, for use in a method for the treatment of polymyositis.

One aspect of the present invention pertains to a salt, a crystalline form, or a pharmaceutical composition, as described herein, for use in a method for the treatment of thyroiditis.

One aspect of the present invention pertains to a salt, a crystalline form, or a pharmaceutical composition, as described herein, for use in a method for the treatment of vitiligo.

One aspect of the present invention pertains to a salt, a crystalline form, or a pharmaceutical composition, as described herein, for use in a method for the treatment of hepatitis.

One aspect of the present invention pertains to a salt, a crystalline form, or a pharmaceutical composition, as described herein, for use in a method for the treatment of biliary cirrhosis.

Pharmaceutical Compositions

A further aspect of the present invention pertains to pharmaceutical compositions comprising one or more compounds as described herein and one or more pharmaceutically acceptable carriers. The embodiments pertain to pharmaceutical compositions comprising a compound of the present invention and a pharmaceutically acceptable carrier.

The embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations.

Parenteral dosage forms may be prepared by dissolving the compound of the invention in a suitable liquid vehicle and filter sterilizing the solution before filling and sealing an appropriate vial or ampule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, *The Science and Practice of Pharmacy*, 20$^{th}$ Edition, 2000, Lippincott Williams & Wilkins, (Editors: Gennaro et al.).

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt, solvate, hydrate or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: *Polymorphism in Pharmaceutical Solids*, ed. Harry G. Brittan, Vol. 95, Marcel Dekker, Inc., New York, 1999, incorporated herein by reference in its entirety.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate, hydrate or physiologically functional derivative thereof can be used as active ingredients in pharmaceutical compositions, specifically as S1P1 receptor modulators. By the term "active ingredient" is defined in the context of a "pharmaceutical composition" and refers to a component of a pharmaceutical composition that provides the primary pharmacological effect, as opposed to an "inactive ingredient" which would generally be recognized as providing no pharmaceutical benefit.

The dose when using the compounds of the present invention can vary within wide limits and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt, solvate or hydrate of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size. The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methyl cellulose, sodium carboxymethylcellulose, a low melting wax, cocoa butter and the like. The term "preparation" refer to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methyl cellulose, sodium carboxymethylcellulose, or other well-known suspending agents.

Also included are solid form preparations which can be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension.

In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well known to the person skilled in the art. For their preparation, for example, solutions or dispersions of the compounds of the present invention in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The present invention is directed to pharmaceutical compositions that include every combination of one or more of the salts, or crystalline forms selected from the following group:

(R)-2-(9-chloro-7-(4-isopropoxy-3-(trifluoromethyl)benzyloxy)-2,3-dihydro-1H-pyrrolo[1,2-a]indol-1-yl)acetic acid L-lysine salt;

(R)-2-(9-chloro-7-(4-isopropoxy-3-(trifluoromethyl)benzyloxy)-2,3-dihydro-1H-pyrrolo[1,2-a]indol-1-yl)acetic acid sodium salt;

(R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate;

(R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate;

(R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt;

(R)-2-(9-chloro-7-(4-isopropoxy-3-(trifluoromethyl)benzyloxy)-2,3-dihydro-1H-pyrrolo[1,2-a]indol-1-yl)acetic acid L-arginine salt;

(R)-2-(9-chloro-7-(4-isopropoxy-3-(trifluoromethyl)benzyloxy)-2,3-dihydro-1H-pyrrolo[1,2-a]indol-1-yl)acetic acid zinc salt;

(R)-2-(9-chloro-7-(4-isopropoxy-3-(trifluoromethyl)benzyloxy)-2,3-dihydro-1H-pyrrolo[1,2-a]indol-1-yl)acetic acid calcium salt;

(R)-2-(9-chloro-7-(4-isopropoxy-3-(trifluoromethyl)benzyloxy)-2,3-dihydro-1H-pyrrolo[1,2-a]indol-1-yl)acetic acid N-methylglucamine salt;

(R)-2-(9-chloro-7-(4-isopropoxy-3-(trifluoromethyl)benzyloxy)-2,3-dihydro-1H-pyrrolo[1,2-a]indol-1-yl)acetic acid potassium salt;

(R)-2-(9-chloro-7-(4-isopropoxy-3-(trifluoromethyl)benzyloxy)-2,3-dihydro-1H-pyrrolo[1,2-a]indol-1-yl)acetic acid magnesium salt; and a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid.

One aspect of the present invention pertains to pharmaceutical compositions comprising (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt and a pharmaceutically acceptable carrier.

One aspect of the present invention pertains to pharmaceutical compositions comprising a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt and a pharmaceutically acceptable carrier.

One aspect of the present invention pertains to pharmaceutical compositions comprising a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid and a pharmaceutically acceptable carrier.

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in *Bioreversible Carriers in Drug Design*, ed. Edward B. Roche, American Pharmaceutical Association and Pergamon Press, 1987, both of which are hereby incorporated by reference in their entirety.

The embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when the S1P1 receptor modulators are utilized as active ingredients in a pharmaceutical composition, these are not intended for use only in humans, but in other non-human mammals as well. Indeed, recent advances in the area of animal health-care mandate that consideration be given for the use of active agents, such as S1P1 receptor modulators, for the treatment of an S1P-associated disease or disorder in companionship animals (e.g., cats, dogs, etc.) and in livestock animals (e.g., cows, chickens, fish, etc.) Those of ordinary skill in the art are readily credited with understanding the utility of such compounds in such settings.

Hydrates and Solvates

It is understood that when the phrase "pharmaceutically acceptable salts, solvates, and hydrates" or the phrase "pharmaceutically acceptable salt, solvate, or hydrate" is used when referring to compounds described herein, it embraces pharmaceutically acceptable solvates and/or hydrates of the compounds, pharmaceutically acceptable salts of the compounds, as well as pharmaceutically acceptable solvates and/or hydrates of pharmaceutically acceptable salts of the compounds. It is also understood that when the phrase "pharmaceutically acceptable solvates and hydrates" or the phrase "pharmaceutically acceptable solvate or hydrate" is used when referring to salts described herein, it embraces pharmaceutically acceptable solvates and/or hydrates of such salts.

It will be apparent to those skilled in the art that the dosage forms described herein may comprise, as the active component, either a compound described herein or a pharmaceutically acceptable salt or as a pharmaceutically acceptable solvate or hydrate thereof. Moreover, various hydrates and solvates of the compounds described herein and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc., New York, 1999. Accordingly, one aspect of the present invention pertains to methods of administering hydrates and solvates of compounds described herein and/or their pharmaceutical acceptable salts, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

One embodiment of the present invention includes (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate.

One embodiment of the present invention is directed compositions comprising (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate.

Compositions Containing Salts and Crystalline Forms

One aspect of the present invention is directed compositions comprising a salt or a crystalline form, as described herein.

One embodiment of the present invention is directed to compositions comprising (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt.

One embodiment of the present invention is directed to compositions comprising (R)-2-(9-chloro-7-(4-isopropoxy-3-(trifluoromethyl)benzyloxy)-2,3-dihydro-1H-pyrrolo[1,2-a]indol-1-yl)acetic acid sodium salt.

One embodiment of the present invention is directed to compositions comprising (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate.

One embodiment of the present invention is directed to compositions comprising (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate.

One embodiment of the present invention is directed to compositions comprising (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt.

One embodiment of the present invention is directed to compositions comprising (R)-2-(9-chloro-7-(4-isopropoxy-3-(trifluoromethyl)benzyloxy)-2,3-dihydro-1H-pyrrolo[1,2-a]indol-1-yl)acetic acid L-arginine salt.

One embodiment of the present invention is directed to compositions comprising (R)-2-(9-chloro-7-(4-isopropoxy-3-(trifluoromethyl)benzyloxy)-2,3-dihydro-1H-pyrrolo[1,2-a]indol-1-yl)acetic acid zinc salt.

One embodiment of the present invention is directed to compositions comprising (R)-2-(9-chloro-7-(4-isopropoxy-3-(trifluoromethyl)benzyloxy)-2,3-dihydro-1H-pyrrolo[1,2-a]indol-1-yl)acetic acid calcium salt.

One embodiment of the present invention is directed to compositions comprising (R)-2-(9-chloro-7-(4-isopropoxy-3-(trifluoromethyl)benzyloxy)-2,3-dihydro-1H-pyrrolo[1,2-a]indol-1-yl)acetic acid N-methylglucamine salt.

One embodiment of the present invention is directed to compositions comprising (R)-2-(9-chloro-7-(4-isopropoxy-3-(trifluoromethyl)benzyloxy)-2,3-dihydro-1H-pyrrolo[1,2-a]indol-1-yl)acetic acid potassium salt.

One embodiment of the present invention is directed to compositions comprising (R)-2-(9-chloro-7-(4-isopropoxy-3-(trifluoromethyl)benzyloxy)-2,3-dihydro-1H-pyrrolo[1,2-a]indol-1-yl)acetic acid magnesium salt.

One embodiment of the present invention is directed to compositions comprising a crystalline form (R)-2-(9-chloro-7-(4-isopropoxy-3-(trifluoromethyl)benzyloxy)-2,3-dihydro-1H-pyrrolo[1,2-a]indol-1-yl)acetic acid, the crystalline form as described herein.

One aspect of the present invention provides for pharmaceutical compositions comprising a salt or crystalline form, as described herein, and a pharmaceutically acceptable carrier. For example, in some embodiments, pharmaceutical compositions of the present invention comprise (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt and a pharmaceutically acceptable carrier.

In some embodiments, pharmaceutical compositions of the present invention comprise a crystalline form of (R)-2-(9-chloro-7-(4-isopropoxy-3-(trifluoromethyl)benzyloxy)-2,3- dihydro-1H-pyrrolo[1,2-a]indol-1-yl)acetic acid, as described herein, and a pharmaceutically acceptable carrier.

The present invention further provides compositions comprising a salt or a crystalline form, as described herein, wherein the salt or crystalline form comprises about 5%, 10%, 15%, 20%, 25%, 30%, 35%, 40%, 45%, 50%, 55%, 60%, 65%, 70%, 75%, 80%, 85%, 90%, 95%, 98%, 99%, or greater by weight of the composition.

The present invention further provides compositions comprising (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt, wherein the salt comprises about 5%, 10%, 15%, 20%, 25%, 30%, 35%, 40%, 45%, 50%, 55%, 60%, 65%, 70%, 75%, 80%, 85%, 90%, 95%, 98%, 99%, or greater by weight of the composition.

The present invention further provides compositions comprising a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid, wherein the crystalline form comprises about 5%, 10%, 15%, 20%, 25%, 30%, 35%, 40%, 45%, 50%, 55%, 60%, 65%, 70%, 75%, 80%, 85%, 90%, 95%, 98%, 99%, or greater by weight of the composition.

In some embodiments, the compositions comprise a salt or a crystalline form, as described herein, wherein the salt or crystalline form comprises about 50% or greater by weight of said composition.

In some embodiments, the compositions comprise a salt or a crystalline form, as described herein, wherein the salt or crystalline form comprises about 75% or greater by weight of said composition.

In some embodiments, the compositions comprise a salt or a crystalline form, as described herein, wherein the salt or crystalline form comprises about 85% or greater by weight of said composition.

In some embodiments, the compositions comprise a salt or a crystalline form, as described herein, wherein the salt or crystalline form comprises about 95% or greater by weight of said composition.

In some embodiments, the compositions comprise a salt or a crystalline form, as described herein, wherein the salt or crystalline form comprises about 97% or greater by weight of said composition.

In some embodiments, the compositions comprise a salt or a crystalline form, as described herein, wherein the salt or crystalline form comprises about 99% or greater by weight of said composition.

Processes of the Present Invention

The present invention is further directed to, inter alia, processes and intermediates for the preparation of (R)-2-(9-chloro-7-(4-isopropoxy-3-(trifluoromethyl)benzyloxy)-2,3-dihydro-1H-pyrrolo[1,2-a]indol-1-yl)acetic acid, salts and crystalline forms thereof.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

In some embodiments, preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis,* 3rd Ed., Wiley & Sons, 1999, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, diisopropyl ether, or t-butyl methyl ether.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran, N,N-dimethylformamide, N,N-dimethylacetamide, 1,3-dimethyl-3,4,5,6-tetrahydro-2(1H)-pyrimidinone, 1,3-dimethyl-2-imidazolidinone, N-methylpyrrolidinone, formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, o, m-, or p-xylene, octane, indane, nonane, or naphthalene.

Supercritical carbon dioxide can also be used as a solvent.

The reactions of the processes described herein can be carried out at appropriate temperatures which can be readily determined by one skilled in the art. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

The reactions of the processes described herein can be carried out in air or under an inert atmosphere. Typically, reactions containing reagents or products that are substantially reactive with air can be carried out using air-sensitive synthetic techniques that are well known to one skilled in the art.

In some embodiments, preparation of compounds can involve the addition of acids or bases to effect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, trifluoroacetic acid, propionic acid, butanoic acid, methanesulfonic acid, p-toluene sulfonic acid, benzenesulfonic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, isopropanol, n-butyl, t-butyl, trimethylsilyl and cyclohexyl substituted amides.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

The processes described herein can be stereoselective such that any given reaction starting with one or more chiral reagents enriched in one stereoisomer forms a product that is also enriched in one stereoisomer. The reaction can be conducted such that the product of the reaction substantially retains one or more chiral centers present in the starting materials. The reaction can also be conducted such that the product of the reaction contains a chiral center that is substantially inverted relative to a corresponding chiral center present in the starting materials.

Resolution of racemic mixtures of compounds can be carried out by any of numerous methods known in the art. An example method includes fractional recrystallization (for example, diastereomeric salt resolution) using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of β-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Upon carrying out preparation of compounds according to the processes described herein, the usual isolation and purification operations such as concentration, filtration, extraction, solid-phase extraction, recrystallization, enantiomeric-enrichment via recrystallization, chromatography, and the like may be used, to isolate the desired products.

Example processes and certain intermediates of the present invention are shown in Schemes I to X below, wherein each substituent of the compounds depicted is defined herein.

Representative indole forming step, and intermediates of Formulae (IIa) or a salt thereof, (IIb), and (IIc) or a salt thereof, of the present invention are provided below in Scheme I, wherein each substituent depicted in the Formulae has the same meaning as defined herein.

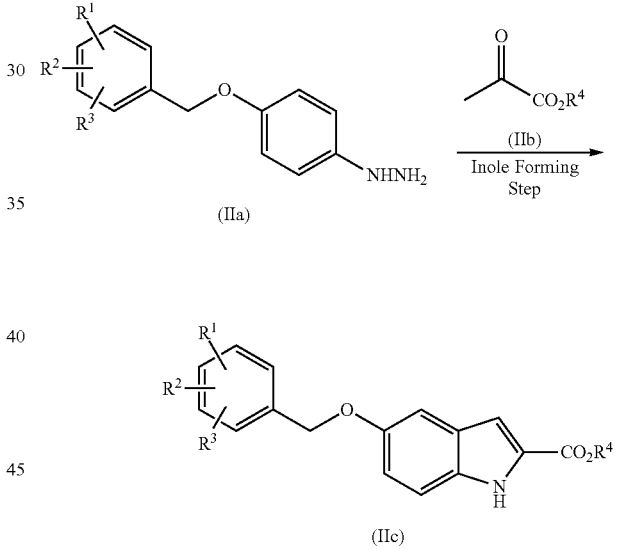

Representative cyclizing step, and intermediates of Formulae (IIc) or a salt thereof, (IId), and (IIe) or a keto tautomer thereof, of the present invention are provided below in Scheme II, wherein each substituent depicted in the Formulae has the same meaning as defined herein.

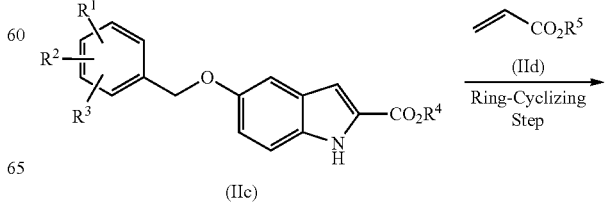

-continued

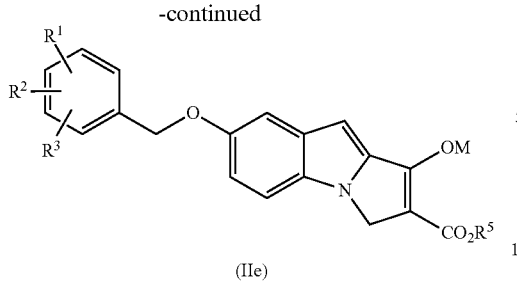

(IIe)

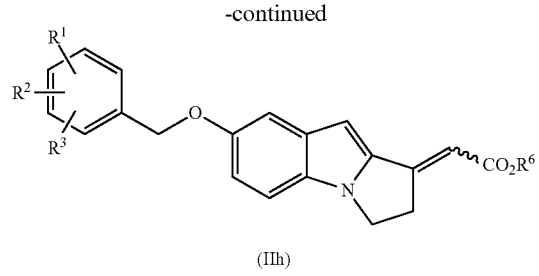

(IIh)

Representative decarboxylating step and intermediates of Formulae (IIe) or a keto tautomer thereof, and (IIf) or a salt thereof, of the present invention are provided below in Scheme III, wherein each substituent depicted in the Formulae has the same meaning as defined herein.

Representative reducing step and intermediates of Formulae (IIh) or a salt thereof, and (IIi) or a salt thereof, of the present invention are provided below in Scheme V, wherein each substituent depicted in the Formulae has the same meaning as defined herein.

Scheme III

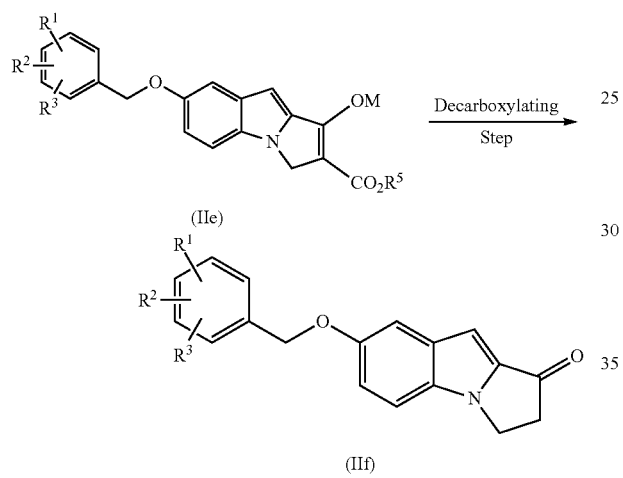

Representative olefinating step and intermediates of Formulae (IIf) or a salt thereof, (IIg), and (IIh) or a salt thereof, of the present invention are provided below in Scheme IV, wherein each substituent depicted in the Formulae has the same meaning as defined herein.

Scheme V

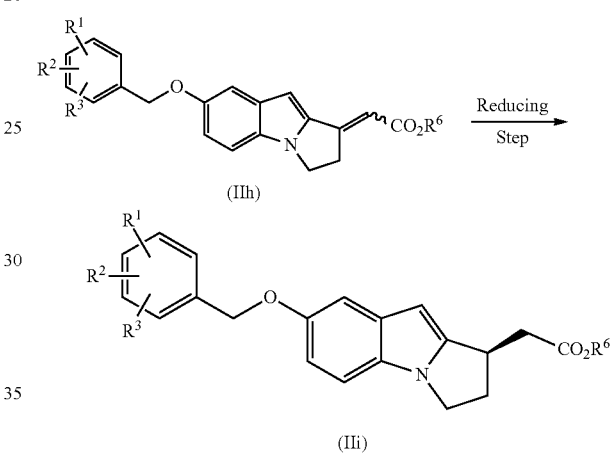

Representative deprotecting step and intermediates of Formulae (IIi) or a salt thereof, and (IIj) or a salt thereof, of the present invention are provided below in Scheme VI, wherein each substituent depicted in the Formulae has the same meaning as defined herein.

Scheme VI

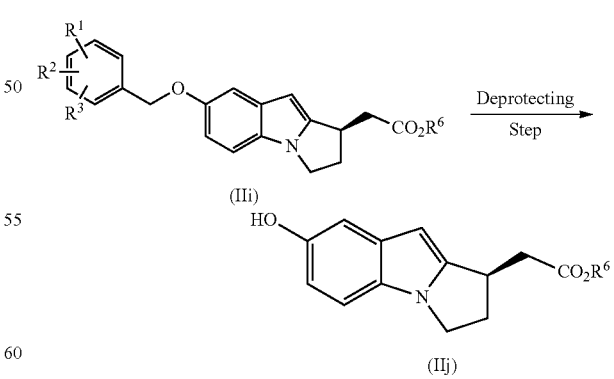

Scheme IV

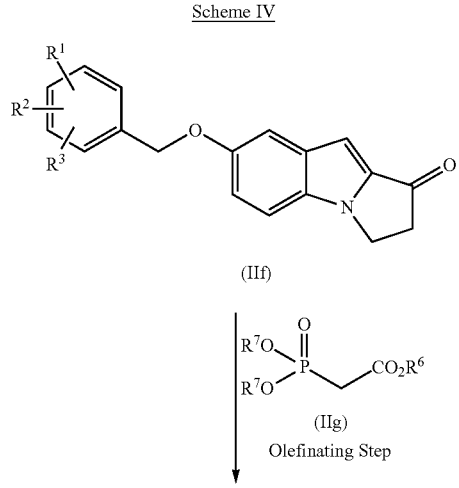

Representative alkylating step and intermediates of Formulae (IIj) or a salt thereof, (IIk), and (IIm) or a salt thereof, is provided below in Scheme VII, wherein each substituent depicted in the Formulae has the same meaning as defined herein.

Scheme VII

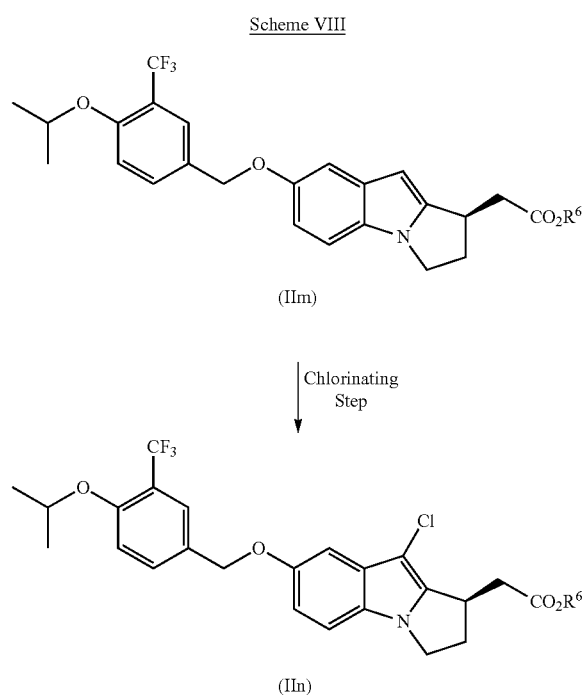

Representative chlorinating step and intermediates of Formulae (IIm) or a salt thereof, and (IIn) or a salt thereof, is provided below in Scheme VIII, wherein each substituent depicted in the Formulae has the same meaning as defined herein.

Scheme VIII

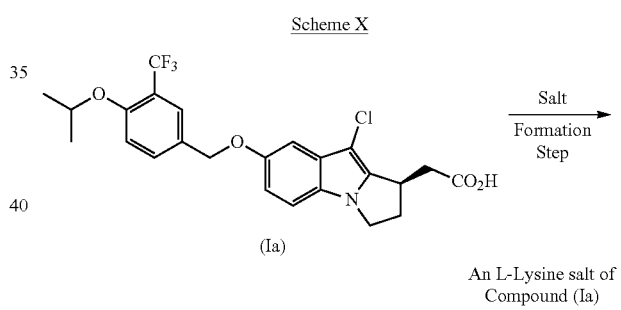

Representative hydrolyzing step and intermediates of Formulae (IIn) or a salt thereof, and (Ia) are provided below in Scheme IX, wherein each substituent depicted in the Formulae has the same meaning as defined herein.

Scheme IX

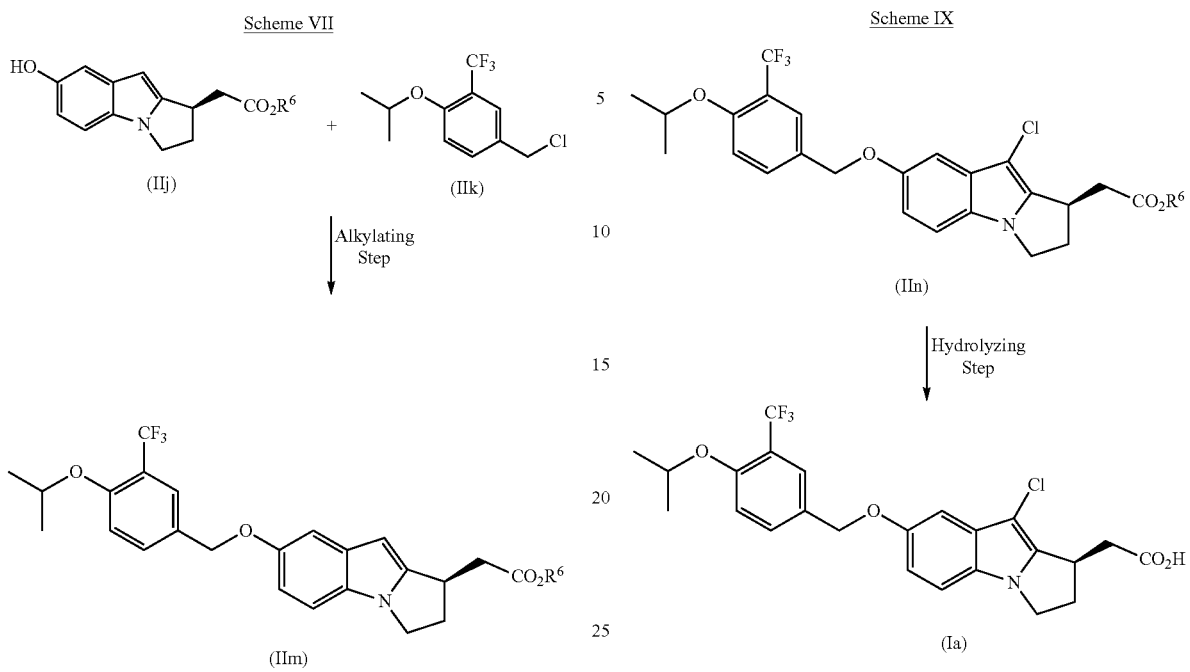

Representative salt formation step from compound of Formula (Ia) to an L-lysine salt of compound of Formula (Ia) is provided below in Scheme X.

Scheme X

One aspect of the present invention includes every combination of one or more process step and intermediates related thereto used in the preparation of (R)-2-(9-chloro-7-(4-isopropoxy-3-(trifluoromethyl)benzyloxy)-2,3-dihydro-1H-pyrrolo[1,2-a]indol-1-yl)acetic acid, and salts, and crystalline forms thereof, such processes as exemplified by Schemes I, II, III, IV, V, VI, VII, VIII, IX, and X (supra) and compounds of Formulae (Ia), (IIa), (IIb), (IIe), (IId), (IIe), (IIf), (IIg), (IIh), (IIi), (IIj), (IIm), and (IIn).

One aspect of the present invention pertains to intermediates, compounds of Formulae (Ia), (IIa), (IIb), (IIe), (IId), (IIe), (IIf), (IIg), (IIh), (IIi), (IIj), (IIm), and (IIn), as exemplified in Schemes I, II, III, IV, V, VI, VII, VIII, IX, and X (supra), useful in the preparation of Compound of Formula (Ia) and salts, and crystalline forms thereof, for example, an L-lysine salt of Compound of Formula (Ia).

One aspect of the present invention pertains to intermediates as exemplified in Schemes I, II, III, IV, V, VI, VII, VIII, IX, and X (supra), that involve compounds of Formulae (Ia), (IIa), (IIb), (IIe), (IId), (IIe), (IIf), (IIg), (IIh), (IIi), (IIj), (IIm), and (IIn), wherein:

$R^1$, $R^2$, and $R^3$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro;

$R^4$ is $C_1$-$C_4$ alkyl;
$R^5$ is $C_1$-$C_4$ alkyl;
$R^6$ is $C_1$-$C_4$ alkyl;
each $R^7$ is independently $C_1$-$C_4$ alkyl; and
M is an alkali metal or H.

In some embodiments, $R^1$, $R^2$, and $R^3$ are each selected independently from the group consisting of H, $C_1$-$C_4$ alkyl, $C_1$-$C_4$ alkoxy, and $C_1$-$C_4$ haloalkyl.

In some embodiments, $R^1$, $R^2$, and $R^3$ are each selected independently from the group consisting of H, $C_1$-$C_4$ alkyl, and $C_1$-$C_4$ alkoxy.

In some embodiments, $R^1$, $R^2$, and $R^3$ are each selected independently from the group consisting of H, $CH_3$, $OCH_3$, $OCH(CH_3)_2$, and $CF_3$.

In some embodiments, $R^1$, $R^2$, and $R^3$ are each selected independently from the group consisting of H, $CH_3$, and $OCH_3$.

In some embodiments, $R^1$, $R^2$, and $R^3$ are each selected independently from the group consisting of H, $OCH(CH_3)_2$, and $CF_3$.

In some embodiments, $R^1$ is H.
In some embodiments, $R^2$ is $OCH(CH_3)_2$.
In some embodiments, $R^3$ is $CF_3$.
In some embodiments, $R^1$, $R^2$, and $R^3$ are each H.
In some embodiments, $R^4$ is $CH_3$, $CH_2CH_3$, $CH_2CH_2CH_3$, or $CH_2(CH_2)_2CH_3$.
In some embodiments, $R^4$ is $CH_3$.
In some embodiments, $R^4$ is $CH_2CH_3$.
In some embodiments, $R^4$ is $CH_2CH_2CH_3$.
In some embodiments, $R^5$ is $CH_3$, $CH_2CH_3$, $CH_2CH_2CH_3$, or $CH_2(CH_2)_2CH_3$.
In some embodiments, $R^5$ is $CH_3$.
In some embodiments, $R^5$ is $CH_2CH_3$.
In some embodiments, $R^5$ is $CH_2CH_2CH_3$.
In some embodiments, M is lithium, sodium or potassium.
In some embodiments, M is sodium.
In some embodiments, M is potassium.
In some embodiments, M is H.
In some embodiments, $R^6$ is $CH_3$, $CH_2CH_3$, $CH_2CH_2CH_3$, $CH_2(CH_2)_2CH_3$, or t-butyl.
In some embodiments, $R^6$ is $CH_3$, $CH_2CH_3$, $CH_2CH_2CH_3$, or $CH_2(CH_2)_2CH_3$.
In some embodiments, $R^6$ is $CH_3$.
In some embodiments, $R^6$ is $CH_2CH_3$.
In some embodiments, $R^6$ is $CH_2CH_2CH_3$.
In some embodiments, $R^6$ is t-butyl.
In some embodiments, $R^7$ is $CH_3$, $CH_2CH_3$, $CH_2CH_2CH_3$, or $CH_2(CH_2)_2CH_3$.
In some embodiments, $R^7$ is $CH_3$.
In some embodiments, $R^7$ is $CH_2CH_3$.
In some embodiments, $R^7$ is $CH_2CH_2CH_3$.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All subcombinations of the chemical groups represented by variables (e.g., $R^1$, $R^2$, $R^3$, $R^4$, $R^5$, $R^6$, $R^7$, and M) contained within the generic chemical formulae described herein, for example, (IIa), (IIb), (IIc), (IId), (IIe), (IIe), (IIf), (IIg), (IIh), (IIi), (IIj), (IIm), (IIIb), (IIIc), (IIId), and (IIIe), are specifically embraced by the present invention just as if each and every combination was individually and explicitly recited, to the extent that such combinations embrace compounds that result in stable compounds (i.e., compounds that can be isolated, and characterized). Further more, all subcombinations of the embodiments pertaining process steps as described herein are specifically embraced by the present invention just as if each process step and every combination was individually and explicitly recited. In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein. In addition, all subcombinations of the salts, solvates, hydrates, and crystalline forms specifically exemplified herein, as well as all subcombinations of uses thereof and medical indications related thereto described herein, are also specifically embraced by the present invention just as if each and every subcombination of salts, solvates, hydrates and crystalline forms specifically exemplified herein and subcombination of uses thereof and medical indications related thereto was individually and explicitly recited herein.

Compounds of the invention can also include tautomeric forms, such as keto-enol tautomers and the like. Tautomeric forms can be in equilibrium or sterically locked into one form by appropriate substitution. It is understood that the various tautomeric forms are within the scope of the compounds of the present invention.

Compounds of the invention can also include all isotopes of atoms occurring in the intermediates and/or final compounds. Isotopes include those atoms having the same atomic number but different mass numbers. For example, isotopes of hydrogen include deuterium and tritium.

It is understood that the present invention embraces each diastereoisomer, each enantiomer and mixtures thereof of each compound and generic formulae disclosed herein just as if they were each individually disclosed with the specific stereochemical designation for each chiral carbon. Separation of the individual isomers (such as, by chiral HPLC, recrystallization of diastereoisomeric mixtures and the like) or selective synthesis (such as, by enantiomeric selective syntheses and the like) of the individual isomers is accomplished by application of various methods which are well known to practitioners in the art.

One aspect of the present invention pertains to the preparation of (R)-2-(9-chloro-7-(4-isopropoxy-3-(trifluoromethyl)benzyloxy)-2,3-dihydro-1H-pyrrolo[1,2-a]indol-1-yl) acetic acid, crystalline forms, and salts thereof, wherein the "deprotecting step" and the "alkylating step", as described herein, are optional. It is appreciated that when the compound of Formula (IIi) is:

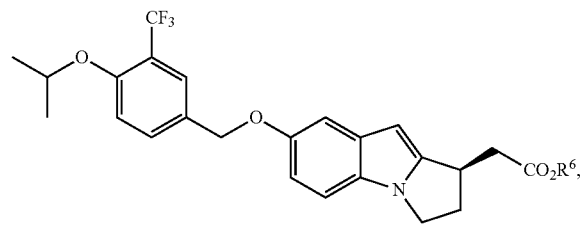

wherein $R^6$ is $C_1$-$C_4$ alkyl,
then the "deprotecting step", see Scheme VI and as described herein, and the subsequent "alkylating step", see Scheme VII and as described herein, are optional as the desired benzyloxy group (i.e., 4-isopropoxy-3-(trifluoromethyl)benzyloxy group) is present and in this regard the deprotecting and alkylating steps are not required. Therefore, one aspect of the present invention pertains to the preparation of (R)-2-(9-chloro-7-(4-isopropoxy-3-(trifluoromethyl)benzyloxy)-2,3-dihydro-1H-pyrrolo[1,2-a]indol-1-yl)acetic acid, crystalline forms, and salts thereof, comprising the following steps: an indole forming step (Scheme I), a cyclizing step (Scheme II), a decarboxylating step (Scheme III), an olefinating step (Scheme IV), a reducing step (Scheme V), a chlorinating step (Scheme VIII), a hydrolyzing step (Scheme IX), and a salt formation step (Scheme X), wherein details of each step are as described herein. In some embodiments, $R^6$ is ethyl.

I. Indole Forming Step

One aspect of the present invention pertains to processes for preparing a compound of Formula (IIc):

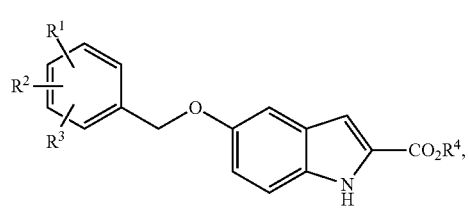

comprising the step:

reacting a compound of Formula (IIa) or a salt thereof:

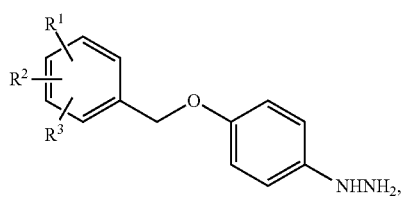

wherein $R^1$, $R^2$, and $R^3$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro; with a compound of:

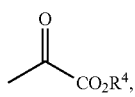

wherein $R^4$ is $C_1$-$C_4$ alkyl;

in the presence of an indole-forming-step acid and an indole-forming-step solvent to form the compound of Formula (IIc).

In some embodiments, $R^1$, $R^2$, and $R^3$ are each selected independently from the group consisting of H, $C_1$-$C_4$ alkyl, and $C_1$-$C_4$ alkoxy.

In some embodiments, $R^1$, $R^2$, and $R^3$ are each selected independently from the group consisting of H, $CH_3$, and $OCH_3$.

In some embodiments, $R^1$, $R^2$, and $R^3$ are each H.

In some embodiments, the compound of Formula (IIa) is (4-(benzyloxy)phenyl)-hydrazine:

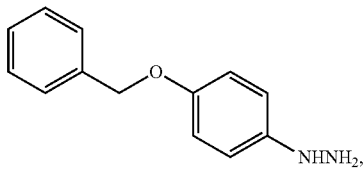 [SMILES: NNc1ccc(OCc2ccccc2)cc1]

or an HCl salt thereof.

In some embodiments, $R^4$ is $CH_3$, $CH_2CH_3$, $CH_2CH_2CH_3$, or $CH_2(CH_2)_2CH_3$.

In some embodiments, $R^4$ is $CH_2CH_3$.

In some embodiments, the compound of Formula (IIb) is ethyl 2-oxopropanoate (i.e., also referred to as ethyl pyruvate):

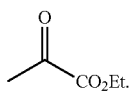

In some embodiments, $R^1$, $R^2$, and $R^3$ are each H; and $R^4$ is $CH_2CH_3$.

In some embodiments, the indole-forming-step acid comprises a Brønsted acid.

In some embodiments, the indole-forming-step acid comprises acetic acid, trifluoroacetic acid, p-TsOH, $H_3PO_4$, $H_2SO_4$, methanesulfonic acid, formic acid, or HCl.

In some embodiments, the indole-forming-step acid comprises p-TsOH, $H_3PO_4$, $H_2SO_4$, or methanesulfonic acid.

In some embodiments, the indole-forming-step acid comprises $H_2SO_4$.

In some embodiments, the indole-forming-step solvent comprises $C_1$-$C_4$ alkylalcohol solvent.

In some embodiments, the indole-forming-step solvent comprises methanol or ethanol.

In some embodiments, the indole-forming-step solvent comprises ethanol.

In some embodiments, the reacting further comprises the step of adding a solution of the compound of Formula (IIb) in the indole-forming-step solvent to a suspension of the compound of Formula (IIa) in the indole-forming-step acid and the indole-forming-step solvent to form a reaction mixture.

In some embodiments, the suspension of the compound of Formula (IIa) in the indole-forming-step acid and the indole-forming-step solvent is at a temperature of about −15° C. to about 25° C.

In some embodiments, the suspension of the compound of Formula (IIa) in the indole-forming-step acid and the indole-forming-step solvent is at a temperature of about −10° C. to about 10° C.

In some embodiments, the suspension of the compound of Formula (IIa) in the indole-forming-step acid and the indole-forming-step solvent is at a temperature of about 0° C.

In some embodiments, the reaction mixture is at a temperature of about 30° C. to about 60° C.

In some embodiments, the reaction mixture is at a temperature of about 40° C. to about 50° C.

In some embodiments, the reaction mixture is at a temperature of about 45° C.

In some embodiments, the suspension of the compound of Formula (IIa) in the indole-forming-step acid and the indole-forming-step solvent is at a temperature of about 0° C.; and the reaction mixture is at a temperature of about 45° C.

In some embodiments, the reacting further comprises the step of cooling the reaction mixture to a temperature of about 10° C. to about 25° C.

In some embodiments, the reacting further comprises the step of isolating (R)-2-(9-chloro-7-(4-isopropoxy-3-(trifluoromethyl)benzyloxy)-2,3-dihydro-1H-pyrrolo[1,2-a]indol-1-yl)acetic acid.

In some embodiments, isolating comprises filtration.

II. Cyclizing Step

One aspect of the present invention pertains to processes for preparing a compound of Formula (IIe), or a keto tautomer thereof:

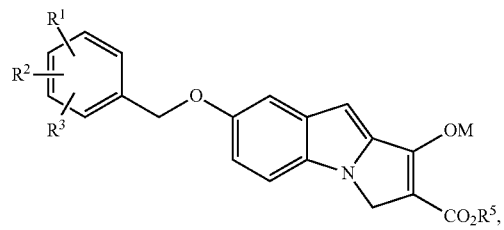

wherein $R^1$, $R^2$, and $R^3$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro; $R^5$ is $C_1$-$C_4$ alkyl; and M is an alkali metal or H;

comprising the step of:

cyclizing a compound of Formula (IIc):

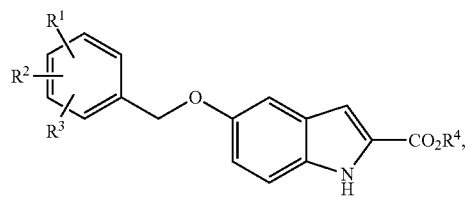

wherein $R^4$ is $C_1$-$C_4$ alkyl;

with a compound of Formula (IId):

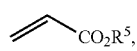

in the presence of an alkali metal $C_1$-$C_4$ alkoxide base and a cyclizing-step solvent to form the compound of Formula (IIe), or a keto tautomer thereof.

In some embodiments, $R^1$, $R^2$, and $R^3$ are each selected independently from the group consisting of H, $C_1$-$C_4$ alkyl, and $C_1$-$C_4$ alkoxy.

In some embodiments, $R^1$, $R^2$, and $R^3$ are each selected independently from the group consisting of H, $CH_3$, and $OCH_3$.

In some embodiments, $R^1$, $R^2$, and $R^3$ are each H.

In some embodiments, $R^4$ is $CH_3$, $CH_2CH_3$, $CH_2CH_2CH_3$, or $CH_2(CH_2)_2CH_3$.

In some embodiments, $R^4$ is $CH_2CH_3$.

In some embodiments, $R^5$ is $CH_3$, $CH_2CH_3$, $CH_2CH_2CH_3$, or $CH_2(CH_2)_2CH_3$.

In some embodiments, $R^5$ is $CH_2CH_3$.

In some embodiments, M is lithium, sodium or potassium.

In some embodiments, M is potassium.

In some embodiments, M is H.

In some embodiments, the compound of Formula (IIe) is:

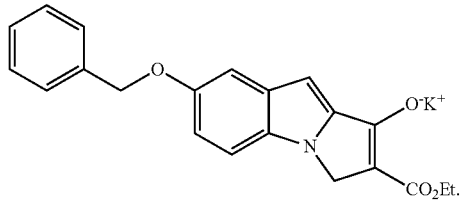

In some embodiments, the compound of Formula (IIc) is:

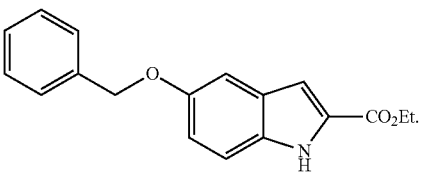 [SMILES: CCOC(=O)c1cc2cc(OCc3ccccc3)ccc2[nH]1]

In some embodiments, the compound of Formula (IId) is ethyl acrylate:

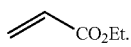

In some embodiments, the alkali metal $C_1$-$C_4$ alkoxide base comprises lithium isopropoxide, lithium t-butoxide, sodium isopropoxide, sodium t-butoxide, potassium isopropoxide, or potassium t-butoxide.

In some embodiments, the alkali metal $C_1$-$C_4$ alkoxide base comprises lithium t-butoxide, sodium t-butoxide, or potassium t-butoxide.

In some embodiments, the alkali metal $C_1$-$C_4$ alkoxide base comprises potassium t-butoxide.

In some embodiments, the cyclizing-step solvent comprises an aprotic solvent.

In some embodiments, the cyclizing-step solvent comprises tetrahydrofuran, diethylether, methyl tert-butyl ether (MTBE), or dioxane.

In some embodiments, the cyclizing-step solvent comprises tetrahydrofuran or methyl tert-butyl ether (MTBE).

In some embodiments, the cyclizing-step solvent comprises tetrahydrofuran.

In some embodiments, the cyclizing step is conducted under a substantially inert atmosphere.

In some embodiments, the cyclizing step is conducted under a substantially inert atmosphere comprising argon or nitrogen.

In some embodiments, the cyclizing step is conducted under a substantially inert atmosphere comprising nitrogen.

In some embodiments, the cyclizing step further comprises the step of:

adding a mixture comprising the alkali metal $C_1$-$C_4$ alkoxide base and the cyclizing-step solvent to a mixture comprising the compound of Formula (IIc) and the cyclizing-step solvent to form a cyclizing-step first mixture.

In some embodiments, the cyclizing step further comprises the step of:

adding the compound of Formula (IId) to the cyclizing-step first mixture to form a cyclizing-step second mixture.

In some embodiments, the cyclizing-step first mixture is at a temperature of about 10° C. to about 40° C.

In some embodiments, the cyclizing-step first mixture is at a temperature of about 15° C. to about 35° C.

In some embodiments, the cyclizing-step first mixture is at a temperature of about 20° C. to about 30° C.

In some embodiments, the cyclizing step further comprises heating the cyclizing-step second mixture to a temperature of about 50° C. to about 75° C. after addition of said compound of Formula (IId) to said cyclizing-step first mixture.

In some embodiments, the cyclizing step further comprises heating said cyclizing-step second mixture to a temperature of about 55° C. to about 70° C. after addition of said compound of Formula (IId) to said cyclizing-step first mixture.

In some embodiments, the cyclizing step further comprises heating said cyclizing-step second mixture to a temperature of about 60° C. to about 65° C. after addition of said compound of Formula (IId) to said cyclizing-step first mixture.

In some embodiments, the cyclizing step further comprises the step of cooling the cyclizing-step second mixture to a temperature of about 0° C. to about 30° C.

In some embodiments, the cyclizing step further comprises the step of cooling the cyclizing-step second mixture to a temperature of about 10° C. to about 30° C.

In some embodiments, the cyclizing step further comprises the step of cooling the cyclizing-step second mixture to a temperature of about 20° C. to about 30° C.

In some embodiments, the cyclizing step further comprises the step of precipitating the compound of Formula (IIe).

In some embodiments, the cyclizing step further comprises the step of isolating the compound of Formula (IIe).

In some embodiments, isolating comprises filtration.

III. Decarboxylating Step

One aspect of the present invention pertains to processes for preparing a compound of Formula (IIf):

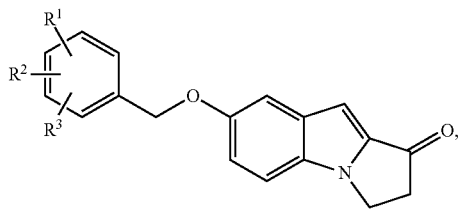

wherein $R^1$, $R^2$, and $R^3$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro;

comprising the step of:

decarboxylating the compound of Formula (IIe), or a keto tautomer thereof,

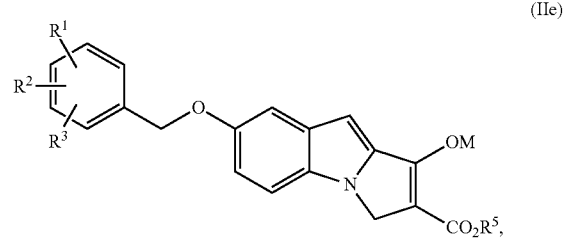

wherein M is an alkali metal or H;

in the presence of a Brønsted acid and water to form the compound of Formula (IIf).

In some embodiments, $R^1$, $R^2$, and $R^3$ are each selected independently from the group consisting of H, $C_1$-$C_4$ alkyl, and $C_1$-$C_4$ alkoxy.

In some embodiments, $R^1$, $R^2$, and $R^3$ are each selected independently from the group consisting of H, $CH_3$, and $OCH_3$.

In some embodiments, $R^1$, $R^2$, and $R^3$ are each H.

In some embodiments, $R^4$ is $CH_3$, $CH_2CH_3$, $CH_2CH_2CH_3$, or $CH_2(CH_2)_2CH_3$.

In some embodiments, $R^4$ is $CH_2CH_3$.

In some embodiments, $R^5$ is $CH_3$, $CH_2CH_3$, $CH_2CH_2CH_3$, or $CH_2(CH_2)_2CH_3$.

In some embodiments, $R^5$ is $CH_2CH_3$.

In some embodiments, the compound of Formula (IIf) is:

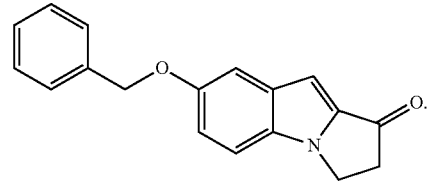 [SMILES: O=C1CCn2c1cc1cc(OCc3ccccc3)ccc12]

In some embodiments, M is lithium, sodium, or potassium.

In some embodiments, M is potassium.

In some embodiments, the compound of Formula (IIe) is:

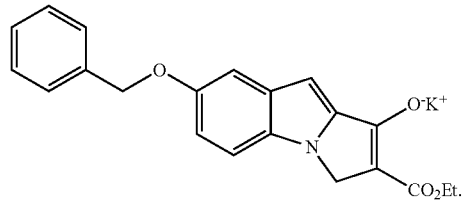

In some embodiments, the Brønsted acid comprises acetic acid, trifluoroacetic acid, p-TsOH, $H_3PO_4$, $H_2SO_4$, methanesulfonic acid, or formic acid.

In some embodiments, the Brønsted acid comprises acetic acid or trifluoroacetic acid.

In some embodiments, the Brønsted acid comprises acetic acid.

In some embodiments, the volume ratio between the Brønsted acid and the water is about 1.0:1.0 to about 10.0:1.0.

In some embodiments, the volume ratio between the Brønsted acid and the water is about 1.5:1.0 to about 5.0:1.0.

In some embodiments, the volume ratio between the Brønsted acid and the water is about 2.0:1.0.

In some embodiments, the decarboxylating step further comprises a step of adding the compound of Formula (IIf) to a mixture comprising the Brønsted acid and the water forming a decarboxylating-step mixture.

In some embodiments, the decarboxylating step further comprises the step of heating the decarboxylating-step mixture to a temperature of about 75° C. to about 120° C.

In some embodiments, the decarboxylating step further comprises the step of heating the decarboxylating-step mixture to a temperature of about 85° C. to about 120° C.

In some embodiments, the decarboxylating step further comprises the step of heating the decarboxylating-step mixture to a temperature of about 95° C. to about 120° C.

In some embodiments, the decarboxylating step further comprises the step of cooling said decarboxylating-step mixture to a temperature of about 0° C. to about 30° C. after heating said decarboxylating-step mixture.

In some embodiments, the decarboxylating step further comprises the step of cooling said decarboxylating-step mixture to a temperature of about 10° C. to about 25° C. after heating said decarboxylating-step mixture.

In some embodiments, the decarboxylating step further comprises the step of cooling said decarboxylating-step mixture to a temperature of about 20° C. to about 30° C. after heating said decarboxylating-step mixture.

In some embodiments, the decarboxylating step further comprises the step of precipitating the compound of Formula (IIf).

In some embodiments, the decarboxylating step further comprises the step of isolating the compound of Formula (IIf).

In some embodiments, isolating comprises filtration.

IV. Olefinating Step

One aspect of the present invention pertains to processes for preparing a compound of Formula (IIh):

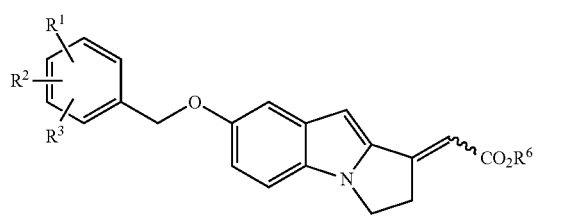

(IIh)

wherein $R^1$, $R^2$, and $R^3$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro; and $R^6$ is $C_1$-$C_4$ alkyl;

comprising the step of:
olefinating a compound of Formula (IIf):

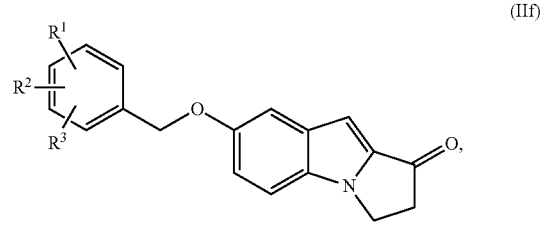

(IIf)

with a compound of Formula (IIg):

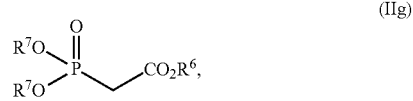

(IIg)

wherein and each $R^7$ is independently $C_1$-$C_4$ alkyl;
in the presence of an olefinating-step base and an olefinating-step solvent to form the compound of Formula (IIh).

It is understood that compounds of Formula (IIh) embrace, E isomers and Z isomers, and that the olefination process embraces processes using substantially pure E isomer, substantially pure Z isomer, and all mixtures of E isomers and Z isomers.

In some embodiments, the compound of Formula (IIh) comprises the E isomer and is of the Formula (IIh)-E:

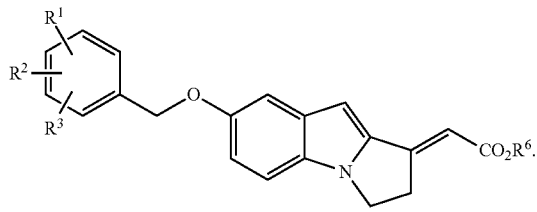

(IIh)-E

In some embodiments, the compound of Formula (IIh) comprises the Z isomer and is of the Formula (IIh)-Z:

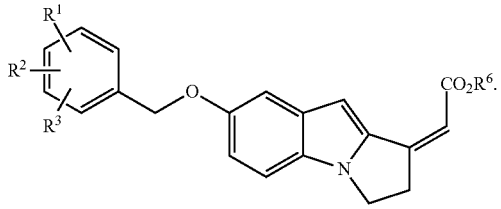

(IIh)-Z

In some embodiments, $R^1$, $R^2$, and $R^3$ are each selected independently from the group consisting of H, $C_1$-$C_4$ alkyl, and $C_1$-$C_4$ alkoxy.

In some embodiments, $R^1$, $R^2$, and $R^3$ are each selected independently from the group consisting of H, $CH_3$, and $OCH_3$.

In some embodiments, $R^1$, $R^2$, and $R^3$ are each H.

In some embodiments, the compound of Formula (IIf) is:

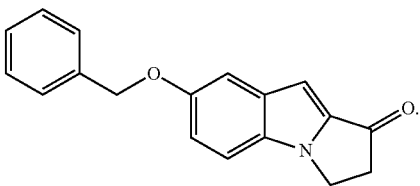 [SMILES: O=C1CCn2c1cc1cc(OCc3ccccc3)ccc12]

In some embodiments, $R^6$ is $CH_3$, $CH_2CH_3$, $CH_2CH_2CH_3$, $CH_2(CH_2)_2CH_3$, or t-butyl.

In some embodiments, $R^6$ is $CH_3$, $CH_2CH_3$, $CH_2CH_2CH_3$, or $CH_2(CH_2)_2CH_3$.

In some embodiments, $R^6$ is $CH_2CH_3$.

In some embodiments, $R^6$ is t-butyl.

In some embodiments, $R^7$ is $CH_3$, $CH_2CH_3$, $CH_2CH_2CH_3$, or $CH_2(CH_2)_2CH_3$.

In some embodiments, $R^7$ is $CH_2CH_3$.

In some embodiments, the compound of Formula (IIg) is:

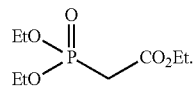

In some embodiments, the olefinating-step base comprises lithium isopropoxide, lithium t-butoxide, sodium isopropoxide, sodium t-butoxide, potassium isopropoxide, or potassium t-butoxide.

In some embodiments, the olefinating-step base comprises lithium t-butoxide, sodium t-butoxide, or potassium t-butoxide.

In some embodiments, the olefinating-step base comprises potassium t-butoxide.

In some embodiments, the olefinating-step solvent comprises an aprotic solvent.

In some embodiments, the olefinating-step solvent comprises tetrahydrofuran, diethylether, methyl tert-butyl ether (MTBE), or dioxane.

In some embodiments, the olefinating-step solvent comprises tetrahydrofuran or methyl tert-butyl ether (MTBE).

In some embodiments, the olefinating-step solvent comprises tetrahydrofuran.

In some embodiments, the olefinating step is conducted under a substantially inert atmosphere.

In some embodiments, the olefinating step is conducted under a substantially inert atmosphere comprising argon or nitrogen.

In some embodiments, the olefinating step is conducted under a substantially inert atmosphere comprising nitrogen.

In some embodiments, the olefinating step further comprises the step of:

adding a mixture comprising the olefinating-step base and the olefinating-step solvent to a mixture comprising the compound of Formula (IIg) and the olefinating-step solvent to form a first olefinating-step mixture comprising the ylide of the compound of Formula (IIg).

In some embodiments, the process further comprises the step of adding the compound of Formula (IIf) to the first olefinating-step mixture comprising the ylide of the compound of Formula (IIg) to form a second olefinating-step mixture.

In some embodiments, the second olefinating-step mixture is maintained at a temperature of about 10° C. to about 50° C. after addition of said compound of Formula (IIf) to said first olefinating-step mixture comprising the ylide of said compound of Formula (IIg).

In some embodiments, the second olefinating-step mixture is maintained at a temperature of about 15° C. to about 35° C. after addition of said compound of Formula (IIf) to said first olefinating-step mixture comprising the ylide of said compound of Formula (IIg).

In some embodiments, the second olefinating-step mixture is maintained at a temperature of about 20° C. to about 30° C. after addition of said compound of Formula (IIf) to said first olefinating-step mixture comprising the ylide of said compound of Formula (IIg).

In some embodiments, the process further comprises the step of concentrating said second olefinating-step mixture to form a concentrate comprising said compound of Formula (IIh).

In some embodiments, the process further comprises the step of adding to said concentrate comprising said compound of Formula (IIh) a mixture comprising isopropanol to form a precipitate comprising said compound of Formula (IIh).

In some embodiments, the process further comprises the step of isolating the precipitate of the compound of Formula (IIh) from the mixture comprising isopropanol.

In some embodiments, the isolating the precipitate of the compound of Formula (IIh) comprises filtration.

In some embodiments, the precipitate of the compound of Formula (IIh) comprises:

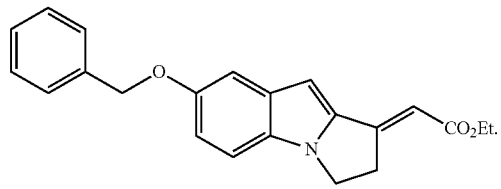 [SMILES: CCOC(=O)/C=C1\CCn2c1cc1cc(OCc3ccccc3)ccc12]

V. Reducing Step

One aspect of the present invention pertains to processes for preparing a compound of Formula (IIi):

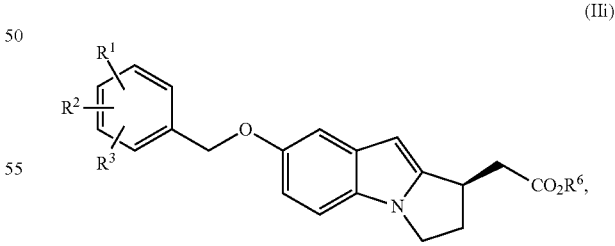

wherein $R^1$, $R^2$, and $R^3$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro; and $R^6$ is $C_1$-$C_4$ alkyl;

comprising the step of:

reducing the compound of Formula (IIh):

(IIh)

[Structure: R¹, R², R³ substituted benzyl ether linked to indoline with =CHCO₂R⁶ group]

in the presence of:
  i) a chiral phosphine ligand;
  ii) a Cu-catalyst;
  iii) hydride-reagent;
  iv) a reducing-step solvent; and
  v) optionally a sterically-hindered $C_3$-$C_8$ alkylalcohol, to form the compound of Formula (IIi).

It is understood that the compound of Formula (IIh) embraces, E isomers and Z isomers, and the olefination process embraces processes using the substantially pure E isomer, the substantially pure Z isomer, and all mixtures of E isomers and Z isomers.

In some embodiments, the sterically-hindered $C_3$-$C_8$ alkylalcohol is present. The term sterically-hindered $C_3$-$C_8$ alkylalcohol refers to a 2° or a 3° alcohol containing $C_3$ to $C_8$ carbons.

In some embodiments, the sterically-hindered $C_3$-$C_8$ alkylalcohol comprises isopropanol, t-butyl alcohol, 2-methylbutan-2-ol, 2,3-dimethylbutan-2-ol, 2,3,3-trimethylbutan-2-ol, 3-methylpentan-3-ol, or 3-ethylpentan-3-ol.

In some embodiments, the sterically-hindered $C_3$-$C_8$ alkylalcohol comprises t-butyl alcohol.

In some embodiments, $R^1$, $R^2$, and $R^3$ are each selected independently from the group consisting of H, $C_1$-$C_4$ alkyl, and $C_1$-$C_4$ alkoxy.

In some embodiments, $R^1$, $R^2$, and $R^3$ are each selected independently from the group consisting of H, $CH_3$, and $OCH_3$.

In some embodiments, $R^1$, $R^2$, and $R^3$ are each H.

In some embodiments, $R^6$ is $CH_3$, $CH_2CH_3$, $CH_2CH_2CH_3$, $CH_2(CH_2)_2CH_3$, or t-butyl.

In some embodiments, $R^6$ is $CH_3$, $CH_2CH_3$, $CH_2CH_2CH_3$, or $CH_2(CH_2)_2CH_3$.

In some embodiments, $R^6$ is $CH_2CH_3$.

In some embodiments, $R^6$ is t-butyl.

In some embodiments, the compound of Formula (IIi) is:

[Structure: benzyl ether linked to indoline with CH₂CO₂Et group with stereochemistry indicated]

Any suitable chiral phosphine ligand, Cu-catalyst, and hydride-reagent can be used in the reducing-step (i.e., reduction of compounds of Formula (IIh) to compound of Formula (IIi)).

Representative examples of chiral phosphine ligands, Cu-catalysts, and hydride-reagents are provided below.

Representative Examples of Chiral Phosphine Ligands

The only requirement for the selection of the chiral phosphine ligand is when the chiral phosphine ligand is utilized in the reducing-step process the product has the correct R steriochemistry (i.e., as shown in Formula (IIi)). The correct R enantiomer can be prepared utilizing either the E isomer or the Z isomer of a compound of Formula (IIh). When the E isomer of the compound of Formula (IIh) is present then any suitable chiral phosphine ligand can be used provided that the correct R stereochemistry is obtained for the compound of Formula (IIi). To illustrate this point, utilizing the E isomer of a compound of Formula (IIh), one useful chiral phosphine ligand for this step is (R)-(−)-1-[(S)-2-(diphenylphosphino)ferrocenyl]ethyldi-tert-butylphosphine. Specific details using this chiral phosphine ligand, as well as additional ligands, are described in Example 1.5, Step E. Alternatively, if the Z isomer of the compound of Formula (IIh) is used then one useful chiral phosphine ligand is (S)-BINAP. Specific details using this chiral phosphine ligand are described in Example 1.7, Step B. Accordingly, either the E-isomer or the Z-isomer of Formula (IIh) can be utilized to prepare the compound of Formula (IIi).

Josiphos Family of Chiral Ligands

Examples of a Josiphos chiral ligand for use in the reducing step of the present invention include: (R)-(−)-1-[(S)-2-(diphenylphosphino)ferrocenyl]ethyldi-t-butylphosphine; (R)-(−)-1-[(S)-2-[bis(3,5-dimethyl-4-methoxyphenyl)phosphino]ferrocenyl]ethyldicyclohexylphosphine; (R)-(−)-1-[(S)-2-(diphenylphosphino)ferrocenyl]ethyldicyclohexylphosphine; (R)-(−)-1-[(S)-2-(diphenylphosphino)ferrocenyl]ethyldi-3,5-xylylphosphine; and the like.

Mandyphos™ Family of Chiral Ligands

Examples of a Mandyphos™ chiral ligand for use in the reducing step of the present invention include: (S,S)-(+)-2,2'-bis[(R)—(N,N-dimethylamino)(phenyl)methyl]-1,1'-bis(dicyclohexylphosphino)ferrocene; (S,S)-(−)-2,2'-bis[(R)—(N,N-dimethylamino)(phenyl)methyl]-1,1'-bis(di(3,5-dimethylphenyl)phosphino)ferrocene; (S,S)-(−)-2,2'-bis[(R)—(N,N-dimethylamino)(phenyl)methyl]-1,1'-bis[di(3,5-dimethyl-4-methoxyphenyl)phosphino]ferrocene; (S,S)-(−)-2,2'-bis[(R)—(N,N-dimethylamino)(phenyl)methyl]-1,1'-bis(diphenylphosphino)ferrocene; and the like.

MeO-biPhep Family of Chiral Ligands

Examples of a MeO-biPhep chiral ligand for use in the reducing step of the present invention include: (R)-(+)-2,2'-bis(diphenylphosphino)-6,6'-dimethoxy-1,1'-biphenyl((R)-MeO-BIPHEP); (R)-(+)-2,2'-bis(di-isopropanolphosphino)-6,6'-dimethoxy-1,1'-biphenyl; (R)-(+)-2,2'-bis(di-p-tolylphosphino)-6,6'-dimethoxy-1,1'-biphenyl; (R)-(−)-2,2'-bis[di(3,5-di-isopropanol-4-dimethylaminophenyl)phosphino]-6,6'-dimethoxy-1,1'-biphenyl; and the like.

Duphos Family of Chiral Ligands

Examples of a MeO-biPhep chiral ligand for use in the reducing step of the present invention include: (−)-1,2-bis((2S,5S)-2,5-diethylphospholano)ethane((S,S)-Et-BPE); (+)-1,2-bis((2R,5R)-2,5-di-isopropanolphospholano)benzene((R,R)-i-Pr-DUPHOS); (+)-1,2-bis((2S,5S)-2,5-diphenylphospholano)ethane((S,S)-Ph-BPE); (+)-1,2-bis((2R,5R)-2,5-dimethylphospholano)ethane((R,R)-Me-BPE); and the like.

BINAP Family of Chiral Ligands

Examples of a BINAP chiral ligand for use in the reducing step of the present invention include: (R)-(+)-2,2'-bis(diphenylphosphino)-1,1'-binaphthyl((R)-BINAP); (S)-BINAP; (R)-(+)-2,2'-bis(diphenylphosphino)-5,5',6,6',7,7',8,8'-octahydro-1(1'-binaphthyl(R)—H8-BINAP); (R)-(+)-2,2'-bis(di-p-tolylphosphino)-1,1'-binaphthyl((R)-Tol-BINAP);

(R)-(+)-2,2'-bis[di(3,5-xylyl)phosphino]-1,1'-binaphthyl ((R)-3,5-xylyl-BINAP); and the like.

N or Phos Family of Chiral Ligands

An example of a N or Phos chiral ligand for use in the reducing step of the present invention includes: (2R,3R)-(−)-2,3-bis(diphenylphosphino)-bicyclo[2.2.1]hept-5-ene((R, R)—NORPHOS), and the like.

P-Phos Family of Chiral Ligands

Examples of a P-Phos chiral ligand for use in the reducing step of the present invention include: (R)-(+)-2,2',6,6'-tetramethoxy-4,4'-bis(diphenylphosphino)-3,3'-bipyridine (TH-(R)-P-Phos); (R)-(+)-2,2',6,6'-tetramethoxy-4,4'-bis(di (3,5-xylyl)phosphino)-3,3'-bipyridine (CTH-(R)-Xylyl-P-Phos); and the like.

Phanephos Family of Chiral Ligands

Examples of a Phanephos chiral ligand for use in the reducing step of the present invention include: (R)-(−)-4,12-bis (diphenylphosphino)-[2.2]-paracyclophane((R)—PHANEPHOS); (R)-(−)-4,12-bis(di(3,5-xylyl)phosphino)-[2.2]-paracyclophane, min (CTH-(R)-3,5-xylyl-PHANEPHOS); and the like.

SegPhos Family of Chiral Ligands

Examples of a SegPhos chiral ligand for use in the reducing step of the present invention include: (R)-(−)-5,5'-bis[di(3,5-di-t-butyl-4-methoxyphenyl)phosphino]-4,4'-bi-1,3-benzodioxole((R)-DTBM-SEGPHOS); (R)-(+)-5,5'-bis(diphenylphosphino)-4,4'-bi-1,3-benzodioxole((R)-SEGPHOS); (R)-(+)-5,5'-bis[di(3,5-xylyl)phosphino]-4,4'-bi-1,3-benzodioxole((R)-DM-SEGPHOS); and the like.

Other Chiral Ligands

Examples of other chiral ligands for use in the reducing step of the present invention include: (−)-2,3-bis[(2R,5R)-2,5-dimethylphospholanyl]-1-[3,5-bis(trifluoromethyl)phenyl]-1H-pyrrole-2,5-dione [catASium® MNXylF(R)]; (−)-2,3-bis[(2R,5R)-2,5-dimethylphospholanyl]maleic anhydride [catASium® M(R)]; (3R,4R)-(+)-bis(diphenylphosphino)-1-benzylpyrrolidine [catASium® D(R)]; (+)-{4-[(1R,4S)-3-(Diphenylphosphino)-1,7,7-trimethylbicyclo[2.2.1]hept-2-en-2-yl]-2,5-dimethyl-3-thien-3-yl}bis(3,5-dimethylphenyl) phosphine [catASium® T3]; and [R,S,-TanIAphos].

Representative Examples of Cu-Catalysts

Examples of a copper catalyst for use in the reducing step of the present invention include: [(PPh$_3$P)CuH]$_6$ (Stryker's reagent); Ph$_3$PCuH; CuCl; (Ph$_3$P)CuF (EtOH)$_2$; Cu(OAc)$_2$.H$_2$O; CuCl$_2$.H$_2$O; [(3,5-xylyl)$_3$P]$_2$CuNO$_3$; CuOt-Bu; CuF$_2$; CuH N-heterocyclic carbene complexes; and the like. Copper catalysts comprising CuH N-heterocyclic carbene (NHC) complexes are described in art, see for example, Herrmann, W. A., Angew. Chem., Int. Ed. 2002, 41, 1290-1309.

Representative Examples of Hydride-Reagents

Examples of a hydride-reagent for use in the reducing step of the present invention include: poly(methylhydrosiloxane) (PMHS); tetramethyldisiloxane (TMDSO, TMDS); H$_2$; Et$_3$SH; PhSiH$_3$; PhMe$_2$SiH; Bu$_3$SnH; Ph$_2$Si$_2$H; and the like.

In some embodiments, the chiral phosphine ligand comprises a Josiphos chiral ligand, a Mandyphos™ chiral ligand, a MeO-biPhep chiral ligand, a MeO-biPhep chiral ligand, a BINAP chiral ligand, a N or Phos chiral ligand, a P-Phos chiral ligand, a Phanephos chiral ligand, or a SegPhos chiral ligand.

Some embodiments of the present invention pertain to the preparation of compounds of Formula (IIi) using an E isomer of the compound of Formula (IIh). Suitable chiral phosphine ligands that can be used with the E isomer include for example, (R)-(+)-2,2'-bis(diphenylphosphino)-1,1'-binaphthyl; (R)-(+)-2,2'-bis[di(3,5-xylyl)phosphino]-1,1'-binaphthyl; (R)-(−)-5,5'-bis[di(3,5-di-t-butyl-4-methoxyphenyl) phosphino]-4,4'-bi-1,3-benzodioxole; (R)-(−)-1-[(S)-2-(diphenylphosphino)ferrocenyl]ethyldi-tert-butylphosphine, and the like.

In some embodiments, the compound of Formula (IIh) is of Formula (IIh)-E:

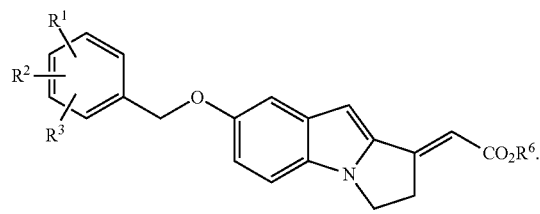

(IIh)-E

In some embodiments, the compound of Formula (IIh) is:

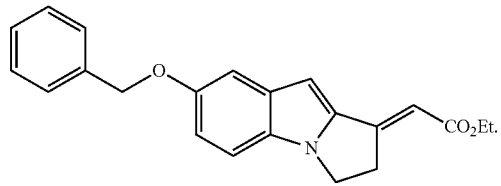 [SMILES: CCOC(=O)/C=C1\CCn2c1cc1cc(OCc3ccccc3)ccc12]

In some embodiments, the chiral phosphine ligand comprises:
(R)-(+)-2,2'-bis(diphenylphosphino)-1,1'-binaphthyl;
(R)-(+)-2,2'-bis[di(3,5-xylyl)phosphino]-1,1'-binaphthyl;
(R)-(−)-5,5'-bis[di(3,5-di-t-butyl-4-methoxyphenyl)phosphino]-4,4'-bi-1,3-benzodioxole; or
(R)-(−)-1-[(S)-2-(diphenylphosphino)ferrocenyl]ethyldi-tert-butylphosphine.

In some embodiments, the chiral phosphine ligand comprises (R)-(−)-1-[(S)-2-(diphenylphosphino)ferrocenyl]ethyldi-tert-butylphosphine, and the like.

Some embodiments of the present invention pertain to the preparation of compounds of Formula (IIi) using a Z isomer of the compound of Formula (IIh). Suitable chiral phosphine ligands that can be used with the Z isomer include for example, (S)-(+)-2,2'-bis(diphenylphosphino)-1,1'-binaphthyl.

In some embodiments, the compound of Formula (IIh) is of Formula (IIh)-Z:

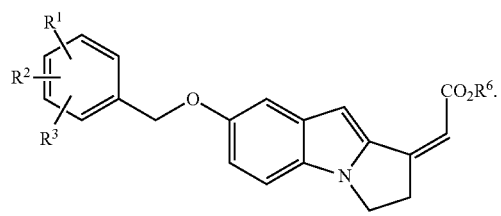

(IIh)-Z

In some embodiments, the compound of Formula (IIh) is:

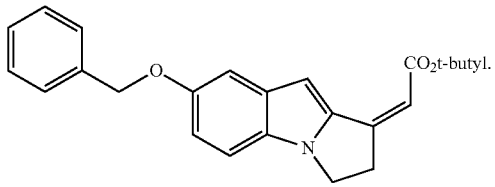

In some embodiments, the chiral phosphine ligand comprises (S)-(+)-2,2'-bis(diphenylphosphino)-1,1'-binaphthyl.

In some embodiments, the Cu-catalyst comprises [(PPh$_3$P)CuH]$_6$, Ph$_3$PCuH, CuCl, (Ph$_3$P)CuF·(EtOH)$_2$, Cu(OAc)$_2$·H$_2$O, CuCl$_2$·H$_2$O, [(3,5-xylyl)$_3$P]$_2$CuNO$_3$, CuOt-Bu, or CuF$_2$.

In some embodiments, the Cu-catalyst comprises Cu(OAc)$_2$·H$_2$O.

In some embodiments, the hydride-reagent comprises poly(methylhydrosiloxane) (PMHS), tetramethyldisiloxane (TMDS), H$_2$, Et$_3$SH, PhSiH$_3$, PhMe$_2$SiH, Bu$_3$SnH, or Ph$_2$Si$_2$H.

In some embodiments, the hydride-reagent comprises poly(methylhydrosiloxane) (PMHS).

In some embodiments, the reducing-step solvent comprises an aprotic solvent.

In some embodiments, the reducing-step solvent comprises tetrahydrofuran (THF), 2-methyl-tetrahydrofuran, diethyl ether, dibutyl ether, tert-butylmethyl ether, or tetrahydropyran.

In some embodiments, the reducing-step solvent comprises tetrahydrofuran (THF).

In some embodiments, the reducing step is conducted under a substantially inert atmosphere.

In some embodiments, the reducing step is conducted under a substantially inert atmosphere comprising argon or nitrogen.

In some embodiments, the reducing step is conducted under a substantially inert atmosphere comprising nitrogen.

In some embodiments, the molar ratio between the compound of Formula (IIh) and the chiral phosphine ligand is about 150.0:1.0 to about 250.0:1.0.

In some embodiments, the molar ratio between the compound of Formula (IIh) and the chiral phosphine ligand is about 200.0:1.0.

In some embodiments, the molar ratio between the compound of Formula (IIh) and the Cu-catalyst is about 150.0:1.0 to about 250.0:1.0.

In some embodiments, the molar ratio between the compound of Formula (IIh) and the Cu-catalyst is about 200.0:1.0.

In some embodiments, the molar ratio between the compound of Formula (IIh), the chiral phosphine ligand, and the Cu-catalyst is about 200.0:1.0:1.0.

In some embodiments, the weight ratio between the compound of Formula (IIh) and the hydride-reagent is about 1.0:0.1 to about 1.0:3.0.

In some embodiments, the weight ratio between the compound of Formula (IIh) and the hydride-reagent is about 1.0:0.3 to about 1.0:1.5.

In some embodiments, the molar ratio between the compound of Formula (IIh) and the hydride-reagent is about 1.0:0.5.

In some embodiments, the reducing step further comprises the step of:
adding a first mixture comprising the chiral phosphine ligand, the Cu-catalyst, and the reducing-step solvent, to a second mixture comprising the compound of Formula (IIh) and the reducing-step solvent, to form a first reducing-step mixture.

In some embodiments, the second mixture comprising the compound of Formula (IIh) and the reducing-step solvent is at a temperature of about −10° C. to about 25° C.

In some embodiments, the second mixture comprising the compound of Formula (IIh) and the reducing-step solvent is at a temperature of about −5° C. to about 15° C.

In some embodiments, the second mixture comprising the compound of Formula (IIh) and the reducing-step solvent is at a temperature of about 5° C.

In some embodiments, the reducing step further comprises adding the sterically-hindered C$_3$-C$_8$ alkylalcohol to the first reducing-step mixture to form a second reducing-step mixture.

In some embodiments, the process further comprises the step of treating the second reducing-step mixture with an aqueous mixture comprising ammonium chloride to form a bi-phasic reducing-step mixture.

In some embodiments, the process further comprises the step of separating the bi-phasic reducing-step mixture into an aqueous phase comprising ammonium chloride and a third reducing-step mixture.

In some embodiments, the process further comprises the step of concentrating the third reducing-step mixture to isolate the compound of Formula (IIi).

VI. Deprotecting Step

One aspect of the present invention pertains to processes for preparing a compound of Formula (IIj), or a salt thereof:

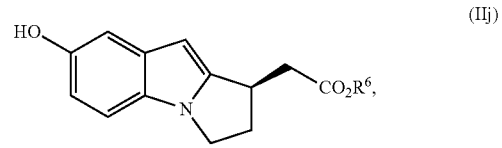

wherein R$^6$ is C$_1$-C$_4$ alkyl;
comprising the step of:
deprotecting a compound of Formula (IIi):

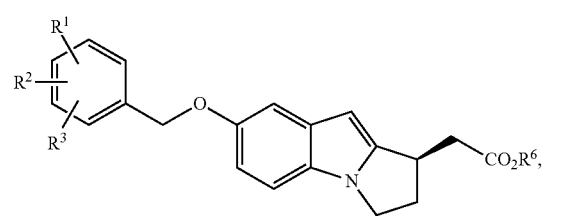

wherein R$^6$ is C$_1$-C$_4$ alkyl;
in the presence of hydrogen, a palladium catalyst, and a deprotecting-step solvent, to form the compound of Formula (IIj).

In some embodiments, R$^1$, R$^2$, and R$^3$ are each selected independently from the group consisting of H, C$_1$-C$_4$ alkyl, and C$_1$-C$_4$ alkoxy.

In some embodiments, $R^1$, $R^2$, and $R^3$ are each selected independently from the group consisting of H, $CH_3$, and $OCH_3$.

In some embodiments, $R^1$, $R^2$, and $R^3$ are each H.

In some embodiments, $R^6$ is $CH_3$, $CH_2CH_3$, $CH_2CH_2CH_3$, $CH_2(CH_2)_2CH_3$, or t-butyl.

In some embodiments, $R^6$ is $CH_3$, $CH_2CH_3$, $CH_2CH_2CH_3$, or $CH_2(CH_2)_2CH_3$.

In some embodiments, $R^6$ is $CH_2CH_3$.

In some embodiments, $R^6$ is t-butyl.

In some embodiments, the compound of Formula (IIi) is:

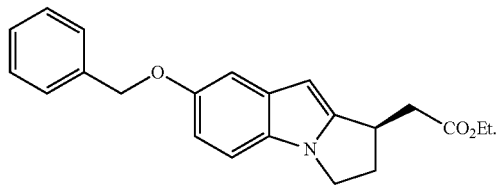 [SMILES: CCOC(=O)C[C@H]1CCn2c1cc1cc(OCc3ccccc3)ccc12]

In some embodiments, the compound of Formula (IIj) is:

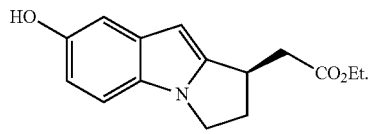 [SMILES: CCOC(=O)C[C@H]1CCn2c1cc1cc(O)ccc12]

In some embodiments, the palladium catalyst comprises palladium on carbon.

In some embodiments, the palladium catalyst comprises about 2% palladium on carbon to about 10% palladium on carbon.

In some embodiments, the palladium catalyst comprises about 10% palladium on carbon.

In some embodiments, the deprotecting-step solvent comprises a suitable solvent.

In some embodiments, the deprotecting-step solvent comprises methanol, ethanol, isopropanol, n-propanol, n-butanol, cyclohexane, pentane, hexane, tetrahydrofuran, methyl tert-butyl ether (MTBE), acetone, ethyl methyl ketone, methyl acetate, ethyl acetate, or isopropyl acetate.

In some embodiments, the deprotecting-step solvent comprises ethyl acetate.

In some embodiments, the ethyl acetate is substantially free of dissolved oxygen.

In some embodiments, the deprotecting step further comprises the step of:

adding the palladium catalyst to a mixture comprising the compound of Formula (IIi) and the deprotecting-step solvent to form a first deprotecting-step mixture.

In some embodiments, the process further comprises the step of:

treating the mixture comprising the compound of Formula (IIi) and the deprotecting-step solvent with HCl prior to adding the palladium catalyst.

In some embodiments, the process further comprises the step of:

exposing the first deprotecting-step mixture to an atmosphere of hydrogen to form a second deprotecting-step mixture.

In some embodiments, the process further comprises the step of:

exposing the first deprotecting-step mixture to an atmosphere of hydrogen at a pressure of about 10 psi to about 70 psi to form a second deprotecting-step mixture.

In some embodiments, the process further comprises the step of:

exposing the first deprotecting-step mixture to an atmosphere of hydrogen at a pressure of about 30 psi to about 60 psi to form a second deprotecting-step mixture.

In some embodiments, the process further comprises the step of:

exposing the first deprotecting-step mixture to an atmosphere of hydrogen at a pressure of about 50 psi to form a second deprotecting-step mixture.

In some embodiments, the process further comprises the step of filtering the second deprotecting-step mixture to form a third deprotecting-step mixture.

In some embodiments, the third deprotecting-step mixture is substantially free of the palladium catalyst.

In some embodiments, the process further comprises the step of concentrating the third deprotecting-step mixture to form a concentrate comprising the compound of Formula (IIj).

In some embodiments, the process further comprises the step of adding to said concentrate comprising said compound of Formula (IIj) a mixture comprising methyl tert-butyl ether (MTBE) and hexanes to form a precipitate comprising said compound of Formula (IIj).

In some embodiments, the volume ratio between the methyl tert-butyl ether (MTBE) and the hexanes is about 1.0:2.0.

In some embodiments, the process further comprises the step of isolating the precipitate of the compound of Formula (IIj) from the mixture comprising methyl tert-butyl ether (MTBE) and hexanes.

In some embodiments, the isolating the precipitate of the compound of Formula (IIj) comprises filtration.

VII. Alkylating Step

One aspect of the present invention pertains to processes for preparing a compound of Formula (IIm) or a salt thereof:

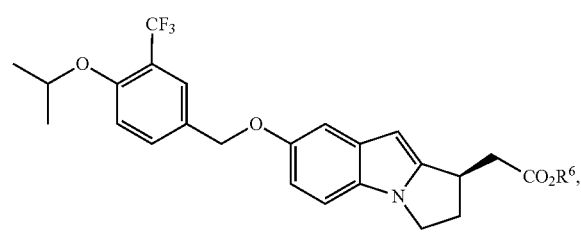

wherein $R^6$ is $C_1$-$C_4$ alkyl;
comprising the step of:
alkylating the compound of Formula (IIj) or a salt thereof:

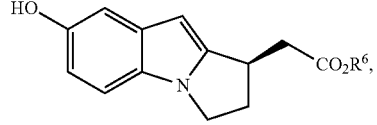

with 4-(chloromethyl)-1-isopropoxy-2-(trifluoromethyl) benzene of Formula (IIk):

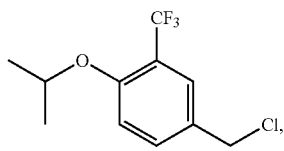

in the presence of an alkylating-step base, and an alkylating-step solvent to form the compound of Formula (IIm).

In some embodiments, $R^6$ is $CH_3$, $CH_2CH_3$, $CH_2CH_2CH_3$, $CH_2(CH_2)_2CH_3$, or t-butyl.

In some embodiments, $R^6$ is $CH_3$, $CH_2CH_3$, $CH_2CH_2CH_3$, or $CH_2(CH_2)_2CH_3$.

In some embodiments, $R^6$ is $CH_2CH_3$.

In some embodiments, $R^6$ is t-butyl.

In some embodiments, the compound of Formula (IIj) is:

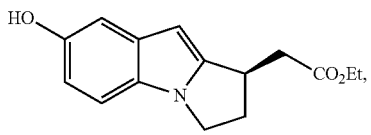 [SMILES: CCOC(=O)C[C@H]1CCn2c1cc1cc(O)ccc12]

or a salt thereof.

In some embodiments, the alkylating-step base comprises an inorganic base.

In some embodiments, the alkylating-step base comprises a carbonate base.

In some embodiments, the alkylating-step base comprises sodium carbonate, potassium carbonate, or cesium carbonate.

In some embodiments, the alkylating-step base comprises cesium carbonate.

In some embodiments, the alkylating-step solvent comprises an aprotic solvent.

In some embodiments, the alkylating-step solvent comprises acetone, 2-butanone, dimethylformamide (DMF), dimethylacetamide (DMA), tetrahydrofuran (THF), or acetonitrile.

In some embodiments, the alkylating-step solvent comprises acetonitrile.

In some embodiments, the alkylating-step solvent comprises dimethylformamide (DMF).

In some embodiments, the alkylating-step solvent is substantially free of water.

In some embodiments, the alkylating step is conducted under a substantially inert atmosphere.

In some embodiments, the alkylating step is conducted under a substantially inert atmosphere comprising argon or nitrogen.

In some embodiments, the alkylating step is conducted under a substantially inert atmosphere comprising nitrogen.

In some embodiments, the molar ratio between the 4-(chloromethyl)-1-isopropoxy-2-(trifluoromethyl)benzene (Formula (IIk)), the compound of Formula (IIj) or a salt thereof, and the alkylating-step base is about 1.0:1.0:0.5 to about 2.0:1.0:3.0.

In some embodiments, the molar ratio between the 4-(chloromethyl)-1-isopropoxy-2-(trifluoromethyl)benzene (Formula (IIk)), the compound of Formula (IIj) or a salt thereof, and the alkylating-step base is about 1.0:1.0:1.0 to about 1.5:1.0:2.0.

In some embodiments, the molar ratio between the 4-(chloromethyl)-1-isopropoxy-2-(trifluoromethyl)benzene (Formula (IIk)), the compound of Formula (IIj) or a salt thereof, and the alkylating-step base is about 1.0:1.0:1.0 to about 1.2:1.0:1.5.

In some embodiments, the molar ratio between the 4-(chloromethyl)-1-isopropoxy-2-(trifluoromethyl)benzene (Formula (IIk)), the compound of Formula (IIj) or a salt thereof, and the alkylating-step base is about 1.0:1.0:1.3.

In some embodiments, the alkylating step is conducted at a temperature of about 20° C. to about 80° C.

In some embodiments, the alkylating step is conducted at a temperature of about 55° C. to about 75° C.

In some embodiments, the alkylating step is conducted at a temperature of about 60° C. to about 70° C.

In some embodiments, the alkylating step is conducted at a temperature of about 65° C.

In some embodiments, the alkylating step further comprises the step of adding the 4-(chloromethyl)-1-isopropoxy-2-(trifluoromethyl)benzene (Formula (IIk)) to a mixture comprising the compound of Formula (IIj) or a salt thereof, the alkylating-step base, and the alkylating-step solvent to form an alkylating-step mixture.

In some embodiments, the adding the 4-(chloromethyl)-1-isopropoxy-2-(trifluoromethyl)benzene (Formula (IIk)) to a mixture comprising the compound of Formula (IIj) or a salt thereof, the alkylating-step base, and the alkylating-step solvent is conducted at a temperature of about 20° C. to about 35° C.

In some embodiments, the alkylating-step mixture is maintained at a temperature of about 25° C. to about 80° C.

In some embodiments, the alkylating-step mixture is maintained at a temperature of about 55° C. to about 75° C.

In some embodiments, the alkylating-step mixture is maintained at a temperature of about 60° C. to about 70° C.

In some embodiments, the alkylating-step mixture is maintained at a temperature of about 65° C.

In some embodiments, the process further comprises the step of isolating the compound of Formula (IIm) from the alkylating-step mixture to form a concentrate comprising the compound of Formula (IIm).

In some embodiments, the process further comprises the step of adding to said concentrate comprising said compound of Formula (IIm) a mixture comprising methyl tert-butyl ether (MTBE) and hexanes to form a precipitate.

In some embodiments, the volume ratio between the methyl tert-butyl ether (MTBE) and the hexanes is about 1.0:1.0.

In some embodiments, the process further comprises the step of isolating the precipitate of the compound of Formula (IIm) from the mixture comprising methyl tert-butyl ether (MTBE) and hexanes.

In some embodiments, the isolating the precipitate of the compound of Formula (IIm) comprises filtration.

VIII. Chlorinating Step

One aspect of the present invention pertains to processes for preparing a compound of Formula (IIn):

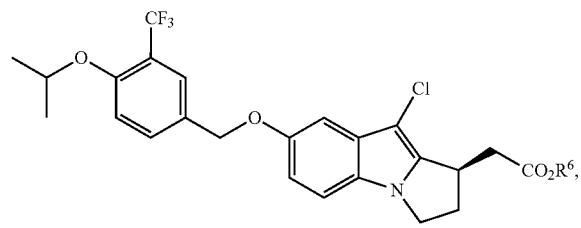

wherein $R^6$ is $C_1$-$C_4$ alkyl;
comprising the step of:
chlorinating a compound of Formula (IIm) or a salt thereof:

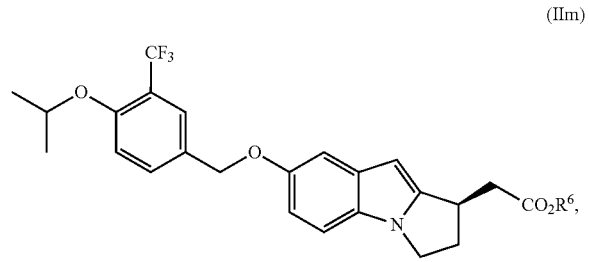

with a chlorinating agent in the presence of a chlorinating-step solvent to form the compound of Formula (IIn).

In some embodiments, $R^6$ is $CH_3$, $CH_2CH_3$, $CH_2CH_2CH_3$, $CH_2(CH_2)_2CH_3$, or t-butyl.

In some embodiments, $R^6$ is $CH_3$, $CH_2CH_3$, $CH_2CH_2CH_3$, or $CH_2(CH_2)_2CH_3$.

In some embodiments, $R^6$ is $CH_2CH_3$.
In some embodiments, $R^6$ is t-butyl.
In some embodiments, the compound of Formula (IIm):

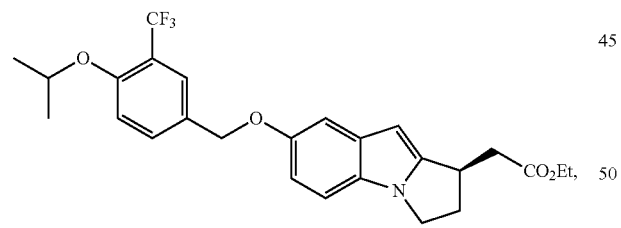

or a salt thereof.

In some embodiments, the chlorinating agent comprises t-butyl hypochlorite, chlorine (i.e, $Cl_2$), N-chlorosuccinamide (NCS), or trichlorocyanuric acid (TCCA).

In some embodiments, the chlorinating agent comprises N-chlorosuccinamide (NCS).

In some embodiments, the chlorinating-step solvent comprises methylene chloride, chloroform, carbon tetrachloride, dimethylformamide (DMF), dimethylacetamide (DMA), tetrahydrofuran (THF), or acetonitrile.

In some embodiments, the chlorinating-step solvent comprises methylene chloride.

In some embodiments, the chlorinating step further comprises the step of adding a mixture of the chlorinating agent and the chlorinating-step solvent to a mixture of the compound of Formula (IIm) or a salt thereof and the chlorinating-step solvent to form a chlorinating-step mixture.

In some embodiments, the mixture of the compound of Formula (IIn) or a salt thereof and the chlorinating-step solvent is at a temperature of about −20° C. to about 30° C.

In some embodiments, the mixture of the compound of Formula (IIn) or a salt thereof and the chlorinating-step solvent is at a temperature of about −15° C. to about 15° C.

In some embodiments, the mixture of the compound of Formula (IIn) or a salt thereof and the chlorinating-step solvent is at a temperature of about −10° C. to about 10° C.

In some embodiments, after addition of the mixture of the chlorinating agent and the chlorinating-step solvent to a mixture of the compound of Formula (IIn) or a salt thereof and the chlorinating-step solvent, the chlorinating-step mixture is at a temperature of about −10° C. to about 30° C.

In some embodiments, the process further comprises the steps of treating the chlorinating-step mixture with an aqueous mixture of sodium thiosulfate to form a chlorinating-step bi-phasic mixture.

In some embodiments, the process further comprises the step of separating the chlorinating-step bi-phasic mixture into an aqueous phase comprising sodium thiosulfate and a second chlorinating-step mixture.

In some embodiments, the process further comprises the step of concentrating the second chlorinating-step mixture to isolate the compound of Formula (IIn).

IX. Hydrolyzing Step

One aspect of the present invention pertains to processes for preparing (R)-2-(9-chloro-7-(4-isopropoxy-3-(trifluoromethyl)benzyloxy)-2,3-dihydro-1H-pyrrolo[1,2-a]indol-1-yl)acetic acid of Formula (Ia):

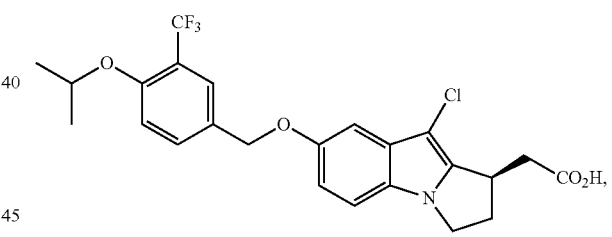

comprising the step of:
hydrolyzing a compound of Formula (IIn):

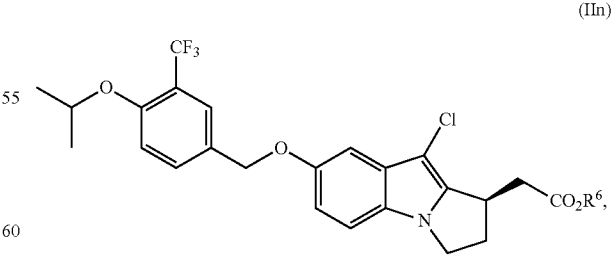

wherein $R^6$ is $C_1$-$C_4$ alkyl; in the presence of a hydrolyzing-step base and a hydrolyzing-step solvent to form the (R)-2-(9-chloro-7-(4-isopropoxy-3-(trifluoromethyl)benzyloxy)-2,3-dihydro-1H-pyrrolo[1,2-a]indol-1-yl)acetic acid (Formula (Ia)).

In some embodiments, $R^6$ is $CH_3$, $CH_2CH_3$, $CH_2CH_2CH_3$, $CH_2(CH_2)_2CH_3$, or t-butyl.

In some embodiments, $R^6$ is $CH_3$, $CH_2CH_3$, $CH_2CH_2CH_3$, or $CH_2(CH_2)_2CH_3$.

In some embodiments, $R^6$ is $CH_2CH_3$.

In some embodiments, $R^6$ is t-butyl.

In some embodiments, the hydrolyzing-step base is an alkali metal hydroxide.

In some embodiments, the hydrolyzing-step base is selected from the group consisting of lithium hydroxide, sodium hydroxide, and potassium hydroxide.

In some embodiments, the hydrolyzing-step base comprises sodium hydroxide.

In some embodiments, the hydrolyzing-step base comprises potassium hydroxide.

In some embodiments, the hydrolyzing-step solvent comprises dioxane, methanol, ethanol, isopropanol, or tetrahydrofuran.

In some embodiments, the hydrolyzing-step solvent comprises dioxane.

In some embodiments, the hydrolyzing-step solvent comprises methanol.

In some embodiments, the hydrolyzing-step solvent comprises dioxane, methanol, and water.

In some embodiments, the hydrolyzing step is conducted in the presence of water.

In some embodiments, the hydrolyzing step is conducted at a temperature of about 10° C. to about 40° C.

In some embodiments, the hydrolyzing step is conducted at a temperature of about 15° C. to about 35° C.

In some embodiments, the hydrolyzing step is conducted at a temperature of about 20° C. to about 30° C.

In some embodiments, the hydrolyzing step is conducted at a temperature of about 25° C.

In some embodiments, the hydrolyzing step further comprises the step of isolating the (R)-2-(9-chloro-7-(4-isopropoxy-3-(trifluoromethyl)benzyloxy)-2,3-dihydro-1H-pyrrolo[1,2-a]indol-1-yl)acetic acid of Formula (Ia).

In some embodiments, isolating comprises filtration.

In some embodiments, after isolating, (R)-2-(9-chloro-7-(4-isopropoxy-3-(trifluoromethyl)benzyloxy)-2,3-dihydro-1H-pyrrolo[1,2-a]indol-1-yl)acetic acid of Formula (Ia) has an enantiomeric excess of about 95% or greater.

In some embodiments, after isolating, (R)-2-(9-chloro-7-(4-isopropoxy-3-(trifluoromethyl)benzyloxy)-2,3-dihydro-1H-pyrrolo[1,2-a]indol-1-yl)acetic acid of Formula (Ia) has an enantiomeric excess of about 97% or greater.

In some embodiments, after isolating, (R)-2-(9-chloro-7-(4-isopropoxy-3-(trifluoromethyl)benzyloxy)-2,3-dihydro-1H-pyrrolo[1,2-a]indol-1-yl)acetic acid of Formula (Ia) has an enantiomeric excess of about 98% or greater.

X. Contacting Step

One aspect of the present invention pertains to processes for preparing an L-lysine salt of (R)-2-(9-chloro-7-(4-isopropoxy-3-(trifluoromethyl)benzyloxy)-2,3-dihydro-1H-pyrrolo[1,2-a]indol-1-yl)acetic acid of Formula (Ia):

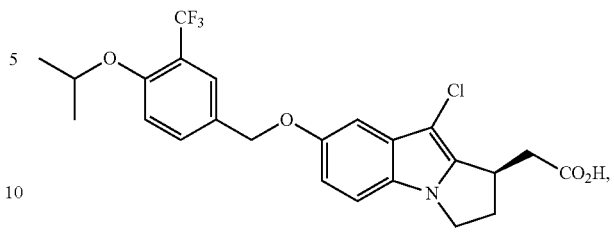

(Ia)

comprising the step of:

contacting the (R)-2-(9-chloro-7-(4-isopropoxy-3-(trifluoromethyl)benzyloxy)-2,3-dihydro-1H-pyrrolo[1,2-a]indol-1-yl)acetic acid with L-lysine or a salt thereof, in the presence of a contacting-step solvent and $H_2O$ to form the L-lysine salt of (R)-2-(9-chloro-7-(4-isopropoxy-3-(trifluoromethyl)benzyloxy)-2,3-dihydro-1H-pyrrolo[1,2-a]indol-1-yl)acetic acid of Formula (Ia).

In some embodiments, the contacting-step solvent comprises a suitable solvent.

In some embodiments, the contacting-step solvent comprises an aprotic solvent.

In some embodiments, the contacting-step solvent comprises acetonitrile, tetrahydrofuran, acetone, or ethyl acetate.

In some embodiments, the contacting-step solvent comprises acetonitrile.

In some embodiments, the contacting-step solvent comprises a protic solvent.

In some embodiments, the contacting-step solvent comprises a $C_1$-$C_6$ alcohol.

In some embodiments, the contacting-step solvent comprises ethanol or isopropanol.

In some embodiments, the contacting step is conducted under a substantially inert atmosphere.

In some embodiments, the contacting step is conducted under a substantially inert atmosphere comprising argon or nitrogen.

In some embodiments, the contacting step is conducted under a substantially inert atmosphere comprising nitrogen.

In some embodiments, the molar ratio between the (R)-2-(9-chloro-7-(4-isopropoxy-3-(trifluoromethyl)benzyloxy)-2,3-dihydro-1H-pyrrolo[1,2-a]indol-1-yl)acetic acid and L-lysine is about 1.0:1.0 to about 1.0:1.2.

In some embodiments, the molar ratio between the (R)-2-(9-chloro-7-(4-isopropoxy-3-(trifluoromethyl)benzyloxy)-2,3-dihydro-1H-pyrrolo[1,2-a]indol-1-yl)acetic acid and L-lysine is about 1.0:1.0.

In some embodiments, the contacting step further comprises the step of adding an aqueous solution of L-lysine to a first contacting mixture comprising the (R)-2-(9-chloro-7-(4-isopropoxy-3-(trifluoromethyl)benzyloxy)-2,3-dihydro-1H-pyrrolo[1,2-a]indol-1-yl)acetic acid and the contacting solvent to form a second contacting mixture.

In some embodiments, the first contacting mixture is at a temperature of about 50° C. to about 80° C.

In some embodiments, the first contacting mixture is at a temperature of about 60° C. to about 75° C.

In some embodiments, the first contacting mixture is at a temperature of about 65° C. to about 75° C.

In some embodiments, the first contacting mixture is at a temperature of about 70° C.

In some embodiments, the process further comprises the steps of cooling the second contacting mixture and crystallizing the L-lysine salt of (R)-2-(9-chloro-7-(4-isopropoxy-3-(trifluoromethyl)benzyloxy)-2,3-dihydro-1H-pyrrolo[1,2-a]indol-1-yl)acetic acid.

In some embodiments, the process further comprises the step of isolating the L-lysine salt of (R)-2-(9-chloro-7-(4-isopropoxy-3-(trifluoromethyl)benzyloxy)-2,3-dihydro-1H-pyrrolo[1,2-a]indol-1-yl)acetic acid.

In some embodiments, isolating comprises filtration.

In some embodiments, after isolating, the L-lysine salt of (R)-2-(9-chloro-7-(4-isopropoxy-3-(trifluoromethyl)benzyloxy)-2,3-dihydro-1H-pyrrolo[1,2-a]indol-1-yl)acetic acid has a purity of about 95% or greater.

In some embodiments, after isolating, the L-lysine salt of (R)-2-(9-chloro-7-(4-isopropoxy-3-(trifluoromethyl)benzyloxy)-2,3-dihydro-1H-pyrrolo[1,2-a]indol-1-yl)acetic acid has a purity of about 97% or greater.

In some embodiments, after isolating, the L-lysine salt of (R)-2-(9-chloro-7-(4-isopropoxy-3-(trifluoromethyl)benzyloxy)-2,3-dihydro-1H-pyrrolo[1,2-a]indol-1-yl)acetic acid has a purity of about 99% or greater.

In some embodiments, after isolating, the L-lysine salt of (R)-2-(9-chloro-7-(4-isopropoxy-3-(trifluoromethyl)benzyloxy)-2,3-dihydro-1H-pyrrolo[1,2-a]indol-1-yl)acetic acid has an enantiomeric excess of about 95% or greater.

In some embodiments, after isolating, the L-lysine salt of (R)-2-(9-chloro-7-(4-isopropoxy-3-(trifluoromethyl)benzyloxy)-2,3-dihydro-1H-pyrrolo[1,2-a]indol-1-yl)acetic acid has an enantiomeric excess of about 97% or greater.

In some embodiments, after isolating, the L-lysine salt of (R)-2-(9-chloro-7-(4-isopropoxy-3-(trifluoromethyl)benzyloxy)-2,3-dihydro-1H-pyrrolo[1,2-a]indol-1-yl)acetic acid has an enantiomeric excess of about 99% or greater.

XI. Processes Related to Intermediate 4-(Chloromethyl)-1-Isopropoxy-2-(trifluoromethyl)benzene of formula (IIk)

One aspect of the present invention pertains to processes for preparing 4-(chloromethyl)-1-isopropoxy-2-(trifluoromethyl)benzene of Formula (IIk):

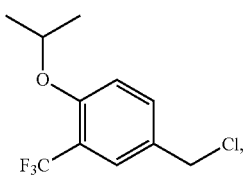
(IIk)

comprising the following steps:

a) adding isopropanol to 4-fluoro-3-(trifluoromethyl)benzonitrile of Formula (IIIb):

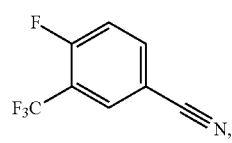
(IIIb)

in the presence of an adding-step base and an adding-step solvent, to form 4-isopropoxy-3-(trifluoromethyl)benzonitrile of Formula (IIIc):

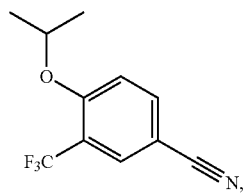
(IIIc)

b) hydrolyzing the 4-isopropoxy-3-(trifluoromethyl)benzonitrile of Formula (IIIc) in the presence of a hydrolyzing-step hydroxide base, a hydrolyzing-step solvent, and water, to form 4-isopropoxy-3-(trifluoromethyl)benzoic acid of Formula (IIId) or salt thereof:

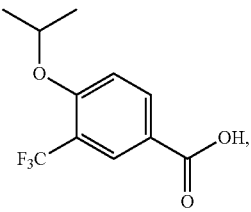
(IIId)

c) reducing the 4-isopropoxy-3-(trifluoromethyl)benzoic acid of Formula (IIId) or salt thereof, in the presence of a reducing agent, and a reducing-step solvent, to form (4-isopropoxy-3-(trifluoromethyl)phenyl)methanol of Formula (IIIe):

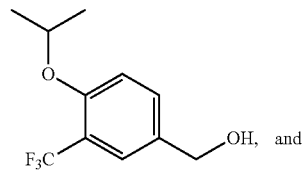
(IIIe)

and d) chlorinating the (4-isopropoxy-3-(trifluoromethyl)phenyl)methanol of Formula (IIIe) in the presence of a chlorinating agent, and a chlorinating-step solvent, to form the 4-(chloromethyl)-1-isopropoxy-2-(trifluoromethyl)benzene of Formula (IIk).

In some embodiments, the adding-step base comprises an alkali-metal $C_3$-$C_8$ alkyloxide.

In some embodiments, the adding-step base comprises an alkali-metal propan-2-olate, an alkali-metal 2-methylpropan-2-olate, an alkali-metal 2-methylbutan-2-olate, an alkali-metal 2,3-dimethylbutan-2-olate, an alkali-metal 2,3,3-trimethylbutan-2-olate, an alkali-metal 3-methylpentan-3-olate, or an alkali-metal 3-ethylpentan-3-olate. In some embodiments, the alkali-metal is lithium, sodium, or potassium.

In some embodiments, the adding-step base comprises potassium propan-2-olate, potassium 2-methylpropan-2-olate, potassium 2-methylbutan-2-olate, potassium 2,3-dimethylbutan-2-olate, potassium 2,3,3-trimethylbutan-2-olate, potassium 3-methylpentan-3-olate, or potassium 3-ethylpentan-3-olate.

In some embodiments, the adding-step base comprises potassium 2-methylpropan-2-olate.

In some embodiments, the adding-step solvent comprises an aprotic solvent.

In some embodiments, the adding-step solvent comprises tetrahydrofuran (THF), 2-methyl-tetrahydrofuran, diethyl ether, dibutyl ether, tert-butylmethyl ether, or tetrahydropyran.

In some embodiments, the adding-step solvent comprises tetrahydrofuran (THF).

In some embodiments, the adding-step solvent is substantially free of water.

In some embodiments, the adding-step is conducted under a substantially inert atmosphere.

In some embodiments, the adding-step is conducted under a substantially inert atmosphere comprising argon or nitrogen.

In some embodiments, the adding-step is conducted under an atmosphere comprising substantially nitrogen.

In some embodiments, the adding-step further comprises the step of:
 adding a mixture comprising adding-step base and the adding-step solvent to a mixture comprising the isopropanol, the 4-fluoro-3-(trifluoromethyl)benzonitrile of Formula (IIIb), and the adding-step solvent, to form an adding-step mixture.

In some embodiments, the mixture comprising the isopropanol, the 4-fluoro-3-(trifluoromethyl)benzonitrile of Formula (IIIb), and the adding-step solvent is at a temperature of about −10° C. to about 10° C.

In some embodiments, the adding-step mixture is at a temperature of about −10° C. to about 35° C.

In some embodiments, the adding-step mixture is at a temperature of about 0° C. to about 35° C.

In some embodiments, the adding-step mixture is at a temperature of about 15° C. to about 35° C.

In some embodiments, the adding-step further comprises the step of:
 quenching the adding-step mixture with water to form a bi-phasic mixture comprising 4-isopropoxy-3-(trifluoromethyl)benzonitrile of Formula (IIIc).

In some embodiments, the adding-step further comprises the step of:
 separating the bi-phasic mixture comprising the 4-isopropoxy-3-(trifluoromethyl)benzonitrile of Formula (IIIc) into an aqueous phase and an organic phase comprising 4-isopropoxy-3-(trifluoromethyl)benzonitrile of Formula (IIIc).

In some embodiments, the adding-step further comprises the step of isolating the 4-isopropoxy-3-(trifluoromethyl) benzonitrile of Formula (IIIc) from the organic phase comprising 4-isopropoxy-3-(trifluoromethyl)benzonitrile of Formula (IIIc).

In some embodiments, the hydrolyzing-step hydroxide base comprises lithium hydroxide, sodium hydroxide, or potassium hydroxide.

In some embodiments, the hydrolyzing-step hydroxide base comprises sodium hydroxide.

In some embodiments, the hydrolyzing-step solvent comprises a $C_1$-$C_4$ alkylalcohol.

In some embodiments, the hydrolyzing-step solvent comprises methanol, ethanol, n-propanol, isopropanol, or n-butanol.

In some embodiments, the hydrolyzing-step solvent comprises ethanol.

In some embodiments, the hydrolyzing-step further comprises the step of:
 adding an aqueous mixture of the hydrolyzing-step hydroxide base to a mixture comprising the 4-isopropoxy-3-(trifluoromethyl)benzonitrile of Formula (IIIc) and the hydrolyzing-step solvent, to form a hydrolyzing-step mixture.

In some embodiments, the hydrolyzing-step mixture is at a temperature of about 20° C. to about 90° C.

In some embodiments, the hydrolyzing-step mixture is at a temperature of about 40° C. to about 85° C.

In some embodiments, the hydrolyzing-step mixture is at a temperature of about 60° C. to about 80° C.

In some embodiments, the hydrolyzing-step further comprises the step of:
 concentrating the hydrolyzing-step mixture to form a concentrate comprising the 4-isopropoxy-3-(trifluoromethyl) benzoic acid of Formula (IIId) or salt thereof.

In some embodiments, the hydrolyzing-step further comprises the step of:
 treating the concentrate comprising the 4-isopropoxy-3-(trifluoromethyl)benzoic acid of Formula (IIId) or salt thereof, with a Brønsted acid to form a suspension comprising the 4-isopropoxy-3-(trifluoromethyl)benzoic acid of Formula (IIId) or salt thereof.

In some embodiments, the Brønsted acid comprises aqueous HCl.

In some embodiments, the hydrolyzing-step further comprises the step of isolating the 4-isopropoxy-3-(trifluoromethyl)benzoic acid of Formula (IIId) or salt thereof from the suspension comprising the 4-isopropoxy-3-(trifluoromethyl) benzoic acid of Formula (IIId) or salt thereof.

In some embodiments, the isolating the 4-isopropoxy-3-(trifluoromethyl)benzoic acid of Formula (IIId) or salt thereof, is conducted by filtration.

In some embodiments, the reducing-step agent comprises $BH_3$ or lithium aluminium hydride (LAH).

In some embodiments, the reducing-step agent comprises $BH_3$.

In some embodiments, the reducing-step agent comprises $BH_3.THF$ or $BH_3.S(CH_3)_2$.

In some embodiments, the reducing-step solvent comprises tetrahydrofuran (THF), 2-methyl-tetrahydrofuran, diethyl ether, dibutyl ether, tert-butylmethyl ether, or tetrahydropyran.

In some embodiments, the reducing-step solvent comprises tetrahydrofuran (THF).

In some embodiments, the reducing-step further comprises the step of:
 adding a mixture comprising the reducing-step agent and the reducing-step solvent to a mixture comprising the 4-isopropoxy-3-(trifluoromethyl)benzoic acid of Formula (IIId) or salt thereof, and the reducing-step solvent, to form a first reducing-step mixture.

In some embodiments, the mixture comprising the 4-isopropoxy-3-(trifluoromethyl)benzoic acid of Formula (IIId) and the reducing-step solvent is at a temperature of about −15° C. to about 15° C.

In some embodiments, the mixture comprising the 4-isopropoxy-3-(trifluoromethyl)benzoic acid of Formula (IIId) and the reducing-step solvent is at a temperature of about −5° C. to about 5° C.

In some embodiments, the reducing-step further comprises the step of warming the first reducing-step mixture to a temperature of about 20° C. to about 35° C.

In some embodiments, the reducing-step further comprises the step of warming the first reducing-step mixture to a temperature of about 20° C. to about 30° C.

In some embodiments, the reducing-step further comprises the step of warming the first reducing-step mixture to a temperature of about 25° C.

In some embodiments, the reducing-step further comprises the step of:

quenching the first reducing-step mixture with a $C_1$-$C_4$ alkylalcohol, or a Brønsted acid, or both, to form a second reducing-step mixture comprising the (4-isopropoxy-3-(trifluoromethyl)phenyl)methanol of Formula (IIIe).

In some embodiments, the $C_1$-$C_4$ alkylalcohol comprises methanol, ethanol, n-propanol, isopropanol, or n-butanol.

In some embodiments, the $C_1$-$C_4$ alkylalcohol comprises methanol.

In some embodiments, the Brønsted acid comprises HCl.

In some embodiments, the Brønsted acid comprises aqueous HCl.

In some embodiments, the step of isolating the (4-isopropoxy-3-(trifluoromethyl)phenyl)methanol of Formula (IIIe) from the second reducing-step mixture.

In some embodiments, the chlorinating-step agent comprises thionyl chloride, trichlorocyanuric acid (TCCA), oxalyl chloride, oxalyl chloride/DMF, $PPh_3/Cl_3CC(O)CCl_3$, or $PPh_3/Cl_3CN$.

In some embodiments, the chlorinating-step agent comprises thionyl chloride.

In some embodiments, the chlorinating-step solvent comprises toluene, benzene, methylene chloride, chloroform, tetrahydrofuran (THF), 2-methyl-tetrahydrofuran, diethyl ether, dibutyl ether, tert-butylmethyl ether, or tetrahydropyran.

In some embodiments, the chlorinating-step solvent comprises toluene.

In some embodiments, the chlorinating-step further comprises the step of:

adding the chlorinating-step agent to a mixture comprising the (4-isopropoxy-3-(trifluoromethyl)phenyl)methanol of Formula (IIIe) and the chlorinating-step solvent to form a first chlorinating-step mixture.

In some embodiments, the first chlorinating-step mixture is at a temperature of about 10° C. to about 55° C.

In some embodiments, the first chlorinating-step mixture is at a temperature of about 15° C. to about 45° C.

In some embodiments, the first chlorinating-step mixture is at a temperature of about 20° C. to about 35° C.

In some embodiments, the chlorinating-step further comprises the step of: concentrating the first chlorinating-step mixture to form a second chlorinating-step mixture comprising the 4-(chloromethyl)-1-isopropoxy-2-(trifluoromethyl) benzene of Formula (IIk).

In some embodiments, the chlorinating-step further comprises the step of treating the second chlorinating-step mixture comprising the 4-(chloromethyl)-1-isopropoxy-2-(trifluoromethyl)benzene of Formula (IIk) with a chlorinating-step base.

In some embodiments, the chlorinating-step further comprises the step of isolating the 4-(chloromethyl)-1-isopropoxy-2-(trifluoromethyl)benzene of Formula (IIk).

In some embodiments, the isolating the 4-(chloromethyl)-1-isopropoxy-2-(trifluoromethyl)benzene of Formula (IIk) comprises distillation.

In some embodiments, the isolating the 4-(chloromethyl)-1-isopropoxy-2-(trifluoromethyl)benzene of Formula (IIk) comprises distillation, wherein the 4-(chloromethyl)-1-isopropoxy-2-(trifluoromethyl)benzene of Formula (IIk) distills at a temperature of about 80° C. to about 90° C. under a vacuum of about 0.1 mTorr.

Uses and Intermediates

One aspect of the present invention provides, inter alia, intermediates prepared by any of the processes described herein.

The present invention further provides pharmaceutical compositions comprising compounds prepared by any of the processes as described herein.

The present invention further provides processes of preparing a pharmaceutical composition comprising admixing compound of Formula (Ia) or a salt thereof with a pharmaceutically acceptable carrier, wherein the compound of Formula (Ia) or a salt thereof is prepared by any of the processes as described herein.

The present invention further provides intermediates, as described herein, for use in processes for preparing pharmaceutical compositions for treating an S1P1 receptor-associated disorder in an individual.

The present invention further provides uses of compounds, as described herein, in processes for preparing pharmaceutical compositions for treating an S1P1 receptor-associated disorder.

One aspect of the present invention pertains to compounds represented by any of the formulae described herein.

One aspect of the present invention pertains to compounds represented by any of the formulae described herein for use in a process for preparing a pharmaceutical composition for treating an S1P1 receptor-associated disorder in an individual.

One aspect of the present invention pertains to compounds represented by any of the formulae described herein prepared according to any of the processes described herein.

One aspect of the present invention pertains to compounds represented by any of the formulae described herein prepared according to any of the processes described herein, for use in a process for preparing a pharmaceutical composition for treating an S1P1 receptor-associated disorder in an individual.

The present invention further provides intermediates that are useful in the preparation of (R)-2-(9-chloro-7-(4-isopropoxy-3-(trifluoromethyl)benzyloxy)-2,3-dihydro-1H-pyrrolo[1,2-a]indol-1-yl)acetic acid of Formula (Ia), salts, and crystalline forms thereof.

1) Compounds of Formula (IIe)

One aspect of the present invention pertains to a compound of Formula (IIe):

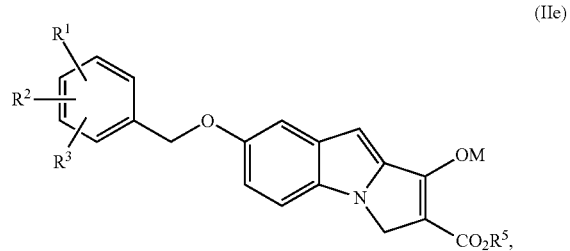

wherein $R^1$, $R^2$, and $R^3$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro; $R^5$ is $C_1$-$C_4$ alkyl; and M is potassium.

In some embodiments, $R^1$, $R^2$, and $R^3$ are each selected independently from the group consisting of H, $C_1$-$C_4$ alkyl, and $C_1$-$C_4$ alkoxy.

In some embodiments, $R^1$, $R^2$, and $R^3$ are each selected independently from the group consisting of H, $CH_3$, and $OCH_3$.

In some embodiments, $R^1$, $R^2$, and $R^3$ are each selected independently from the group consisting of H, $OCH(CH_3)_2$, and $CF_3$.

In some embodiments, $R^1$ is H.
In some embodiments, $R^2$ is $OCH(CH_3)_2$.
In some embodiments, $R^3$ is $CF_3$.
In some embodiments, $R^1$, $R^2$, and $R^3$ are each H.
In some embodiments, $R^5$ is $CH_3$, $CH_2CH_3$, $CH_2CH_2CH_3$, or $CH_2(CH_2)_2CH_3$.
In some embodiments, $R^5$ is $CH_2CH_3$.
In some embodiments, the compound of Formula (IIe) is:

[Structure: benzyloxy-indole with O⁻K⁺ and CO₂Et substituents]

2) Compounds of Formula (IIh)

One aspect of the present invention pertains to a compound of Formula (IIh), or a salt thereof:

(IIh)

[Structure with R¹, R², R³ on phenyl, linked via CH₂-O to indole-pyrrolidine fused system with CO₂R⁶]

wherein $R^1$, $R^2$, and $R^3$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro; and $R^6$ is $C_1$-$C_4$ alkyl.

In some embodiments, the compound of Formula (IIh) is of Formula (IIh)-E:

(IIh)-E

[Structure with E-configured double bond to CO₂R⁶]

In some embodiments, the compound of Formula (IIh) is of Formula (IIh)-Z:

(IIh)-Z

[Structure with Z-configured double bond to CO₂R⁶]

In some embodiments, $R^1$, $R^2$, and $R^3$ are each selected independently from the group consisting of H, $C_1$-$C_4$ alkyl, and $C_1$-$C_4$ alkoxy.
In some embodiments, $R^1$, $R^2$, and $R^3$ are each selected independently from the group consisting of H, $CH_3$, and $OCH_3$.
In some embodiments, $R^1$, $R^2$, and $R^3$ are each H.
In some embodiments, $R^6$ is $CH_3$, $CH_2CH_3$, $CH_2CH_2CH_3$, $CH_2(CH_2)_2CH_3$, or t-butyl.
In some embodiments, $R^6$ is $CH_3$, $CH_2CH_3$, $CH_2CH_2CH_3$, or $CH_2(CH_2)_2CH_3$.
In some embodiments, $R^6$ is $CH_2CH_3$.
In some embodiments, $R^6$ is t-butyl.
In some embodiments, the compound of Formula (IIh) is:

[Structure: benzyloxy-indole-pyrrolidine with =CH-CO₂Et]

or a salt thereof.
In some embodiments, the compound of Formula (IIh) is:

[Structure: benzyloxy-indole-pyrrolidine with =CH-CO₂t-butyl]

or a salt thereof.

3) Compounds of Formula (IIi)

One aspect of the present invention pertains to a compound of Formula (IIi):

(IIi)

[Structure with saturated pyrrolidine bearing CH₂-CO₂R⁶]

wherein $R^1$, $R^2$, and $R^3$ are each selected independently from the group consisting of H, $C_1$-$C_4$ alkyl, $C_1$-$C_4$ alkoxy, halogen, $C_1$-$C_4$ haloalkyl, $C_1$-$C_4$ haloalkoxy, and nitro; and $R^6$ is $C_1$-$C_4$ alkyl.

In some embodiments, $R^1$, $R^2$, and $R^3$ are each selected independently from the group consisting of H, $C_1$-$C_4$ alkyl, and $C_1$-$C_4$ alkoxy.

In some embodiments, $R^1$, $R^2$, and $R^3$ are each selected independently from the group consisting of H, $CH_3$, and $OCH_3$.

In some embodiments, $R^1$, $R^2$, and $R^3$ are each H.

In some embodiments, $R^6$ is $CH_3$, $CH_2CH_3$, $CH_2CH_2CH_3$, $CH_2(CH_2)_2CH_3$, or t-butyl.

In some embodiments, $R^6$ is $CH_3$, $CH_2CH_3$, $CH_2CH_2CH_3$, or $CH_2(CH_2)_2CH_3$.

In some embodiments, $R^6$ is $CH_2CH_3$.

In some embodiments, $R^6$ is t-butyl.

In some embodiments, the compound of Formula (IIh) is:

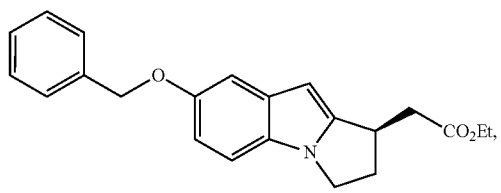 [SMILES: CCOC(=O)C[C@H]1CCn2c1cc1cc(OCc3ccccc3)ccc12]

or a salt thereof.

In some embodiments, the compound of Formula (IIh) is:

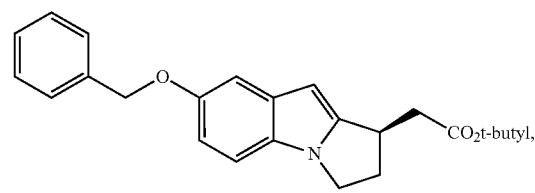

or a salt thereof.

3) Compounds of Formula (IIj)

One aspect of the present invention pertains to a compound of Formula (IIj), or a salt thereof:

(IIj)

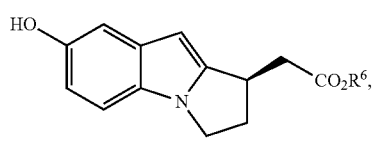

wherein $R^6$ is $C_1$-$C_4$ alkyl.

In some embodiments, $R^6$ is $CH_3$, $CH_2CH_3$, $CH_2CH_2CH_3$, $CH_2(CH_2)_2CH_3$, or t-butyl.

In some embodiments, $R^6$ is $CH_3$, $CH_2CH_3$, $CH_2CH_2CH_3$, or $CH_2(CH_2)_2CH_3$.

In some embodiments, $R^6$ is $CH_2CH_3$.

In some embodiments, $R^6$ is t-butyl.

In some embodiments, the compound of Formula (IIj) is:

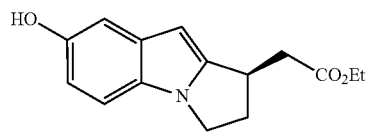 [SMILES: CCOC(=O)C[C@H]1CCn2c1cc1cc(O)ccc12]

or a salt thereof.

In some embodiments, the compound of Formula (IIj) is:

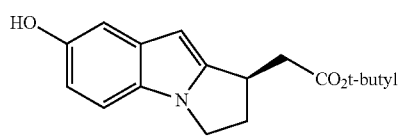

or a salt thereof.

4) Compounds of Formula (IIm)

One aspect of the present invention pertains to a compound of Formula (IIm) or a salt thereof:

(IIm)

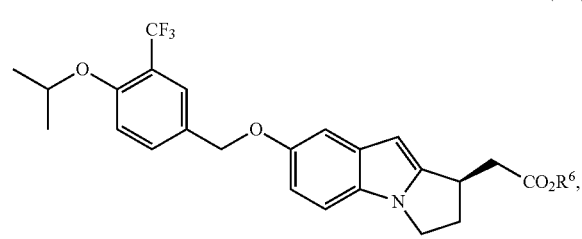

wherein $R^6$ is $C_1$-$C_4$ alkyl.

In some embodiments, $R^6$ is $CH_3$, $CH_2CH_3$, $CH_2CH_2CH_3$, $CH_2(CH_2)_2CH_3$, or t-butyl.

In some embodiments, $R^6$ is $CH_3$, $CH_2CH_3$, $CH_2CH_2CH_3$, or $CH_2(CH_2)_2CH_3$.

In some embodiments, $R^6$ is $CH_2CH_3$.

In some embodiments, $R^6$ is t-butyl.

In some embodiments, the compound of Formula (IIm) is:

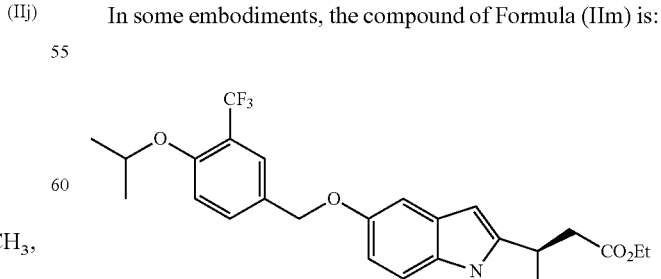

or a salt thereof.

In some embodiments, the compound of Formula (IIm) is:

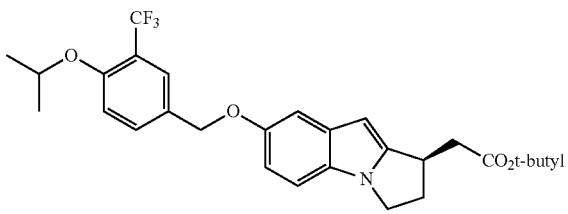

or a salt thereof.

5) Compounds of Formula (IIn)

One aspect of the present invention pertains to a compound of Formula (IIn) or a salt thereof:

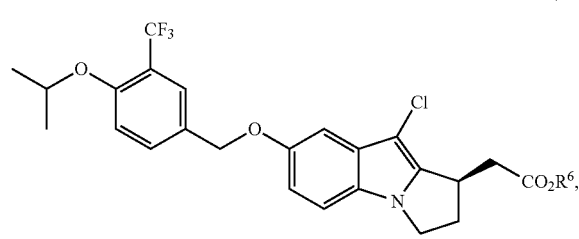

wherein $R^6$ is $C_1$-$C_4$ alkyl.

In some embodiments, $R^6$ is $CH_3$, $CH_2CH_3$, $CH_2CH_2CH_3$, $CH_2(CH_2)_2CH_3$, or t-butyl.

In some embodiments, $R^6$ is $CH_3$, $CH_2CH_3$, $CH_2CH_2CH_3$, or $CH_2(CH_2)_2CH_3$.

In some embodiments, $R^6$ is $CH_2CH_3$.

In some embodiments, $R^6$ is t-butyl.

In some embodiments, the compound of Formula (IIn) is:

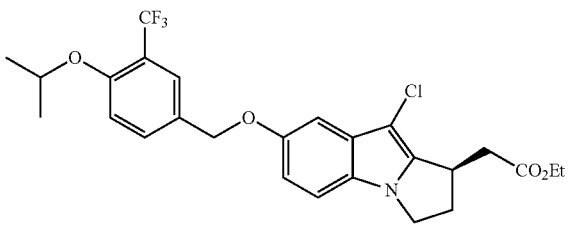 [SMILES: CCOC(=O)C[C@H]1CCn2c1c(Cl)c1cc(OCc3ccc(OC(C)C)c(C(F)(F)F)c3)ccc12]

or a salt thereof.

In some embodiments, the compound of Formula (IIn) is:

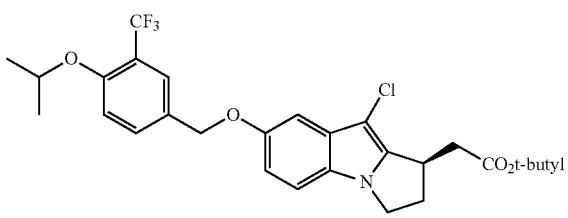

or a salt thereof.

Other Utilities

Another object of the present invention relates to radio-labeled compounds of the present invention that would be useful not only in radio-imaging but also in assays, both in vitro and in vivo, for localizing and quantitating the S1P1 receptor in tissue samples, including human and for identifying S1P1 receptor ligands by inhibition binding of a radio-labeled compound. It is a further object of this invention to develop novel S1P1 receptor assays of which comprise such radio-labeled compounds.

The present invention embraces isotopically-labeled compounds of the present invention. Isotopically or radio-labeled compounds are those which are identical to compounds disclosed herein, but for the fact that one or more atoms are replaced or substituted by an atom having an atomic mass or mass number different from the atomic mass or mass number most commonly found in nature. Suitable radionuclides that may be incorporated in compounds of the present invention include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}F$, $^{35}S$, $^{36}Cl$, $^{75}Br$, $^{76}Br$, $^{77}Br$, $^{82}Br$, $^{123}I$, $^{124}I$, $^{125}I$, and $^{131}I$. The radionuclide that is incorporated in the instant radio-labeled compounds will depend on the specific application of that radio-labeled compound. For example, for in vitro S1P1 receptor labeling and competition assays, compounds that incorporate $^3H$, $^{14}C$, $^{82}Br$, $^{125}I$, $^{131}I$ or $^{35}S$ will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound of Formula (Ia), (IIa), (IIb), (IIc), (IId), (IIe), (IIe), (IIf), (IIg), (IIh), (IIi), (IIj), (IIm), (IIIb), (IIIc), (IIId), or (IIIe) that has incorporated at least one radionuclide; in some embodiments the radionuclide is selected from the group consisting of $^3H$, $^{14}C$, $^{125}I$, $^{35}S$ and $^{82}Br$.

Certain isotopically-labeled compounds of the present invention are useful in compound and/or substrate tissue distribution assays. In some embodiments the radionuclide $^3H$ and/or $^{14}C$ isotopes are useful in these studies. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Schemes and Examples herein by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the scarcer radio-isotope or nonradioactive isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^3H$]: This procedure is rather inexpensive and requires precursors containing reducible functional groups such as aldehydes, ketones, lactones, esters and the like.

C. Reduction with Lithium Aluminum Hydride [³H]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [³H]: This procedure is usually employed to prepare O-methyl or N-methyl (³H) products by treating appropriate precursors with high specific activity methyl iodide (³H). This method in general allows for higher specific activity, such as for example, about 70-90 Ci/mmol.

Synthetic methods for incorporating activity levels of $^{125}$I into target molecules include:

A. Sandmeyer and like reactions: This procedure transforms an aryl amine or a heteroaryl amine into a diazonium salt, such as a diazonium tetrafluoroborate salt and subsequently to $^{125}$I labeled compound using Na$^{125}$I. A represented procedure was reported by Zhu, G-D. and co-workers in *J. Org. Chem.*, 2002, 67, 943-948.

B. Ortho $^{125}$Iodination of phenols: This procedure allows for the incorporation of $^{125}$I at the ortho position of a phenol as reported by Collier, T. L. and co-workers in *J. Labelled Compd. Radiopharm.*, 1999, 42, S264-S266.

C. Aryl and heteroaryl bromide exchange with $^{125}$I: This method is generally a two step process. The first step is the conversion of the aryl or heteroaryl bromide to the corresponding tri-alkyltin intermediate using for example, a Pd catalyzed reaction [i.e. Pd(Ph₃P)₄] or through an aryl or heteroaryl lithium, in the presence of a tri-alkyltinhalide or hexaalkylditin [e.g., (CH₃)₃SnSn(CH₃)₃]. A representative procedure was reported by Le Bas, M.-D. and co-workers in *J. Labelled Compd. Radiopharm.* 2001, 44, S280-S282.

A radiolabeled S1P1 receptor compound of Formula (Ia) can be used in a screening assay to identify/evaluate compounds. In general terms, a newly synthesized or identified compound (i.e., test compound) can be evaluated for its ability to reduce binding of the "radio-labeled compound of Formula (Ia)" to the S1P1 receptor. Accordingly, the ability of a test compound to compete with the "radio-labeled compound of Formula (Ia)" for the binding to the S1P1 receptor directly correlates to its binding affinity.

The labeled compounds of the present invention bind to the S1P1 receptor. In one embodiment the labeled compound has an IC$_{50}$ less than about 500 μM, in another embodiment the labeled compound has an IC$_{50}$ less than about 100 μM, in yet another embodiment the labeled compound has an IC$_{50}$ less than about 10 μM, in yet another embodiment the labeled compound has an IC$_{50}$ less than about 1 μM and in still yet another embodiment the labeled inhibitor has an IC$_{50}$ less than about 0.1 μM.

Other uses of the disclosed receptors and methods will become apparent to those skilled in the art based upon, inter alia, a review of this disclosure.

As will be recognized, the steps of the methods of the present invention need not be performed any particular number of times or in any particular sequence. Additional objects, advantages and novel features of this invention will become apparent to those skilled in the art upon examination of the following examples thereof, which are intended to be illustrative and not intended to be limiting.

EXAMPLES

Example 1

Syntheses of Compounds of the Present Invention

The compounds of the invention and their syntheses are further illustrated by the following examples. The following examples are provided to further define the invention without, however, limiting the invention to the particulars of these examples. The compounds described herein, supra and infra, are named according to the CS ChemDraw Ultra Version 7.0.1, AutoNom version 2.2, or CS ChemDraw Ultra Version 9.0.7. In certain instances common names are used and it is understood that these common names would be recognized by those skilled in the art.

Chemistry: Proton nuclear magnetic resonance (¹H NMR) spectra were recorded on a Bruker Avance-400 equipped with a QNP (Quad Nucleus Probe) or a BBI (Broad Band Inverse) and z-gradient. Chemical shifts are given in parts per million (ppm) with the residual solvent signal used as reference. NMR abbreviations are used as follows: s=singlet, d=doublet, dd=doublet of doublets, ddd=doublet of doublet of doublets, dt=doublet of triplets, t=triplet, td=triplet of doublets, tt=triplet of triplets, q=quartet, m=multiplet, bs=broad singlet, bt=broad triplet, sep=septet. Microwave irradiations were carried out using a Smith Synthesizer™ or an Emrys Optimizer™ (Biotage). Thin-layer chromatography (TLC) was performed on silica gel 60 F$_{254}$ (Merck), preparatory thin-layer chromatography (prep TLC) was preformed on PK6F silica gel 60 A 1 mm plates (Whatman) and column chromatography was carried out on a silica gel column using Kieselgel 60, 0.063-0.200 mm (Merck). Evaporation was done under reduced pressure on a Büchi rotary evaporator.

LCMS spec: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2.

Example 1.1

Preparation of 4-(Chloromethyl)-1-isopropoxy-2-(trifluoromethyl)benzene

Step A: Preparation of 4-Isopropoxy-3-(trifluoromethyl)benzonitrile

To a solution of 4-fluoro-3-(trifluoromethyl)benzonitrile (154 g, 814 mmol) in THF (1.5 L) was added isopropanol (73.4 g, 1.22 mol). The reaction flask was purged with N₂ and cooled in an ice bath (1.5° C. internal temperature). t-BuOK (1.0 M in THF, 847 mL, 847 mmol) was added slowly over 10 minutes via addition funnel (slight exotherm to 31° C. was observed) and let stir at that temperature for 30 min (temp decreased to 18° C. during this time). The ice bath was removed and allowed to stir at room temperature until starting material was consumed as observed by LC/MS (~20 min). The resulting mixture was quenched with water (500 mL) and the layers were separated. The organic layer was concentrated and the aqueous layer was extracted with MTBE (1 L). The organics were combined and washed with H₂O (750 mL) and brine (750 mL). Dried organics over MgSO₄, filtered, and concentrated to give 4-isopropoxy-3-(trifluoromethyl)benzonitrile (183 g, 798 mmol, 98% yield) as a yellow solid. Exact mass calculated for $C_{11}H_{10}F_3NO$: 229.1, found: LCMS m/z=230.2, [M+H$^+$]; $^1$H NMR (400 MHz, CDCl$_3$) δ ppm 1.41 (d, J=6.1 Hz, 6 H), 4.73 (sep, J=6.1 Hz, 1 H), 7.06 (d, J=8.7 Hz, 1 H), 7.75 (dd, J$_1$=8.7, J$_2$=2.1 Hz, 1 H), 7.85 (d, J=1.9 Hz, 1 H).

Step B: Preparation of
4-Isopropoxy-3-(trifluoromethyl)benzoic acid

To a solution of 4-isopropoxy-3-(trifluoromethyl)benzonitrile (183 g, 798 mmol) in EtOH (1 L) was added 5 N NaOH (559 mL, 2.80 mol). The reaction mixture was heated to 80° C. for 18 h. Volatiles were removed in vacuo and 3 N HCl was added until the mixture was acidic. A precipitate formed that was collected by vacuum filtration. The solid was washed with water and hexanes. The solid was dissolved in EtOAc and dried over MgSO$_4$ to give 4-isopropoxy-3-(trifluoromethyl)benzoic acid (191 g, 770 mmol, 96% yield) as a white solid. Exact mass calculated for $C_{11}H_{11}F_3O_3$: 248.1, found: LCMS m/z=249.3, [M+H$^+$]; $^1$H NMR (400 MHz, CDCl$_3$) δ ppm 1.41 (d, J=6.0 Hz, 6 H), 4.76 (sep, J=6.0 Hz, 1 H), 7.05 (d, J=8.8 Hz, 1 H), 8.22 (dd, J$_1$=8.8, J$_2$=2.2 Hz, 1 H), 8.33 (d, J=2.0 Hz, 1 H).

Step C: Preparation of
(4-Isopropoxy-3-(trifluoromethyl)phenyl)methanol

To a solution of 4-isopropoxy-3-(trifluoromethyl)benzoic acid (191 g, 770 mmol) in THF (2 L) at 0° C. in a 5-L round bottomed flask under N$_2$ was added BH$_3$·THF (1M solution in THF, 1.08 L, 1.08 mol) slowly over 15 min. The mixture was allowed to stir at 0° C. for 30 min at which time the ice bath was removed and the reaction warmed to room temperature. The reaction was quenched with MeOH (80.0 mL, 506 mmol) followed by aq. HCl (1 M, 1000 mL, 1000 mmol) (slight exotherm to 36° C. was observed). The volatile organics were removed in vacuo and the aqueous phase was extracted with EtOAc (2×1 L). The organic layers were combined and washed with sat. NaHCO$_3$ (750 mL) and brine (750 mL). Dried organics over MgSO$_4$, filtered, and concentrated to give (4-isopropoxy-3-(trifluoromethyl)phenyl)methanol (181 g, 763 mmol, 99% yield) as a clear oil. $^1$H NMR (400 MHz, CDCl$_3$) δ ppm 1.37 (d, J=6.1 Hz, 6 H), 1.66 (s, 1H) 4.59-4.69 (m, 3 H), 6.99 (d, J=8.5 Hz, 1 H), 7.46 (dd, J$_1$=8.5, J$_2$=2.2 Hz, 1 H), 7.56 (d, J=1.9 Hz, 1 H).

Step D: Preparation of 4-(Chloromethyl)-1-isopropoxy-2-(trifluoromethyl)benzene

To a solution of (4-isopropoxy-3-(trifluoromethyl)phenyl)methanol (181 g, 773 mmol) in toluene (1 L) was added SOCl$_2$ (338 mL, 4637 mmol) (slight exotherm to 35° C. after addition of SOCl$_2$) and was stirred overnight in a 2-L round bottomed flask. The reaction mixture was concentrated in vacuo and diluted with hexanes (1 L). The solution was washed with sat. NaHCO$_3$ (2×750 mL), dried over MgSO$_4$, and filtered. The solvents were removed under reduced pressure to give 4-(chloromethyl)-1-isopropoxy-2-(trifluoromethyl)benzene (194 g, 768 mmol, 99% yield) as an orange oil. Optionally the product can be further purified by distillation (bp=85° C. at 0.1 mTorr) to obtain a clear oil. $^1$H NMR (400 MHz, CDCl$_3$) δ ppm 1.37 (d, J=6.1 Hz, 6 H), 4.56 (s, 2H) 4.65 (sep, J=6.1 Hz, 1 H), 6.98 (d, J=8.6 Hz, 1 H), 7.48 (dd, J$_1$=8.6, J$_2$=2.3 Hz, 1 H), 7.57 (d, J=2.2 Hz, 1 H).

Example 1.2

Preparation of tert-Butyl 2-methyl-4-(triisocarpropylsilyloxy)phenylcarbamate

Step A: Preparation of
2-Methyl-4-(triisopropylsilyloxy)aniline

To a solution of 4-amino-3-methylphenol (75.0 g, 609 mmol) in THF (1.5 L) was added imidazole (83 g, 1.22 mol). The reaction was cooled to 0° C. and triisopropylsilyl chloride (123 mL, 579 mmol) was added. The reaction mixture was allowed to warm to room temperature, stirred for 3 h, diluted with MTBE (1.5 L) and filtered. The filtrate was washed with water (1.0 L). The aqueous phase was back-extracted with MTBE (500 mL). The organics were combined, washed with 0.5 N NaOH (2×500 mL), brine (500 mL), and dried over MgSO$_4$. The organics were filtered and concentrated to give 2-methyl-4-(triisopropylsilyloxy)aniline (135 g, 482 mmol, 83% yield) as a red oil. Exact mass calculated for $C_{16}H_{29}NOSi$: 279.2, found: LCMS m/z=280.5, [M+H$^+$]; $^1$H NMR (400 MHz, CDCl$_3$) δ ppm 1.09 (d, J=7.0 Hz, 18 H), 1.21 (m, 3 H), 2.12 (s, 3 H), 3.31 (bs, 2 H), 6.53 (d, J=8.4 Hz, 1 H), 6.57 (dd, J$_1$=8.4, J$_2$=2.7 Hz, 1 H), 6.62 (d, J=2.7 Hz, 1 H).

Step B: Preparation of tert-Butyl
2-methyl-4-(triisopropylsilyloxy)phenylcarbamate To a solution of 2-methyl-4-(triisopropylsilyloxy)aniline (130 g, 465 mmol) in THF (1.0 L) was added di-tert-butyl dicarbonate (102 g, 465 mmol). The resulting reaction mixture was allowed to stir overnight at room temperature and N,N,N'-trimethylethylenediamine (10 mL) was added and stirred for 30 minutes. The mixture was concentrated in vacuo to approximately half the total volume and diluted with MTBE (1.0 L). The resulting mixture was washed with 1 N HCl (2×500 mL), brine (500 mL), dried over MgSO$_4$, and filtered. The mixture was concentrated and purified with silica gel plug filtration (hexanes) and concentrated to give tert-butyl 2-methyl-4-(triisopropylsilyloxy)phenylcarbamate (100 g, 263 mmol, 56.6% yield) as a red oil in approx. 90% purity ($^1$H NMR). Exact mass calculated for $C_{21}H_{37}NO_3Si$: 379.3, found: LCMS m/z=380.4, [M+H]; $^1$H NMR (400 MHz, CDCl$_3$) δ ppm 1.09 (d, J=7.0 Hz, 18 H), 1.23 (m, 3 H), 1.50 (s, 9 H), 2.18 (s, 3 H), 6.05 (bs, 1 H), 6.69 (m, 2 H), 7.44 (m, 1 H).

Example 1.3

Preparation of (R)-4-tert-Butyl 1-methyl 2-(2-(benzyloxy)ethyl)succinate

Step A: Preparation of (R)-2-(2-(Benzyloxy)ethyl)-4-tert-butoxy-4-oxobutanoic acid To a solution of (S)-4-benzyl-3-(4-(benzyloxy)butanoyl)oxazolidin-2-one (170 g, 482 mmol) in THF (1.0 L) at −78° C. was added LiHMDS (1.0 M in THF, 530 mL, 530 mmol) over 10 minutes via cannula. After stirring for 1 h at −78° C. tert-butyl bromoacetate (82.0 mL, 554 mmol) was added slowly over 45 min via syringe pump. The mixture was slowly allowed to warm to room temperature overnight. The reaction mixture was quenched with sat. ammonium chloride (300 mL) and stirred for 10 min, diluted further with H$_2$O (500 mL), and extracted with MTBE (1.0 L). The organic layer was isolated, treated with N,N,N'-trimethylethylenediamine (5 mL) and shaken for 2 min in order to remove excess tert-butyl bromoacetate. The mixture was washed with 1 N HCl (2×750 mL), and brine (1.0 L). The organics were dried over MgSO$_4$, filtered, and concentrated to give 262 g of crude (R)-tert-butyl 3-((S)-4-benzyl-2-oxooxazolidine-3-carbonyl)-5-(benzyloxy)pentanoate.

To a solution of the (R)-tert-butyl 3-((S)-4-benzyl-2-oxooxazolidine-3-carbonyl)-5-(benzyloxy)pentanoate in THF:H$_2$O (4:1, 3.0 L) was added 30% aq. H$_2$O$_2$ (230 mL) at 0° C. over 20 min. To the mixture was added lithium hydroxide monohydrate (31.0 g, 738 mmol) in H$_2$O (300 mL), warmed to room temperature, and stirred overnight. The mixture was cooled to 0° C. and sodium sulfite (264 g, 2.10 mol) suspended in water (350 mL) was added in portions over 20 min (CAUTION-exotherm!). The mixture was stirred for 1.0 h and acidified to pH 5 with 2 N HCl. The mixture was concentrated to remove THF and reduce the volume. The resulting mixture was diluted with MTBE (1.0 L), the organics separated, and the aqueous phase was back-extracted with MTBE (2×500 mL). The organics were combined, washed with brine, dried over MgSO$_4$, filtered, and concentrated to provide a mixture of (R)-2-(2-(benzyloxy)ethyl)-4-tert-butoxy-4-oxobutanoic acid and chiral oxazolidinone auxiliary.

The crude oil was dissolved in MTBE (~1 L) and 1 N NaOH (1.0 L) was added to move the acid product into the aqueous phase as the carboxylate anion. The organic layer was back-extracted with 1 N NaOH (750 mL). The basic aqueous phase was extracted with MTBE (500 mL). The organic phases were discarded. The aqueous phase was diluted with MTBE (1.0 L) and the aqueous phase was acidified to pH 2 with 6 N HCl to fully protonate the carboxylate group and partition the compound into the organic phase. The phases were separated and the organics were washed with brine (1.0 L), dried over MgSO$_4$, filtered, and concentrated. The crude oil still contained up to 25% of the chiral auxiliary, the following cycle described above was repeated as follows.

The organics were dissolved in MTBE (1.0 L) and washed with 1 N NaOH (1.0 L). The phases were separated and the aqueous layer was extracted with MTBE (2×500 mL). The organic phases were discarded. The aqueous phase was diluted with MTBE (1.0 L) and the aqueous phase was acidified with 6 N HCl until pH~2 to move the acid back into the organic phase. The organics were isolated and washed with brine, dried over MgSO$_4$, filtered, and concentrated to give (R)-2-(2-(benzyloxy)ethyl)-4-tert-butoxy-4-oxobutanoic acid (137 g, 378 mmol, 78% yield, 91% ee) as a pale yellow oil; approx. 85% purity by $^1$H NMR. Exact mass calculated for C$_{17}$H$_{24}$O$_5$: 308.2, found: LCMS m/z=309.6, [M+H$^+$]; $^1$H NMR (400 MHz, CDCl$_3$) δ ppm 1.42 (s, 9 H), 1.83 (m, 1 H), 2.03 (m, 1 H), 2.45 (dd, J=16.5, J$_2$=5.4 Hz, 1 H), 2.64 (dd, J=16.5, J$_2$=8.6 Hz, 1 H), 2.98 (m, 1 H), 3.57 (t, J=6.2 Hz, 2 H), 4.50 (s, 2 H), 7.32 (m, 5 H).

The enantiomeric excess was determined by conversion of the acid to the corresponding (S)-Phg-OMe amide and (R)-Phg-OMe amide separately. The $^1$H NMR spectra from each amide derivative contained 4.5% of the corresponding diastereomer (91% de).

Step B: Preparation of (R)-4-tert-Butyl 1-methyl 2-(2-(benzyloxy)ethyl)succinate To a solution of (R)-2-(2-(benzyloxy)ethyl)-4-tert-butoxy-4-oxobutanoic acid (120 g, 388 mmol) in DMA (750 mL) was added NaHCO$_3$ (65.2 g, 776 mmol) followed by MeI (36.4 mL, 582 mmol) and stirred overnight at room temperature. Additional NaHCO$_3$ (130 g, 1.55 mol), and MeI (72.8 mL, 1.16 mol) were added and stirring was continuted for an additional 20 h. The mixture was filtered and the filtrate partitioned between MTBE (1.5 L) and H$_2$O (1.5 L). The aqueous phase was separated and back-extracted with MTBE (1.0 L). The combined organics were washed with H$_2$O (2×1.5 L), brine (1 L), dried over MgSO$_4$, and filtered. The filtrate was concentrated to give a pale yellow oil containing (R)-4-tert-butyl 1-methyl 2-(2-(benzyloxy)ethyl)succinate (140 g, 379 mmol, 98% yield). Exact mass calculated for C$_{18}$H$_{26}$O$_5$: 322.2, found: LCMS m/z=323.3, [M+H$^+$]; $^1$H NMR (400 MHz, CDCl$_3$) δ ppm 1.43 (s, 9 H), 1.82 (m, 1 H), 1.97 (m, 1 H), 2.42 (dd, J$_1$=16.3, J$_2$=5.3 Hz, 1 H), 2.63 (dd, J$_1$=16.5, J$_2$=9.0 Hz, 1 H), 2.96 (m, 1 H), 3.50 (t, J=6.2 Hz, 2 H), 3.65 (s, 3 H), 4.48 (s, 2 H), 7.32 (m, 5 H).

Example 1.4

Preparation of Preparation of (R)-Methyl 2-(7-hydroxy-2,3-dihydro-1H-pyrrolo[1,2-a]indol-1-yl)acetate Step A: Preparation of (R)-5-(Benzyloxy)-3-(5-(triisopropylsilyloxy)-1H-indol-2-yl)pentanoic acid To a solution of tert-butyl 2-methyl-4-(triisopropylsilyloxy)phenylcarbamate (181 g, 477 mmol) in THF (1 L) under N$_2$ at −40° C. (ACN/dry ice bath) was added sec-butyllithium (1.4 M in cyclohexane, 797 mL, 1.12 mol) over approximately 15 minutes via cannula/transfer needle. Stirring was continued for 1 h at which time the dilthiate was added via cannula/transfer needle to a solution of (R)-4-tert-butyl 1-methyl 2-(2-(benzyloxy)ethyl)succinate (98.5 g, 306 mmol) in THF (600 mL) cooled to −78° C. under N$_2$. The mixture was stirred at −78° C. for 30 min, and quenched w/aq. 10% citric acid solution (100 mL) while still cold. Let warm to approx 0° C. and added additional aq. 10% citric acid (400 mL) and EtOAc (1 L). Separated phases and washed organics w/aq. 10% citric acid (500 mL), and brine (500 mL). Dried organics over MgSO$_4$, filtered, and concentrated.

The concentrate was dissolved in DCM (1 L) and cooled to 0° C. in an ice bath (internal temp 15° C.). TMS-I (306 g, 1.53 mol) was added over 15 minutes (bubbling occurred likely due to the liberation of CO$_2$ from residual EtOAc, no increase in temp). The mixture was warmed to room temperature and stirred overnight. Added additional TMSI (100 g, 0.500 mol) and stirred for 1.5 h at room temperature. The mixture was added slowly to a solution of DCM/MeOH/Et$_3$N (1:1:1, 900 mL) cooled to 0° C. Concentrated mixture in vacuo. Diluted w/EtOAc (1.0 L) and washed w/2 N HCl (2×800 mL). Washed organics w/brine (800 mL), dried over MgSO$_4$, filtered, and concentrated.

The concentrate was dissolved in MTBE (600 mL). Cyclohexylamine (58.1 g, 586 mmol) was added followed by hexanes (75 mL) and heated gently for 2-3 minutes. The resulting mixture was cooled to room temperature and a white precipitate formed. After 0.5 h the mixture was filtered. The solid was re-suspended in MTBE (1 L) and heated gently. The suspension was filtered to provide the desired product as the cyclohexylamine salt. All filtrates combined and concentrated for later use (see below).

The solid was suspended in EtOAc (1.5 L) and treated with 2 N aq. HCl (1.0 L, to free cyclohexylamine). Separated phases and washed organics with 2 N HCl (750 mL) and brine (750 mL). Dried over MgSO$_4$, filtered, and concentrated to give 54 g of (R)-5-(benzyloxy)-3-(5-(triisopropylsilyloxy)-1H-indol-2-yl)pentanoic acid as a light brown oil (10 wt. % EtOAc). Exact mass calculated for C$_{29}$H$_{41}$NO$_4$Si: 495.3, found: LCMS m/z=496.3, [M+H$^+$]; $^1$H NMR (400 MHz, CDCl$_3$) δ ppm 1.12 (d, J=7.2 Hz, 18 H), 1.27 (m, 3 H), 2.03 (m, 2 H), 2.79 (m, 2 H), 3.51 (m, 3 H), 4.46 (d, J=11.7 Hz, 1 H), 4.53 (d, J=11.7 Hz, 1 H), 6.09 (d, J=1.7 Hz, 1 H), 6.71 (dd, J$_1$=8.6, J$_2$=2.4 Hz, 1 H), 6.98 (m, 2 H), 7.34 (m, 5 H), 8.36 (bs, 1 H).

The initial filtrates were treated with additional cyclohexylamine (10 mL) and loaded onto a silica gel column. Eluted w/50:50 hexanes/EtOAc containing 0.1% triethylamine for approximately 3 column volumes. The eluants were discarded. Flushed column w/25% EtOAc in hexanes (containing no triethylamine) for approx 2 column volumes and discarded eluant. A solvent system containing 0.5% AcOH in EtOAc was passed through the column to elute the desired acid. The fractions were concentrated in vacuo, dissolved in MTBE:EtOAc (1:1, 500 mL), and washed sequentially with sat. NaHCO$_3$ (2×500 mL), 1 N HCl (2×250 mL), and brine (250 mL) to give 25 g of a brown oil that contained additional (R)-5-(benzyloxy)-3-(5-(triisopropylsilyloxy)-1H-indol-2-yl)pentanoic acid.

Step B: Preparation of (R)-Methyl 5-(benzyloxy)-3-(5-(triisopropylsilyloxy)-1H-indol-2-yl)pentanoate To a solution of (R)-5-(benzyloxy)-3-(5-(triisopropylsilyloxy)-1H-indol-2-yl)pentanoic acid (54 g) in DMA (150 mL) was added NaHCO$_3$ (28.8 g, 343 mmol) followed by MeI (41.7 g, 294 mmol) and stirred overnight at room temperature. To the resulting mixture was added an additional amount of NaHCO$_3$ (15 g, 179 mmol) and MeI (25.0 g, 176 mmol) and the mixture was stirred an additional 20 h. To this mixture was added more NaHCO$_3$ (25 g, 297 mmol), and MeI (35.0 g, 247 mmol), and stirred overnight. The mixture was diluted with MTBE (1 L) and filtered. The filtrate was sequentially washed with H$_2$O (2×500 mL), sat. aqueous sodium bisulfite (500 mL), and brine (500 mL). The organics were dried organics over MgSO$_4$, filtered, and concentrated to give 59.6 g of an orange oil containing desired product.

The material isolated via column chromatography from above, Example 1.4, Step A, (25 g mixture) was dissolved in DMA (60 mL) and NaHCO$_3$ (14.0 g, 167 mmol) was added followed by MeI (54.7 g, 386 mmol) and stirred overnight at room temperature. To the resulting mixture was added an additional amount of NaHCO$_3$ (4.00 g, 47.6 mmol) and MeI (7.00 g, 49.3 mmol), and stirred at room temperature for an additional 2 h. The mixture was diluted with MTBE (500 mL). The organics were washed with H$_2$O (2×250 mL), brine (250 mL), and dried over MgSO$_4$. The organics were filtered, concentrated, and purified by silica gel chromatography (5% EtOAc in hexanes gradient to 30% EtOAc in hexanes) to give 4.43 g of the desired ester as a brown oil (~75 wt. %), along with higher molecular weight impurities.

In total, (R)-methyl 5-(benzyloxy)-3-(5-(triisopropylsilyloxy)-1H-indol-2-yl)pentanoate (52.5 g, 103 mmol, 33.7% yield) was obtained from (R)-4-tert-butyl 1-methyl 2-(2-(benzyloxy)ethyl)succinate (98.5 g, 306 mmol). Exact mass calculated for C$_{30}$H$_{43}$NO$_4$Si: 509.3, found: LCMS m/z=510.4, [M+H$^+$]; $^1$H NMR (400 MHz, CDCl$_3$) δ ppm 1.12 (d, J=7.2 Hz, 18 H), 1.27 (m, 3 H), 2.03 (m, 2 H), 2.74 (m, 2 H), 3.52 (m, 3 H), 3.66 (s, 3 H), 4.46 (d, J=11.7 Hz, 1 H), 4.52 (d, J=11.7 Hz, 1 H), 6.08 (d, J=1.7 Hz, 1 H), 6.71 (dd, J$_1$=8.6, J$_2$=2.3 Hz, 1 H), 6.97 (d, J=2.3 Hz, 1 H), 7.01 (d, J=8.6 Hz, 1 H), 7.34 (m, 5 H), 8.48 (bs, 1 H).

Step C: Preparation of (R)-Methyl 5-hydroxy-3-(5-(triisopropylsilyloxy)-1H-indol-2-yl)pentanoate To a solution of (R)-methyl 5-(benzyloxy)-3-(5-(triisopropylsilyloxy)-1H-indol-2-yl)pentanoate (52.5 g, 103 mmol in EtOAc (150 mL) was added 10% Pd/C (wet, 15 g) and placed in a Parr shaker under 45 psi of hydrogen for 2.5 h (dropped 10 psi during the 2.5 h). The mixture was filtered through celite and concentrated to give (R)-methyl 5-hydroxy-3-(5-(triisopropylsilyloxy)-1H-indol-2-yl)pentanoate (47.6 g, 93 mmol, 92% yield) as a viscous yellow oil. Exact mass calculated for C$_{23}$H$_{37}$NO$_4$Si: 419.2, found: LCMS m/z=420.3, [M+H$^+$]; $^1$H NMR (400 MHz, CDCl$_3$) δ ppm 1.11 (d, J=7.2 Hz, 18 H), 1.27 (m, 3 H), 1.97 (m, 2 H), 2.75 (m, 2 H), 3.49 (m, 1 H), 3.69 (m, 5 H), 6.13 (d, J=2.0 Hz, 1 H), 6.73 (dd, J$_1$=8.6, J$_2$=2.3 Hz, 1 H), 6.99 (d, J=2.3 Hz, 1 H), 7.21 (d, J=8.6 Hz, 1 H), 8.58 (bs, 1 H).

Step D: Preparation of (R)-Methyl 2-(7-hydroxy-2,3-dihydro-1H-pyrrolo[1,2-a]indol-1-yl)acetate To a solution of (R)-methyl 5-hydroxy-3-(5-(triisopropylsilyloxy)-1H-indol-2-yl)pentanoate (39.0 g, 93 mmol) in DCM (250 mL) at 0° C. was added MsCl (8.33 mL, 107 mmol) followed by DMAP (34.1 g, 279 mmol). The mixture was stirred with warming to room temperature over 1.5 h. The resulting mixture was concentrated to remove DCM and partitioned between MTBE (350 mL) and 1 N HCl (250 mL). The phases were separated and the organics washed with 1 N HCl (2×250 mL), sat. NaHCO$_3$ (250 mL), and brine (250 mL). The organics were dried over MgSO$_4$, filtered, and concentrated to give the intermediate mesylate. Exact mass calculated for C$_{24}$H$_{39}$NO$_6$SSi: 497.2, found: LCMS m/z=498.3, [M+H$^+$].

To a solution of the resulting mesylate dissolved in DMF (150 mL) at 0° C. was added NaI (2.79 g, 18.6 mmol) followed by addition of NaH (2.0 equiv., 60% dispersion in mineral oil) over 2 min. The resulting mixture was stirred for 2.0 h and quenched by addition to ice water. The mixture was acidified with 1 N HCl and extracted w/MTBE (3×500 mL). The organics were washed with water (2×500 mL), and brine (500 mL). The phases were separated, and the organics were dried over MgSO$_4$, filtered, and concentrated.

The concentrate was dissolved in THF (250 mL) and treated with TBAF (1.0M in THF, (139 mL, 139 mmol). After stirring at room temperature for 2 h the resulting mixture was diluted with MTBE (500 mL), washed with 1 N HCl (2×250 mL), and brine (250 mL). The phases were separated and the organics were dried over MgSO$_4$, filtered, and concentrated. The crude material obtained contained a significant amount of free acid as determined by LC/MS. The crude material was subsequently dissolved in PhMe:MeOH (2:1, 450 mL) and cooled to 0° C. To the resulting mixture was added TMS-Diazomethane (2.0 M in Et$_2$O, 67.4 mL, 135 mmol) slowly over 10 min and stirred for 15 min. The reaction mixture was quenched with AcOH (10 mL), stirred for 10 min, and the solution was concentrated in vacuo.

The resulting concentrate was treated with MTBE:hexanes (3:1, 100 mL) and heated gently. Upon cooling, the suspension was filtered to provide (R)-methyl 2-(7-hydroxy-2,3-dihydro-1H-pyrrolo[1,2-a]indol-1-yl)acetate as a light pink solid (batch 1: 12.2 g, 90% purity, 98% ee). The filtrate was concentrated and the above precipitation process was repeated to give an additional 1.00 g of (R)-methyl 2-(7-hydroxy-2,3-dihydro-1H-pyrrolo[1,2-a]indol-1-yl)acetate as a yellow solid (90% purity, 80% ee).

All remaining filtrates were concentrated and purified by silica gel chromatography (40% EtOAc in hexanes gradient to 85% EtOAc in hexanes). The fractions containing product were concentrated and precipitated by treatment w/MTBE/ hexanes to give (R)-methyl 2-(7-hydroxy-2,3-dihydro-1H-pyrrolo[1,2-a]indol-1-yl)acetate as a white solid (1.99 g, 45% ee) after filtration.

In total, (R)-methyl 2-(7-hydroxy-2,3-dihydro-1H-pyrrolo[1,2-a]indol-1-yl)acetate (15.5 g, 56.9 mmol, 61.2% yield) was obtained. Exact mass calculated for $C_{14}H_{15}NO_3$: 245.1, found: LCMS m/z=246.1, [M+H$^+$]; $^1$H NMR (400 MHz, d$_6$-DMSO) δ ppm 2.20 (m, 1 H), 2.66 (dd, $J_1$=16.1, $J_2$=7.8 Hz, 1 H), 2.75 (m, 2 H), 3.58 (m, 1 H), 3.66 (s, 3 H), 3.92 (m, 1 H), 4.05 (m, 1 H), 5.88 (s, 1 H), 6.54 (dd, $J_1$=8.6, $J_2$=2.3 Hz, 1 H), 6.77 (d, J=2.3 Hz, 1 H), 7.06 (d, J=8.6 Hz, 1 H), 8.55 (s, 1 H).

Enantiomeric excess was determined via chiral HPLC analysis [250 mm×4.6 mm Chiralcel® OD-H column, 20% IPA in hexanes containing 0.05% TFA, 1 mL/min. 1st peak (S)-enantiomer, t$_r$=15.2 min; 2nd peak (R)-enantiomer, t$_r$=16.8 min].

Example 1.5

(R)-Ethyl 2-(7-Hydroxy-2,3-dihydro-1H-pyrrolo[1,2-a]indol-1-yl)acetate

Step A: Preparation of Ethyl 5-(Benzyloxy)-1H-indole-2-carboxylate

To a mixture of sulfuric acid (80.0 mL, 1.50 mol) dissolved in Ethanol (450 mL) at 0° C. was added (4-(benzyloxy)phenyl)hydrazine hydrochloride (90.0 g, 359 mmol) to form a suspension. To the suspension was added ethyl 2-oxopropanoate (43.9 mL, 395 mmol) in EtOH (90 mL) and mechanically stirred for 2 h using a mechanical stirrer. The mixture was heated to 45° C. and maintained for 16 h. The mixture was cooled to room temperature and cold EtOH (200 mL) was added. The mixture was filtered through a course frit. The collected solid was washed sequentially with cold EtOH, hexanes, and water. The solid was dried in a vacuum oven (45° C., 2 Ton) to give ethyl 5-(benzyloxy)-1H-indole-2-carboxylate (73.1 g, 247 mmol, 69% yield). Exact mass calculated for $C_{18}H_{17}NO_3$: 295.1, found: LCMS m/z=296.2, [M+H$^+$]; $^1$H NMR (400 MHz, CDCl$_3$) δ ppm 1.41 (t, J=7.1 Hz, 3 H), 4.40 (q, J=7.1 Hz, 2 H), 5.10 (s, 2 H), 7.08 (dd, $J_1$=8.9, $J_2$=2.4 Hz, 1 H), 7.14 (d, J=1.6 Hz, 1 H), 7.20 (d, J=2.3 Hz, 1 H), 7.32 (m, 2 H), 7.39 (m, 2 H), 7.47 (m, 2 H), 8.75 (bs, 1 H).

Step B: Preparation of Potassium 7-(Benzyloxy)-2-(ethoxycarbonyl)-3H-pyrrolo[1,2-a]indol-1-olate To a 5000 mL, 3-neck round bottom flask equipped with a mechanical stirrer, a temperature probe, a nitrogen inlet, and a heating mantle was added ethyl 5-(benzyloxy)-1H-indole-2-carboxylate (150 g, 508 mmol) followed by anhydrous THF (2000 mL). To the resulting mixture was added potassium t-butoxide (1.0 M in THF, 762 mL, 762 mmol) via an addition funnel over 15 min (temperature increased from 20° C. to 26° C. over the addition time). The mixture was stirred for 1 h and ethyl acrylate (166 mL, 1.52 mol) was added via addition funnel over 15 min (temp increase to 34° C.). The addition funnel was replaced with a reflux condenser and the mixture heated to reflux and stirred for 18 h (the product started to appear as a white precipitate after only 0.5 h of heating). The flask was cooled to room temperature. The resulting precipitate was collected by vacuum filtration. The filtrate was concentrated to approximately 750 mL and diluted with MTBE (approx. 500 mL). Additional product precipitated and this material was filtered and added to the original filter cake. The combined solids were washed with cold THF:MTBE (1:1) and vacuum oven dried (45° C., 2 Ton) to give potassium 7-(benzyloxy)-2-(ethoxycarbonyl)-3H-pyrrolo[1,2-a]indol-1-olate as an off-white solid (120 g, 61% yield). Exact mass calculated for $C_{21}H_{19}NO_4$ (protonated keto-enol form): 349.1, found: LCMS m/z=350.3, [M+H$^+$]; $^1$H NMR (400 MHz, d$_6$-DMSO) δ ppm 1.18 (t, J=7.1 Hz, 3 H), 3.99 (q, J=7.1 Hz, 2 H), 4.59 (s, 2 H), 5.09 (s, 2 H), 6.14 (s, 1 H), 6.80 (dd, $J_1$=8.8, $J_2$=2.3 Hz, 1 H), 7.11 (d, J=2.3 Hz, 1 H), 7.30 (m, 2 H), 7.38 (m, 2 H), 7.46 (m, 2 H).

Step C: Preparation of 7-(Benzyloxy)-2,3-dihydro-1H-pyrrolo[1,2-a]indol-1-one; this rxn was run as 4 separate batches in parallel as described below To a 3-neck, 5L RB flask equipped w/a mechanical stirrer, temperature probe, and a reflux condenser was added potassium 7-(benzyloxy)-2-(ethoxycarbonyl)-3H-pyrrolo[1,2-a]indol-1-olate (206 g, 530 mmol) followed by AcOH:H$_2$O (2:1, v/v, 2.65 L). The mixture was heated to reflux for 40 h and cooled to room temperature. Upon cooling a light brown precipitate formed. The mixtures from all four batches were combined and filtered. The solid was washed with H$_2$O and hexanes. The filtrates were further diluted with water (1 L) and an additional solid precipitated. The 2$^{nd}$ crop was filtered and the solid washed with water and hexanes. Both crops were combined and dried in a vacuum oven (50° C., 2 Ton) to give 7-(benzyloxy)-2,3-dihydro-1H-pyrrolo[1,2-a]indol-1-one (493 g from all 4 batches, 1.72 mol, 81% yield) as a brown solid. Exact mass calculated for $C_{18}H_{15}NO_2$: 277.1, found: LCMS m/z=278.2, [M+H$^+$]; $^1$H NMR (400 MHz, CDCl$_3$) δ ppm 3.20 (t, J=6.4 Hz, 2 H), 4.40 (t, J=6.4 Hz, 2 H), 5.11 (s, 2 H), 6.91 (s, 1 H), 7.13 (dd, $J_1$=9.0, $J_2$=2.3 Hz, 1 H), 7.20 (d, J=2.3 Hz, 1 H), 7.33 (m, 2 H), 7.39 (m, 2 H), 7.47 (m, 2 H).

Step D: Preparation of (E)-Ethyl 2-(7-(Benzyloxy)-2,3-dihydro-1H-pyrrolo[1,2-a]indol-1-ylidene)acetate, this reaction was run as 4 separate batches in parallel as described below To a 5000 mL 3-neck round bottom flask at room temperature under N$_2$ equipped with a mechanical stirrer, an addition funnel, and a temperature probe containing a solution of ethyl 2-(diethoxyphosphoryl)acetate (114 mL, 577 mmol) in THF (2.0 L) was added potassium t-butoxide (1.0 M in THF, 554 mL, 554 mmol) via addition funnel over 10 minutes (temp increase from 22° C. to 29° C.). The reaction mixture was stirred for 2 h and 7-(benzyloxy)-2,3-dihydro-1H-pyrrolo[1,2-a]indol-1-one (123 g, 444 mmol) was added in 4 portions. An additional amount of THF (750 mL) was added to further dissolve ketone. The mixture was stirred at room temperature for 16 h. Anaylasis of an aliquat from the reaction mixture using LC/MS revealed approximately 75-85% conversion to the title compound.

A separate solution of ylide (0.4 equiv. total, 710 mmol) was prepared as described below.

To a 5000 mL flask with a mechanical stirrer and nitrogen inlet at room temperature under N$_2$ containing a solution of ethyl 2-(diethoxyphosphoryl)acetate (167 g, 745.5 mmol) in THF (1.25 L) was added potassium t-butoxide (1 M in THF, 710 mL, 710 mmol) over 10 min via addition funnel. After stirring for 1.5 h, 500 mL of this solution was added to each of the four reaction mixtures via addition funnel and the mixture was stirred an additional 20 h at room temperature.

The resulting reaction mixtures were separately filtered through a pad of sand (approx 3 cm×15 cm) atop celite (approx 5 cm×15 cm) in a 3000 mL course fritted buchner funnel to remove insoluble phosphate salts. The filter cake was washed with THF and the organics were concentrated for each filtrate to approximately half volume. All combined filtrates were combined in a 20L heavy-walled SCHOTT/Duran filter flask (9 L total volume). The mixture was placed in an ice bath and agitated with a mechanical stirrer as IPA (enough to double volume, 8 L) was added to precipitate product. To the mixture was added a small batch of seed crystals and the resulting mixture was agitated overnight. The mixture was filtered to leave behind a beige solid that was vacuum oven-dried (45° C., 2 Torr) to give 249 g of (E)-ethyl 2-(7-(benzyloxy)-2,3-dihydro-1H-pyrrolo[1,2-a]indol-1-ylidene)acetate.

The filtrates were concentrated to half volume (8 L) and allowed to sit overnight. Filtration gave a $2^{nd}$ crop (190 g) of a dark-brown solid that was ~75% pure as determined by LC/MS analysis. The $2^{nd}$ crop was suspended in IPA:ACN (2:1, v/v, 450 mL) and heated to 80° C. for 3 h. Cooled to 40° C. and filtered through a medium-fritted filter. The filter cake was washed sequentially with warm IPA:ACN (2:1), cold IPA, and hexanes to give additional (E)-ethyl 2-(7-(benzyloxy)-2,3-dihydro-1H-pyrrolo[1,2-a]indol-1-ylidene)acetate as a light brown solid (90.5 g).

In total (E)-ethyl 2-(7-(benzyloxy)-2,3-dihydro-1H-pyrrolo[1,2-a]indol-1-ylidene)acetate (339 g, 974 mmol, 58% yield) was obtained as a light brown solid. Exact mass calculated for $C_{22}H_{21}NO_3$: 347.2, found: LCMS m/z=348.3, [M+H$^+$]; $^1$H NMR (400 MHz, CDCl$_3$) δ ppm 1.34 (t, J=7.1 Hz, 3 H), 3.79 (td, J$_1$=6.6, J$_2$=2.4 Hz, 2 H), 4.23 (m, 4 H), 5.11 (s, 2 H), 6.30 (t, J=2.4 Hz, 1 H), 6.62 (s, 1 H), 6.99 (dd, J$_1$=8.9, J$_2$=2.3 Hz, 1 H), 7.13 (d, J=2.3 Hz, 1 H), 7.22 (d, J=8.9 Hz, 1 H), 7.33 (m, 1 H), 7.39 (m, 2 H), 7.48 (m, 2 H).

Step E: Preparation of (R)-Ethyl 2-(7-(Benzyloxy)-2,3-dihydro-1H-pyrrolo[1,2-a]indol-1-yl)acetate In a 500 mL round flask under N$_2$ was added a mixture of copper(II) acetate hydrate (259 mg, 1.30 mmol) and (R)-(−)-1-[(S)-2-(diphenylphosphino)ferrocenyl]ethyldi-tert-butylphosphine (710 mg, 1.30 mmol) in anhydrous THF (100 mL) and the mixture was stirred for 30 min. To the resulting mixture was added poly(methylhydrosiloxane) (PMHS) (49.0 mL) and stirred for an additional 30 min. The mixture was transferred via cannula into a 3000 mL flask containing a solution of (E)-ethyl 2-(7-(benzyloxy)-2,3-dihydro-1H-pyrrolo[1,2-a]indol-1-ylidene)acetate (90.0 g, 259 mmol) in anhydrous THF (1500 mL) cooled to 5° C. (external ice-salt bath, internal temperature). To the resulting mixture was added t-BuOH (74.3 mL, 777 mmol) and the mixture was mechanically stirred under N$_2$ while slowly warming to 10° C. over 16 h. The mixture was diluted with MTBE (1000 mL), washed with sat. aq. NH$_4$Cl (500 mL), and brine (500 mL). The organics were dried over MgSO$_4$, filtered, and concentrated in vacuo. The product was recrystallized from methanol and the resulting solid (crop 1) was washed with hexanes. The filtrate was concentrated and the above process was repeated to give two additional crops of product.

In total (R)-ethyl 2-(7-(benzyloxy)-2,3-dihydro-1H-pyrrolo[1,2-a]indol-1-yl)acetate (81.1 g, 232 mmol, 90% yield) was obtained as a tan crystalline solid. Exact mass calculated for $C_{22}H_{23}NO_3$: 349.2, found: LCMS m/z=350.3, [M+H$^+$]; $^1$H NMR (400 MHz, CDCl$_3$) δ ppm 1.30 (t, J=7.2 Hz, 3 H), 2.38 (m, 1 H), 2.57 (dd, J$_1$=16.0, J$_2$=8.6 Hz, 1 H), 2.83 (dd, J$_1$=16.0, J$_2$=6.3 Hz, 1 H), 2.88 (m, 1 H), 3.75 (m, 1 H), 3.99 (dt, J$_1$=9.8, J$_2$=7.4 Hz, 1 H), 4.11 (ddd, J$_1$=9.8, J$_2$=8.7 Hz, J$_3$=4.3 Hz, 1 H), 4.21 (q, J=7.2 Hz, 2 H), 5.10 (s, 2 H), 6.08 (s, 1 H), 6.88 (dd, J$_f$=8.7, J$_2$=2.4 Hz, 1 H), 7.12 (m, 2 H), 7.30 (m, 1 H), 7.38 (m, 2 H), 7.47 (m, 2 H).

A number of other chiral phosphine ligands were employed utilizing conditions as shown in the following table to provide the R enantiomer with at least an ee % of 69% or greater.

Table of Phosphine Ligands, Conditions and % ee

| Chiral Phosphine Ligand | Solvent | Temp ° C. | % ee (Configuration) |
|---|---|---|---|
| (R)-BINAP | THF | 5 | 76% (R) |
| (R)-BINAP | Toluene | 5 | 69% (R) |
| (R)-BINAP | THF | 25 | 77% (R) |
| (R)-BINAP | Toluene | 25 | 89% (R) |
| (R)-xylyl-BINAP | THF | 5 | 83% (R) |
| (R)-xylyl-BINAP | Toluene | 5 | 75% (R) |
| (R)-xylyl-BINAP | THF | 25 | 79% (R) |
| (R)-xylyl-BINAP | Toluene | 25 | 76% (R) |
| (R)-DTBM-SEGPHOS | THF | 5 | 97% (R) |
| (R)-DTBM-SEGPHOS | Toluene | 5 | 97% (R) |
| (R)-DTBM-SEGPHOS | THF | 25 | 95% (R) |
| (R)-DTBM-SEGPHOS | Toluene | 25 | 96% (R) |
| (R,S)-PPF-P(t-Bu)$_2$ | THF | 5 | 96% (R) |
| (R,S)-PPF-P(t-Bu)$_2$ | Toluene | 5 | 99% (R) |
| (R,S)-PPF-P(t-Bu)$_2$ | Toluene | 25 | 79% (R) |

(R)-BINAP is (R)-(+)-2,2'-bis(diphenylphosphino)-1,1'-binaphthyl;
(R)-xylyl-BINAP is (R)-(+)-2,2'-bis[di(3,5-xylyl)phosphino]-1,1'-binaphthyl;
(R)-DTBM-SEGPHOS is (R)-(−)-5,5'-bis[di(3,5-di-t-butyl-4-methoxyphenyl)phosphino]-4,4'-bi-1,3-benzodioxole; and
(R,S)-PPF-P(t-Bu)$_2$ is (R)-(−)-1-[(S)-2-(diphenylphosphino)ferrocenyl]ethyldi-tert-butylphosphine.

Step F: Preparation of (R)-ethyl 2-(7-hydroxy-2,3-dihydro-1H-pyrrolo[1,2-a]indol-1-yl)acetate (R)-ethyl 2-(7-(benzyloxy)-2,3-dihydro-1H-pyrrolo[1,2-a]indol-1-yl)acetate (81.1 g, 232 mmol was dissolved in EtOAc (1.0 L) and washed w/aq. 0.5 N HCl (2×350 mL). The organics were dried over MgSO$_4$, filtered, and concentrated to a total volume of approximately 600 mL. The solution was transferred to a Parr bottle and 10% Pd/C (22 g) was added. The mixture was placed on a Parr shaker under 50 psi of hydrogen for 3.5 h. The mixture was filtered through celite and concentrated in vacuo. The crude material was treated with hexanes:MTBE (1:1, v/v, 500 mL), and concentrated to give a white paste. The resulting paste was suspended in a mixture of hexanes:MTBE (2:1, v/v, 350 mL) and filtered. The filter cake was washed with hexanes (twice) to provide a $1^{st}$ crop of (R)-ethyl 2-(7-hydroxy-2,3-dihydro-1H-pyrrolo[1,2-a]indol-1-yl)acetate as a white solid (~70 g, wet). Upon standing the combined filtrates contained additional precipitated product that was filtered and washed with hexanes (twice) to give a 2nd crop (~7 g, wet) of (R)-ethyl 2-(7-hydroxy-2,3-dihydro-1H-pyrrolo[1,2-a]indol-1-yl)acetate. All remaining filtrates were concentrated and purified by silica gel chromatography (45% EtOAc in hexanes gradient to 85% EtOAc in hexanes). Concentration of the fractions containing the product provided a white solid that was filtered and washed with hexanes to give an additional 6.73 g of desired product.

All solids were combined and dried in an vacuum oven (45° C., 2 Torr) to give (R)-ethyl 2-(7-hydroxy-2,3-dihydro-1H-pyrrolo[1,2-a]indol-1-yl)acetate (53.86 g, 204 mmol, 88% yield, >98% ee) as a white solid. Exact mass calculated for $C_{15}H_{17}NO_3$: 259.1, found: LCMS m/z=260.2, [M+H$^+$]; $^1$H NMR (400 MHz, d$_6$-DMSO) δ ppm 1.21 (t, J=7.1 Hz, 3 H), 2.20 (m, 1 H), 2.63 (dd, J$_1$=16.0, J$_2$=7.7 Hz, 1 H), 2.75 (m, 2 H), 3.58 (m, 1 H), 3.92 (dt, J$_1$=9.9, J$_2$=7.4 Hz, 1 H), 4.05 (ddd, J$_1$=9.9, J$_2$=8.5 Hz, J$_3$=4.4 Hz, 1 H), 4.13 (qd, J$_1$=7.1, J$_2$=1.3 Hz, 1 H), 5.87 (s, 1 H), 6.54 (dd, J$_1$=8.6, J$_2$=2.3 Hz, 1 H), 6.77 (d, J=2.3 Hz, 1 H), 7.06 (d, J=8.6 Hz, 1 H), 8.54 (s, 1 H).

Enantiomeric excess was determined via chiral HPLC analysis [250 mm×4.6 mm Chiralcel® OD-H column, 7% IPA in hexanes, 1 mL/min. 1st peak-minor enantiomer (S) $t_r$=45.3 min, 2nd peak-major enantiomer (R) $t_r$=50.2 min].

Example 1.6

Preparation of (R)-2-(9-chloro-7-(4-isopropoxy-3-(trifluoromethyl)benzyloxy)-2,3-dihydro-1H-pyrrolo[1,2-a]indol-1-yl)acetic acid Step A: Preparation of (R)-ethyl 2-(7-(4-isopropoxy-3-(trifluoromethyl)benzyloxy)-2,3-dihydro-1H-pyrrolo[1,2-a]indol-1-yl)acetate To a solution of (R)-ethyl 2-(7-hydroxy-2,3-dihydro-1H-pyrrolo[1,2-a]indol-1-yl)acetate (35.0 g, 135 mmol) in DMF (250 mL) was added $Cs_2CO_3$ (66.0 g, 202 mmol). After stirring for 5 min, 4-(chloromethyl)-1-isopropoxy-2-(trifluoromethyl)benzene (34.1 g, 135 mmol) was added and the mixture was stirred overnight at 65° C. (oil bath temp) under $N_2$. The mixture was cooled to room temperature, filtered, and concentrated in vacuo via rotary evaporator (5 Torr, 45° C. water bath temperature) to near dryness. The concentrate was partitioned between EtOAc:MTBE (3:1, v/v, 1.5 L was needed to see phase separation) and $H_2O$ (1 L). The phases were separated and the aqueous phase was acidified with aqueous 2 N HCl. The aqueous phased was extracted with EtOAc (1 L). The organics were combined, dried over $MgSO_4$, filtered, and concentrated. The concentrate was treated with MTBE:hexanes (1:1, v/v, 300 mL) to precipitate the product. The mixture was filtered and the solid was washed with hexanes (twice) to give a $1^{st}$. crop (40 g) of product. The combined filtrates contained additional precipitated product that was filtered and washed with hexanes (twice) to give a $2^{nd}$ crop of product (1.5 g).

All filtrates were concentrated and purified by silica gel chromatography (10% EtOAc in hexanes gradient to 45% EtOAc in hexanes). The product containing fractions were concentrated to near dryness to give a white solid that was filtered and washed with hexanes.

All solids were combined and dried in a vacuum oven (45° C., 2 Torr, 1 h) to give (R)-ethyl 2-(7-(4-isopropoxy-3-(trifluoromethyl)benzyloxy)-2,3-dihydro-1H-pyrrolo[1,2-a]indol-1-yl)acetate (52.81 g, 111 mmol, 82% yield) as a white solid. Exact mass calculated for $C_{26}H_{28}F_3NO_4$: 475.2, found: LCMS m/z=476.2, [M+H$^+$]; $^1$H NMR (400 MHz, CDCl$_3$) δ ppm 1.30 (t, J=7.1 Hz, 3 H), 1.37 (d, J=6.1 Hz, 6 H), 2.28 (m, 1 H), 2.58 (dd, $J_1$=16.0, $J_2$=8.5 Hz, 1 H), 2.82 (dd, $J_1$=16.0, $J_2$=6.3 Hz, 1 H), 2.88 (m, 1 H), 3.75 (m, 1 H), 4.00 (dt, $J_1$=9.9, $J_2$=7.5 Hz, 1 H), 4.11 (ddd, $J_1$=9.9, $J_2$=8.5 Hz, $J_3$=4.2 Hz 1 H), 4.21 (qd, $J_1$=7.1, $J_2$=0.8 Hz, 2 H), 4.64 (sep, J=6.1 Hz, 1 H), 5.02 (s, 2 H), 6.08 (s, 1 H), 6.85 (dd, $J_1$=8.7, $J_2$=2.4 Hz, 1 H), 7.00 (d, J=8.5 Hz, 1 H), 7.09 (d, J=2.3 Hz, 1 H), 7.13 (d, J=8.7 Hz, 1 H), 7.55 (dd, $J_1$=8.5, $J_2$=2.0 Hz, 1 H), 7.66 (d, J=2.0 Hz, 1 H).

Step B: Preparation of (R)-ethyl 2-(9-chloro-7-(4-isopropoxy-3-(trifluoromethyl)benzyloxy)-2,3-dihydro-1H-pyrrolo[1,2-a]indol-1-yl)acetate To a solution of (R)-ethyl 2-(7-(4-isopropoxy-3-(trifluoromethyl)benzyloxy)-2,3-dihydro-1H-pyrrolo[1,2-a]indol-1-yl)acetate (52.8 g, 111 mmol) in DCM (350 mL) at −5° C. (ice-salt bath) was added a solution of NCS (14.8 g, 111 mmol) in DCM (350 mL) slowly over 20 min via addition funnel. After stirring for 0.5 h the mixture was washed w/sat. aq. sodium thiosulfate (300 mL). The organics were concentrated to about 300 mL and filtered using a column (60 cm×80 cm) containing sodium sulfate (top layer), sand (middle layer), and silica gel (bottom) using DCM as the eluant. The filtrate was concentrated to give (R)-ethyl 2-(9-chloro-7-(4-isopropoxy-3-(trifluoromethyl)benzyloxy)-2,3-dihydro-1H-pyrrolo[1,2-a]indol-1-yl)acetate (54.6 g, 107 mmol, 96% yield) as a white/mildly yellow solid. Exact mass calculated for $C_{26}H_{27}ClF_3NO_4$: 509.2, found: LCMS m/z=510.3, [M+H$^+$]; $^1$H NMR (400 MHz, CDCl$_3$) δ ppm 1.28 (t, J=7.1 Hz, 3 H), 1.37 (d, J=6.1 Hz, 6 H), 2.34 (m, 1 H), 2.52 (dd, $J_1$=16.3, $J_2$=10.2 Hz, 1 H), 2.93 (m, 1 H), 3.22 (dd, $J_1$=16.3, $J_2$=4.0 Hz, 1 H), 3.81 (m, 1 H), 4.00 (m, 1 H), 4.12 (m, 1 H), 4.20 (qd, $J_1$=7.1, $J_2$=1.7 Hz, 2 H), 4.65 (sep, J=6.1 Hz, 1 H), 5.04 (s, 2 H), 6.89 (dd, $J_1$=8.8, $J_2$=2.4 Hz, 1 H), 7.01 (d, J=8.6 Hz, 1 H), 7.06 (d, J=2.4 Hz, 1 H), 7.12 (d, J=8.8 Hz, 1 H), 7.56 (dd, $J_1$=8.5, $J_2$=1.9 Hz, 1 H), 7.67 (d, J=1.9 Hz, 1 H).

Step C: Preparation of (R)-2-(9-chloro-7-(4-isopropoxy-3-(trifluoromethyl)benzyloxy)-2,3-dihydro-1H-pyrrolo[1,2-a]indol-1-yl)acetic acid To a solution of (R)-ethyl 2-(9-chloro-7-(4-isopropoxy-3-(trifluoromethyl)benzyloxy)-2,3-dihydro-1H-pyrrolo[1,2-a]indol-1-yl)acetate (54.6 g, 107 mmol) in dioxane (750 mL) and MeOH (75 mL) was added NaOH (aq. 3N, 89.0 mL, 268 mmol). The mixture was stirred at room temperature for 17 h, concentrated in vacuo to approx 150 mL, and acidified with aqueous 3N HCl (300 mL). The resulting slurry was shaken and the solid filtered, washed with $H_2O$ (twice), hexanes and dried in a vacuum oven (50° C., 2 Torr, 15 h) to give (R)-2-(9-chloro-7-(4-isopropoxy-3-(trifluoromethyl)benzyloxy)-2,3-dihydro-1H-pyrrolo[1,2-a]indol-1-yl)acetic acid (51.3 g, 101 mmol, 94% yield, >98% ee) as a white solid. Exact mass calculated for $C_{24}H_{23}ClF_3NO_4$: 481.1, found: LCMS m/z=482.2, [M+H$^+$]; $^1$H NMR (400 MHz, CD$_3$CN) δ ppm 1.33 (d, J=6.0 Hz, 6 H), 2.34 (m, 1 H), 2.58 (dd, $J_1$=16.5, $J_2$=9.7 Hz, 1 H), 2.86 (m, 1 H), 3.06 (dd, $J_1$=16.5, $J_2$=4.2 Hz, 1 H), 3.73 (m, 1 H), 4.01 (m, 1 H), 4.14 (ddd, $J_1$=9.9, $J_2$=8.5 Hz, $J_3$=4.9 Hz 1 H), 4.75 (sep, J=6.0 Hz, 1 H), 5.08 (s, 2 H), 6.87 (dd, $J_1$=8.8, $J_2$=2.4 Hz, 1 H), 7.01 (d, J=2.4 Hz, 1 H), 7.18 (d, J=8.6 Hz, 1 H), 7.21 (d, J=8.8 Hz, 1 H), 7.63 (dd, $J_1$=8.6, $J_2$=2.1 Hz, 1 H), 7.68 (d, J=2.1 Hz, 1 H), 9.10 (bs, 1 H).

Enantiomeric excess was determined via chiral HPLC analysis [250 mm×10 mm Chiralpak® IA column, 35% MTBE in hexanes containing 0.1% TFA, 8 mL/min. 1st peak-minor enantiomer (S) $t_r$=27.9 min, 2nd peak-major enantiomer. (R) $t_r$=29.0 min].

Example 1.7

Preparation of (R)-tert-Butyl 2-(7-hydroxy-2,3-dihydro-1H-pyrrolo[1,2-a]indol-1-yl)acetate Step A: Preparation of (Z)-tert-Butyl 2-(7-(benzyloxy)-2,3-dihydro-1H-pyrrolo[1,2-a]indol-1-ylidene)acetate

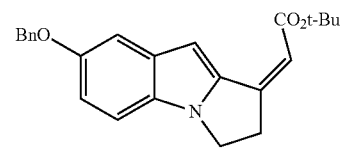 [SMILES: CC(C)(C)OC(=O)/C=C1/CCn2c1cc1cc(OCc3ccccc3)ccc12]

A mixture of 7-(benzyloxy)-2,3-dihydro-1H-pyrrolo[1,2-a]indol-1-one (20.0 g, 72.1 mmol) and tert-Butyl(triphenylphosphoranylidene)acetate (136 g, 361 mmol) in THF (700 mL) was heated at reflux for 4 days. Additional and tert-Butyl(triphenylphosphoranylidene)acetate (27.1 g, 72.1 mmol) was added and stirring at reflux was continued for an additional 24 h. The mixture was cooled to room temperature and the solvent was removed under reduced pressure. Recrystallization from hot IPA gave (E)-tert-butyl 2-(7-(benzyloxy)-2,3-dihydro-1H-pyrrolo[1,2-a]indol-1-ylidene)acetate as a white solid. Exact mass calculated for $C_{24}H_{25}NO_3$: 375.2, found: LCMS m/z=376.2, (M+H$^+$); $^1$H NMR (400 MHz, CDCl$_3$) δ ppm 1.53 (s, 9 H), 3.75 (td, $J_1$=6.4, $J_2$=2.4 Hz, 2 H), 4.20 (t, J=6.4 Hz, 2 H), 5.11 (s, 2 H), 6.23 (t, J=2.4 Hz, 1 H), 6.58 (s, 1 H), 6.98 (dd, $J_1$=8.9, $J_2$=2.3 Hz, 1 H), 7.13 (d, J=2.3 Hz, 1 H), 7.21 (d, J=8.9 Hz, 1 H), 7.33 (m, 1 H), 7.39 (m, 2 H), 7.48 (m, 2 H).

Isolation of pure (Z)-tert-butyl 2-(7-(benzyloxy)-2,3-dihydro-1H-pyrrolo[1,2-a]indol-1-ylidene)acetate was accomplished as follows. The filtrates from the recyrstallization above were concentrated under reduced pressure and suspended in ether which precipitated tert-butyl(triphenylphosphoranylidene)acetate as a white solid that was removed via vacuum filtration. The solid was discarded and the filtrates were treated with hexanes to precipitate triphenylphosphine oxide which was removed by filtration. The remaining solvent was removed under reduced pressure and the crude residue purified via column chromatography (0% EtOAc in hexanes gradient to 40% EtOAc/hexanes, silica) to give pure (Z)-tert-butyl 2-(7-(benzyloxy)-2,3-dihydro-1H-pyrrolo[1,2-a]indol-1-ylidene)acetate. Exact mass calculated for $C_{24}H_{25}NO_3$: 375.2, found: LCMS m/z=376.2, [M+H$^+$]; $^1$H NMR (400 MHz, CDCl$_3$) δ ppm 1.56 (s, 9 H), 3.40 (m, 2 H), 4.13 (t, J=6.6 Hz, 2 H), 5.11 (s, 2 H), 5.80 (s, 1 H), 7.00 (dd, $J_1$=9.0, $J_2$=2.2 Hz, 1 H), 7.18 (m, 2 H), 7.33 (m, 1 H), 7.39 (m, 2 H), 7.48 (m, 2 H), 7.55 (s, 1 H).

Step B: Preparation of (R)-tert-Butyl 2-(7-(benzyloxy)-2,3-dihydro-1H-pyrrolo[1,2-a]indol-1-yl)acetate from (Z)-tert-butyl 2-(7-(benzyloxy)-2,3-dihydro-1H-pyrrolo[1,2-a]indol-1-ylidene)acetate and (S)-BINAP A mixture of copper(II) acetate hydrate (13.0 mg, 0.067 mmol) and (S)-2,2'-bis(diphenylphosphino)-1,1'-binaphthyl (41.0 mg, 0.067 mmol) were stirred for 30 min in toluene (2 mL) at room temperature under nitrogen. To this mixture was added Polymethyl hydrosiloxane (0.330 mL) and the mixture was allowed to stir for an additional 30 min. A solution of (Z)-tert-butyl 2-(7-(benzyloxy)-2,3-dihydro-1H-pyrrolo[1,2-a]indol-1-ylidene)acetate (0.332 g, 0.880 mmol) in toluene (2 mL) was added followed by t-BuOH (0.509 mL, 5.33 mmol). The mixture was sealed in a vial under nitrogen and allowed to stir overnight.

Sat. NH$_4$Cl (20 mL) was added and the mixture was extracted with ether. The organics were washed with brine, dried (MgSO$_4$), filtered, and concentrated. The solvent was removed under reduced pressure. The residue was purified via silica gel chromatography (0% EtOAc in hexanes gradient to 30% EtOAc in hexanes) to give (R)-tert-butyl 2-(7-(benzyloxy)-2,3-dihydro-1H-pyrrolo[1,2-a]indol-1-yl)acetate as a white solid. Exact mass calculated for $C_{24}H_{27}NO_3$: 377.2, found: LCMS m/z=378.4, [M+H$^+$]; $^1$H NMR (400 MHz, CDCl$_3$) δ ppm 1.50 (s, 9 H), 2.27 (m, 1 H), 2.49 (dd, $J_1$=15.8, $J_2$=8.5 Hz, 1 H), 2.73 (dd, $J_1$=15.8, $J_2$=6.4 Hz, 1 H), 2.86 (m, 1 H), 3.71 (m, 1 H), 3.99 (m, 1 H), 4.10 (ddd, $J_1$=9.8, $J_2$=8.6 Hz, $J_3$=4.2 Hz 1 H), 5.10 (s, 2 H), 6.08 (s, 1 H), 6.87 (dd, $J_1$=8.7, $J_2$=2.5 Hz, 1 H), 7.12 (m, 2 H), 7.30 (m, 1 H), 7.38 (m, 2 H), 7.47 (m, 2 H).

Step C: Preparation of (R)-tert-Butyl 2-(7-hydroxy-2,3-dihydro-1H-pyrrolo[1,2-a]indol-1-yl)acetate A mixture of (R)-tert-butyl 2-(7-(benzyloxy)-2,3-dihydro-1H-pyrrolo[1,2-a]indol-1-yl)acetate (0.320 g, 0.848 mmol), Pd(OAc)$_2$ (0.019 g, 0.085 mmol) and ammonium formate (0.214 g, 3.39 mmol) in methanol (20 mL) was heated under reflux overnight. After cooling the mixture was filtered through celite and then the solvent was removed under reduced pressure. Water (10 mL) and DCM (10 mL) were added and the 2 layers separated. The aqueous layer was extracted with DCM then the combined organics dried by passing through a phase separator cartridge. The solvent was removed under reduced pressure to give (R)-tert-butyl 2-(7-hydroxy-2,3-dihydro-1H-pyrrolo[1,2-a]indol-1-yl)acetate (0.240 g, 0.835 mmol, 99% yield, >70% ee) as a colorless oil. Exact mass calculated for $C_{17}H_{21}NO_3$: 287.2, found: LCMS m/z=288.2, [M+H$^+$]; $^1$H NMR (400 MHz, CDCl$_3$) δ ppm 1.56 (s, 9 H), 3.40 (m, 2 H), 4.13 (t, J=6.6 Hz, 2 H), 5.11 (s, 2 H), 5.80 (s, 1 H), 7.00 (dd, $J_1$=9.0, $J_2$=2.2 Hz, 1 H), 7.18 (m, 2 H), 7.33 (m, 1 H), 7.39 (m, 2 H), 7.48 (m, 2 H), 7.55 (s, 1 H) $^1$H NMR (400 MHz, d$_6$-DMSO) δ ppm 1.44 (s, 9 H), 2.18 (m, 1 H), 2.52 (dd, $J_1$=15.9, $J_2$=7.7 Hz, 1 H), 2.62 (dd, $J_1$=15.9, $J_2$=7.1 Hz, 1 H), 2.74 (m, 1 H), 3.54 (m, 1 H), 3.91 (m, 1 H), 4.05 (ddd, $J_1$=9.8, $J_2$=8.5 Hz, $J_3$=4.3 Hz 1 H), 5.88 (s, 1 H), 6.54 (m, 1 H), 6.76 (d, J=2.3 Hz, 1 H), 7.06 (d, J=8.6 Hz, 1 H), 8.54 (s, 1 H).

Enantiomeric excess can be determined via chiral HPLC analysis [250 mm×4.6 mm Chiralcel® AD-H column, 15% IPA in hexanes, 1 mL/min. 1st peak-(S)-tert-butyl 2-(7-hydroxy-2,3-dihydro-1H-pyrrolo[1,2-a]indol-1-yl)acetate $t_r$=13.8 min, 2nd peak-(R)-tert-butyl 2-(7-hydroxy-2,3-dihydro-1H-pyrrolo[1,2-a]indol-1-yl)acetate $t_r$=15.0 min].

Example 1.8

Powder X-ray Diffraction

Powder X-ray Diffraction (PXRD) data were collected on an X'Pert PRO MPD powder diffractometer (PANalytical, Inc.) with a Cu source set at 45 kV and 40 mA, Cu(Kα) radiation and an X'Celerator detector. Samples were added to the sample holder and smoothed flat with a spatula and weigh paper. With the samples spinning, X-ray diffractograms were obtained by a 12-min scan over the 2-theta range 5-40° 2θ. Diffraction data were viewed and analyzed with the X'Pert Data Viewer Software, version 1.0a and X'Pert HighScore Software, version 1.0b.

Example 1.9

Differential Scanning Calorimetry

Differential scanning calorimetry (DSC) studies were conducted using a TA Instruments, Q2000 at heating rate 10° C./min. The instruments were calibrated for temperature and energy using the melting point and enthalpy of fusion of an indium standard. Thermal events (desolvation, melting, etc.) were evaluated using Universal Analysis 2000 software, version 4.1D, Build 4.1.0.16.

Example 1.10

Thermal Gravimetric Analysis

Thermogravimetric analyses (TGA) were conducted using a TA Instruments TGA Q500 or Q5000 at heating rate 10° C./min. The instruments were calibrated using a standard weight for the balance, and Alumel and Nickel standards for the furnace (Curie point measurements). Thermal events such as weight-loss are calculated using the Universal Analysis 2000 software, version 4.1D, Build 4.1.0.16.

Example 1.11

Dynamic Moisture Sorption (DMS)

Samples are prepared for dynamic moisture-sorption analysis by placing ~5 mg to ~20 mg of compound in a tarred sample holder on the VTI balance. The instrument is a dynamic moisture-sorption analyzer, VTI Corporation, SGA-100. A drying step is run at 40° C. and ~1% RH for 1 h. The isotherm temperature is 25° C. A % weight change over 10 min (5 weight readings) of dm/dt=0.010 or 2 h, whichever occurs first, is required before continuing to the next step. The water content of the sample equilibrated as described above was determined from 30% RH to 90% RH and then back down to 10% RH.

Example 1.12

Preparation of the Crystalline From of (R)-2-(9-Chloro-7-(4-isopropoxy-3-(trifluoromethyl)benzyloxy)-2,3-dihydro-1H-pyrrolo[1,2-a]indol-1-yl)acetic Acid of Formula (Ia)

Figure 3:
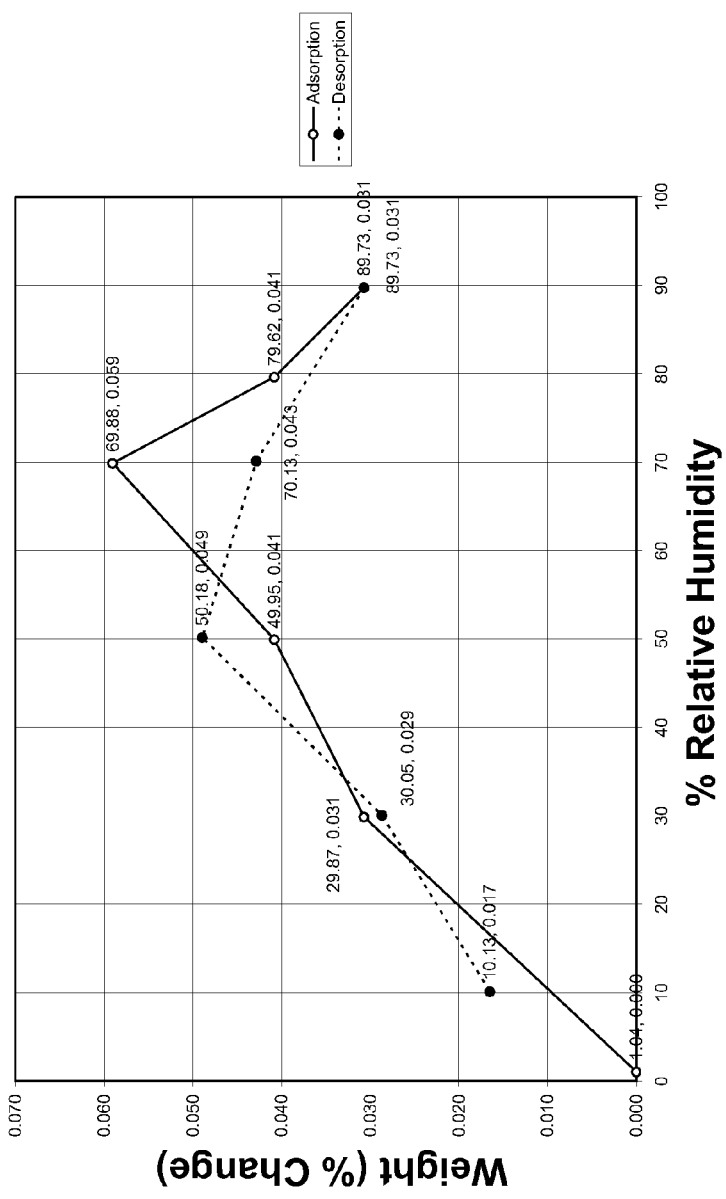
FIG. 3 shows a dynamic moisture sorption profile for a sample containing a crystalline form of (R)-2-(9-chloro-7-(4-isopropoxy-3-(trifluoromethyl)benzyloxy)-2,3-dihydro-1H-pyrrolo[1,2-a]indol-1-yl)acetic acid.

(R)-2-(9-Chloro-7-(4-isopropoxy-3-(trifluoromethyl)benzyloxy)-2,3-dihydro-1H-pyrrolo[1,2-a]indol-1-yl)acetic acid (102 mg) was slurried in IPA (0.5 mL) for 16 h and collected by vacuum filtration to provide 88 mg of the title compound as a solid. The PXRD pattern of the title compound is shown in FIG. 1; the DSC and TGA are shown in FIG. 2, and the DMS is shown in FIG. 3.

Example 1.13

Preparation of (R)-2-(9-Chloro-7-(4-isopropoxy-3-(trifluoromethyl)benzyloxy)-2,3-dihydro-1H-pyrrolo[1,2-a]indol-1-yl)acetic acid L-lysine salt The (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt was successfully prepared using a variety of different solvents, such as, IPA, MeCN, THF, Acetone, EtOAc, and EtOH. Each preparation utilizing these different solvents provided the same crystalline form as determined by PXRD. Two representative methods are described below.

Method 1:
(R)-2-(9-Chloro-7-(4-isopropoxy-3-(trifluoromethyl)benzyloxy)-2,3-dihydro-1H-pyrrolo[1,2-a]indol-1-yl)acetic acid (2.7265 g, 5.6579 mmol) was dissolved in acetone (90 mL) and heated to 45° C. using an external oil bath. Aqueous L-lysine (2.829 mL, 2.0 M) was added causing formation of a white precipitate. The oil bath was turned off and the solution was allowed to slowly cool to room temperature. After cooling, stirring was continued for a total of 18 h. The solids were collected by filtration to afford 2.58 g of the L-lysine salt (R)-2-(9-chloro-7-(4-isopropoxy-3-(trifluoromethyl)benzyloxy)-2,3-dihydro-1H-pyrrolo[1,2-a]indol-1-yl)acetic acid.

The PXRD pattern of the title compound is shown in FIG. 4; and the DSC and TGA are shown in FIG. 5.

Method 2:
(R)-2-(9-Chloro-7-(4-isopropoxy-3-(trifluoromethyl)benzyloxy)-2,3-dihydro-1H-pyrrolo[1,2-a]indol-1-yl)acetic acid (2.0 g, 4.15 mmol) was dissolved in acetonitrile (66 mL) with heating (70° C., oil bath) and a 2.0 M aqueous L-lysine solution (2.075 mL, 4.15 mmol) was added. After addition, the oil bath was turned off, and the reaction was allowed to slowly cool to room temperature and stirred for 16 h. The white solid was collected by vacuum filtration to afford 2.365 grams of the desired (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt (91% yield).

Example 1.14

Preparation of (R)-2-(9-chloro-7-(4-isopropoxy-3-(trifluoromethyl)benzyloxy)-2,3-dihydro-1H-pyrrolo[1,2-a]indol-1-yl)acetic acid sodium salt hydrate (R)-2-(9-Chloro-7-(4-isopropoxy-3-(trifluoromethyl)benzyloxy)-2,3-dihydro-1H-pyrrolo[1,2-a]indol-1-yl)acetic acid (20 mg) was dissolved in IPA (0.5 mL) with heating, and 2.0 M NaOH (21 uL) was added. The solution was allowed to cool to room temperature and stir for 24 h. The resultant solids that had formed were collected after decanting off the IPA.

The PXRD pattern of the title compound is shown in FIG. 7; and the DSC and TGA are shown in FIG. 8. The TGA thermogram shows a weight loss of about 6.6%, indicating that the salt is a di-hydrate.

Example 1.15

Preparation of (R)-2-(9-chloro-7-(4-isopropoxy-3-(trifluoromethyl)benzyloxy)-2,3-dihydro-1H-pyrrolo[1,2-a]indol-1-yl)acetic acid ethylenediamine salt hydrate (R)-2-(9-Chloro-7-(4-isopropoxy-3-(trifluoromethyl)benzyloxy)-2,3-dihydro-1H-pyrrolo[1,2-a]indol-1-yl)acetic acid (15 mg) was dissolved in THF (0.5 mL) and aqueous ethylenediamine (16 uL, 2.27 M) was added. The homogeneous solution was left to stir at room temperature for 2d. ACN (300 µL) was then added and the reaction was stirred at room temperature for one additional day. The reaction mixture was evaporated to dryness and 0.5 mL of EtOAc was added. After stiffing for 24 h at room temperature, a solid had formed which was collected by filtration. The PXRD pattern of the title compound is shown in FIG. 10; and the DSC and TGA are shown in FIG. 11.

Example 1.16

Preparation of (R)-2-(9-chloro-7-(4-isopropoxy-3-(trifluoromethyl)benzyloxy)-2,3-dihydro-1H-pyrrolo[1,2-a]indol-1-yl)acetic acid 2-amino-2-hydroxymethyl-propane-1,3-diol (TRIS) salt (R)-2-(9-Chloro-7-(4-isopropoxy-3-(trifluoromethyl)benzyloxy)-2,3-dihydro-1H-pyrrolo[1,2-a]indol-1-yl)acetic acid (15 mg, 0.0311 mmol) was dissolved in EtOAc (0.5 mL) and warmed to 60° C. Aqueous 2-amino-2-hydroxymethyl-propane-1,3-diol (TRIS, 8.0 uL, 4.0 M) was added. The reaction mixture was allowed to cool to room temperature over 24 h and the solids were collected by filtration. The PXRD pattern of the title compound is shown in FIG. 13; and the DSC and TGA are shown in FIG. 14.

Example 1.17

Preparation of (R)-2-(9-chloro-7-(4-isopropoxy-3-(trifluoromethyl)benzyloxy)-2,3-dihydro-1H-pyrrolo [1,2-a]indol-1-yl)acetic acid L-arginine salt (R)-2-(9-Chloro-7-(4-isopropoxy-3-(trifluoromethyl)benzyloxy)-2,3-dihydro-1H-pyrrolo[1,2-a]indol-1-yl)acetic acid (15 mg) was dissolved in acetone (0.5 mL) and heated to 60° C. Aqueous L-arginine (14 uL, 2.22 M) was added and the reaction mixture was cooled to 35° C. Water (14 uL) was then added and the mixture was stirred for 24 h. The reaction mixture was concentrated to dryness and EtOAc was added to provide a white solid which was collected by filtration.

Example 1.18

Preparation of (R)-2-(9-chloro-7-(4-isopropoxy-3-(trifluoromethyl)benzyloxy)-2,3-dihydro-1H-pyrrolo [1,2-a]indol-1-yl)acetic acid zinc salt (R)-2-(9-Chloro-7-(4-isopropoxy-3-(trifluoromethyl)benzyloxy)-2,3-dihydro-1H-pyrrolo[1,2-a]indol-1-yl)acetic acid [15 mg] was dissolved in THF [0.5 mL] and heated to 60° C. Aqueous Zn(OAc)$_2$ [8.0 uL, 1.95 M] was added and the reaction mixture was cooled to 35° C. over 24 h. Water [8 uL] was added and the mixture was stirred at room temperature for 24 h. The reaction mixture was concentrated to dryness and EtOAc was added to provide a white solid which was collected by filtration.

Example 1.19

Preparation of (R)-2-(9-chloro-7-(4-isopropoxy-3-(trifluoromethyl)benzyloxy)-2,3-dihydro-1H-pyrrolo [1,2-a]indol-1-yl)acetic acid calcium salt (R)-2-(9-Chloro-7-(4-isopropoxy-3-(trifluoromethyl)benzyloxy)-2,3-dihydro-1H-pyrrolo[1,2-a]indol-1-yl)acetic acid (15 mg) was dissolved in acetone and heated to 60° C. for 10 minutes. Aqueous Ca(OAc)$_2$ (15 uL, 1.04 M) was added. The reaction mixture was allowed to cool to 35° C. over 24 h and the solids were collected by filtration.

Example 1.20

Preparation of (R)-2-(9-chloro-7-(4-isopropoxy-3-(trifluoromethyl)benzyloxy)-2,3-dihydro-1H-pyrrolo [1,2-a]indol-1-yl)acetic acid N-methylglucamine salt (R)-2-(9-Chloro-7-(4-isopropoxy-3-(trifluoromethyl)benzyloxy)-2,3-dihydro-1H-pyrrolo[1,2-a]indol-1-yl)acetic acid (15 mg, 0.0311 mmol) was dissolved in acetone (0.5 mL) and warmed to 50° C. Aqueous N-methylglucamine (14 uL, 2.27M) was added and the mixture was allowed to slowly cool to 30° C. over 24 h. The reaction mixture was evaporated to dryness, and EtOAc (0.5 mL) was added to provide a solid which was collected by filtration.

Example 1.21

Preparation of (R)-2-(9-chloro-7-(4-isopropoxy-3-(trifluoromethyl)benzyloxy)-2,3-dihydro-1H-pyrrolo [1,2-a]indol-1-yl)acetic acid potassium salt (R)-2-(9-Chloro-7-(4-isopropoxy-3-(trifluoromethyl)benzyloxy)-2,3-dihydro-1H-pyrrolo[1,2-a]indol-1-yl)acetic acid (15 mg, 0.031 mmol) was dissolved in a suitable solvent (THF or acetone, 0.5 mL) and heated to 60° C. 2.08 M aqueous KOH (15 mL, 0.031 mmol) was added and the reaction mixture was cooled to 35° C. and stirred for 24 h. No solid product was obtained.

Example 1.22

Preparation of (R)-2-(9-chloro-7-(4-isopropoxy-3-(trifluoromethyl)benzyloxy)-2,3-dihydro-1H-pyrrolo [1,2-a]indol-1-yl)acetic acid magnesium salt (R)-2-(9-Chloro-7-(4-isopropoxy-3-(trifluoromethyl)benzyloxy)-2,3-dihydro-1H-pyrrolo[1,2-a]indol-1-yl)acetic acid (15 mg, 0.031 mmol) was dissolved in a suitable solvent (THF or acetone, 0.5 mL) and heated to 60° C. 1.04 M aqueous Mg(OAc)$_2$ (15 mL, 0.0156 mmol) was added and the reaction mixture was allowed to cool to 35° C. and stir for 24 h. The reaction was allowed to evaporate to dryness. No solid product was obtained.

Example 2

Homogeneous Time-Resolved Fluorescence (HTRF®) Assay For Direct cAMP Measurement Compounds were screened for agonists of the S1P1 receptor (e.g., human S1P1 receptor) using the HTRF® assay for direct cAMP measurement (Gabriel et al., Assay and Drug Development Technologies, 1:291-303, 2003) and recombinant CHO-K1 cells stably transfected with S1P1. CHO-K1 cells were obtained from ATCC® (Manassas, Va.; Catalog #CCL-61). An agonist of the S1P1 receptor was detected in the HTRF® assay for direct cAMP measurement as a compound which decreased cAMP concentration. HTRF® assay also was used to determine $EC_{50}$ values for S1P1 receptor agonists.

Principle of the Assay: HTRF® assay kit was purchased from Cisbio-US, Inc. (Bedford, Mass.; Catalog #62AM4PEC). The HTRF® assay supported by the kit is a competitive immunoassay between endogenous cAMP produced by the CHO-K1 cells and tracer cAMP labeled with the dye d2. The tracer binding is visualized by a monoclonal anti-cAMP antibody labeled with Cryptate. The specific signal (i.e., fluorescence resonance energy transfer, FRET) is inversely proportional to the concentration of unlabeled cAMP in the standard or sample.

Standard Curve: The fluorescence ratio (665 nm/620 nm) of the standards (0.17 to 712 nM cAMP) included in the assay was calculated and used to generate a cAMP standard curve according to the kit manufacturer's instructions. The fluorescence ratio of the samples (test compound or compound buffer) was calculated and used to deduce respective cAMP concentrations by reference to the cAMP standard curve.

Setup of the Assay: The HTRF® assay was carried out using a two-step protocol essentially according to the kit manufacturer's instructions, in 20 μL total volume per well in 384-well plate format (ProxiPlates; PerkinElmer, Fremont, Calif.; catalog #6008280). To each of the experimental wells was transferred 1500 recombinant CHO-K1 cells in 5 μL phosphate buffered saline containing calcium chloride and magnesium chloride (PBS+; Invitrogen, Carlsbad, Calif.; catalog #14040) supplemented with IBMX (250 μM) and rolipram (20 μM) (phosphodiesterase inhibitors; Sigma-Aldrich, St. Louis, Mo.; catalog #I5879 and catalog #R6520, respectively), followed by test compound in 5 μL compound buffer (PBS+ supplemented with 10 μL NKH477 (watersoluble forskolin derivative; SignaGen Laboratories, Gaithersburg, Md.; catalog #PKI-NKH477-010)) or 5 μL compound buffer. The plate was then incubated at room temperature for 1 h. To each well was then added 5 μL cAMP-d₂ conjugate in lysis buffer and 5 μL Cryptate conjugate in lysis buffer according to the kit manufacturer's instructions. The plate was then further incubated at room temperature for 1 hour, after which the assay plate was read.

Assay readout: HTRF® readout was accomplished using a PHERAstar (BMG LABTECH Inc., Durham, N.C.) or EnVision™ (PerkinElmer, Fremont Calif.) microplate reader.

The corresponding activity for (R)-2-(9-chloro-7-(4-isopropoxy-3-(trifluoromethyl)benzyloxy)-2,3-dihydro-1H-pyrrolo[1,2-a]indol-1-yl)acetic acid (Compound (Ia)) in the HTRF assay is shown in Table 11.

TABLE 11

| Compound | EC$_{50}$ S1P1 |
|---|---|
| (R)-2-(9-chloro-7-(4-isopropoxy-3-(trifluoromethyl)benzyloxy)-2,3-dihydro-1H-pyrrolo[1,2-a]indol-1-yl)acetic acid | 28 pM |

Example 3

Cellular/Functional Ca$^{2+}$ Assay for Agonist Activity on S1P3 Receptor

A compound of the invention can be shown to have no or substantially no agonist activity on the S1P3 receptor by using in assay a human neuroblastoma cell line which endogenously expresses S1P3 (predominantly), S1P2 and S1P5 receptors, but not S1P1 or S1P4 receptors, based on mRNA analysis (Villullas et al., *J. Neurosci. Res.*, 73:215-226, 2003). Of these, S1P3 and S1P2 receptors respond to agonists, such as S1P, with an intracellular calcium increase. No or substantially no increase of intracellular calcium in response to a test compound is indicative of the test compound exhibiting no or substantially no agonist activity on the S1P3 receptor. Such an assay can be performed commercially, e.g. by Caliper LifeSciences (Hopkinton, Mass.).

Assay: The human neuroblastoma cells are washed and resuspended in physiological buffer. The cells are then loaded with dye that measures intracellular calcium. S1P is used as a reference agonist. After addition of S1P or a test compound, fluorescence is measured at 485 nm excitation/525 nm emission every 2 s for at least 60 s. Calcium ionophore A23187 is then added as an internal positive control.

Example 4

Effect of (R)-2-(9-chloro-7-(4-isopropoxy-3-(trifluoromethyl)benzyloxy)-2,3-dihydro-1H-pyrrolo[1,2-a]indol-1-yl)acetic acid L-Lysine Salt in Peripheral Lymphocyte Lowering (PLL) Assay in Male BALB/c Mice Mouse PLL Assay.

Animals: Male BALB/c mice (Charles River Laboratories, Wilmington, Mass.) were housed four per cage and maintained in a humidity-controlled (40 to 60%) and temperature-controlled (68 to 72° F.) facility on a 12 h:12 h light/dark cycle (lights on at 6:30 am) with free access to food (Harlan Teklad, Orange, Calif., Rodent Diet 8604) and water. Mice were allowed (approximately) one week of habituation to the animal facility before testing.

Figure 15:
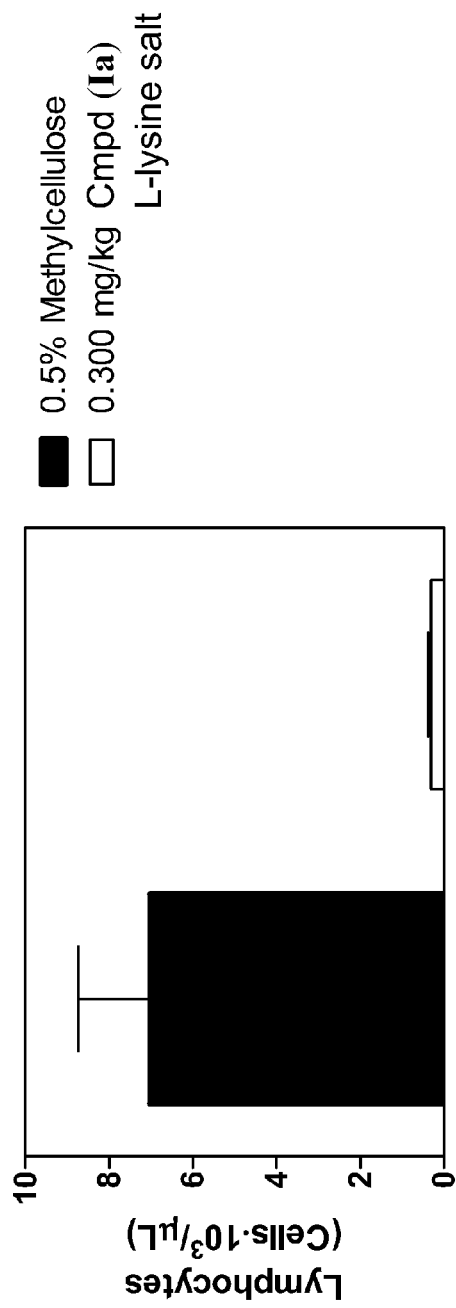
FIG. 15 shows the effect of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt in the Peripheral Lymphocyte Lowering (PLL) Assay after a 0.3 mg/kg oral dose (0.5% methyl cellulose in water) in BALB/c mice.

PLL Assay: Mice were given a 0.300 mg/kg oral dose of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt or dosing vehicle (0.5% methyl cellulose in water) in a total volume of 10 mL/kg. Peripheral blood samples were collected at 5 hours post-dose. The mice were anesthetized with isoflurane and blood was collected via cardiac puncture. A complete cell count (CBC), including lymphocyte count, was obtained using a CELL-DYN® 3700 (Abbott Laboratories, Abbott Park, Ill.) instrument. Results are presented in FIG. 15, in which peripheral blood lymphocyte (PBL) count is shown for the 5 hour group. Reduction of the PBL count by the test compound in comparison with vehicle is indicative of the test compound exhibiting activity or inducing peripheral lymphocyte lowering. It is apparent from inspection of FIG. 15 that (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt exhibited activity for inducing PBL lowering (lymphopenia) in the mouse.

Example 5

Effect of (R)-2-(9-chloro-7-(4-isopropoxy-3-(trifluoromethyl)benzyloxy)-2,3-dihydro-1H-pyrrolo[1,2-a]indol-1-yl)acetic acid in Peripheral Lymphocyte Lowering (PLL) Assay in Male Sprague-Dawley Rats Rat PLL Assay.

Animals: Male Sprague-Dawley rats (Charles River Laboratories, Hollister, Calif.) were housed and maintained in humidity (40 to 60%) and temperature (68 to 72° F.) controlled facility on a 12 h:12 h light/dark cycle (lights on at 6:30 am) with free access to food (Harlan Teklad, Orange, Calif., Rodent Diet 8604) and water. Rats were allowed (approximately) one week of habituation to the animal facility before testing.

Figure 16:
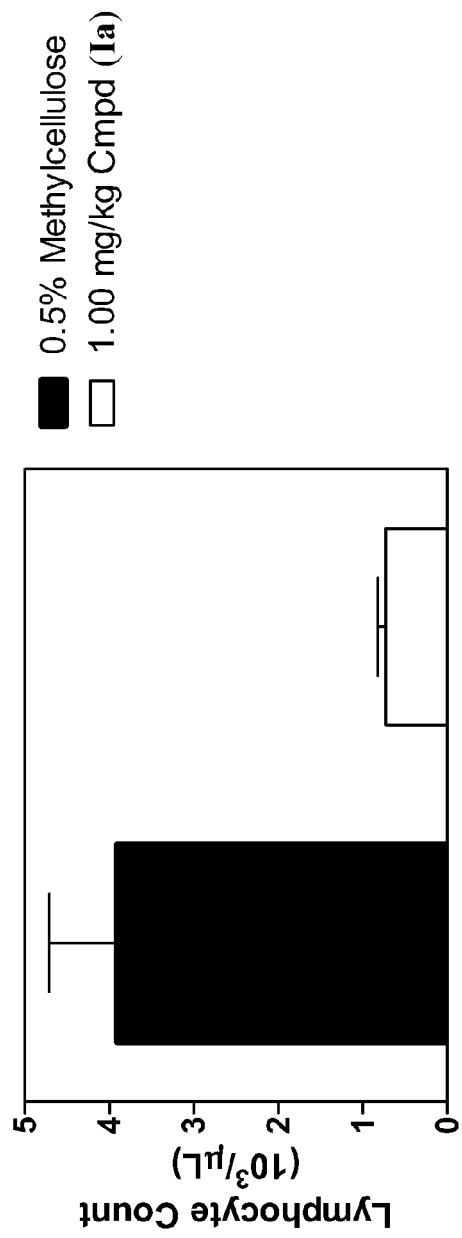
FIG. 16 shows the effect of (R)-2-(9-chloro-7-(4-isopropoxy-3-(trifluoromethyl)benzyloxy)-2,3-dihydro-1H-pyrrolo[1,2-a]indol-1-yl)acetic acid in the Peripheral Lymphocyte Lowering (PLL) Assay after a 1.0 mg/kg oral dose (0.5% methyl cellulose in water) in male Sprague-Dawley rats.

PLL Assay: Rats were given a 1.0 mg/kg oral dose of (R)-2-(9-chloro-7-(4-isopropoxy-3-(trifluoromethyl)benzyloxy)-2,3-dihydro-1H-pyrrolo[1,2-a]indol-1-yl)acetic acid or or dosing vehicle (0.5% methyl cellulose in water) in a total volume of 1 mL/kg. Peripheral blood samples were collected at 5 h post-dose. Blood was collected via indwelling catheter. A complete cell count (CBC), including lymphocyte count, was obtained using a CELL-DYN® 3700 (Abbott Laboratories, Abbott Park, Ill.) instrument. Results are presented in FIG. 16, in which peripheral blood lymphocyte (PBL) count is shown for the 5 hour group. Reduction of the PBL count by the test compound in comparison with vehicle is indicative of the test compound exhibiting activity or inducing peripheral lymphocyte lowering. It is apparent from inspection of FIG. 16 that (R)-2-(9-chloro-7-(4-isopropoxy-3-(trifluoromethyl)benzyloxy)-2,3-dihydro-1H-pyrrolo[1,2-a]indol-1-yl)acetic acid exhibited activity for inducing PBL lowering (lymphopenia) in the rat.

Example 6

Effect of (R)-2-(9-chloro-7-(4-isopropoxy-3-(trifluoromethyl)benzyloxy)-2,3-dihydro-1H-pyrrolo[1,2-a]indol-1-yl)acetic acid L-Lysine Salt on Experimental Autoimmune Encephalomyelitis (EAE)

A compound of the invention can be shown to have therapeutic efficacy in multiple sclerosis by showing it to have therapeutic efficacy in experimental autoimmune encephalomyelitis (EAE), an animal model for multiple sclerosis. In certain exemplary well-established models, EAE is induced in rodents by injection of myelin oligodendrocyte glycoprotein (MOG) peptide, by injection of myelin basic protein (MBP) or by injection of proteolipid protein (PLP) peptide.

A. MOG-induced EAE in Mice.

Animals: Female C57BL/6 mice (8 to 10 weeks of age at start of study) (Jackson Laboratory, Bar Harbor, Me.) were housed four per cage and maintained in a humidity-controlled (40-60%) and temperature-controlled (68-72° F.) facility on a 12 h:12 h light/dark cycle (lights on at 6:30 am) with free access to food (Harlan Teklad, Orange, Calif., Rodent Diet 8604) and water. Mice were allowed one week of habituation to the animal facility before testing.

Induction of EAE: Mice were immunized subcutaneously, 50 μL per hind flank, with a total of 100 μg $MOG_{35-55}$ peptide emulsified 1:1 with complete Freund's adjuvant containing 4 mg/mL heat-killed *Mycobacterium tuberculosis*. Mice also receive 200 ng pertussis toxin intraperitoneally on the day of immunization and 48 h later.

Clinical Scoring: Severity of disease symptoms were scored as follows (in increasing order of severity): 0=normal; 1=limp tail OR hind limb weakness; 2=limp tail AND limb weakness/weakness of 2 or more limbs; 3=severe limb weakness or single limb paralysis; 4=paralysis of 2 or more limbs; 5=death.

Figure 17:
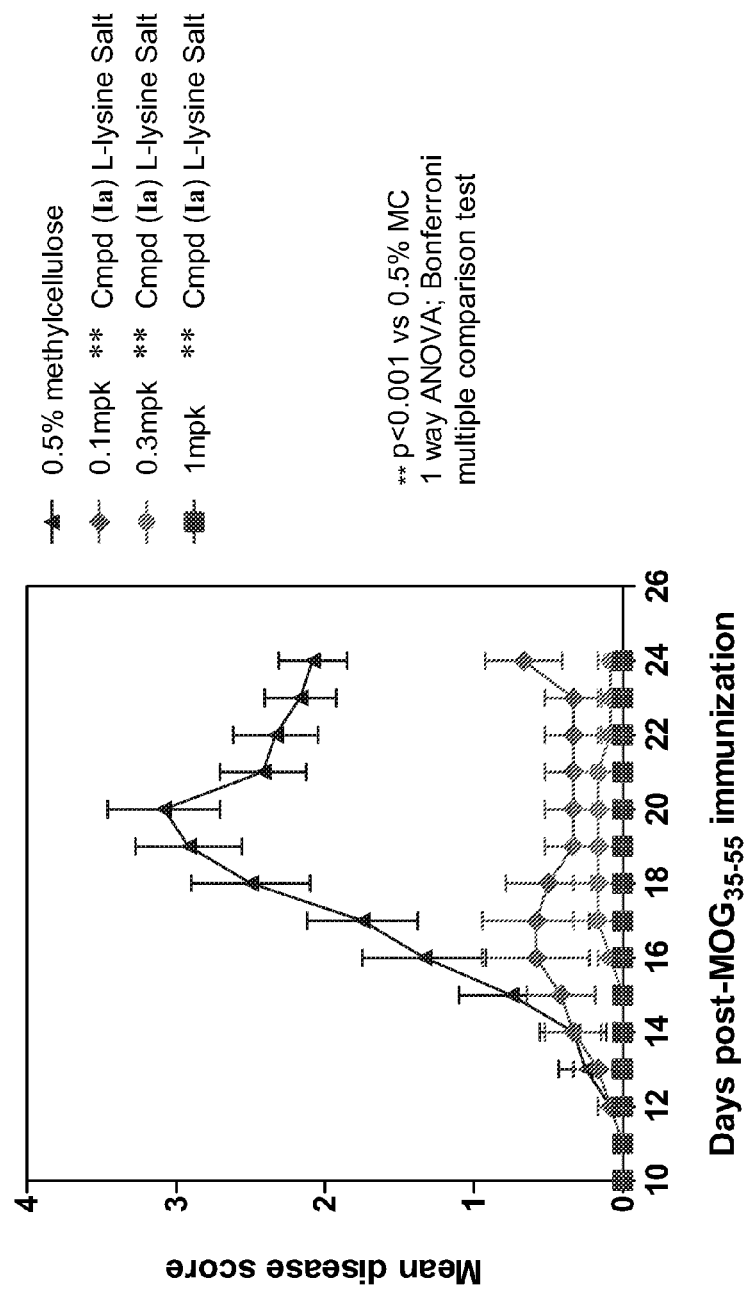
FIG. 17 shows the effect of (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt in the experimental autoimmune encephalomyelitis (EAE) assay after daily oral dosing of 0.1 mg/kg, 0.3 mg/kg, and 1.0 mg/kg from day 3 to day 21.

Drug Treatment: Mice were dosed orally, with vehicle or (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt, once a day from day 3 until day 21. Dosing volume was 5 mL/kg. Compound (Ia) was dosed at, e.g., 0.1 mg/kg, 0.3 mg/kg, and 1.0 mg/kg. Mice were weighed daily. Mice were monitored daily from day 7 onward for disease symptoms. After the last dose on day 21, disease progression was monitored daily for 2 more weeks. Reduction of the severity of disease symptoms by (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt in comparison with vehicle is shown in FIG. 17 and clearly shows that (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt exhibits therapeutic efficacy in EAE.

B. PLP-induced EAE in Mice.

Animals: Female SJL/J mice (8 to 10 weeks of age at start of study) (Jackson Laboratory, Bar Harbor, Me.) are housed four per cage and maintained in a humidity-controlled (40-60%) and temperature-controlled (68-72° F.) facility on a 12 h:12 h light/dark cycle (lights on at 6:30 am) with free access to food (Harlan-Teklad Western Res, Orange, Calif., Rodent Diet 8604) and water. Mice are allowed one week of habituation to the animal facility before testing.

Induction of EAE: Mice are immunized subcutaneously with 100 μg $PLP_{139-151}$ peptide emulsified 1:1 with complete Freund's adjuvant containing 4 mg/mL heat-killed *Mycobacterium tuberculosis*. Mice also receive 200 ng pertussis toxin intraperitoneally on the day of immunization and a second 200 ng dose after 48 hours.

Clinical Scoring: Severity of disease symptoms is scored as follows (in increasing order of severity): 0=normal; 1=limp tail OR hind limb weakness; 2=limp tail AND limb weakness/weakness of 2 or more limbs; 3=severe limb weakness or single limb paralysis; 4=paralysis of 2 or more limbs; 5=death.

Drug Treatment: Mice are dosed orally, with vehicle or a test compound, once a day from day 3 until day 21. Dosing volume is 5 ml/kg. The test compound is dosed at, e.g., 1 mg/kg, 3 mg/kg, 10 mg/kg or 30 mg/kg. Mice are weighed daily. Mice are monitored daily from day 7 onward for disease symptoms. After the last dose on day 21, disease progression is monitored daily for two more weeks.

C. MBP-induced EAE in Rats.

Animals: Male Lewis rats (325-375 g at start of study) (Harlan, San Diego, Calif.) are housed two per cage and maintained in a humidity-controlled (30-70%) and temperature-controlled (20-22° C.) facility on a 12 h:12 h light/dark cycle (lights on at 6:30 A.M.) with free access to food (Harlan-Teklad Western Res., Orange, Calif., Rodent Diet 8604) and water. Rats are allowed one week of habituation to the animal facility before testing. During the study, rats are weighed daily prior to clinical scoring at 11 am.

Induction of EAE: Myelin basic protein (MBP; guinea pig) is dissolved in sterile saline at a concentration of 1 mg/ml, and then emulsified 1:1 with complete Freund's adjuvant (1 mg/ml). 50 μL of this emulsion is administered by intraplantar (ipl) injection into both hind paws of each rat, for a total injected volume of 100 μL per rat and a total dose of 50 μg of MBP per rat.

Clinical Scoring: Severity of disease symptoms is scored daily after body weighing and before drug dosing. Severity of disease symptoms is scored as follows (in increasing order of severity): 0=normal; 1=tail OR limb weakness; 2=tail AND limb weakness; 3=severe hind limb weakness or single limb paralysis; 4=loss of tail tone and paralysis of 2 or more limbs; 5=death.

Drug Treatment: Rats are dosed orally, with vehicle or a test compound, 1 hour prior to MBP injection on day 0 and daily thereafter, after clinical scoring, for the duration of the study. Dosing volume is 5 mL/kg. The test compound is dosed at, e.g., 1 mg/kg, 3 mg/kg, 10 mg/kg or 30 mg/kg. Reduction of the severity of disease symptoms by the test compound in comparison with vehicle is indicative of the test compound exhibiting therapeutic efficacy in EAE.

Example 7

Effect of a Compound on Type I Diabetes

A compound of the invention can be shown to have therapeutic efficacy in type I diabetes using an animal model for type I diabetes, such as cyclophosphamide-induced type I diabetes in mice.

Animals: Baseline blood glucose measurements are taken from 9-10 week old female NOD/Ltj mice (Jackson Laboratory, Bar Harbor, Me.) to ensure that they are normoglycemic (blood glucose is 80-120 mg/dL) prior to initiation of the experiment. Blood glucose is measured from tail bleeds using a OneTouch® Ultra® meter and test strips (LifeScan, Milpitas, Calif.).

Cyclophosphamide Induction of Type I Diabetes: On day 0 and day 14, normoglycemic NOD mice are injected intraperitoneally with 4 mg cyclophosphamide monohydrate (200 mg/kg) dissolved in 0.9% saline. If mice are diabetic (blood glucose is >250 mg/dL), they are not given a booster dose of cyclophosphamide on day 14.

Drug Treatment: Mice are dosed orally, with vehicle or test compound, once a day from day 0 until day 25. Compounds are suspended in 0.5% methyl cellulose vehicle using a sonicator to ensure uniform suspension. Mice are weighed twice weekly and are dosed according to weight. Dosing volume is 5 mL/kg. The test compound is dosed at, e.g., 1 mg/kg, 3 mg/kg, 10 mg/kg or 30 mg/kg. Blood glucose is measured twice weekly. After dosing is completed at day 25, the mice continue to be monitored and blood glucose measurements are taken once a week for 3 weeks. Promotion of normoglycemia by the test compound in comparison with vehicle is indicative of the test compound exhibiting therapeutic efficacy in type I diabetes.

Example 8

Allograft Survival

A compound of the invention can be shown to have therapeutic efficacy in prolonging allograft survival by showing it to have therapeutic efficacy in prolonging, e.g., survival of a skin allograft in an animal model.

Animals: Female Balb/c mice (6 to 7 weeks of age at start of study) (Jackson Laboratory, Bar Harbor, Me.) are housed four per cage and maintained in a humidity-controlled (40-60%) and temperature-controlled (68-72° F.) facility on a 12 h:12 h light/dark cycle (lights on at 6:30 am) with free access to food (Harlan Teklad, Orange, Calif., Rodent Diet 8604) and water. Female C57BL/6 mice (8 to 10 weeks of age at start of study) (Jackson Laboratory, Bar Harbor, Me.) are similarly housed and maintained. Mice are allowed one week of habituation to the animal facility before testing.

Skin Allograft: Balb/c and C57BL/6 mice are used as donors and recipients, respectively, in a model of skin allograft transplantation. Donor Balbc/J mice are anesthetized, and 0.5 cm—diameter full thickness areas of abdominal skin are surgically removed. Skin grafts harvested from the Balb/c mice are sutured onto the dorsum of anesthetized recipient C57BL/6 mice. Sutured allografts are covered with Vaseline gauze and Bolster dressing for 7 days. The allografted mice are divided into 8 groups of 8 mice each.

Clinical Scoring: Skin allografts are inspected and digital images recorded daily until rejection, which is defined as the first day on which more than 80% of the graft is necrotic. Histological analysis of the rejected graft is carried out on hematoxylin and eosin (H&E)-stained sections. In an optional related study, on post-transplantation day 5 isolated lymphocytes from peripheral lymph nodes and spleen are counted and characterized for activation markers (e.g., T-cell activation markers) by flow cytometry. Also on day 5, grafts are removed from transplanted recipients, cut into small fragments, digested with collagenase and sedimented over Ficoll-Paque (Pharmacia Biotech, Uppsala, Sweden) to isolate graft-infiltrating lymphocytes, which are counted and characterized for activation markers (e.g., T-cell activation markers) by flow cytometry. Histological analysis of the graft on day 5 can be carried out on hematoxylin and eosin (H&E)-stained sections.

Drug Treatment: Mice are dosed orally, with vehicle or test compound, once a day from the day of transplantation until the end of the study, e.g. until day 14, 21, or 28. Dosing volume is 5 mL/kg. The test compound is dosed at, e.g., 1 mg/kg, 3 mg/kg, 10 mg/kg or 30 mg/kg. Delay of time of rejection of the skin allograft by the test compound in comparison with vehicle is indicative of the test compound exhibiting therapeutic efficacy in prolonging skin allograft survival.

Example 9

Effect of a Compound on Colitis

A compound of the invention can be shown to have therapeutic efficacy in colitis using an animal model for colitis. Suitable animal models are known in the art (Boismenu et al., J. Leukoc. Biol., 67:267-278, 2000). A first exemplary animal model for colitis is trinitrobenzenesulfonic acid (TNBS)-induced colitis, which presents clinical and histopathological findings that resemble those in Crohn's disease (Neurath et al., J. Exp. Med., 182:1281-1290, 1995; Boismenu et al., J. Leukoc. Biol., 67:267-278, 2000). A second exemplary animal model for colitis is dextran sulfate sodium (DSS)-induced colitis, which presents clinical and histopathological findings that resemble those in ulcerative colitis (Okayasu et al., Gastroenterology, 98:694-702, 1990; Boismenu et al., J. Leukoc. Biol., 67:267-278, 2000). Compounds can be commercially tested for efficacy in at least DSS-induced colitis and TNBS-induced colitis, e.g. by the Jackson Laboratory (Bar Harbor, Me.).

A. Mouse Model for Colitis.

Animals: Male BALB/c mice (6 weeks of age at start of study) (Jackson Laboratory, Bar Harbor, Me.) are housed four per cage and maintained in a humidity-controlled (40-60%) and temperature-controlled (68-72° F.) facility on a 12 h:12 h light/dark cycle (lights on at 6:30 am) with free access to food (Harlan Teklad, Orange Calif., Rodent Diet 8604) and water. Mice are allowed one week of habituation to the animal facility before testing.

TNBS Induction of Colitis: Mice are weighed for baseline body weights and fasted later that day beginning at 6:15 pm just prior to lights-out (day 0). Body weights are taken again the following morning (day 1) at approximately 7:30 am. Mice are anesthetized with isoflurane prior to induction of colitis. Colitis is induced in the mice by intracolonic injection of about 150 mg/kg TNBS in 50% ethanol (in a volume of 150 µL) using an intubation needle (22 g, 1.5 in) inserted completely into the anus with the mouse held by the tail in a vertical position. The mouse is held vertically for 30 additional seconds to allow thorough absorption and minimize leakage, after which the mouse is returned to its cage. Mice are then fed, following the preceding approximately 14 hour of fasting. Each morning thereafter, the mice are weighed. In control experiments, mice receive 50% ethanol alone using the same protocol.

Drug Treatment: Drug treatment begins on day 2. Mice are dosed orally, with vehicle or a test compound, once a day from day 2 until the conclusion of the experiment on, e.g., day 7, 14, or 21. Dosing volume is 5 mL/kg. The test compound is dosed at, e.g., 1 mg/kg, 3 mg/kg, 10 mg/kg, or 30 mg/kg.

Clinical Scoring: Upon conclusion of the experiment, colons are extracted and measured. Mice are euthanized with $CO_2$ and colon is removed from anus to cecum. Excised colon is measured for entire length, length from anus to end of inflamed area and length of inflamed (affected) area. After measurements, colon is cleared of excrement by flushing with saline and then cut open to clear more thoroughly. Colon is then weighed and preserved in neutral buffered formalin (NBF; 10% formalin, pH 6.7-7.0). The colon tissue is embedded in paraffin and processed for hematoxylin and eosin (H & E)-stained sections. Severity of disease symptoms is scored histologically from the stained sections as follows: 0=no evidence of inflammation; 1=low level of leukocyte infiltration with infiltration seen in <10% of high-power fields AND no structural changes; 2=moderate leukocyte infiltration with infiltration seen in 10% to 25% of high-power fields AND crypt elongation AND bowel wall thickening that does not extend beyond the mucosal layer AND no ulcerations; 3=high level of leukocyte infiltration seen in 25% to 50% of high-power fields AND crypt elongation AND infiltration beyond the mucosal layer AND thickening of the bowel wall AND superficial ulcerations; 4=marked degree of transmural leukocyte infiltration seen in >50% of high-power fields AND elongated and distorted crypts AND bowel wall thickening AND extensive ulcerations. Reduction of the severity of the disease symptoms by the test compound in comparison with vehicle is indicative of the test compound exhibiting therapeutic efficacy in colitis.

B. Rat Model for Colitis.

Animals: Male Wistar rats (175-200 g at start of study) (Charles River Laboratories, Wilmington, Mass.) are housed two per cage and maintained in a humidity-controlled (40-60%) and temperature-controlled (68-72° F.) facility on a 12 h:12 h light/dark cycle (lights on at 6:30 am) with free access to food (Harlan Teklad, Orange Calif., Rodent Diet 8604) and water. Rats are allowed one week of habituation to the animal facility before testing.

TNBS Induction of Colitis: Rats are weighed for baseline body weights and fasted later that day beginning at 6:15 pm just prior to lights-out (day 0). Body weights are taken again the following morning (day 1) at approximately 7:30 am. Rats are anesthetized with isoflurane prior to induction of colitis. Colitis is induced in the rats by intracolonic injection of about 60 mg/kg TNBS in 50% ethanol (in a volume of 500 µL) using a fabricated intubation needle (7.5 Fr umbilical catheter and 14 g hub) inserted 8 cm into the anus with the rat held by the tail in a vertical position. The rat is held vertically for 30 additional s to allow thorough absorption and minimize leakage, after which the rat is returned to its cage. Rats are then fed, following the preceding approximately 14 h of fasting. Each morning thereafter, the rats are weighed. In control experiments, rats receive 50% ethanol alone using the same protocol.

Drug Treatment: Drug treatment begins on day 2. Rats are dosed orally, with vehicle or test compound, once a day from day 2 until the conclusion of the experiment on, e.g., day 7, 14 or 21. Dosing volume is 5 mL/kg. Test compound is dosed at, e.g., 1 mg/kg, 3 mg/kg, 10 mg/kg, or 30 mg/kg.

Clinical Scoring: Upon conclusion of the experiment, colons are extracted and measured. Rats are euthanized with $CO_2$ and colon is removed from anus to cecum. Excised colon is measured for entire length, length from anus to end of inflamed area, and length of inflamed (affected) area. After measurements, colon is cleared of excrement by flushing with saline and then cut open to clear more thoroughly. Colon is then weighed and preserved in neutral buffered formalin (NBF; 10% formalin, pH 6.7-7.0). The colon tissue is embedded in paraffin and processed for hematoxylin and eosin (H & E)-stained sections. Severity of disease symptoms is scored histologically from the stained sections as follows: 0=no evidence of inflammation; 1=low level of leukocyte infiltration with infiltration seen in <10% of high-power fields AND no structural changes; 2=moderate leukocyte infiltration with infiltration seen in 10% to 25% of high-power fields AND crypt elongation AND bowel wall thickening that does not extend beyond the mucosal layer AND no ulcerations; 3=high level of leukocyte infiltration seen in 25% to 50% of high-power fields AND crypt elongation AND infiltration beyond the mucosal layer AND thickening of the bowel wall AND superficial ulcerations; 4=marked degree of transmural leukocyte infiltration seen in >50% of high-power fields AND elongated and distorted crypts AND bowel wall thickening AND extensive ulcerations. Reduction of the severity of the disease symptoms by the test compound in comparison with vehicle is indicative of the test compound exhibiting therapeutic efficacy in colitis.

Example 10

Effects of a Compound on Cardiac Telemetry in the Rat

Animals: Male Sprague-Dawley rats (250-300 g at time of surgery) are implanted by Charles River Laboratories (Wilmington, Mass.) with cardiac transmitting devices (Data Sciences PhysioTel C50-PXT) into the peritoneal space, with a pressure-sensing catheter inserted into the descending aorta. Rats are allowed at least one week to recover. Rats are housed in individual cages and maintained in a humidity-controlled (30-70%) and temperature-controlled (20-22° C.) facility on a 12 h:12 h light/dark cycle (lights on at 7:00 am) with free access to food (Harlan-Teklad, Orange, Calif., Rodent Diet 8604) and water. Rats are allowed one week of habituation to the animal facility before testing.

Measurement of Cardiovascular Parameters: The implanted transmitting devices transmit continuous measurements of blood pressure (systolic, diastolic, mean arterial, pulse), heart rate, body temperature, and motor activity in freely moving conscious animals. These data are transmitted via radiofrequency to a computer which bin the data into 1 min averages using DataSciences Aroom temperature software. Telemetry recording takes place over a 21-h period, starting at noon and continuing until 9:00 am the following day. A maximum of eight rats are tested at a time, and the same eight rats are utilized for all treatment groups in a within-subject design.

Drug Treatment: Rats are injected orally with vehicle or compound at 1:00 pm. A full study (vehicle+3 doses) requires four separate testing sessions, which occur on Mondays-Tuesdays and Thursdays-Fridays. During each of the testing sessions, the eight rats are divided into four treatment groups such that each group comprises N=2 for any given session. Rats are re-tested in subsequent testing sessions in a crossover design such that by the end of the four sessions, all animals receive all treatments in a pseudo-random order, and each group comprises N=8.

Exemplary bradycardia assay: It is expressly contemplated that the rats can be used to show that a compound of the invention has no or substantially no activity for bradycardia. By way of illustration and not limitation, the rats are administered vehicle or a test compound and heart rate is then measured over a 120 min period. No or substantially no reduction of heart rate in response to the test compound in comparison with vehicle is indicative of the test compound exhibiting no or substantially no activity for bradycardia.

Those skilled in the art will recognize that various modifications, additions, substitutions and variations to the illustrative examples set forth herein can be made without departing from the spirit of the invention and are, therefore, considered within the scope of the invention. All documents referenced above, including, but not limited to, printed publications and provisional and regular patent applications, are incorporated herein by reference in their entirety.

Citation of any reference throughout this application is not to be construed as an admission that such reference is prior art to the present application.

What is claimed is:

1. A salt that is (R)-2-(9-chloro-7-(4-isopropoxy-3-(trifluoromethyl)benzyloxy)-2,3-dihydro-1H-pyrrolo[1,2-a]indol-1-yl)acetic acid L-lysine salt.

2. A crystalline form of the salt according to claim 1 having an X-ray powder diffraction pattern comprising peaks, in terms of 2θ, at about 6.9° and about 11.4°.

3. A crystalline form of the salt according to claim 1 having an X-ray powder diffraction pattern comprising peaks, in terms of 2θ, at about 6.9°, about 11.4°, about 13.7°, about 21.7°, and about 22.9°.

4. A crystalline form of the salt according to claim 1 having an X-ray powder diffraction pattern comprising peaks, in terms of 2θ, at about 6.9°, about 11.4°, about 13.6°, about 13.7°, about 19.8°, about 20.6°, about 21.7°, about 22.1°, and about 22.9°.

5. A crystalline form of the salt according to claim 1 having an X-ray powder diffraction pattern substantially as shown in FIG. 4.

6. A crystalline form of the salt according to claim 1 having a differential scanning calorimetry thermogram comprising an endotherm with an extrapolated onset temperature between about 213° C. and about 217° C.

7. A crystalline form of the salt according to claim 1 having a differential scanning calorimetry thermogram comprising an endotherm with an extrapolated onset temperature between about 220° C. and about 224° C.

8. A crystalline form of the salt according to claim 1 having a differential scanning calorimetry thermogram comprising an endotherm with a first extrapolated onset temperature between about 213° C. and about 217° C.; and a second extrapolated onset temperature between about 220° C. and about 224° C.

9. A crystalline form of the salt according to claim 1 having a differential scanning calorimetry thermogram substantially as shown in FIG. 5.

10. A crystalline form of the salt according to claim 1 having a thermogravimetric analysis profile showing less than about 0.1% weight loss up to about 110° C.

11. A crystalline form of the salt according to claim 1 having a thermogravimetric analysis profile substantially as shown in FIG. 5.

12. A crystalline form of the salt according to claim 1 having:
1) an X-ray diffraction pattern comprising peaks, expressed in terms of 2θ, at about 6.9°, about 11.4°, about 13.7°, about 21.7°, and about 22.9°;
2) a differential scanning calorimetry thermogram comprising an endotherm with an extrapolated onset temperature between about 213° C. and about 217° C.; and/or
3) a thermogravimetric analysis profile showing less than about 0.1% weight loss up to about 110° C.

13. A crystalline form of the salt according to claim 1 having:
1) an X-ray diffraction pattern comprising peaks, expressed in terms of 2θ, at about 6.9°, about 11.4°, about 13.6°, about 13.7°, about 19.8°, about 20.6°, about 21.7°, about 22.1°, and about 22.9°;
2) a differential scanning calorimetry thermogram comprising an endotherm with a first extrapolated onset temperature between about 213° C. and about 217° C.; and a second extrapolated onset temperature between about 220° C. and about 224° C.; and/or
3) a thermogravimetric analysis profile showing less than about 0.1% weight loss up to about 110° C.

14. A salt that is an L-lysine salt of (R)-2-(9-chloro-7-(4-isopropoxy-3-(trifluoromethyl)benzyloxy)-2,3-dihydro-1H-pyrrolo[1,2-a]indol-1-yl)acetic acid, wherein the salt is prepared by a process comprising the steps of:

a) hydrolyzing a compound of Formula (IIn):

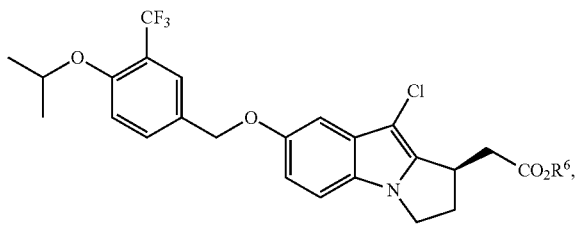

(IIn)

wherein $R^6$ is $C_1$-$C_4$ alkyl;
in the presence of a hydrolozing-step base and a hydrolyzing-step solvent to form said (R)-2-(9-chloro-7-(4-isopropoxy-3-(trifluoromethyl)benzyloxy)-2,3-dihydro-1H-pyrrolo[1,2-a]indol-1-yl)acetic acid; and b) contacting said (R)-2-(9-chloro-7-(4-isopropoxy-3-(trifluoromethyl)benzyloxy)-2,3-dihydro-1H-pyrrolo[1,2-a]indol-1-yl)acetic acid with L-lysine or a salt thereof, in the presence of a contacting-step solvent and $H_2O$ to form said L-lysine salt of (R)-2-(9-chloro-7-(4-isopropoxy-3-(trifluoromethyl)benzyloxy)-2,3-dihydro-1H-pyrrolo[1,2-a]indol-1-yl)acetic acid.

15. A composition comprising said salt according to claim 1.

16. The composition according to claim 15, wherein said salt or said crystalline form comprises about 97% or greater by weight of said composition.

17. A pharmaceutical composition comprising said salt according to claim 1, and a pharmaceutically acceptable carrier.

18. A method for treating an S1P1 receptor-associated disorder selected from the group consisting of psoriasis, psoriatic arthritis, inflammatory bowel disease, rheumatoid arthritis, Crohn's disease, transplant rejection, multiple sclerosis, systemic lupus erythematosus, ulcerative colitis, type I diabetes, acne, myocardial ischemia-reperfusion injury, hypertensive nephropathy, glomerulosclerosis, gastritis, polymyositis, thyroiditis, vitiligo, hepatitis, and biliary cirrhosis in an individual comprising administering to said individual in need thereof a therapeutically effective amount of a salt according to claim 1.

19. A compound of Formula (IIm), or a salt thereof:

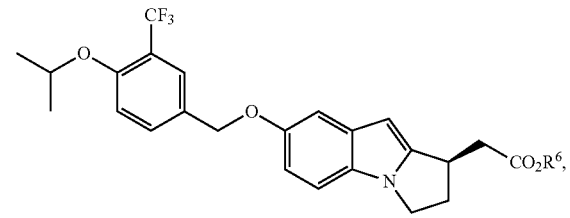

(IIm)

wherein $R^6$ is $C_1$-$C_4$ alkyl.

20. The compound according to claim 19, wherein $R^6$ is $CH_2CH_3$ or t-butyl.

21. A compound of Formula (IIn), or a salt thereof:

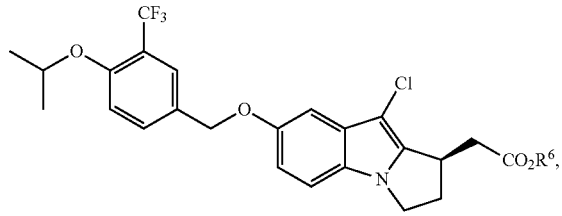

(IIn)

wherein $R^6$ is $C_1$-$C_4$ alkyl.

22. The compound according to claim 21, wherein $R^6$ is $CH_2CH_3$ or t-butyl.

23. The method according to claim 18, wherein said S1P1 receptor-associated disorder is biliary cirrhosis.

24. The method according to claim 18, wherein said S1P1 receptor-associated disorder is multiple sclerosis.

25. A method according to claim 18, wherein said S1P1 receptor-associated disorder disorder is psoriasis.

26. A method according to claim 18, wherein said S1P1 receptor-associated disorder disorder is rheumatoid arthritis.

27. A method according to claim 18, wherein said S1P1 receptor-associated disorder disorder is psoriatic arthritis.

28. A method according to claim 18, wherein said S1P1 receptor-associated disorder disorder is inflammatory bowel disease.

29. A method according to claim 18, wherein said S1P1 receptor-associated disorder disorder is Crohn's disease.

30. A method according to claim 18, wherein said S1P1 receptor-associated disorder disorder is ulcerative colitis.

* * * * *

UNITED STATES PATENT AND TRADEMARK OFFICE
CERTIFICATE OF CORRECTION

PATENT NO.        : 9,085,581 B2
APPLICATION NO.   : 13/581846
DATED             : July 21, 2015
INVENTOR(S)       : Jones et al.

Page 1 of 1

It is certified that error appears in the above-identified patent and that said Letters Patent is hereby corrected as shown below:

On the Title Page item [56]:

Col. 2, line 1 (Other Publications), delete "efficent" and insert -- efficient --;

Col. 2, line 15 (Other Publications), delete "autoimmunue" and insert -- autoimmune --;

On the Title Page item [57]:

Col. 2, lines 2-3, delete "chloro -7" and insert -- chloro-7 --;

In the Claims:

Claim 14, Col. 124, line 17, delete "hydrolozing-step" and insert -- hydrolyzing-step --;

Claim 25, Col. 126, line 6, delete "disorder disorder" and insert -- disorder --;

Claim 26, Col. 126, line 8, delete "disorder disorder" and insert -- disorder --;

Claim 27, Col. 126, line 10, delete "disorder disorder" and insert -- disorder --;

Claim 28, Col. 126, line 12, delete "disorder disorder" and insert -- disorder --;

Claim 29, Col. 126, line 15, delete "disorder disorder" and insert -- disorder --;

Claim 30, Col. 126, line 17, delete "disorder disorder" and insert -- disorder --.

Signed and Sealed this
Nineteenth Day of January, 2016

Michelle K. Lee
*Director of the United States Patent and Trademark Office*